US008563570B2

(12) United States Patent
Yao et al.

(10) Patent No.: US 8,563,570 B2
(45) Date of Patent: *Oct. 22, 2013

(54) LACTAM COMPOUNDS AND THEIR USE AS PHARMACEUTICALS

(75) Inventors: Wenqing Yao, Kennett Square, PA (US);
Chunhong He, Boothwyn, PA (US);
David M. Burns, Philadelphia, PA (US);
Jincong Zhuo, Garnett Valley, PA (US);
Meizhong Xu, Hockessin, DE (US);
Colin Zhang, Ambler, PA (US);
Ding-Quan Qian, Newark, DE (US);
Brian Metcalf, Moraga, CA (US)

(73) Assignee: Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/355,219

(22) Filed: Jan. 20, 2012

(65) Prior Publication Data

US 2012/0122858 A1    May 17, 2012

Related U.S. Application Data

(63) Continuation of application No. 12/252,700, filed on Oct. 16, 2008, now Pat. No. 8,110,581, which is a continuation-in-part of application No. 11/269,984, filed on Nov. 9, 2005, now abandoned.

(60) Provisional application No. 60/715,020, filed on Sep. 8, 2005, provisional application No. 60/626,617, filed on Nov. 10, 2004.

(51) Int. Cl.
*C07D 471/10*      (2006.01)
*A61K 31/4439*     (2006.01)

(52) U.S. Cl.
USPC ............... 514/278; 514/228.8; 514/253.04; 514/275; 514/255.05; 514/263.22; 514/266.21; 514/253.06; 514/256; 514/265.1; 546/16; 546/20; 544/230; 544/70

(58) Field of Classification Search
USPC ............ 514/278, 228.8, 253.04, 275, 255.05, 514/263.22, 266.21, 253.06, 256, 265.1; 546/16, 20; 544/230, 70
See application file for complete search history.

(56) References Cited

U.S. PATENT DOCUMENTS

| 4,439,606 | A | 3/1984 | Du et al. |
|---|---|---|---|
| 5,442,064 | A | 8/1995 | Pieper et al. |
| 5,614,534 | A | 3/1997 | Binet et al. |
| 5,668,138 | A | 9/1997 | Baziard-Mouysset et al. |
| 5,981,754 | A | 11/1999 | Badone et al. |
| 6,547,958 | B1 | 4/2003 | Elomari et al. |
| 8,110,581 | B2 * | 2/2012 | Yao et al. ............ 514/278 |
| 2003/0229119 | A1 | 12/2003 | Kym et al. |
| 2004/0009998 | A1 | 1/2004 | Dhar et al. |
| 2004/0097511 | A1 | 5/2004 | Habashita et al. |
| 2005/0020645 | A1 | 1/2005 | Ohta et al. |
| 2005/0080078 | A1 | 4/2005 | Aquila et al. |
| 2005/0282858 | A1 | 12/2005 | Yao et al. |
| 2005/0288317 | A1 | 12/2005 | Yao et al. |
| 2005/0288329 | A1 | 12/2005 | Yao et al. |
| 2005/0288338 | A1 | 12/2005 | Yao et al. |
| 2006/0004049 | A1 | 1/2006 | Yao et al. |
| 2006/0009471 | A1 | 1/2006 | Yao et al. |
| 2006/0009491 | A1 | 1/2006 | Yao et al. |
| 2006/0019977 | A1 | 1/2006 | Habashita et al. |
| 2006/0106045 | A1 | 5/2006 | Hughes et al. |
| 2006/0116382 | A1 | 6/2006 | Yao et al. |
| 2006/0122197 | A1 | 6/2006 | Yao et al. |
| 2006/0122210 | A1 | 6/2006 | Yao et al. |
| 2006/0149070 | A1 | 7/2006 | Rohde et al. |
| 2006/0199816 | A1 | 9/2006 | Gillespie et al. |
| 2007/0066584 | A1 | 3/2007 | Yao et al. |
| 2007/0129345 | A1 | 6/2007 | Zhuo et al. |
| 2007/0197506 | A1 | 8/2007 | Yao et al. |
| 2007/0197530 | A1 | 8/2007 | Li et al. |
| 2007/0208001 | A1 | 9/2007 | Zhuo et al. |
| 2007/0213311 | A1 | 9/2007 | Li et al. |
| 2007/0270424 | A1 | 11/2007 | Li et al. |
| 2007/0293529 | A1 | 12/2007 | Li et al. |
| 2008/0318991 | A1 | 12/2008 | Yao et al. |

FOREIGN PATENT DOCUMENTS

| EP | 0743312 A1 | 11/1996 |
|---|---|---|
| EP | 1683797 | 7/2006 |
| WO | WO 97/11940 | 4/1997 |
| WO | WO 03/037847 | 5/2003 |
| WO | WO 03/057698 | 7/2003 |
| WO | WO 2004/056745 | 7/2004 |
| WO | WO 2004/065351 | 8/2004 |
| WO | WO 2004/082687 | 9/2004 |
| WO | WO 2004/089470 | 10/2004 |
| WO | WO 2004/089896 | 10/2004 |

(Continued)

OTHER PUBLICATIONS

Chalmers (TiPS vol. 17, pp. 166-172 Apr. 1996).*
Alberts et al. Endocrinology (2003) 144: 4755-4762.
Albiston et al. (1994) Mol. Cell. Endocrin. 105: R11-R17.
Barf et al. (2002) J. Med. Chem. 45: 3813-3815.
Bellows et al. (1998) Bone 23: 119-125.
Bhargava et al., (2001), Endo 142: 1587-1594.
Billaudel and Sutter (1979) Horm. Metab. Res. 11: 555-560.
Blum, et al., (2003) Prog. Nucl. Acid Res. Mol. Biol. 75:173-216.
Bujalska et al. (1997) Lancet 349: 1210-1213.
Canalis (1996) J. Clin. Endocrinol. Metab. 81: 3441-3447.
Conn, (1955), J. Lab. Clin. Med. 45: 6-17.
Cooper et al. (2000) Bone 27: 375-381.

(Continued)

*Primary Examiner* — Kahsay Habte
(74) *Attorney, Agent, or Firm* — Fish & Richardson P.C.

(57) ABSTRACT

The present invention relates to inhibitors of 11-β hydroxyl steroid dehydrogenase type 1, antagonists of the mineralocorticoid receptor (MR), and pharmaceutical compositions thereof. The compounds of the invention can be useful in the treatment of various diseases associated with expression or activity of 11-β hydroxyl steroid dehydrogenase type 1 and/or diseases associated with aldosterone excess.

31 Claims, No Drawings

(56) References Cited

FOREIGN PATENT DOCUMENTS

| WO | WO 2005/047286 | 5/2005 |
|----|----------------|--------|
| WO | WO 2005/063745 | 7/2005 |
| WO | WO 2006/012226 | 2/2006 |
| WO | WO 2006/020598 | 2/2006 |
| WO | WO2006/039639  | 4/2006 |
| WO | WO 2006/047196 | 5/2006 |
| WO | WO2006/065908  | 6/2006 |

OTHER PUBLICATIONS

Database CAPLUS on STN (Columbus, OH, USA) No. 126:317635, "Alpha-amino acids derived from ornithine as building blocks for peptide synthesis" abstract, Gescrinier et al. j. Pep. Res. 49(2):183-189 (1997).
Database CAPLUS on STN (Columbus, OH, USA) No. 143:78479, "Preparation of amino acid derivatives as novel M3 muscarinic acetylcholine receptor antagonists" abstract, Busch et al. (2005), see RN 902149-23-9 and 854750-92-8.
Davani et al. (2000) J. Biol. Chem. 275: 34841-34844.
Draper et al. (2003) Nat. Genet. 34: 434-439.
Edwards et al. (1988) Lancet 2: 986-989.
Engeli, et al., (2004) Obes. Res. 12: 9-17.
Funder et al. (1988), Science 242: 583-585.
Greene, et al., Protective Groups in Organic Synthesis, 2d. Ed., Wiley & Sons, 1991.
Gu et al., "Discovery of 4-heteroarylbicyclo[2.2.2]octyltriazoles as potent and selective inhibitors of 11β-HSD1: Novel therapeutic agents for the treatment of metabolic syndrome," Bioorg. Med. Chem. Lett., 15:5266-5269 (2005).
Jausons-Loffreda et al. J. Biolumin and Chemilumin, 9:217-221 (1994).
Journal of Pharmaceutical Science, 66, 2 (1977).
Kotelevstev et al. (1997) Proc. Natl. Acad. Sci. 94: 14924-14929.
Kurukulasuriya , et al., (2003) Curr. Med. Chem. 10: 123-53.
Lindsay et al. (2003) J. Clin. Endocrinol. Metab. 88: 2738-2744.
Livingstone et al. (2000) Endocrinology 131: 560-563.
Low et al. (1994) J. Mol. Endocrin. 13: 167-174.
Lupien et al. (1998) Nat. Neurosci. 1: 69-73.
Masuzaki et al. (2001) Science 294: 2166-2170.
Masuzaki et al. (2003) J. Clinical Invest. 112: 83-90.
Masuzaki, et al., (2003) Curr. Drug Targets Immune Endocr. Metabol. Disord. 3: 255-62.
Matsuzawa et al, (1999) Ann. N.Y. Acad. Sci. 892: 146-154.
McEwen and Sapolsky (1995) Curr. Opin. Neurobiol. 5: 205-216.
Miller and Chrousos (2001) Endocrinology and Metabolism, eds. Felig and Frohman (McGraw-Hill, New York), 4th Ed.: 387-524.
Morton et al. (2001) J. Biol. Chem. 276: 41293-41300.
Morton et al. (2004) Diabetes 53: 931-938).
Ogawa et al. (1992) J. Clin. Invest. 90: 497-504.
Pitt et al., New England J. Med. (1999), 341: 709-719.
Pitt et al., New England J. Med. (2003), 348: 1309-1321.
Rajan et al. (1996) J. Neurosci. 16: 65-70.
Rask et al. (2001) J. Clin. Endocrinol. Metab. 86: 1418-1421.
Rauz et al. (2001) Invest. Ophthalmol. Vis. Sci. 42: 2037-2042.
Reaven (1993) Ann. Rev. Med. 44: 121-131.
Remington's Pharmaceutical Sciences, 17th ed., Mack Publishing Company, Easton, Pa., 1985, p. 1418.
Sandeep et al. (2004) Proc. Natl. Acad. Sci Early Edition: 1-6).
Stokes et al. (2000) Invest. Ophthalmol. Vis. Sci. 41: 1629-1683.
T. Higuchi and V. Stella, "Pro-drugs as Novel Delivery Systems," vol. 14 of the A.C.S. Symposium Series, and in Bioreversible Carriers in Drug Design, ed. Edward B. Roche, American Pharmaceutical Association and Pergamon Press, 1987.
Wajchenberg (2000) Endocr. Rev. 21: 697-738).
Wake et al. (2003) J. Clin. Endocrinol. Metab. 88: 3983-3988.
Walker et al. (1979) Hypertension 1: 287-291.
Wilson et al. (1998) Proc. Natl. Acad. Sci. 95: 10200-10205.
Yau et al. (2001) Proc. Natl. Acad. Sci. 98: 4716-4721.
Yeh et al., "Discovery of orally active butyrolactam 11β-HSD1 inhibitors," Bioorg. Med. Chem. Lett., 16:5555-5560 (2006).
Yeh et al., "Synthesis and biological evaluation of heterocycle containing adamantine 11β-HSD1 inhibitors," Bioorg. Med. Chem. Lett., 16:5414-5419 (2006).
International Search Report for PCT/US05/28201 dated Nov. 6, 2006, 5 pgs.
Alper et al., "Facile, Novel Methodology for the Synthesis of Spiro[pyrrolidin-3,3'-oxindoles]: Catalyzed Ring Expansion Reactions of Cyclopropanes by Aldimines", Angewandte Chemie. International Edition, Wiley Vch Verlag. Weinheim, Jan. 1, 1999, vol. 38, No. 21, pp. 3186-3189.
Brindley et al., "Possible connections between stress, diabetes, obesity, hypertension and altered lipoprotein metabolism that may result in atherosclerosis", Clinical Science, London, England : 1979), Nov. 1989, vol. 77, No. 5, pp. 453-461 (Database Accession No. NLM2684477—Database Medline, US National Library of Medicine (NLM)).
Marti et al., "Total synthesis of (−)-spirotryprostatin B: synthesis and related studies.", Journal of the American Chemical Society, Aug. 17, 2005, vol. 127, No. 32, pp. 11505-11515.
Nagata et al., "Synthetic approach towards nakadomarin A: efficient synthesis of the central tetracyclic core", Tetrahedron Letters, 2001, vol. 42, pp. 8345-8349.
Nishida et al., "Synthetic study of nakadomarin", Tennen Yuki Kagobutsu Toronkai Koen Yoshishu, 2001, 43rd, pp. 617-622 (with English abstract).
Patschan et al., "Molecular mechanisms of glucocorticoid-induced osteoporosis", Bone, Dec. 2001, vol. 29, No. 6, pp. 498-505.
Search Report dated Aug. 14, 2009 for Singapore Appln. No. 200703242-8 (5 pgs.).
Supplementary European Search Report dated Aug. 14, 2009 for European Appln. No. EP05818772 (12 pgs.).
European Search Report dated Mar. 16, 2012 for European Appln. No. 12153931.6 (11 pgs.).

\* cited by examiner

LACTAM COMPOUNDS AND THEIR USE AS PHARMACEUTICALS

CROSS REFERENCE TO RELATED APPLICATIONS

This application is a continuation of U.S. Ser. No. 12/252,700 filed Oct. 16, 2008 which is pending, which is a continuation-in-part of U.S. Ser. No. 11/269,984, filed Nov. 9, 2005, which is abandoned, which claims the benefit of U.S. Ser. Nos. 60/626,617, filed Nov. 10, 2004 and 60/715,020, filed Sep. 8, 2005. The disclosure of each of the prior applications is hereby incorporated herein by reference in its entirety.

FIELD OF THE INVENTION

The present invention relates to modulators of 11-β hydroxyl steroid dehydrogenase type 1 (11βHSD1) and/or mineralocorticoid receptor (MR), compositions thereof and methods of using the same.

BACKGROUND OF THE INVENTION

Glucocorticoids are steroid hormones that regulate fat metabolism, function and distribution. In vertebrates, glucocorticoids also have profound and diverse physiological effects on development, neurobiology, inflammation, blood pressure, metabolism and programmed cell death. In humans, the primary endogenously-produced glucocorticoid is cortisol. Cortisol is synthesized in the zona fasciculate of the adrenal cortex under the control of a short-term neuroendocrine feedback circuit called the hypothalamic-pituitary-adrenal (HPA) axis. Adrenal production of cortisol proceeds under the control of adrenocorticotrophic hormone (ACTH), a factor produced and secreted by the anterior pituitary. Production of ACTH in the anterior pituitary is itself highly regulated, driven by corticotropin releasing hormone (CRH) produced by the paraventricular nucleus of the hypothalamus. The HPA axis maintains circulating cortisol concentrations within restricted limits, with forward drive at the diurnal maximum or during periods of stress, and is rapidly attenuated by a negative feedback loop resulting from the ability of cortisol to suppress ACTH production in the anterior pituitary and CRH production in the hypothalamus.

Aldosterone is another hormone produced by the adrenal cortex; aldosterone regulates sodium and potassium homeostasis. Fifty years ago, a role for aldosterone excess in human disease was reported in a description of the syndrome of primary aldosteronism (Conn, (1955), J. Lab. Clin. Med. 45: 6-17). It is now clear that elevated levels of aldosterone are associated with deleterious effects on the heart and kidneys, and are a major contributing factor to morbidity and mortality in both heart failure and hypertension.

Two members of the nuclear hormone receptor superfamily, glucocorticoid receptor (GR) and mineralocorticoid receptor (MR), mediate cortisol function in vivo, while the primary intracellular receptor for aldosterone is the MR. These receptors are also referred to as 'ligand-dependent transcription factors,' because their functionality is dependent on the receptor being bound to its ligand (for example, cortisol); upon ligand-binding these receptors directly modulate transcription via DNA-binding zinc finger domains and transcriptional activation domains.

Historically, the major determinants of glucocorticoid action were attributed to three primary factors: 1) circulating levels of glucocorticoid (driven primarily by the HPA axis), 2) protein binding of glucocorticoids in circulation, and 3) intracellular receptor density inside target tissues. Recently, a fourth determinant of glucocorticoid function was identified: tissue-specific pre-receptor metabolism by glucocorticoid-activating and -inactivating enzymes. These 11-beta-hydroxysteroid dehydrogenase (11-β-HSD) enzymes act as pre-receptor control enzymes that modulate activation of the GR and MR by regulation of glucocorticoid hormones. To date, two distinct isozymes of 11-beta-HSD have been cloned and characterized: 11βHSD1 (also known as 11-beta-HSD type 1, 11betaHSD1, HSD11B1, HDL, and HSD11L) and 11βHSD2. 11βHSD1 and 11βHSD2 catalyze the interconversion of hormonally active cortisol (corticosterone in rodents) and inactive cortisone (11-dehydrocorticosterone in rodents). 11βHSD1 is widely distributed in rat and human tissues; expression of the enzyme and corresponding mRNA have been detected in lung, testis, and most abundantly in liver and adipose tissue. 11βHSD1 catalyzes both 11-beta-dehydrogenation and the reverse 11-oxoreduction reaction, although 11βHSD1 acts predominantly as a NADPH-dependent oxoreductase in intact cells and tissues, catalyzing the activation of cortisol from inert cortisone (Low et al. (1994) J. Mol. Endocrin. 13: 167-174) and has been reported to regulate glucocorticoid access to the GR. Conversely, 11βHSD2 expression is found mainly in mineralocorticoid target tissues such as kidney, placenta, colon and salivary gland, acts as an NAD-dependent dehydrogenase catalyzing the inactivation of cortisol to cortisone (Albiston et al. (1994) Mol. Cell. Endocrin. 105: R11-R17), and has been found to protect the MR from glucocorticoid excess, such as high levels of receptor-active cortisol (Blum, et al., (2003) Prog. Nucl. Acid Res. Mol. Biol. 75:173-216).

In vitro, the MR binds cortisol and aldosterone with equal affinity. The tissue specificity of aldosterone activity, however, is conferred by the expression of 11βHSD2 (Funder et al. (1988), Science 242: 583-585). The inactivation of cortisol to cortisone by 11βHSD2 at the site of the MR enables aldosterone to bind to this receptor in vivo. The binding of aldosterone to the MR results in dissociation of the ligand-activated MR from a multiprotein complex containing chaperone proteins, translocation of the MR into the nucleus, and its binding to hormone response elements in regulatory regions of target gene promoters. Within the distal nephron of the kidney, induction of serum and glucocorticoid inducible kinase-1 (sgk-1) expression leads to the absorption of $Na^+$ ions and water through the epithelial sodium channel, as well as potassium excretion with subsequent volume expansion and hypertension (Bhargava et al., (2001), Endo 142: 1587-1594).

In humans, elevated aldosterone concentrations are associated with endothelial dysfunction, myocardial infarction, left ventricular atrophy, and death. In attempts to modulate these ill effects, multiple intervention strategies have been adopted to control aldosterone overactivity and attenuate the resultant hypertension and its associated cardiovascular consequences. Inhibition of angiotensin-converting enzyme (ACE) and blockade of the angiotensin type 1 receptor (AT1R) are two strategies that directly impact the rennin-angiotensin-aldosterone system (RAAS). However, although ACE inhibition and AT1R antagonism initially reduce aldosterone concentrations, circulating concentrations of this hormone return to baseline levels with chronic therapy (known as 'aldosterone escape'). Importantly, co-administration of the MR antagonist Spironolactone or Eplerenone directly blocks the deleterious effects of this escape mechanism and dramatically reduces patient mortality (Pitt et al., New England J. Med. (1999), 341: 709-719; Pitt et al., New England J. Med. (2003), 348: 1309-1321). Therefore, MR antagonism may be an important treatment strategy for many patients with hypertension and cardiovascular disease, particularly those hypertensive patients at risk for target-organ damage.

Mutations in either of the genes encoding the 11-beta-HSD enzymes are associated with human pathology. For example, 11βHSD2 is expressed in aldosterone-sensitive tissues such as the distal nephron, salivary gland, and colonic mucosa where its cortisol dehydrogenase activity serves to protect the intrinsically non-selective MR from illicit occupation by cortisol (Edwards et al. (1988) Lancet 2: 986-989). Individuals with mutations in 11βHSD2 are deficient in this cortisol-inactivation activity and, as a result, present with a syndrome of apparent mineralocorticoid excess (also referred to as 'SAME') characterized by hypertension, hypokalemia, and sodium retention (Wilson et al. (1998) Proc. Natl. Acad. Sci. 95: 10200-10205). Likewise, mutations in 11βHSD1, a primary regulator of tissue-specific glucocorticoid bioavailability, and in the gene encoding a co-localized NADPH-generating enzyme, hexose 6-phosphate dehydrogenase (H6PD), can result in cortisone reductase deficiency (CRD), in which activation of cortisone to cortisol does not occur, resulting in adrenocorticotropin-mediated androgen excess. CRD patients excrete virtually all glucocorticoids as cortisone metabolites (tetrahydrocortisone) with low or absent cortisol metabolites (tetrahydrocortisols). When challenged with oral cortisone, CRD patients exhibit abnormally low plasma cortisol concentrations. These individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

The importance of the HPA axis in controlling glucocorticoid excursions is evident from the fact that disruption of homeostasis in the HPA axis by either excess or deficient secretion or action results in Cushing's syndrome or Addison's disease, respectively (Miller and Chrousos (2001) Endocrinology and Metabolism, eds. Felig and Frohman (McGraw-Hill, New York), $4^{th}$ Ed.: 387-524). Patients with Cushing's syndrome (a rare disease characterized by systemic glucocorticoid excess originating from the adrenal or pituitary tumors) or receiving glucocorticoid therapy develop reversible visceral fat obesity. Interestingly, the phenotype of Cushing's syndrome patients closely resembles that of Reaven's metabolic syndrome (also known as Syndrome X or insulin resistance syndrome) the symptoms of which include visceral obesity, glucose intolerance, insulin resistance, hypertension, type 2 diabetes and hyperlipidemia (Reaven (1993) Ann. Rev. Med. 44: 121-131). However, the role of glucocorticoids in prevalent forms of human obesity has remained obscure because circulating glucocorticoid concentrations are not elevated in the majority of metabolic syndrome patients. In fact, glucocorticoid action on target tissue depends not only on circulating levels but also on intracellular concentration, locally enhanced action of glucocorticoids in adipose tissue and skeletal muscle has been demonstrated in metabolic syndrome. Evidence has accumulated that enzyme activity of 11βHSD1, which regenerates active glucocorticoids from inactive forms and plays a central role in regulating intracellular glucocorticoid concentration, is commonly elevated in fat depots from obese individuals. This suggests a role for local glucocorticoid reactivation in obesity and metabolic syndrome.

Given the ability of 11βHSD1 to regenerate cortisol from inert circulating cortisone, considerable attention has been given to its role in the amplification of glucocorticoid function. 11βHSD1 is expressed in many key GR-rich tissues, including tissues of considerable metabolic importance such as liver, adipose, and skeletal muscle, and, as such, has been postulated to aid in the tissue-specific potentiation of glucocorticoid-mediated antagonism of insulin function. Considering a) the phenotypic similarity between glucocorticoid excess (Cushing's syndrome) and the metabolic syndrome with normal circulating glucocorticoids in the latter, as well as b) the ability of 11βHSD1 to generate active cortisol from inactive cortisone in a tissue-specific manner, it has been suggested that central obesity and the associated metabolic complications in syndrome X result from increased activity of 11βHSD1 within adipose tissue, resulting in 'Cushing's disease of the omentum' (Bujalska et al. (1997) Lancet 349: 1210-1213). Indeed, 11βHSD1 has been shown to be upregulated in adipose tissue of obese rodents and humans (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Additional support for this notion has come from studies in mouse transgenic models. Adipose-specific overexpression of 11βHSD1 under the control of the aP2 promoter in mouse produces a phenotype remarkably reminiscent of human metabolic syndrome (Masuzaki et al. (2001) Science 294: 2166-2170; Masuzaki et al. (2003) J. Clinical Invest. 112: 83-90). Importantly, this phenotype occurs without an increase in total circulating corticosterone, but rather is driven by a local production of corticosterone within the adipose depots. The increased activity of 11βHSD1 in these mice (2-3 fold) is very similar to that observed in human obesity (Rask et al. (2001) J. Clin. Endocrinol. Metab. 86: 1418-1421). This suggests that local 11βHSD1-mediated conversion of inert glucocorticoid to active glucocorticoid can have profound influences whole body insulin sensitivity.

Based on this data, it would be predicted that the loss of 11βHSD1 would lead to an increase in insulin sensitivity and glucose tolerance due to a tissue-specific deficiency in active glucocorticoid levels. This is, in fact, the case as shown in studies with 11βHSD1-deficient mice produced by homologous recombination (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). These mice are completely devoid of 11-keto reductase activity, confirming that 11βHSD1 encodes the only activity capable of generating active corticosterone from inert 11-dehydrocorticosterone. 11βHSD1-deficient mice are resistant to diet- and stress-induced hyperglycemia, exhibit attenuated induction of hepatic gluconeogenic enzymes (PEPCK, G6P), show increased insulin sensitivity within adipose, and have an improved lipid profile (decreased triglycerides and increased cardio-protective HDL). Additionally, these animals show resistance to high fat diet-induced obesity. Taken together, these transgenic mouse studies confirm a role for local reactivation of glucocorticoids in controlling hepatic and peripheral insulin sensitivity, and suggest that inhibition of 11βHSD1 activity may prove beneficial in treating a number of glucocorticoid-related disorders, including obesity, insulin resistance, hyperglycemia, and hyperlipidemia.

Data in support of this hypothesis has been published. Recently, it was reported that 11βHSD1 plays a role in the pathogenesis of central obesity and the appearance of the metabolic syndrome in humans. Increased expression of the 11βHSD1 gene is associated with metabolic abnormalities in obese women and that increased expression of this gene is suspected to contribute to the increased local conversion of cortisone to cortisol in adipose tissue of obese individuals (Engeli, et al., (2004) Obes. Res. 12: 9-17).

A new class of 11βHSD1 inhibitors, the arylsulfonamidothiazoles, was shown to improve hepatic insulin sensitivity and reduce blood glucose levels in hyperglycemic strains of mice (Barf et al. (2002) J. Med. Chem. 45: 3813-3815; Alberts et al. Endocrinology (2003) 144: 4755-4762). Furthermore, it was recently reported that selective inhibitors of 11βHSD1 can ameliorate severe hyperglycemia in genetically diabetic obese mice. Thus, 11βHSD1 is a promising pharmaceutical target for the treatment of the Metabolic Syndrome (Masuzaki, et al., (2003) Curr. Drug Targets Immune Endocr. Metabol. Disord. 3: 255-62).

A. Obesity and Metabolic Syndrome

As described above, multiple lines of evidence suggest that inhibition of 11βHSD1 activity can be effective in combating obesity and/or aspects of the metabolic syndrome cluster, including glucose intolerance, insulin resistance, hyperglycemia, hypertension, and/or hyperlipidemia. Glucocorticoids are known antagonists of insulin action, and reductions in local glucocorticoid levels by inhibition of intracellular cortisone to cortisol conversion should increase hepatic and/or peripheral insulin sensitivity and potentially reduce visceral adiposity. As described above, 11βHSD1 knockout mice are resistant to hyperglycemia, exhibit attenuated induction of key hepatic gluconeogenic enzymes, show markedly increased insulin sensitivity within adipose, and have an improved lipid profile. Additionally, these animals show resistance to high fat diet-induced obesity (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). Thus, inhibition of 11βHSD1 is predicted to have multiple beneficial effects in the liver, adipose, and/or skeletal muscle, particularly related to alleviation of component(s) of the metabolic syndrome and/or obesity.

B. Pancreatic Function

Glucocorticoids are known to inhibit the glucose-stimulated secretion of insulin from pancreatic beta-cells (Billaudel and Sutter (1979) Horm. Metab. Res. 11: 555-560). In both Cushing's syndrome and diabetic Zucker fa/fa rats, glucose-stimulated insulin secretion is markedly reduced (Ogawa et al. (1992) J. Clin. Invest. 90: 497-504). 11βHSD1 mRNA and activity has been reported in the pancreatic islet cells of ob/ob mice and inhibition of this activity with carbenoxolone, an 11βHSD1 inhibitor, improves glucose-stimulated insulin release (Davani et al. (2000) J. Biol. Chem. 275: 34841-34844). Thus, inhibition of 11βHSD1 is predicted to have beneficial effects on the pancreas, including the enhancement of glucose-stimulated insulin release.

C. Cognition and Dementia

Mild cognitive impairment is a common feature of aging that may be ultimately related to the progression of dementia. In both aged animals and humans, inter-individual differences in general cognitive function have been linked to variability in the long-term exposure to glucocorticoids (Lupien et al. (1998) Nat. Neurosci. 1: 69-73). Further, dysregulation of the HPA axis resulting in chronic exposure to glucocorticoid excess in certain brain subregions has been proposed to contribute to the decline of cognitive function (McEwen and Sapolsky (1995) Curr. Opin. Neurobiol. 5: 205-216). 11βHSD1 is abundant in the brain, and is expressed in multiple subregions including the hippocampus, frontal cortex, and cerebellum (Sandeep et al. (2004) Proc. Natl. Acad. Sci. Early Edition: 1-6). Treatment of primary hippocampal cells with the 11βHSD1 inhibitor carbenoxolone protects the cells from glucocorticoid-mediated exacerbation of excitatory amino acid neurotoxicity (Rajan et al. (1996) J. Neurosci. 16: 65-70). Additionally, 11βHSD1-deficient mice are protected from glucocorticoid-associated hippocampal dysfunction that is associated with aging (Yau et al. (2001) Proc. Natl. Acad. Sci. 98: 4716-4721). In two randomized, double-blind, placebo-controlled crossover studies, administration of carbenoxolone improved verbal fluency and verbal memory (Sandeep et al. (2004) Proc. Natl. Acad. Sci. Early Edition: 1-6). Thus, inhibition of 11βHSD1 is predicted to reduce exposure to glucocorticoids in the brain and protect against deleterious glucocorticoid effects on neuronal function, including cognitive impairment, dementia, and/or depression.

D. Intra-Ocular Pressure

Glucocorticoids can be used topically and systemically for a wide range of conditions in clinical ophthalmology. One particular complication with these treatment regimens is corticosteroid-induced glaucoma. This pathology is characterized by a significant increase in intra-ocular pressure (IOP). In its most advanced and untreated form, IOP can lead to partial visual field loss and eventually blindness. IOP is produced by the relationship between aqueous humour production and drainage. Aqueous humour production occurs in the non-pigmented epithelial cells (NPE) and its drainage is through the cells of the trabecular meshwork. 11βHSD1 has been localized to NPE cells (Stokes et al. (2000) Invest. Ophthalmol. Vis. Sci. 41: 1629-1683; Rauz et al. (2001) Invest. Ophthalmol. Vis. Sci. 42: 2037-2042) and its function is likely relevant to the amplification of glucocorticoid activity within these cells. This notion has been confirmed by the observation that free cortisol concentration greatly exceeds that of cortisone in the aqueous humour (14:1 ratio). The functional significance of 11βHSD1 in the eye has been evaluated using the inhibitor carbenoxolone in healthy volunteers (Rauz et al. (2001) Invest. Ophthalmol. Vis. Sci. 42: 2037-2042). After seven days of carbenoxolone treatment, IOP was reduced by 18%. Thus, inhibition of 11βHSD1 in the eye is predicted to reduce local glucocorticoid concentrations and IOP, producing beneficial effects in the management of glaucoma and other visual disorders.

E. Hypertension

Adipocyte-derived hypertensive substances such as leptin and angiotensinogen have been proposed to be involved in the pathogenesis of obesity-related hypertension (Matsuzawa et al. (1999) Ann. N.Y. Acad. Sci. 892: 146-154; Wajchenberg (2000) Endocr. Rev. 21: 697-738). Leptin, which is secreted in excess in aP2-11βHSD1 transgenic mice (Masuzaki et al. (2003) J. Clinical Invest. 112: 83-90), can activate various sympathetic nervous system pathways, including those that regulate blood pressure (Matsuzawa et al. (1999) Ann. N.Y. Acad. Sci. 892: 146-154). Additionally, the renin-angiotensin system (RAS) has been shown to be a major determinant of blood pressure (Walker et al. (1979) Hypertension 1: 287-291). Angiotensinogen, which is produced in liver and adipose tissue, is the key substrate for renin and drives RAS activation. Plasma angiotensinogen levels are markedly elevated in aP2-11βHSD1 transgenic mice, as are angiotensin II and aldosterone (Masuzaki et al. (2003) J. Clinical Invest. 112: 83-90). These forces likely drive the elevated blood pressure observed in aP2-11βHSD1 transgenic mice. Treatment of these mice with low doses of an angiotensin II receptor antagonist abolishes this hypertension (Masuzaki et al. (2003) J. Clinical Invest. 112: 83-90). This data illustrates the importance of local glucocorticoid reactivation in adipose tissue and liver, and suggests that hypertension may be caused or exacerbated by 11βHSD1 activity. Thus, inhibition of 11βHSD1 and reduction in adipose and/or hepatic glucocorticoid levels is predicted to have beneficial effects on hypertension and hypertension-related cardiovascular disorders.

F. Bone Disease

Glucocorticoids can have adverse effects on skeletal tissues. Continued exposure to even moderate glucocorticoid doses can result in osteoporosis (Cannalis (1996) J. Clin. Endocrinol. Metab. 81: 3441-3447) and increased risk for fractures. Experiments in vitro confirm the deleterious effects of glucocorticoids on both bone-resorbing cells (also known as osteoclasts) and bone forming cells (osteoblasts). 11βHSD1 has been shown to be present in cultures of human primary osteoblasts as well as cells from adult bone, likely a mixture of osteoclasts and osteoblasts (Cooper et al. (2000) Bone 27: 375-381), and the 11βHSD1 inhibitor carbenoxolone has been shown to attenuate the negative effects of glucocorticoids on bone nodule formation (Bellows et al. (1998) Bone 23: 119-125). Thus, inhibition of 11βHSD1 is predicted to decrease the local glucocorticoid concentration within osteoblasts and osteoclasts, producing beneficial effects in various forms of bone disease, including osteoporosis.

Small molecule inhibitors of 11βHSD1 are currently being developed to treat or prevent 11βHSD1-related diseases such as those described above. For example, certain amide-based inhibitors are reported in WO 2004/089470, WO 2004/089896, WO 2004/056745, and WO 2004/065351.

Antagonists of 11βHSD1 have been evaluated in human clinical trials (Kurukulasuriya, et al., (2003) Curr. Med. Chem. 10: 123-53).

In light of the experimental data indicating a role for 11βHSD1 in glucocorticoid-related disorders, metabolic syndrome, hypertension, obesity, insulin resistance, hyperglycemia, hyperlipidemia, type 2 diabetes, androgen excess (hirsutism, menstrual irregularity, hyperandrogenism) and polycystic ovary syndrome (PCOS), therapeutic agents aimed at augmentation or suppression of these metabolic pathways, by modulating glucocorticoid signal transduction at the level of 11βHSD1 are desirable.

Furthermore, because the MR binds to aldosterone (its natural ligand) and cortisol with equal affinities, compounds that are designed to interact with the active site of 11βHSD1 (which binds to cortisone/cortisol) may also interact with the MR and act as antagonists. Because the MR is implicated in heart failure, hypertension, and related pathologies including atherosclerosis, arteriosclerosis, coronary artery disease, thrombosis, angina, peripheral vascular disease, vascular wall damage, and stroke, MR antagonists are desirable and may also be useful in treating complex cardiovascular, renal, and inflammatory pathologies including disorders of lipid metabolism including dyslipidemia or hyperlipoproteinaemia, diabetic dyslipidemia, mixed dyslipidemia, hypercholesterolemia, hypertriglyceridemia, as well as those associated with type 1 diabetes, type 2 diabetes, obesity, metabolic syndrome, and insulin resistance, and general aldosterone-related target-organ damage.

As evidenced herein, there is a continuing need for new and improved drugs that target 11βHSD1 and/or MR. The compounds, compositions and methods described herein help meet this and other needs.

SUMMARY OF THE INVENTION

The present invention provides, inter alia, compounds of Formula I:

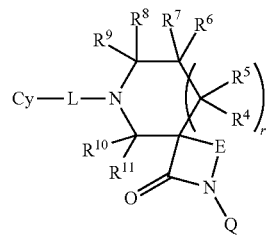

or pharmaceutically acceptable salts or prodrugs thereof, wherein constituent members are defined herein.

The present invention further provides compositions comprising compounds of the invention and a pharmaceutically acceptable carrier.

The present invention further provides methods of modulating 11βHSD1 or MR by contacting 11βHSD1 or MR with a compound of the invention.

The present invention further provides methods of inhibiting 11βHSD1 or MR by contacting 11βHSD1 or MR with a compound of the invention.

The present invention further provides methods of inhibiting the conversion of cortisone to cortisol in a cell by contacting the cell with a compound of the invention.

The present invention further provides methods of inhibiting the production of cortisol in a cell by contacting the cell with a compound of the invention.

The present invention further provides methods of treating diseases associated with activity or expression of 11βHDS1 or MR.

DETAILED DESCRIPTION

The present invention provides, inter alia, compounds of Formula I:

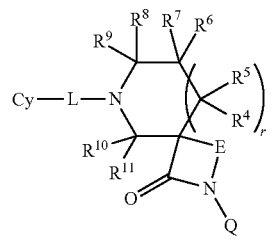

or pharmaceutically acceptable salt or prodrug thereof, wherein:

Cy is aryl, heteroaryl, cycloalkyl, or heterocycloalkyl, each optionally substituted with 1, 2, 3, 4 or 5 —W—X—Y—Z;

L is $(CR^{12}R^{13})_{q1}$, $(CR^{12}R^{13})_{q1}O(CR^{12}R^{13})_{q2}$, $(CR^{12}R^{13})_{q1}S(CR^{12}R^{13})_{q2}$, $(CR^{12}R^{13})_{q1}SO_2(CR^{12}R^{13})_{q2}$, $(CR^{12}R^{13})_{q1}SO(CR^{12}R^{13})_{q2}$, or $(CR^{12}R^{13})_{q1}CO(CR^{12}R^{13})_{q2}$;

Q is —$(CR^1R^2)_m$-A;

A is aryl, heteroaryl, cycloalkyl, or heterocycloalkyl, each optionally substituted with 1, 2, 3, 4 or 5 —W'—X'—Y'—Z';

E is —$(CR^{3a}R^{3b})_{n1}$—, —$(CR^{3a}R^{3b})_{n2}CO$—, —$(CR^{3a}R^{3b})_{n2}OCO$—, —$(CR^{3a}R^{3b})_{n2}SO$—, —$(CR^{3a}R^{3b})_{n2}SO_2$—, —$(CR^{3a}R^{3b})_{n2}NR^{3c}$—, —$(CR^{3a}R^{3b})_{n3}CONR^{3c}$—, —$(CR^{3a}R^{3b})_{n2}NR^{3c}CO$—, or a group of formula:

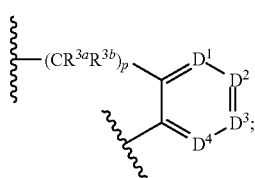

$D^1$, $D^2$, $D^3$ and $D^4$ are each N or $CR^{15}$;

$R^1$ and $R^2$ are each, independently, H or $C_{1-8}$ alkyl;

$R^{3a}$ and $R^{3b}$ are each, independently, H, $OC(O)R^{a'}$, $OC(O)OR^{b'}$, $C(O)OR^{b'}$, $OC(O)NR^{c'}R^{d'}$, $NR^{c'}R^{d'}$, $NR^{c'}C(O)R^{a'}$, $NR^{c'}C(O)OR^{b'}$, $S(O)R^{a'}$, $S(O)NR^{c'}R^{d'}$, $S(O)_2R^{a'}$, $S(O)_2NR^{c'}R^{d'}$, $OR^{b'}$, $SR^{b'}$, halo, $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl or heterocycloalkylalkyl, wherein said $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl or heterocycloalkylalkyl is optionally substituted by $R^{16}$;

$R^{3c}$ is H, $C_{1-4}$ alkyl, $C_{1-4}$ haloalkyl, $C_{2-4}$ alkenyl, $C_{2-4}$ alkynyl, or $CO$—($C_{1-4}$ alkyl);

$R^4$, $R^5$, $R^6$, $R^7$, $R^8$, $R^9$, $R^{10}$ and $R^{11}$ are each, independently, H, $OC(O)R^{a'}$, $OC(O)OR^{b'}$, $C(O)OR^{b'}$, $OC(O)NR^{c'}R^{d'}$, $NR^{c'}R^{d'}$, $NR^{c'}C(O)R^{a'}$, $NR^{c'}C(O)OR^{b'}$, $S(O)R^{a'}$, $S(O)NR^{c'}R^{d'}$, $S(O)_2R^{a'}$, $S(O)_2NR^{c'}R^{d'}$, $OR^{b'}$, $SR^{b'}$, halo, $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl or heterocycloalkylalkyl, wherein said $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl or heterocycloalkylalkyl is optionally substituted by $R^{14}$;

or $R^4$ and $R^5$ together with the carbon atom to which they are attached form a 3-14 membered cycloalkyl or heterocycloalkyl group which is optionally substituted by $R^{14}$;

or $R^6$ and $R^7$ together with the carbon atom to which they are attached form a 3-14 membered cycloalkyl or heterocycloalkyl group which is optionally substituted by $R^{14}$;

or $R^8$ and $R^9$ together with the carbon atom to which they are attached form a 3-14 membered cycloalkyl or heterocycloalkyl group which is optionally substituted by $R^{14}$;

or $R^{10}$ and $R^{11}$ together with the carbon atom to which they are attached form a 3-14 membered cycloalkyl or heterocycloalkyl group which is optionally substituted by $R^{14}$;

or $R^4$ and $R^6$ together with the carbon atom to which they are attached form a 3-7 membered fused cycloalkyl group or 3-7 membered fused heterocycloalkyl group which is optionally substituted by $R^{14}$;

or $R^6$ and $R^8$ together with the carbon atom to which they are attached form a 3-7 membered fused cycloalkyl group or 3-7 membered fused heterocycloalkyl group which is optionally substituted by $R^{14}$;

or $R^4$ and $R^9$ together form a $C_{1-3}$ alkylene bridge which is optionally substituted by $R^{14}$; or $R^4$ and $R^{10}$ together form a $C_{1-3}$ alkylene bridge which is optionally substituted by $R^{14}$;

or $R^6$ and $R^{10}$ together form a $C_{1-3}$ alkylene bridge which is optionally substituted by $R^{14}$;

or $R^9$ and $R^{10}$ together form a $C_{1-3}$ alkylene bridge which is optionally substituted by $R^{14}$;

$R^{12}$ and $R^{13}$ are each, independently, H, halo, $C_{1-4}$ alkyl, $C_{1-4}$ haloalkyl, aryl, cycloalkyl, heteroaryl, heterocycloalkyl, CN, $NO_2$, $OR^{a'}$, $SR^{a'}$, $C(O)R^{b'}$, $C(O)NR^{c'}R^{d'}$, $C(O)OR^{a'}$, $OC(O)R^{b'}$, $OC(O)NR^{c'}R^{d'}$, $NR^{c'}R^{d'}$, $NR^{c'}C(O)R^{a'}$, $NR^{c'}C(O)OR^{a'}$, $S(O)R^{b'}$, $S(O)NR^{c'}R^{d'}$, $S(O)_2R^{b'}$, or $S(O)_2NR^{c'}R^{d'}$;

$R^{14}$ is halo, $C_{1-4}$ alkyl, $C_{1-4}$ haloalkyl, aryl, cycloalkyl, heteroaryl, heterocycloalkyl, CN, $NO_2$, $OR^{a'}$, $SR^{a'}$, $C(O)R^{b'}$, $C(O)NR^{c'}R^{d'}$, $C(O)OR^{a'}$, $OC(O)R^{b'}$, $OC(O)NR^{c'}R^{d'}$, $NR^{c'}R^{d'}$, $NR^{c'}C(O)R^{d'}$, $NR^{c'}C(O)OR^{a'}$, $S(O)R^{b'}$, $S(O)NR^{c'}R^{d'}$, $S(O)_2R^{b'}$, or $S(O)_2NR^{c'}R^{d'}$;

$R^{15}$ is H, halo, $C_{1-4}$ alkyl, $C_{1-4}$ haloalkyl, aryl, cycloalkyl, heteroaryl, heterocycloalkyl, CN, $NO_2$, $OR^{a''}$, $SR^{a''}$, $C(O)R^{b''}$, $C(O)NR^{c''}R^{d''}$, $C(O)OR^{a''}$, $OC(O)R^{b''}$, $OC(O)NR^{c''}R^{d''}$, $NR^{c''}R^{d''}$, $NR^{c''}C(O)R^{d''}$, $NR^{c''}C(O)OR^{a''}$, $S(O)R^{b''}$, $S(O)NR^{c''}R^{d''}$, $S(O)_2R^{b''}$, or $S(O)_2NR^{c''}R^{d''}$;

$R^{16}$ is halo, $C_{1-4}$ alkyl, $C_{1-4}$ haloalkyl, aryl, cycloalkyl, heteroaryl, heterocycloalkyl, CN, $NO_2$, $OR^{a'}$, $SR^{a'}$, $C(O)R^{b'}$, $C(O)NR^{c'}R^{d'}$, $C(O)OR^{a'}$, $OC(O)R^{b'}$, $OC(O)NR^{c'}R^{d'}$, $NR^{c'}R^{d'}$, $NR^{c'}C(O)R^{d'}$, $NR^{c'}C(O)OR^{a'}$, $S(O)R^{b'}$, $S(O)NR^{c'}R^{d'}$, $S(O)_2R^{b'}$, or $S(O)_2NR^{c'}R^{d'}$;

W, W' and W" are each, independently, absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, or $NR^eCONR^f$, wherein said $C_{1-6}$ alkylenyl, $C_{2-6}$ alkenylenyl, $C_{2-6}$ alkynylenyl are each optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

X, X' and X" are each, independently, absent, $C_{1-6}$ alkylenyl, $C_{2-6}$ alkenylenyl, $C_{2-6}$ alkynylenyl, aryl, cycloalkyl, heteroaryl or heterocycloalkyl, wherein said $C_{1-6}$ alkylenyl, $C_{2-6}$ alkenylenyl, $C_{2-6}$ alkynylenyl, aryl, cycloalkyl, heteroaryl or heterocycloalkyl is optionally substituted by one or more halo, oxo, CN, $NO_2$, OH, $C_{1-4}$ alkoxy, $C_{1-4}$ haloalkoxy, amino, $C_{1-4}$ alkylamino or $C_{2-8}$ dialkylamino;

Y, Y' and Y" are each, independently, absent, $C_{1-6}$ alkylenyl, $C_{2-6}$ alkenylenyl, $C_{2-6}$ alkynylenyl, O, S, $NR^e$, CO, COO, $CONR^e$, SO, $SO_2$, $SONR^e$, or $NR^eCONR^f$, wherein said $C_{1-6}$ alkylenyl, $C_{2-6}$ alkenylenyl, $C_{2-6}$ alkynylenyl are each optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

Z, Z' and Z" are each, independently, H, halo, CN, $NO_2$, OH, $C_{1-4}$ alkoxy, $C_{1-4}$ haloalkoxy, amino, $C_{3-4}$ alkylamino, $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, oxo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, ORB, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^eS(O)_2R^b$, $S(O)R^b$, $S(O)NR^cR^d$, $S(O)_2R^b$, or $S(O)_2NR^cR^d$;

wherein two —W—X—Y—Z attached to the same atom optionally form a 3-20 membered cycloalkyl or heterocycloalkyl group, each optionally substituted by 1, 2 or 3 —W"—X"—Y"—Z";

wherein two —W'—X'—Y'—Z' attached to the same atom optionally form a 3-20 membered cycloalkyl or heterocycloalkyl group, each optionally substituted by 1, 2 or 3 —W"—X"—Y"—Z";

wherein —W—X—Y—Z is other than H;
wherein —W'—X'—Y'—Z' is other than H;
wherein —W"—X"—Y"—Z" is other than H;

$R^a$, $R^{a'}$ and $R^{a''}$ are each, independently, H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl; heterocycloalkyl, heterocycloalkylalkyl is optionally substituted with H, OH, amino, halo, $C_{1-6}$ alkyl, $C_{1-6}$ haloalkyl, aryl, arylalkyl, heteroaryl, heteroarylalkyl, cycloalkyl or heterocycloalkyl;

$R^b$, $R^{b'}$ and $R^{b''}$ are each, independently, H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

$R^c$ and $R^d$ are each, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^c$ and $R^d$ together with the N atom to which they are attached form a 4-, 5-, 6- or 7-membered heterocycloalkyl group;

$R^{c'}$ and $R^{d'}$ are each, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^{c'}$ and $R^{d'}$ together with the N atom to which they are attached form a 4-, 5-, 6- or 7-membered heterocycloalkyl group;

$R^{c''}$ and $R^{d''}$ are each, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^{c''}$ and $R^{d''}$ together with the N atom to which they are attached form a 4-, 5-, 6- or 7-membered heterocycloalkyl group;

$R^e$ and $R^f$ are each, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^e$ and $R^f$ together with the N atom to which they are attached form a 4-, 5-, 6- or 7-membered heterocycloalkyl group;

m is 0, 1, 2 or 3;
n1 is 1, 2, 3 or 4;
n2 is 0, 1, 2, 3 or 4;
n3 is 0, 1, 2, 3 or 4;
p is 0, 1 or 2;
q1 is 0, 1 or 2;
q2 is 0, 1 or 2; and
r is 0, 1 or 2.

In some embodiments, when A is aryl optionally substituted with 1, 2, 3, 4 or 5 —W'—X'—Y'—Z' or heteroaryl optionally substituted with 1, 2, 3, 4 or 5 —W'—X'—Y'—Z'; L is $SO_2$, $SO_2CH_2$ or $CH_2$; and m is 0, then Cy is other than unsubstituted aryl, monosubstituted aryl, unsubstituted heteroaryl, or monosubstituted heteroaryl.

In some embodiments, when A is aryl optionally substituted with 1, 2, 3, 4 or 5 —W'—X'—Y'—Z' or heteroaryl optionally substituted with 1, 2, 3, 4 or 5 —W'—X'—Y'—Z'; L is $SO_2$, $SO_2CH_2$ or $CH_2$; m is 0; and Cy is di-, tri-, tetra- or penta-substituted aryl or di-, tri-, tetra- or penta-substituted heteroaryl, then said di-, tri-, tetra- or penta-substituted aryl or di-, tri-, tetra- or penta-substituted heteroaryl is substituted by at least one $C_{1-6}$ alkyl and at least one halo.

In some embodiments, when A is aryl optionally substituted with 1, 2, 3, 4 or 5 —W'—X'—Y'—Z' or heteroaryl optionally substituted with 1, 2, 3, 4 or 5 —W'—X'—Y'—Z'; L is $SO_2$, $SO_2CH_2$ or $CH_2$; and m is 0, then Cy is other than 2-chloro-6-methyl-phenyl.

In some embodiments, when A is phenyl or 4-phenoxyphenyl; L is $SO_2$ or $SO_2CH_2$; and m is 0 or 1, then Cy is other than cyclohexyl or 1,1-dioxo-tetrahydro-thien-3-yl.

In some embodiments, when Cy is aryl optionally substituted with 1, 2, 3, 4 or 5 —W—X—Y—Z or heteroaryl optionally substituted with 1, 2, 3, 4 or 5 —W—X—Y—Z; L is $SO_2$, $SO_2CH_2$ or $CH_2$; and m is 0, then A is other than tetrahydropyran-4-yl, 2,3-dihydroinden-2-yl or 2,2-difluoro-1,3-benzodioxol-5-yl.

In some embodiments, when Cy is aryl optionally substituted with 1, 2, 3, 4 or 5 —W—X—Y—Z or heteroaryl optionally substituted with 1, 2, 3, 4 or 5 —W—X—Y—Z; L is $SO_2$, $SO_2CH_2$ or $CH_2$; and m is 1, then A is other than pyridine-4-yl, phenyl, 2-chloro-6-fluoro-phenyl, 4-methoxyphenyl or 4-phenoxy-phenyl.

In some embodiments, $R^{3a}$ and $R^{3b}$ are each, independently, H, halo, $C_{1-4}$ alkyl, $C_{1-4}$ haloalkyl, $C_{2-4}$ alkenyl, or $C_{2-4}$ alkynyl.

In some embodiments, X, X' and X'' are each, independently, absent, $C_{1-6}$ alkylenyl, $C_{2-6}$ alkenylenyl, $C_{2-6}$ alkynylenyl, aryl, cycloalkyl, heteroaryl or heterocycloalkyl, wherein said $C_{1-6}$ alkylenyl, $C_{2-6}$ alkenylenyl, $C_{2-6}$ alkynylenyl, cycloalkyl, heteroaryl or heterocycloalkyl is optionally substituted by one or more halo, oxo, CN, $NO_2$, OH, $C_{1-4}$ alkoxy, $C_{1-4}$ haloalkoxy, amino, $C_{1-4}$ alkylamino or $C_{2-8}$ dialkylamino.

In some embodiments, Z, Z' and Z'' are each, independently, H, halo, CN, $NO_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, oxo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$.

In some embodiments, when r is 1 and $R^4$ and $R^5$ together with the carbon atom to which they are attached form a 3, 4, 5 or 6-membered heterocycloalkyl group, then m is other than 1.

In some embodiments, Cy is aryl or heteroaryl, each optionally substituted with 1, 2, 3, 4 or 5-W—X—Y—Z.

In some embodiments, Cy is aryl or heteroaryl, each optionally substituted with 1, 2, 3, 4 or 5-W—X—Y—Z wherein W is O or absent, X is absent, and Y is absent.

In some embodiments, Cy is phenyl, naphthyl, pyridyl, pyrimidinyl, triazinyl, furanyl, thiazolyl, pyrazinyl, purinyl, quinazolinyl, quinolinyl, isoquinolinyl, pyrrolo[2,3-d]pyrimidinyl, or 1,3-benzothiazolyl, each optionally substituted with 1, 2, 3, 4 or 5 —W—X—Y—Z.

In some embodiments, Cy is phenyl, naphthyl, pyridyl, pyrimidinyl, triazinyl, furanyl or thienyl, each optionally substituted with 1, 2, 3, 4 or 5 —W—X—Y—Z.

In some embodiments, Cy is phenyl, naphthyl, pyridyl, pyrimidinyl, triazinyl, furanyl thiazolyl, pyrazinyl, purinyl, quinazolinyl, quinolinyl, isoquinolinyl, pyrrolo[2,3-d]pyrimidinyl, or 1,3-benzothiazolyl, each optionally substituted with 1, 2, 3 or 4 halo, CN, $NO_2$, $C_{1-4}$ alkoxy, heteroaryloxy, $C_{2-6}$ alkynyl, $C_{1-4}$ haloalkoxy, $NR^cC(O)R^d$, $NR^cC(O)OR^a$, $C(O)NR^cR^d$, $NR^cR^d$, $NR^eS(O)_2R^b$, $C_{1-4}$ haloalkyl, $C_{1-6}$ alkyl, heterocycloalkyl, aryl or heteroaryl, wherein each of said $C_{1-6}$ alkyl, aryl or heteraryl is optionally substituted by 1, 2 or 3 halo, $C_{1-6}$ alkyl, $C_{1-4}$ haloalkyl, CN, $NO_2$, $OR^a$, $SR^a$, $C(O)NR^cR^d$, $NR^cC(O)R^d$ or $COOR^a$.

In some embodiments, Cy is phenyl, naphthyl, pyridyl, pyrimidinyl, triazinyl, furanyl thienyl, thiazolyl, pyrazinyl, purinyl, quinazolinyl, quinolinyl, isoquinolinyl, pyrrolo[2,3-d]pyrimidinyl, or 1,3-benzothiazolyl, each optionally substituted with 1, 2, 3 or 4 substituents independently selected form:

halo, CN, $NO_2$, $C_{1-4}$ alkoxy, pyridin-2-yloxy, pyridin-3-yloxy, pyridin-4-yloxy, $C_{2-6}$ alkynyl, $C_{1-4}$ haloalkoxy, $NR^cC(O)R^d$, $NR^cC(O)OR^a$, $C(O)NR^cR^d$, $NR^cR^d$, $NR^eS(O)_2R^b$, $C_{1-4}$ haloalkyl, $C_{1-6}$ alkyl, phenyl, pyridyl, pyrimidinyl, isoxazolyl, pyrazolyl, 1,2,3,6-tetrahydro-pyridinyl, 2-oxo-(2H)-pyridinyl, 2-oxo-[1,3]oxazolidinyl, 2-oxo-pyrrolidinyl, pyrrolidinyl, 2-oxopiperidinyl, and 2-oxo-[1,3]oxazinanyl; wherein each of said $C_{1-6}$ alkyl, phenyl, pyridyl, pyrimidinyl, isoxazolyl, pyrazolyl, 1,2,3,6-tetrahydro-pyridinyl, 2-oxo-(2H)-pyridinyl, 2-oxo-[1,3]oxazolidinyl, 2-oxo-pyrrolidinyl, pyrrolidinyl, 2-oxopiperidinyl, or 2-oxo-[1,3]oxazinanyl is optionally substituted by 1, 2 or 3 halo, $C_{1-6}$ alkyl, $C_{1-4}$ haloalkyl, CN, $NO_2$, $OR^a$, $SR^a$, $C(O)NR^cR^d$, $NR^cC(O)R^d$ or $COOR^a$.

In some embodiments, Cy is phenyl, naphthyl, pyridyl, pyrimidinyl, triazinyl, furanyl or thienyl, each optionally substituted with 1, 2, or 3 halo, CN, $C_{1-4}$ alkoxy, $C_{1-4}$ haloalkoxy, $C_{1-6}$ alkyl or aryl, wherein said $C_{1-6}$ alkyl or aryl is optionally substituted by 1, 2 or 3 halo, $C_{1-6}$ alkyl, $C_{1-4}$ haloalkyl, CN, $NO_2$, $OR^a$, or $SR^a$.

In some embodiments, Cy is phenyl, naphthyl, pyridyl, pyrimidinyl, triazinyl, furanyl or thienyl, each optionally substituted with 1, 2, or 3 halo, CN, $C_{1-4}$ alkoxy, $C_{1-4}$ haloalkoxy, $C_{1-6}$ alkyl or aryl, wherein said $C_{1-6}$ alkyl or aryl is optionally substituted by 1, 2 or 3 halo or $C_{1-6}$ alkyl.

In some embodiments, Cy is phenyl, pyridyl, pyrimidinyl, quinolinyl, or isoquinolinyl, each optionally substituted with 1, 2, 3, 4 or 5 —W—X—Y—Z.

In some embodiments, Cy is phenyl, pyridyl, pyrimidinyl, quinolinyl, or isoquinolinyl, each optionally substituted with 1, 2, or 3 halo, CN, $C_{1-6}$ alkyl, $C_{1-6}$ haloalkyl, $C_{1-6}$ alkoxy, —$NR^eC(O)O$—Z, —$C(O)O$—Z, or $NR^eC(O)$—Z.

In some embodiments, Cy is cycloalkyl or heterocloalkyl, each optionally substituted with 1, 2, 3, 4 or 5 —W—X—Y—Z.

In some embodiments, Cy is piperidinyl, pyrrolindinyl, 1,2,3,6-tetrahydropyridinyl, 2-oxo-[1,3]oxazinanyl, or piperizinyl, each optionally substituted with 1, 2, 3, 4 or 5 —W—X—Y—Z.

In some embodiments, Cy is piperidinyl, pyrrolindinyl, 1,2,3,6-tetrahydropyridinyl, or piperizinyl, each optionally substituted with 1, 2, 3, 4 or 5 —W—X—Y—Z.

In some embodiments, Cy is piperidinyl, pyrrolindinyl, 1,2,3,6-tetrahydropyridinyl, 2-oxo-[1,3]oxazinanyl, or piperizinyl, each optionally substituted with 1, 2, or 3 aryl or heteroayl, wherein each of said aryl or heteroaryl is optionally substituted by 1, 2 or 3 halo, CN, $C_{1-4}$ alkyl, phenyl, pyridyl, $C_{1-4}$ alkoxy, or $C_{1-4}$ haloalkyl.

In some embodiments, Cy is piperidinyl, pyrrolindinyl, 1,2,3,6-tetrahydropyridinyl, 2-oxo-[1,3]oxazinanyl, or piperizinyl, each optionally substituted with 1, 2, or 3 phenyl, pyridyl or quinolinyl, wherein each of said phenyl, pyridyl, quinolinyl is optionally substituted by 1, 2 or 3 halo, CN, $C_{1-4}$ alkyl, phenyl, $C_{1-4}$ alkoxy, or $C_{1-4}$ haloalkyl.

In some embodiments, Cy is piperidinyl, pyrrolindinyl, 1,2,3,6-tetrahydropyridinyl, or piperizinyl, each optionally substituted with 1, 2, or 3 aryl, wherein said aryl is optionally substituted by 1, 2 or 3 halo or $C_{1-4}$ haloalkyl.

In some embodiments, L is $(CR^{12}R^{13})_{q1}S(CR^{12}R^{13})_{q2}$, $(CR^{12}R^{13})_{q1}SO_2(CR^{12}R^{13})_{q2}$, or $(CR^{12}R^{13})_{q1}SO(CR^{12}R^{13})_{q2}$.

In some embodiments, L is $(CR^{12}R^{13})_{q1}SO_2(CR^{12}R^{13})_{q2}$.

In some embodiments, L is S, SO or $SO_2$.

In some embodiments, L is $SO_2$.

In some embodiments, L is CO.

In some embodiments, L is $(CR^{12}R^{13})_{q1}$.

In some embodiments, L is $(CR^{12}R^{13})_{q1}$ and q1 is 0.

In some embodiments, Q is aryl, heteroaryl, cycloalkyl, or heterocycloalkyl, each optionally substituted with 1, 2, 3, 4 or 5 —W'—X'—Y'—Z'.

In some embodiments, Q is aryl or heteroaryl, each optionally substituted with 1, 2, 3, 4 or 5 halo, $C_{1-4}$ alkyl, CN, $NR^cC(O)R^d$ or $NR^eS(O)_2R^b$.

In some embodiments, Q is phenyl, pyridyl or quinolinyl, each optionally substituted with 1 or 2 halo, $C_{1-4}$ alkyl, CN, $NR^cC(O)R^d$ or $NR^eS(O)_2R^b$.

In some embodiments, Q is cycloalkyl or heterocycloalkyl, each optionally substituted with 1, 2, 3, 4 or 5 —W'—X'—Y'—Z'.

In some embodiments, Q is cycloalkyl or heterocycloalkyl, each optionally substituted with 1 or 2-W'—X'—Y'—Z'.

In some embodiments, Q is cycloalkyl or heterocycloalkyl, each optionally substituted with 1, 2, 3, 4 or 5 OH, $C_{1-4}$ alkoxy, CN, $C_{1-4}$ alkyl, —O-heteroaryl, —($C_{1-4}$ alkyl)-CN, $COOR^a$, $C(O)NR^cR^d$ or $NR^cC(O)OR^a$.

In some embodiments, Q is cyclopropyl, cyclohexyl, cycloheptyl, adamantyl, tetrahydro-2H-pyranyl or piperidinyl, each optionally substituted with 1OH, $C_{1-4}$ alkoxy, CN, $C_{1-4}$ alkyl, —O-heteroaryl, —($C_{1-4}$ alkyl)-CN, $COOR^a$, $C(O)NR^cR^d$ or $NR^cC(O)OR^a$.

In some embodiments, Q is cycloalkyl or heterocycloalkyl, each optionally substituted with 1, 2, 3, 4 or 5 OH, halo, CN, $C_{1-4}$ alkyl, $C_{1-4}$ alkoxy, $NR^eCOO(C_{1-4}$ alkyl), $NR^eCO(C_{1-4}$ alkyl), aryl, heteroaryl, —O-aryl, —O-heteroaryl, or —($C_{1-4}$ alkyl)-OH.

In some embodiments, Q is cycloalkyl or heterocycloalkyl, each optionally substituted with 1, 2, 3, 4 or 5 OH, CN, —O-heteroaryl, or $C(O)O$—Z'.

In some embodiments, Q is cycloalkyl or heterocycloalkyl, each substituted with at least two —W'—X'—Y'—Z', wherein two of said at least two —W'—X'—Y'—Z' are attached to the same atom and together with the atom to which they are attached form a 3-20 membered cycloalkyl or heterocyloalkyl group, each optionally substituted by 1, 2 or 3-W"—X"—Y"—Z".

In some embodiments, Q is phenyl, pyridyl, cyclopropyl, cyclobutyl, cyclopentyl, cyclohexyl, cycloheptyl, adamantyl, indanyl, or 1,2,3,4-tetrahydronaphthalene, each optionally substituted with 1, 2, 3, 4 or 5 —W'—X'—Y'—Z'.

In some embodiments, Q is phenyl, pyridyl, cyclopropyl, cyclopentyl, cyclohexyl, cycloheptyl, or adamantyl, each optionally substituted with 1, 2, 3, 4 or 5 OH, CN, halo, $C_{1-6}$ alkyl, —O-heteroaryl, or C(O)O—Z'.

In some embodiments, Q is cyclohexyl substituted at the 4-position with at least one —W'—X'—Y'—Z'.

In some embodiments, Q is cyclohexyl substituted at the 4-position with at least one OH, CN, or —O—X'—Y'—Z'.

In some embodiments, Q is —(CR$^1$R$^2$)$_m$-A and m is 1, 2 or 3.

In some embodiments, Q is —(CR$^1$R$^2$)$_m$-A and m is 2.

In some embodiments, A is aryl or heteroaryl, each optionally substituted with 1, 2, 3, 4 or 5-W'—X'—Y'—Z'.

In some embodiments, A is aryl optionally substituted with 1, 2, 3, 4 or 5 —W'—X'—Y'—Z'.

In some embodiments, A is heteroaryl optionally substituted with 1, 2, 3, 4 or 5 —W'—X'—Y'—Z'.

In some embodiments, A is cycloalkyl or heterocycloalkyl, each optionally substituted with 1, 2, 3, 4 or 5 —W'—X'—Y'—Z'.

In some embodiments, A is cycloalkyl or heterocycloalkyl, each optionally substituted with 1 or 2-W'—X'—Y'—Z'.

In some embodiments, A is cycloalkyl optionally substituted with 1, 2, 3, 4 or 5 —W'—X'—Y'—Z'.

In some embodiments, A is cycloalkyl or heterocycloalkyl, each optionally substituted with 1, 2, 3, 4 or 5 OH, halo, CN, $C_{1-4}$ alkyl, $C_{1-4}$ alkoxy, NR$^e$COO(C$_{1-4}$ alkyl), NR$^e$CO(C$_{1-4}$ alkyl), aryl, heteroaryl, —O-aryl, —O-heteroaryl, or —(C$_{1-4}$ alkyl)-OH.

In some embodiments, A is cyclopropyl, cyclopentyl, cyclohexyl, cycloheptyl, or adamantyl, each optionally substituted with 1, 2, 3, 4 or 5 OH, CN, halo, $C_{1-6}$ alkyl, —O-heteroaryl, or C(O)O—Z'.

In some embodiments, A is cyclopropyl, cyclopentyl, cyclohexyl, cycloheptyl, or adamantyl, each optionally substituted with 1, 2, 3, 4 or 5 OH, CN, halo, $C_{1-6}$ alkyl, —O-heteroaryl, or C(O)O—(C$_{1-4}$ alkyl).

In some embodiments, A is cycloalkyl or heterocycloalkyl, each optionally substituted with 1, 2, 3, 4 or 5 OH, CN, —O-heteroaryl, or C(O)O—Z'.

In some embodiments, A is cycloalkyl or heterocycloalkyl, each optionally substituted with 1, 2, 3, 4 or 5 OH, CN, —O-heteroaryl, or C(O)O—(C$_{1-4}$ alkyl).

In some embodiments, A is cycloalkyl or heterocycloalkyl, each substituted with at least two —W'—X'—Y'—Z', wherein two of said at least two —W'—X'—Y'—Z' are attached to the same atom and together with the atom to which they are attached form a 3-20 membered cycloalkyl or heterocyloalkyl group, each optionally substituted by 1, 2 or 3-W"—X"—Y"—Z".

In some embodiments, A is phenyl, pyridyl, cyclopropyl, cyclobutyl, cyclopentyl, cyclohexyl, cycloheptyl, adamantyl, indanyl, or 1,2,3,4-tetrahydronaphthalene, each optionally substituted with 1, 2, 3, 4 or 5 —W'—X'—Y'—Z'.

In some embodiments, A is phenyl, pyridyl, cyclopropyl, cyclopentyl, cyclohexyl, cycloheptyl, or adamantyl, each optionally substituted with 1, 2, 3, 4 or 5 OH, CN, halo, $C_{1-6}$ alkyl, —O-heteroaryl, or C(O)O—Z'.

In some embodiments, A is phenyl, pyridyl, cyclopropyl, cyclopentyl, cyclohexyl, cycloheptyl, or adamantyl, each optionally substituted with 1, 2, 3, 4 or 5 OH, CN, halo, $C_{1-6}$ alkyl, —O-heteroaryl, or C(O)O—(C$_{1-4}$ alkyl).

In some embodiments, A is cyclohexyl substituted at the 4-position with at least one —W'—X'—Y'—Z'.

In some embodiments, A is cyclohexyl substituted at the 4-position with at least one OH, CN, or —O—X'—Y'—Z'.

In some embodiments, E is methylene, ethylene, or propylene.

In some embodiments, E is ethylene.

In some embodiments, E is —(CR$^{3a}$R$^{3b}$)$_{n3}$CONR$^{3c}$— or —(CR$^{3a}$R$^{3b}$)$_{n2}$NR$^{3e}$CO—.

In some embodiments, E is —CONR$^{3c}$—.

In some embodiments, E is —CONR$^{3e}$—, wherein R$^{3c}$ is H, C$_{1-4}$ alkyl, or CO—(C$_{1-4}$ alkyl).

In some embodiments, E is —CONH—.

In some embodiments, E is a group of formula:

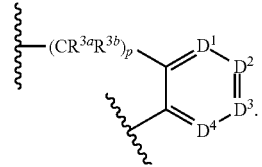

In some embodiments, D$^1$, D$^2$, D$^3$ and D$^4$ are each CR$^{15}$.

In some embodiments, one or two of D$^1$, D$^2$, D$^3$ and D$^4$ is N.

In some embodiments, R$^4$, R$^5$, R$^6$, R$^7$, R$^8$, R$^9$, R$^{10}$ and R$^{11}$ are each, independently, H, OC(O)R$^{a'}$, OC(O)OR$^{b'}$, C(O)OR$^{b'}$, OC(O)NR$^{c'}$R$^{d'}$, NR$^{c'}$R$^{d'}$, NR$^{c'}$C(O)R$^{a'}$, NR$^{c'}$C(O)OR$^{b'}$, S(O)R$^{a'}$, S(O)NR$^{c'}$R$^{d'}$, S(O)$_2$R$^{a'}$, S(O)$_2$NR$^{c'}$R$^{d'}$, OR$^{b'}$, SR$^{b'}$, C$_{1-10}$ alkyl, C$_{1-10}$ haloalkyl, C$_{2-10}$ alkenyl, C$_{2-10}$ alkynyl, aryl, cycloalkyl, heteroaryl, heterocycloalkyl, arylalkyl, heteroarylalkyl, cycloalkylalkyl or heterocycloalkylalkyl.

In some embodiments, R$^4$, R$^5$, R$^6$, R$^7$, R$^8$, R$^9$, R$^{10}$ and R$^{11}$ are each, independently, H, C$_{1-10}$ alkyl or C$_{1-10}$ haloalkyl.

In some embodiments, R$^4$, R$^5$, R$^6$, R$^7$, R$^8$, R$^9$, R$^{10}$ and R$^{11}$ are each H.

In some embodiments, R$^{3a}$ and R$^{3b}$ are each H.

In some embodiments, r is 1.

In some embodiments, r is 0.

In some embodiments, the sum of q1 and q2 is 0, 1 or 2.

In some embodiments, the sum of q1 and q2 is 0.

In some embodiments, R$^{12}$ and R$^{13}$ are each H.

In some embodiments, at least one of W and R$^2$ is C$_{1-4}$ alkyl.

In some embodiments, m is 0.

In some embodiments, m is 1 or 2.

In some embodiments, n1 is 1.

In some embodiments, n1 is 2.

In some embodiments, n2 is 0.

In some embodiments, n2 is 1.

In some embodiments, n3 is 0.

In some embodiments, n3 is 1, 2, 3 or 4;

In some embodiments, p is 0.

In some embodiments, p is 1.

In some embodiments, each —W—X—Y—Z is, independently, —NR$^e$C(O)O—Z, —C(O)O—Z, —NR$^e$C(O)—Z, —CO—Z, —SO—Z, —SO$_2$—Z, —SONR$^e$—Z, —NR$^e$CONR$^f$—Z, halo, CN, NO$_2$, OH, C$_{1-4}$ alkoxy, C$_{1-4}$ haloalkoxy, amino, C$_{1-4}$ alkylamino, C$_{2-8}$ dialkylamino, C$_{1-6}$ alkyl, C$_{2-6}$ alkenyl, C$_{2-6}$ alkynyl, aryl, cycloalkyl, heteroaryl or heterocycloalkyl, wherein said C$_{1-6}$ alkyl, C$_{2-6}$ alkenyl, C$_{2-6}$ alkynyl, aryl, cycloalkyl, heteroaryl or heterocycloalkyl is optionally substituted by 1, 2 or 3 halo, oxo, C$_{1-6}$ alkyl, C$_{2-6}$ alkenyl, C$_{2-6}$ alkynyl, C$_{1-4}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, or S(O)$_2$NR$^c$R$^d$.

In some embodiments, each —W—X—Y—Z is, independently, —NHC(O)O—C$_{1-4}$ alkyl, —NR$^c$C(O)O—C$_{1-4}$ alkynyl, —C(O)O—$C_{1-4}$ alkyl, —NHC(O)—$C_{1-4}$ alkyl, —NHC(O)—$C_{3-9}$ cycloalkyl, halo, CN, $NO_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, oxo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$.

In some embodiments, each —W—X—Y—Z is, independently, halo, CN, $C_{1-6}$ alkyl, $C_{1-6}$ haloalkyl, $C_{1-6}$ alkoxy, —$NR^eC(O)O$—Z, —$C(O)O$—Z, —$NR^eC(O)$—Z or aryl, wherein said aryl is optionally substituted by 1, 2 or 3 halo or $C_{1-4}$ haloalkyl.

In some embodiments, each —W—X—Y—Z is, independently, halo, CN, $C_{1-4}$ alkyl, $C_{1-4}$ haloalkyl, $C_{1-4}$ alkoxy, —NHC(O)O—($C_{1-4}$ alkyl), —NHC(O)O—($C_{1-4}$ alkynyl), —C(O)O—($C_{1-4}$ alkyl), —NHC(O)—($C_{1-4}$ alkyl), —NHC(O)—($C_{3-9}$ cycloalkyl) or phenyl, wherein said phenyl is optionally substituted by 1, 2 or 3 halo or $C_{1-4}$ haloalkyl.

In some embodiments, each —W—X—Y—Z is, independently, halo, CN, $NO_2$, $C_{1-4}$ alkoxy, heteroaryloxy, $C_{2-6}$ alkynyl, $C_{1-4}$ haloalkoxy, $NR^cC(O)R^d$, $NR^eC(O)OR^a$, $C(O)NR^cR^d$, $NR^cR^d$, $NR^eS(O)_2R^b$, $C_{1-4}$ haloalkyl, $C_{1-6}$ alkyl, heterocycloalkyl, aryl or hetaryl, wherein each of said $C_{1-6}$ alkyl, aryl or hetaryl is optionally substituted by 1, 2 or 3 halo, $C_{1-6}$ alkyl, $C_{1-4}$ haloalkyl, CN, $NO_2$, $OR^a$, $SR^a$, $C(O)NR^cR^d$, $NR^cC(O)R^d$ or $COOR^4$.

In some embodiments, each —W—X—Y—Z is, independently, halo, CN, $NO_2$, $C_{1-4}$ alkoxy, pyridin-2-yloxy, pyridin-3-yloxy, pyridin-4-yloxy, $C_{2-6}$ alkynyl, $C_{1-4}$ haloalkoxy, $NR^c$-$C(O)R^d$, $NR^eC(O)OR^a$, $C(O)NR^{ad}$, $NR^cR^d$, $NR^eS(O)_2R^b$, $C_{1-4}$ haloalkyl, $C_{1-6}$ alkyl, phenyl, pyridyl, pyrimidinyl, isoxazolyl, pyrazolyl, 1,2,3,6-tetrahydro-pyridinyl, 2-oxo-(2H)-pyridinyl, 2-oxo-[1,3]oxazolidinyl, 2-oxo-pyrrolidinyl, pyrrolidinyl, 2-oxopiperidinyl, or 2-oxo-[1,3]oxazinanyl, wherein each of said $C_{1-6}$ alkyl, phenyl, pyridyl, pyrimidinyl, isoxazolyl, pyrazolyl, 1,2,3,6-tetrahydro-pyridinyl, 2-oxo-(2H)-pyridinyl, 2-oxo-[1,3]oxazolidinyl, 2-oxo-pyrrolidinyl, pyrrolidinyl, 2-oxopiperidinyl, or 2-oxo-[1,3]oxazinanyl is optionally substituted by 1, 2 or 3 halo, $C_{1-6}$ alkyl, $C_{1-4}$ haloalkyl, CN, $NO_2$, $OR^a$, $SR^a$, $C(O)NR^cR^d$, $NR^cC(O)R^d$ or $COOR^a$.

In some embodiments, each —W—X—Y—Z is, independently, aryl or heteroayl, wherein each of said aryl or heteroaryl is optionally substituted by 1, 2 or 3 halo, CN, $C_{1-4}$ alkyl, phenyl, pyridyl, $C_{1-4}$ alkoxy, or $C_{1-4}$ haloalkyl.

In some embodiments, each —W—X—Y—Z is, independently, phenyl, pyridyl or quinolinyl, wherein each of said phenyl, pyridyl, quinolinyl is optionally substituted by 1, 2 or 3 halo, CN, $C_{1-4}$ alkyl, phenyl, $C_{1-4}$ alkoxy, or $C_{1-4}$ haloalkyl.

In some embodiments, each —W'—X'—Y'—Z' is, independently, OH, CN, halo, $C_{1-6}$ alkyl, $C_{1-6}$ haloalkyl, aryl, heteroaryl, cycloalkyl, heterocycloalkyl, —O—Z', —C(O)—Z' or —C(O)O—Z', wherein said $C_{1-6}$ alkyl, aryl, heteroaryl, cycloalkyl, or heterocycloalkyl are each optionally substituted by 1, 2 or 3 halo, oxo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, or $S(O)_2NR^cR^d$.

In some embodiments, each —W'—X'—Y'—Z' is, independently, OH, $C_{1-4}$ alkoxy, CN, $C_{1-4}$ alkyl, —O-heteroaryl, —($C_{1-4}$ alkyl)-CN, $COOR^a$, $C(O)NR^cR^d$ or $NR^cC(O)OR^a$.

In some embodiments, each —W'—X'—Y'—Z' is, independently, halo, $C_{1-4}$ alkyl, CN, $NR^eC(O)R^d$ or $NR^eS(O)_2R^b$.

In some embodiments, each —W'—X'—Y'—Z' is, independently, OH, CN, halo, $C_{1-6}$ alkyl, —O-heteroaryl, or C(O)O—Z'.

In some embodiments, each —W'—X'—Y'—Z' is, independently, OH, CN, halo, $C_{1-6}$ alkyl, —O-heteroaryl, or —C(O)O—$C_{1-4}$ alkyl.

In some embodiments, each —W"—X"—Y"—Z" is halo, CN, $NO_2$, OH, $C_{1-4}$ alkoxy, $C_{1-4}$ haloalkoxy, amino, $C_{1-4}$ alkylamino, $C_{2-8}$ dialkylamino, $NR^eS(O)_2R^b$, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, oxo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $NR^eS(O)_2R^6$, $S(O)R^b$, $S(O)NR^cR^d$, $S(O)_2R^b$, or $S(O)_2NR^cR^d$.

In some embodiments, each —W"—X"—Y"—Z" is halo, CN, $NO_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, oxo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^eC(O)OR^a$, $S(O)R^b$, $S(O)NR^cR^d$, $S(O)_2R^b$, or $S(O)_2NR^cR^d$.

In some embodiments, each —W"—X"—Y"—Z" is halo, CN, $NO_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl.

In some embodiments, compounds of the invention have Formula II:

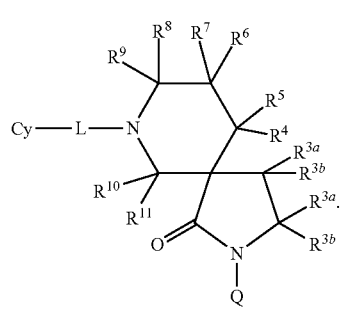

II

In some embodiments, compounds of the invention have Formula IIIa:

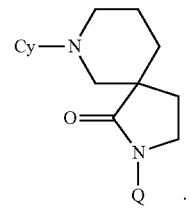

IIIa

In some embodiments, compounds of the invention have Formula IIIb:

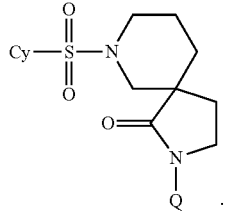

IIIb

In some embodiments, compounds of the invention have Formula IIIc:

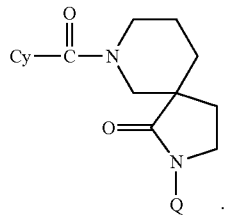

IIIc

In some embodiments, compounds of the invention have Formula IV:

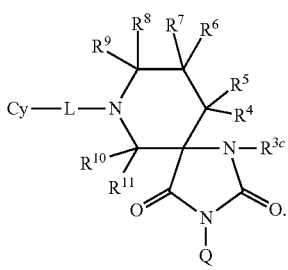

IV

In some embodiments, compounds of the invention have Formula IVa:

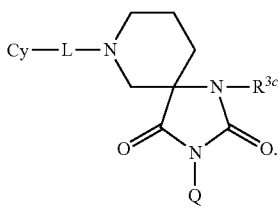

IVa

In some embodiments, compounds of the invention have Formula IVb:

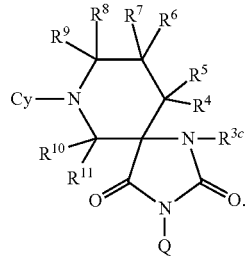

IVb

In some embodiments, compounds of the invention have Formula IVc:

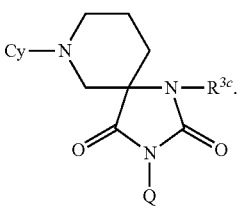

IVc

In some embodiments, compounds of the invention have Formula IV, Formula IVa, Formula IVb, or Formula IVc, wherein $R^{3c}$ is H, $C_{1-4}$ alkyl, or CO—($C_{1-4}$ alkyl). In some further embodiments, $R^{3c}$ is H.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, piperidinyl is an example of a 6-membered heterocycloalkyl ring and 1,2,3,4-tetrahydro-naphthalene is an example of a 10-membered cycloalkyl group.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. The term "alkylenyl" refers to a divalent alkyl linking group.

As used herein, "alkenyl" refers to an alkyl group having one or more double carbon-carbon bonds. Example alkenyl groups include ethenyl, propenyl, cyclohexenyl, and the like. The term "alkenylenyl" refers to a divalent linking alkenyl group.

As used herein, "alkynyl" refers to an alkyl group having one or more triple carbon-carbon bonds. Example alkynyl groups include ethynyl, propynyl, and the like. The term "alkynylenyl" refers to a divalent linking alkynyl group.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic cyclic hydrocarbons including cyclized alkyl, alkenyl, and alkynyl groups. Cycloalkyl groups can include mono- or polycyclic (e.g., having 2, 3 or 4 fused rings) groups. Ring-forming carbon atoms of a cycloalkyl group can be optionally substituted by oxo or sulfido. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo or thienyl derivatives of pentane, pentene, hexane, and the like.

As used herein, "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 4 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles including cyclized alkyl, alkenyl, and alkynyl groups where one or more of the ring-forming carbon atoms is replaced by a heteroatom such as an O, N, or S atom. Heterocycloalkyl groups include monocyclic and polycyclic (e.g., having 2, 3 or 4 fused rings) systems. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Ring-forming carbon atoms and heteroatoms of a heterocycloalkyl group can be optionally substituted by oxo or sulfido. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles such as indolene and isoindolene groups. In some embodiments, the heterocycloalkyl group has from 1 to about 20 carbon atoms, and in further embodiments from about 3 to about 20 carbon atoms. In some embodiments, the heterocycloalkyl group contains 3 to about 14, 4 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double or triple bonds. In some embodiments, the heterocycloalkyl group contains 0 to 2 double or triple bonds.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used here, "haloalkoxy" refers to an —O-haloalkyl group. An example haloalkoxy group is $OCF_3$.

As used herein, "heteroaryloxy" refers to —O-heteroaryl. An example heteroaryloxy is pyridine-2-yloxy [i.e., —O-(pyridine-2-yl)].

As used herein, "arylalkyl" refers to alkyl substituted by aryl and "cycloalkylalkyl" refers to alkyl substituted by cycloalkyl. An example arylalkyl group is benzyl.

As used herein, "amino" refers to $NH_2$.

As used herein, "alkylamino" refers to an amino group substituted by an alkyl group.

As used herein, "dialkylamino" refers to an amino group substituted by two alkyl groups.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C═N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms, such as keto-enol tautomers.

Compounds of the invention further include hydrates and solvates, as well as anhydrous and non-solvated forms.

Compounds of the invention can also include all isotopes of atoms occurring in the intermediates or final compounds. Isotopes include those atoms having the same atomic number but different mass numbers. For example, isotopes of hydrogen include tritium and deuterium.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Synthesis

The novel compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatograpy (HPLC) or thin layer chromatography.

Preparation of Compounds can Involve the Protection and Deprotection of Various Chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of the invention can be prepared, for example, using the reaction pathways and techniques described below.

Compounds of the invention can be generally prepared by the method outlined in Scheme 1. Reagents of formula 1-1 (X is a leaving group such as halo) can be reacted with an amines of formula 1-2 (or its salts) in an appropriate solvent (e.g., CH$_2$Cl$_2$) and optionally in the presence of a base such as diisopropyl ethyl amine to provide the desired products 1-3. As an example, sulfonyl chlorides of formula 1-4 can be reacted with the amines of formula 1-2 to provide sulfonyl linked compounds of formula 1-5.

Scheme 1

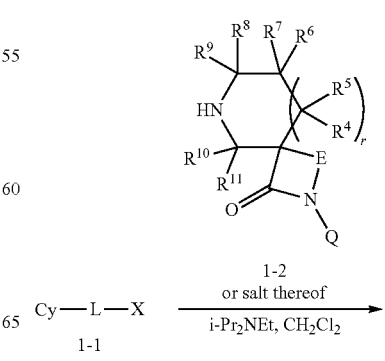

-continued

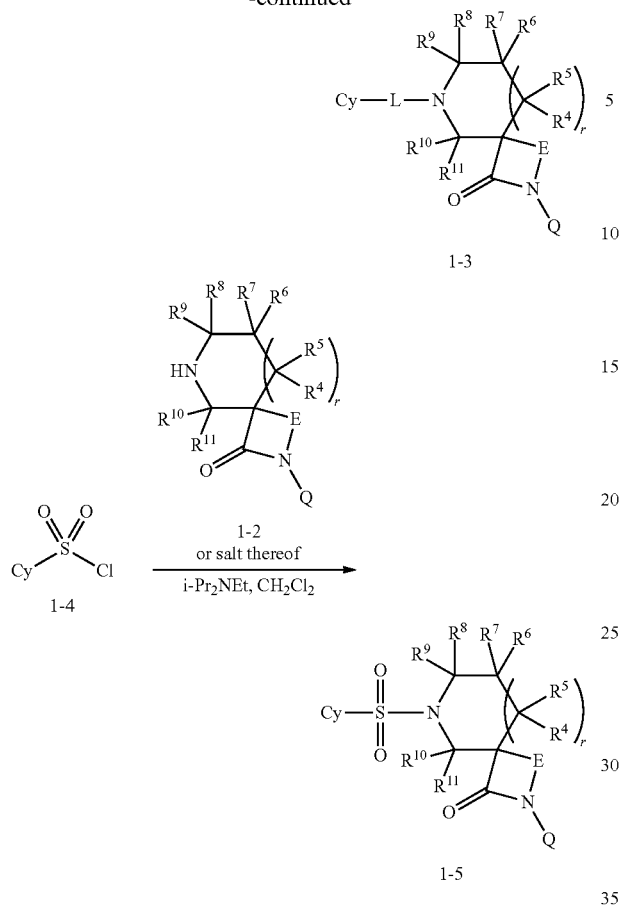

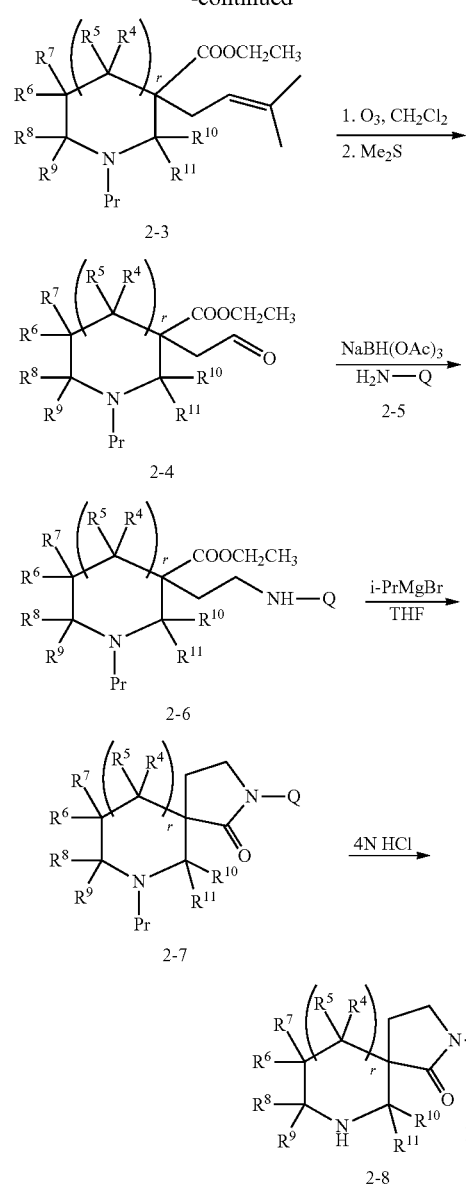

A series of spirocyclyl amines of formula 2-8 can be prepared according to the procedure outlined in Scheme 2. N-protected 2-1 (Pr is an amino protecting group such as Boc) can be treated with a base such as LDA at low temperature in a solvent such as tetrahydrofuran followed by addition of 1-bromo-3-methyl-2-butene (2-2). The resulting intermediate (2-3) can be treated with ozone and then reduced with methyl sulfide to provide the aldehyde 2-4. Reductive amination of 2-4 with amines 2-5 can be conducted in a solvent such as methanol and using a reducing agent such as sodium triacetoxyborohydride, and the product 2-6 can be cyclized in the presence of a base such as isopropylmagnesium bromide to provide the lactam 2-7 which upon acidic cleavage of the Boc group yields the desired amine 2-8.

Scheme 2

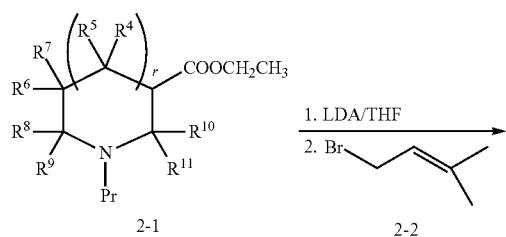

A series of amines of formula 3-7 can be prepared according to the procedure outlined in Scheme 3. Treatment of Boc protected nipecotic ethyl ester 3-1 with a base such as LDA at low temperature in a solvent such as tetrahydrofuran followed by addition of 1-bromo-3-methyl-2-butene can result in an intermediate 3-2, which can be treated with ozone followed by reduction with methyl sulfide to provide the aldehyde 3-3. Reductive amination of 3-3 with amines 3-4 (where $Q_1$ is, e.g., substituted or unsubstituted cycloalkyl or aryl) can be conducted in a solvent such as methanol and using a reducing agent such as sodium triacetoxyborohydride. The resulting intermediate 3-5 can be cyclized in the presence of a base such as isopropylmagnesium bromide to provide the lactam 3-6 which upon acidic cleavage of the Boc group yields the desired piperidine 3-7.

Scheme 3

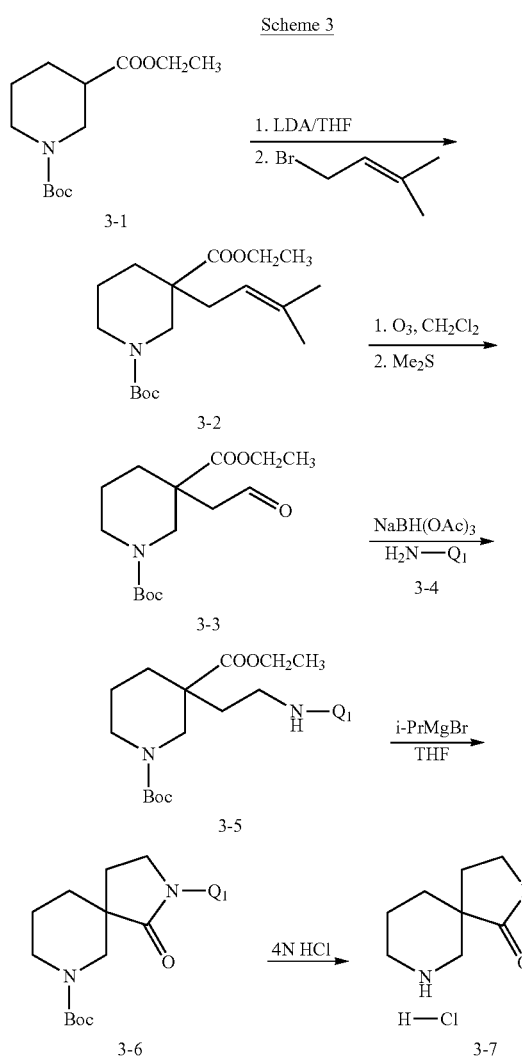

A series of piperidines of 4-4 can be prepared by the method outlined in Scheme 4. Compound 4-1 can be readily converted to the spirohydantoin 4-2 under Bucherer-Bergs conditions, using, e.g., ammonium carbonate and either sodium cyanide or potassium cyanide in aqueous ethanol. Alkylation of compound 4-2 with one equivalent of alkyl halide QX (X is a leaving group such as halo) in the presence of potassium carbonate in DMF, followed by a second alkylation with $R^{3c}X$ (X is a leaving group such as halo) in the presence of sodium hydride in DMF provides substituted hydantoins 4-3, which upon acidic cleavage of the Boc group yields the desired piperidines 4-4.

Scheme 4

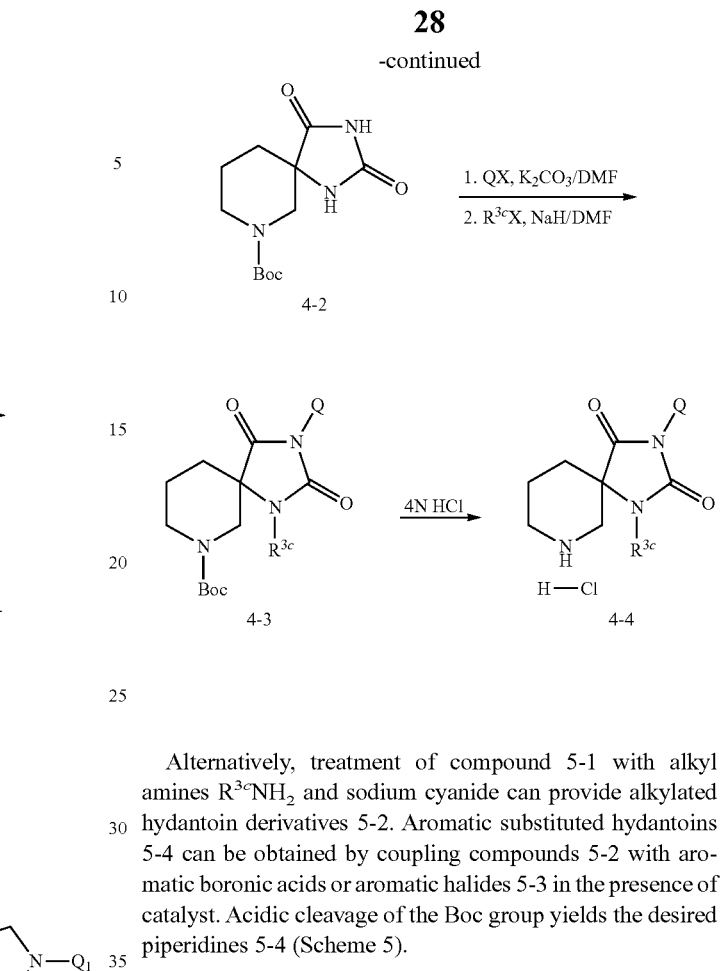

Alternatively, treatment of compound 5-1 with alkyl amines $R^{3c}NH_2$ and sodium cyanide can provide alkylated hydantoin derivatives 5-2. Aromatic substituted hydantoins 5-4 can be obtained by coupling compounds 5-2 with aromatic boronic acids or aromatic halides 5-3 in the presence of catalyst. Acidic cleavage of the Boc group yields the desired piperidines 5-4 (Scheme 5).

Scheme 5

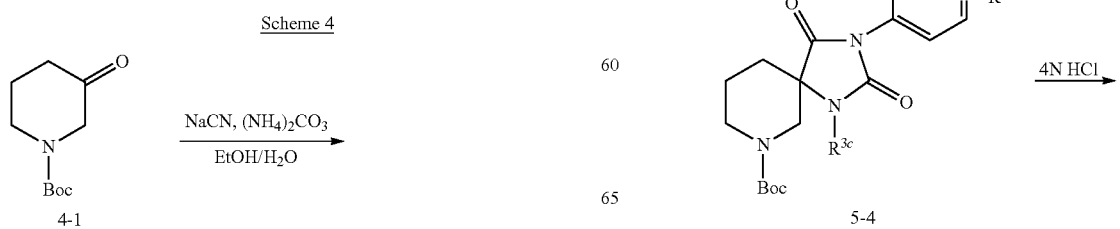

-continued

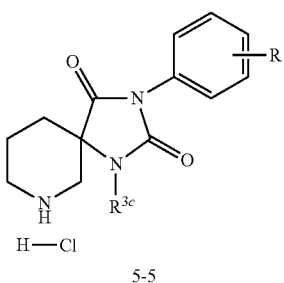

5-5

In a further alternative route, piperidines 6-6 can also be prepared by the method outlined in Scheme 6. The protected amino acid 6-1 can be coupled with an amine Q-NH$_2$ using a coupling agent such as BOP to provide compound 6-2 which, in turn, can be hydrogenated at the presence of Pd catalyst to yield compound 6-3. Compound 6-3 can be treated with methyl chloroformate and a base such as triethyl amine in CH$_2$Cl$_2$ to complete the ring closure and form hydantoin 6-4. As described previously, N alkylation with R$^{3c}$X (X is a leaving group such as halo) can yield compounds of formula 6-5 and acid cleavage can yield compounds of formula 6-6.

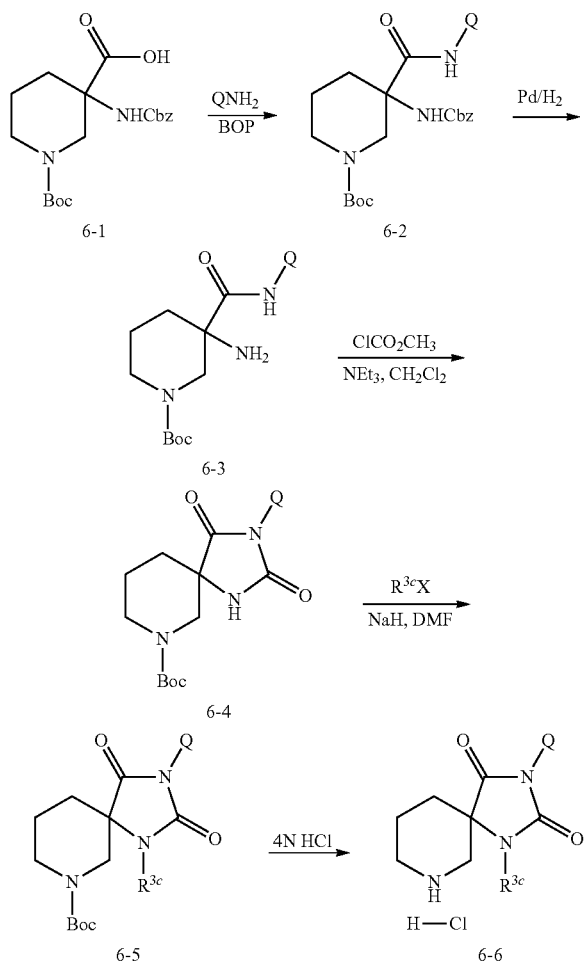

Methods

Compounds of the invention can modulate activity of 11βHSD1 and/or MR. The term "modulate" is meant to refer to an ability to increase or decrease activity of an enzyme or receptor. Accordingly, compounds of the invention can be used in methods of modulating 11βHSD1 and/or MR by contacting the enzyme or receptor with any one or more of the compounds or compositions described herein. In some embodiments, compounds of the present invention can act as inhibitors of 11βHSD1 and/or MR. In further embodiments, the compounds of the invention can be used to modulate activity of 11βHSD1 and/or MR in an individual in need of modulation of the enzyme or receptor by administering a modulating amount of a compound of the invention.

The present invention further provides methods of inhibiting the conversion of cortisone to cortisol in a cell, or inhibiting the production of cortisol in a cell, where conversion to or production of cortisol is mediated, at least in part, by 11βHSD1 activity. Methods of measuring conversion rates of cortisone to cortisol and vice versa, as well as methods for measuring levels of cortisone and cortisol in cells, are routine in the art.

The present invention further provides methods of increasing insulin sensitivity of a cell by contacting the cell with a compound of the invention. Methods of measuring insulin sensitivity are routine in the art.

The present invention further provides methods of treating disease associated with activity or expression, including abnormal activity and overexpression, of 11βHSD1 and/or MR in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the enzyme or receptor. An 11βHSD1-associated disease can also include any disease, disorder or condition that can be prevented, ameliorated, or cured by modulating enzyme activity.

Examples of 11βHSD1-associated diseases include obesity, diabetes, glucose intolerance, insulin resistance, hyperglycemia, hypertension, hyperlipidemia, cognitive impairment, dementia, depression (e.g., psychotic depression), glaucoma, cardiovascular disorders, osteoporosis, and inflammation. Further examples of 11βHSD1-associated diseases include metabolic syndrome, type 2 diabetes, androgen excess (hirsutism, menstrual irregularity, hyperandrogenism) and polycystic ovary syndrome (PCOS).

The present invention further provides methods of modulating MR activity by contacting the MR with a compound of the invention, pharmaceutically acceptable salt, prodrug, or composition thereof. In some embodiments, the modulation can be inhibition. In further embodiments, methods of inhibiting aldosterone binding to the MR (optionally in a cell) are provided. Methods of measuring MR activity and inhibition of aldosterone binding are routine in the art.

The present invention further provides methods of treating a disease associated with activity or expression of the MR. Examples of diseases associated with activity or expression of the MR include, but are not limited to hypertension, as well as cardiovascular, renal, and inflammatory pathologies such as heart failure, atherosclerosis, arteriosclerosis, coronary artery disease, thrombosis, angina, peripheral vascular disease, vascular wall damage, stroke, dyslipidemia, hyperlipoproteinaemia, diabetic dyslipidemia, mixed dyslipidemia, hypercholesterolemia, hypertriglyceridemia, and those associated with type 1 diabetes, type 2 diabetes, obesity metabolic syndrome, insulin resistance and general aldosterone-related target organ damage.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal. In some embodiments, the cell is an adipocyte, a pancreatic cell, a hepatocyte, neuron, or cell comprising the eye.

As used herein, the term "contacting" refers to the bringing together of indicated moieties in an in vitro system or an in vivo system. For example, "contacting" the 11βHSD1 enzyme with a compound of the invention includes the administration of a compound of the present invention to an individual or patient, such as a human, having 11βHSD1, as well as, for example, introducing a compound of the invention into a sample containing a cellular or purified preparation containing the 11βHSD1 enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease (non-limiting examples are preventing metabolic syndrome, hypertension, obesity, insulin resistance, hyperglycemia, hyperlipidemia, type 2 diabetes, androgen excess (hirsutism, menstrual irregularity, hyperandrogenism) and polycystic ovary syndrome (PCOS);

(2) inhibiting the disease; for example, inhibiting a disease, condition or disorder in an individual who is experiencing or displaying the pathology or symptomatology of the disease, condition or disorder (i.e., arresting further development of the pathology and/or symptomatology) such as inhibiting the development of metabolic syndrome, hypertension, obesity, insulin resistance, hyperglycemia, hyperlipidemia, type 2 diabetes, androgen excess (hirsutism, menstrual irregularity, hyperandrogenism) or polycystic ovary syndrome (PCOS), stabilizing viral load in the case of a viral infection; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of metabolic syndrome, hypertension, obesity, insulin resistance, hyperglycemia, hyperlipidemia, type 2 diabetes, androgen excess (hirsutism, menstrual irregularity, hyperandrogenism) and polycystic ovary syndrome (PCOS), or lowering viral load in the case of a viral infection.

Pharmaceutical Formulations and Dosage Forms

When employed as pharmaceuticals, the compounds of Formula I can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, antibodies, immune suppressants, anti-inflammatory agents and the like.

Labeled Compounds and Assay Methods

Another aspect of the present invention relates to labeled compounds of the invention (radio-labeled, fluorescent-labeled, etc.) that would be useful not only in radio-imaging but also in assays, both in vitro and in vivo, for localizing and quantitating the enzyme in tissue samples, including human, and for identifying ligands by inhibition binding of a labeled compound. Accordingly, the present invention includes enzyme assays that contain such labeled compounds.

The present invention further includes isotopically-labeled compounds of the invention. An "isotopically" or "radiolabeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2H$ (also written as D for deuterium), $^3H$ (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{72}$Br, $^{123}$I, $^{124}$I, $^{125}$I and $^{131}$I. The radionuclide that is incorporated in the instant radio-labeled compounds will depend on the specific application of that radio-labeled compound. For example, for in vitro receptor labeling and competition assays, compounds that incorporate $^{3}$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled compound" is a compound that has incorporated at least one radionuclide. In some embodiments the radionuclide is selected from the group consisting of $^{3}$H, $^{14}$C, $^{125}$I, $^{35}$S and $^{82}$Br.

In some embodiments, the labeled compounds of the present invention contain a fluorescent label.

Synthetic methods for incorporating radio-isotopes and fluorescent labels into organic compounds are well known in the art.

A labeled compound of the invention (radio-labeled, fluorescent-labeled, etc.) can be used in a screening assay to identify/evaluate compounds. For example, a newly synthesized or identified compound (i.e., test compound) which is labeled can be evaluated for its ability to bind a 11βHSD1 or MR by monitoring its concentration variation when contacting with the 11βHSD1 or MR, through tracking the labeling. For another example, a test compound (labeled) can be evaluated for its ability to reduce binding of another compound which is known to bind to 11βHSD1 or MR (i.e., standard compound). Accordingly, the ability of a test compound to compete with the standard compound for binding to the 11βHSD1 or MR directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of 11βHSD1- or MR-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results. The compound of the Examples were found to inhibitors of 11βHSD1 and/or MR according to one or more of the assays provided herein.

EXAMPLES

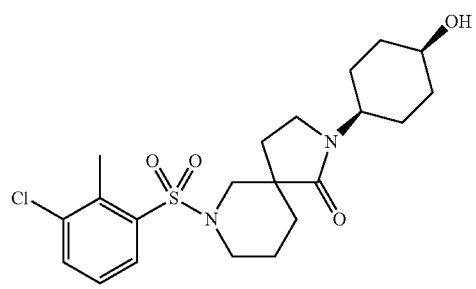 [SMILES: Cc1c(Cl)cccc1S(=O)(=O)N1CCCC2(CCN([C@H]3CC[C@@H](O)CC3)C2=O)C1]

Example 1

7-[(3-Chloro-2-methylphenyl)sulfonyl]-2-(cis-4-hydroxycyclohexyl)-2,7-diazaspiro[4.5]decan-1-one Step 1. 1-tert-butyl 3-ethyl 3-(3-methylbut-2-en-1-yl) piperidine-1,3-dicarboxylate

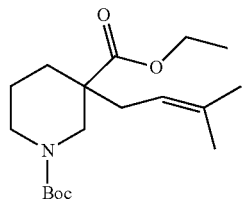 [SMILES: CCOC(=O)C1(CC=C(C)C)CCCN(C(=O)OC(C)(C)C)C1]

To a solution of 1-tert-butyl 3-ethyl piperidine-1,3-dicarboxylate (2.6 g, 10.0 mmol) in THF (30 mL) was slowly added LDA (6.7 mL, 12.0 mmol, 1.8 M solution in heptane-/tetrahydrofuran/ethylbenzene) at −78° C. and the mixture was slowly warmed to −55° C. over 1 h. To this mixture, 1-bromo-3-methyl-2-butene (1.55 g, 10.5 mmol) was slowly added and the reaction was warmed to room temperature and stirred for 4 h. The mixture was quenched with saturated NH$_4$Cl and extracted with diethyl ether, and the combined extracts were washed with brine, dried and concentrated. The product (2.75 g, 85%) was purified by CombiFlash eluted with hexane/ethyl acetate.

Step 2. 1-tert-butyl 3-ethyl 3-(2-oxoethyl)piperidine-1,3-dicarboxylate

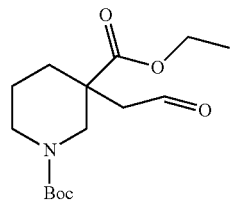 [SMILES: CCOC(=O)C1(CC=O)CCCN(C(=O)OC(C)(C)C)C1]

1-tert-Butyl 3-ethyl 3-(3-methylbut-2-en-1-yl)piperidine-1,3-dicarboxylate (2.75 g, 8.5 mmol) in CH$_2$Cl$_2$ (100 mL) was cooed to −78° C., and ozone was passed into the reaction mixture until a light blue color was observed (ca. 15 min).

Nitrogen was then bubbled through the solution to remove the excess ozone. Dimethyl sulfide (10 mL) was added and the reaction was slowly warmed to room temperature and stirred overnight. The reaction was then washed with water and brine, dried and concentrated to give the product (2.5 g).

Step 3. 1-tert-butyl 3-ethyl 3-{2-[(cis-4-hydroxycyclohexyl)amino]ethyl}piperidine-1,3-dicarboxylate

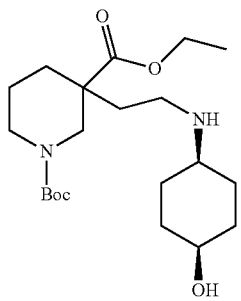 [SMILES: CCOC(=O)C1(CCN[C@H]2CC[C@@H](O)CC2)CCCN(C(=O)OC(C)(C)C)C1]

DIPEA (1.05 eq.) was added to a solution of cis-4-aminocyclohexanol hydrochloride (0.080 g, 0.53 mmol) in methanol (2.0 mL) and stirred for 5 min. To this solution 1-tert-butyl 3-ethyl 3-(2-oxoethyl)-piperidine-1,3-dicarboxylate (0.15 g, 0.5 mmol) was added followed by sodium triacetoxyborohydride (0.21 g, 1.0 mmol) and the mixture was stirred for 2 h. The reaction was acidified by adding AcOH and diluted with water and extracted with ether. The aqueous phase was then basified by adding 1 N NaOH and extracted with ethyl acetate which was then washed with water then brine, dried, and concentrated to give the desired product (0.17 g, 85%). LC-MS: 399.2 (M+H)$^+$.

Step 4. tert-butyl 2-(cis-4-hydroxycyclohexyl)-1-oxo-2,7-diazaspiro[4.5]decane-7-carboxylate

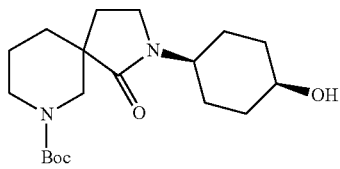 [SMILES: CC(C)(C)OC(=O)N1CCCC2(CCN([C@H]3CC[C@@H](O)CC3)C2=O)C1]

iso-Propylmagnesium bromide (1.0 M in THF, 1.5 mL) was slowly added to a solution of 1-tert-butyl 3-ethyl 3-{2-[(cis-4-hydroxycyclohexyl)amino]ethyl}piperidine-1,3-dicarboxylate (0.15 g, 0.38 mmol) at 0° C. and the mixture was stirred at this temperature for 1 h. The reaction was then poured into cold water and extracted with ethyl acetate, dried and concentrated to give the desired product (0.11 g, 85%). LC-MS: 353.2 (M+H)$^+$, 297.1 (M+H-56)$^+$.

Step 5. 2-(cis-4-hydroxycyclohexyl)-2,7-diazaspiro[4.5]decan-1-one hydrochloride

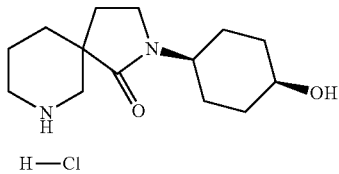

Hydrogen chloride (2.0 mL, 4.0 M in 1,4-dioxane) was added to a solution of tert-butyl 2-(cis-4-hydroxycyclohexyl)-1-oxo-2,7-diazaspiro[4.5]decane-7-carboxylate (0.10 g) in ethyl acetate (0.5 mL) at room temperature and the mixture was stirred for 1 h. The solvent was then removed under vacuum to give the product. LC-MS: 253.2 (M+H)$^+$.

Step 6. 7-[(3-chloro-2-methylphenyl)sulfonyl]-2-(cis-4-hydroxycyclohexyl)-2,7-diazaspiro[4.5]decan-1-one A solution of 3-chloro-2-methylbenzenesulfonyl chloride (0.050 g, 0.22 mmol) in CH$_2$Cl$_2$ (1.0 mL) was slowly added to a mixture of 2-(cis-4-hydroxycyclohexyl)-2,7-diazaspiro[4.5]decan-1-one hydrochloride (0.060 g, 0.2 mmol) and DIPEA (0.10 mL, 0.6 mmol) in CH$_2$Cl$_2$ (1.0 mL) at 0° C. and the reaction was stirred for 1 h. The mixture was diluted with ethyl acetate and then washed with diluted HCl, water and brine, dried and concentrated. The product was purified by CombiFlash eluted with CH$_2$Cl$_2$/EtOAc. LC-MS: 441.2/443.2 (M+H)$^+$.

Example 2

7-[(3-Chloro-2-methylphenyl)sulfonyl]-2-(trans-4-hydroxycyclohexyl)-2,7-diazaspiro[4.5]decan-1-one

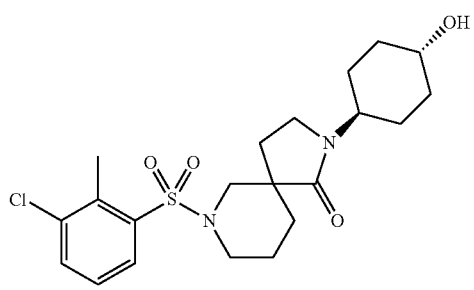 [SMILES: Cc1c(Cl)cccc1S(=O)(=O)N1CCCC2(CCN([C@H]3CC[C@H](O)CC3)C2=O)C1]

This compound was prepared using procedures analogous to those of for example 1. LC-MS: 441.1/443.1 (M+H)$^+$.

Example 3

7-[(3-Chloro-2-methylphenyl)sulfonyl]-2-(2-methylphenyl)-2,7-diazaspiro[4.5]decan-1-one

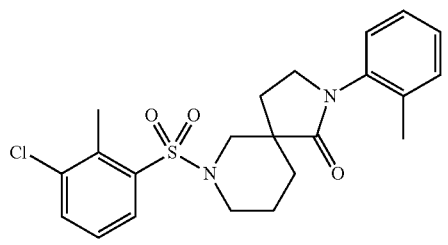 [SMILES: Cc1ccccc1N1CCC2(CCCN(S(=O)(=O)c3cccc(Cl)c3C)C2)C1=O]

This compound was prepared using procedures analogous to those of example 1. LC-MS: 433.1/435.1 (M+H)$^+$.

Example 4

7-[(3-Chloro-2-methylphenyl)sulfonyl]-2-phenyl-2,7-diazaspiro[4.5]decan-1-one

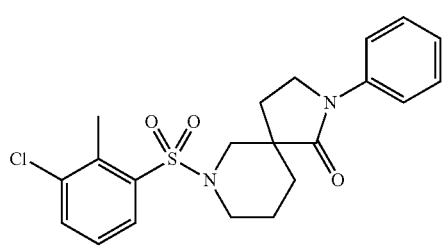 [SMILES: Cc1c(Cl)cccc1S(=O)(=O)N1CCCC2(CCN(c3ccccc3)C2=O)C1]

This compound was prepared using procedures analogous to those of example 1. LC-MS: 419.2/421.2 (M+H)$^+$.

Example 5

Trans-4-{7-[(3-chloro-2-methylphenyl)sulfonyl]-1-oxo-2,7-diazaspiro[4.5]dec-2-yl}cyclohexanecarbonitrile

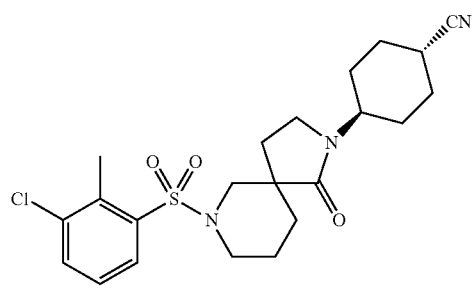

This compound was prepared using procedures analogous to those of example 1. LC-MS: 450.2/452.2 (M+H)$^+$.

Example 6

7-[(3-Chloro-2-methylphenyl)sulfonyl]-2-cycloheptyl-2,7-diazaspiro[4.5]decan-1-one

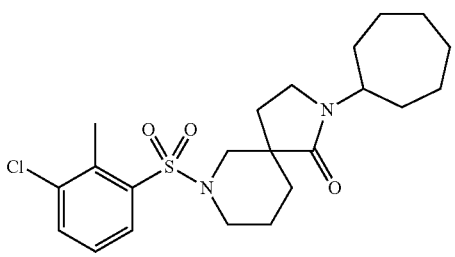 [SMILES: Cc1c(Cl)cccc1S(=O)(=O)N1CCCC2(CCN(C3CCCCCC3)C2=O)C1]

This compound was prepared using procedures analogous to those of example 1. LC-MS: 439.1/441.1 (M+H)$^+$.

Example 7

7-[(3-Chloro-2-methylphenyl)sulfonyl]-2-cyclohexyl-2,7-diazaspiro[4.5]decan-1-one

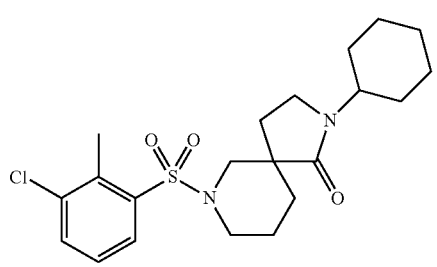 [SMILES: Cc1c(Cl)cccc1S(=O)(=O)N1CCCC2(CCN(C3CCCCC3)C2=O)C1]

This compound was prepared using procedures analogous to those of example 1. LC-MS: 425.1/427.1 (M+H)$^+$.

Example 8

7-[(3-Chloro-2-methylphenyl)sulfonyl]-2-(4-methylpyridin-3-yl)-2,7-diazaspiro[4.5]decan-1-one

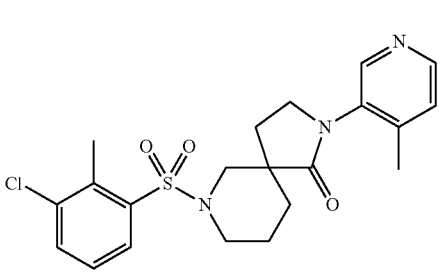 [SMILES: Cc1ccncc1N1CCC2(CCCN(S(=O)(=O)c3cccc(Cl)c3C)C2)C1=O]

This compound was prepared using procedures analogous to those of example 1. LC-MS: 434.1/435.1 (M+H)$^+$.

Example 9

7-[(3-Chloro-2-methylphenyl)sulfonyl]-2-[cis-4-(pyridin-2-yloxy)cyclohexyl]-2,7-diazaspiro[4.5]decan-1-one

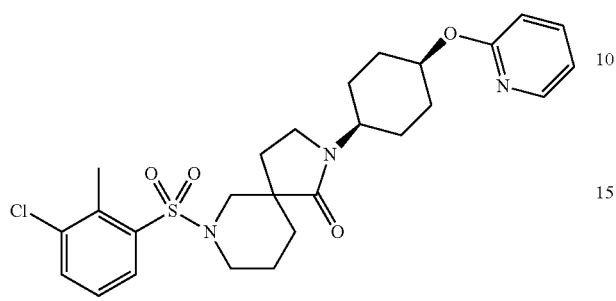

This compound was prepared using procedures analogous to those of example 1. LC-MS: 518.2/520.2 (M+H)$^+$.

Example 10

7-[(3-Chloro-2-methylphenyl)sulfonyl]-2-[cis-4-(pyridin-3-yloxy)cyclohexyl]-2,7-diazaspiro[4.5]decan-1-one

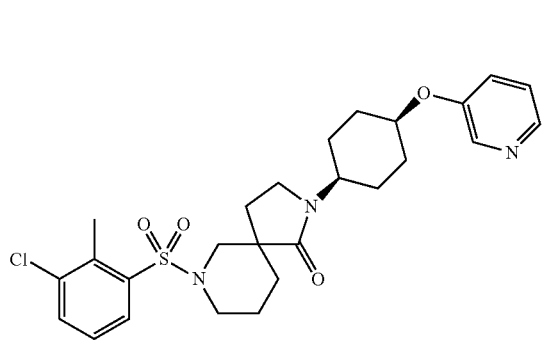 [SMILES: Cc1c(Cl)cccc1S(=O)(=O)N1CCCC2(CCN([C@H]3CC[C@@H](Oc4cccnc4)CC3)C2=O)C1]

This compound was prepared using procedures analogous to those of example 1. LC-MS: 518.2/520.2 (M+H)$^+$.

Example 11

7-[(3-Chloro-2-methylphenyl)sulfonyl]-2-[cis-4-(pyridin-4-yloxy)cyclohexyl]-2,7-diazaspiro[4.5]decan-1-one

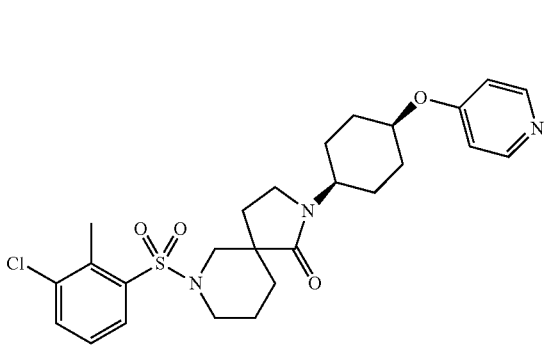 [SMILES: Cc1c(Cl)cccc1S(=O)(=O)N1CCCC2(CCN([C@H]3CC[C@@H](Oc4ccncc4)CC3)C2=O)C1]

This compound was prepared using procedures analogous to those of example 1. LC-MS: 518.2/520.2 (M+H)$^+$.

Example 12

2-(1-Adamantyl)-7-[(3-chloro-2-methylphenyl)sulfonyl]-2,7-diazaspiro[4.5]decan-1-one

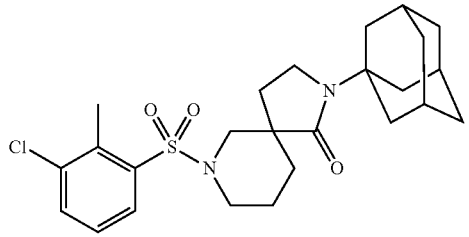 [SMILES: Cc1c(Cl)cccc1S(=O)(=O)N1CCCC2(CCN(C34CC5CC(CC(C5)C3)C4)C2=O)C1]

This compound was prepared using procedures analogous to those of example 1. LC-MS: 477.2/479.2 (M+H)$^+$.

Example 13

7-[(3-Chloro-2-methylphenyl)sulfonyl]-2-(1-methyl-2-phenylethyl)-2,7-diazaspiro[4.5]decan-1-one

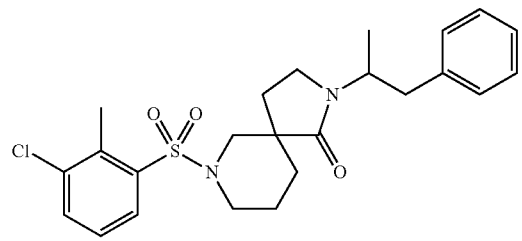 [SMILES: Cc1c(Cl)cccc1S(=O)(=O)N1CCCC2(CCN(C(C)Cc3ccccc3)C2=O)C1]

This compound was prepared using procedures analogous to those of example 1. LC-MS: 461.1/463.1 (M+H)$^+$.

Example 14

(5R)-7-[(3-Chloro-2-methylphenyl)sulfonyl]-2-cycloheptyl-2,7-diazaspiro[4.5]decan-1-one

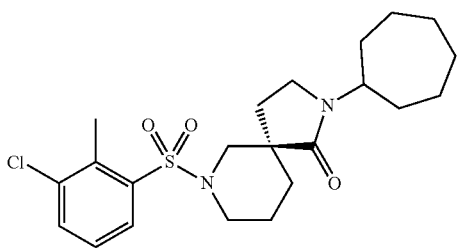 [SMILES: Cc1c(Cl)cccc1S(=O)(=O)N1CCC[C@@]2(CCN(C3CCCCCC3)C2=O)C1]

This compound was prepared by using a chiral column to separate the enantiomers of example 6. Prep Chiral LC conditions: Column: ChiralCel OD-H, 20×250 mm, 5 μm (Chiral Technologies, Inc.); Mobile phase: 15% Ethanol/85% Hexanes; Flow rate: 15 mL/min; Detection: 220 nm; Retention time: t=7.22 min for peak 1; t=9.39 min for peak 2. This compound corresponded to peak 1. LC-MS: 439.1/441.1 (M+H)$^+$.

Example 15

(5S)-7-[(3-Chloro-2-methylphenyl)sulfonyl]-2-cycloheptyl-2,7-diazaspiro[4.5]decan-1-one

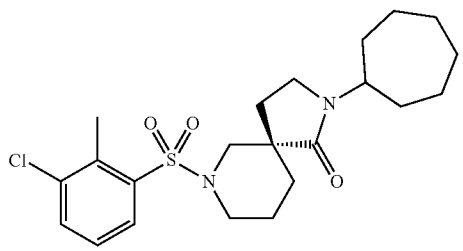 [SMILES: Cc1c(Cl)cccc1S(=O)(=O)N1CCC[C@]2(CCN(C3CCCCCC3)C2=O)C1]

This compound was prepared using procedures analogous to those for the synthesis of example 14. This compound corresponded to peak 2 of the chiral column. LC-MS: 439.1/441.1 (M+H)+.

Example 16 cis-4-{7-[(3-Chloro-2-methylphenyl)sulfonyl]-1-oxo-2,7-diazaspiro[4.5]dec-2-yl}cyclohexanecarbonitrile

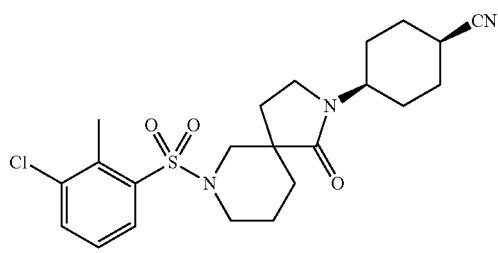 [SMILES: Cc1c(Cl)cccc1S(=O)(=O)N1CCCC2(CCN([C@H]3CC[C@@H](C#N)CC3)C2=O)C1]

This compound was prepared using procedures analogous to those for the synthesis of example 1. LC-MS: 450.2/452.2 (M+H)+.

Example 17

2-Cyclohexyl-7-(2-fluorophenyl)-2,7-diazaspiro[4.5]decan-1-one

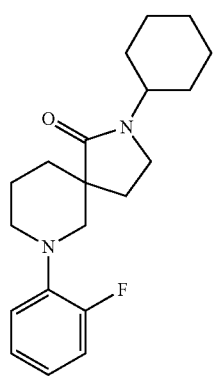 [SMILES: O=C1N(C2CCCCC2)CCC12CCCN(c1ccccc1F)C2]

This compound was prepared by using procedures that were analogous to those described for the synthesis of example 1, steps 1-5, followed by the following microwave mediated amine/aryl coupling procedure:

A mixture of 2-cyclohexyl-2,7-diazaspiro[4.5]decan-1-one hydrochloride (0.025 g, 0.000092 mol), 1-bromo-2-fluorobenzene (0.032 g, 0.00018 mol), and sodium tert-butoxide (0.026 g, 0.00027 mol) in DMSO (0.5 mL) was microwave irradiated at 180° C. for 5 min. After cooling the reaction mixture to ambient temperature the crude product was purified by prep.-HPLC. LC-MS: 331.2 (M+H)+.

Example 18

2-Cyclohexyl-7-(4-fluorophenyl)-2,7-diazaspiro[4.5]decan-1-one

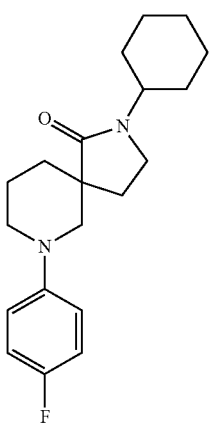 [SMILES: O=C1N(C2CCCCC2)CCC12CCCN(c1ccc(F)cc1)C2]

This compound was prepared using procedures analogous to those for the synthesis of example 17. LC-MS: 331.2 (M+H)+.

Example 19

2-Cyclohexyl-7-(3-fluorophenyl)-2,7-diazaspiro[4.5]decan-1-one

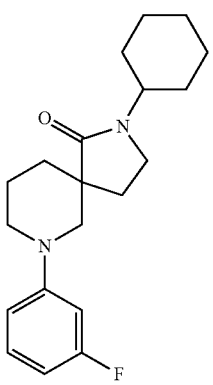 [SMILES: O=C1N(C2CCCCC2)CCC12CCCN(c1cccc(F)c1)C2]

This compound was prepared using procedures analogous to those for the synthesis of example 17. LC-MS: 331.2 (M+H)+.

Example 20

2-Cyclohexyl-7-phenyl-2,7-diazaspiro[4.5]decan-1-one

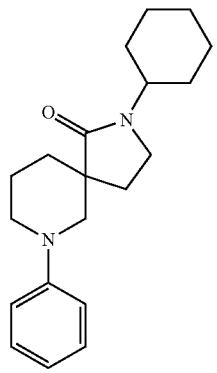

This compound was prepared using procedures analogous to those for the synthesis of example 17. LC-MS: 313.2 (M+H)⁺.

Example 21

7-(4-Fluorophenyl)-2-(trans-4-hydroxycyclohexyl)-2,7-diazaspiro[4.5]decan-1-one

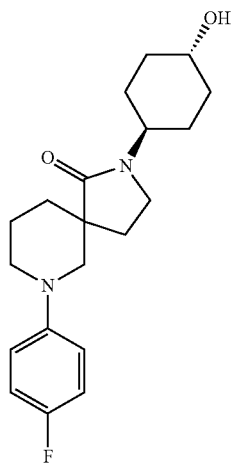 [SMILES: O=C1N([C@H]2CC[C@H](O)CC2)CCC12CCCN(c1ccc(F)cc1)C2]

This compound was prepared using procedures analogous to those for the synthesis of example 17. LC-MS: 347.2 (M+H)⁺.

Example 22

7-(3-Fluorophenyl)-2-(trans-4-hydroxycyclohexyl)-2,7-diazaspiro[4.5]decan-1-one

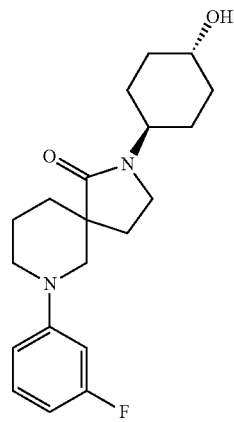 [SMILES: O=C1N([C@H]2CC[C@H](O)CC2)CCC12CCCN(c1cccc(F)c1)C2]

This compound was prepared using procedures analogous to those for the synthesis of example 17. LC-MS: 347.2 (M+H)⁺.

Example 23

2-(trans-4-Hydroxycyclohexyl)-7-phenyl-2,7-diazaspiro[4.5]decan-1-one

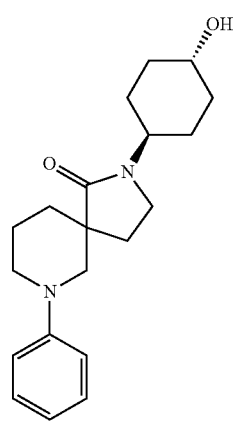 [SMILES: O=C1N([C@H]2CC[C@H](O)CC2)CCC12CCCN(c1ccccc1)C2]

This compound was prepared using procedures analogous to those for the synthesis of example 17. LC-MS: 329.2 (M+H)⁺.

Example 26

Methyl 1-[7-(2-fluorophenyl)-1-oxo-2,7-diazaspiro[4.5]dec-2-yl]cyclopropanecarboxylate

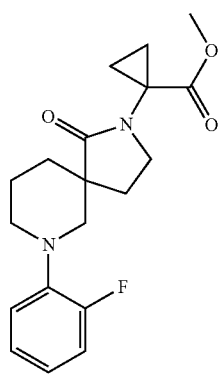 [SMILES: COC(=O)C1(N2CCC3(CCCN(c4ccccc4F)C3)C2=O)CC1]

This compound was prepared by using procedures that were analogous to those described for the synthesis of example 1, steps 1-3, followed by the following reductive amination/cyclization and amine/aryl coupling procedure as described in example 17:

1-Aminocyclopropanecarboxylic acid (0.10 g, 0.00099 mol) in MeOH (3 mL) with 4 N HCl (1.5 mL) was stirred at rt for 2 h. LCMS analysis indicated that the carboxylic acid was successfully converted to methyl ester. (m/z 116.3). The volatiles were removed in-vacuo to afford 150 mg of the methyl ester HCl salt. To this methyl ester, 1-tert-butyl 3-ethyl 3-(2-oxoethyl)piperidine-1,3-dicarboxylate (0.25 g, 0.00084 mol), and triethylamine (190 µL, 0.0013 mol) in 1,2-dichloroethane (1.5 mL, 0.019 mol) was stirred at rt for 30 min. To the mixture was added sodium triacetoxyborohydride (0.35 g, 0.0017 mol) with stirring. After stirring at rt for 2 h, the reaction mixture then was heated to 70° C. and stirred for 16 h. LCMS data indicated that the spiro-ring formed and the methyl ester was hydrolyzed (m/z 283.0, (M−Bu+2H)+). The reaction mixture was diluted with ethyl acetate and the organic solution was washed with 1N HCl, water, brine, and dried over $Na_2SO_4$. After filtration, the filtrate was concentrated to yield 300 mg of crude material. The residue was stirred with a solution of MeOH (2 mL) in 4 N HCl-dioxane solution for 2 h to form the methyl ester. The volatiles were removed in-vacuo to yield 268 mg of the desired product. LC-MS: 253.2 (M+H)+.

Example 27

2-(trans-4-Hydroxycyclohexyl)-7-[5-(trifluoromethyl)pyridin-2-yl]-2,7-diazaspiro[4.5]decan-1-one

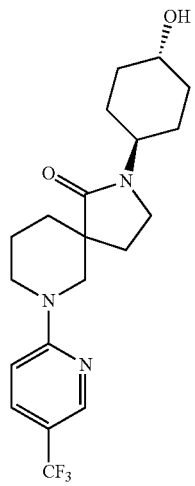 [SMILES: O=C1N([C@H]2CC[C@H](O)CC2)CCC12CCCN(c1ccc(C(F)(F)F)cn1)C2]

This compound was prepared by using procedures that were analogous to those described for the synthesis of example 1, steps 1-5, and by the following microwave mediated amine/aryl coupling procedure:

A mixture of 2-(trans-4-hydroxycyclohexyl)-2,7-diazaspiro[4.5]decan-1-one hydrochloride (5 mg, 0.00002 mol), 2-chloro-5-(trifluoromethyl)pyridine (6 mg, 0.00003 mol), and triethylamine (20 µL, 0.0001 mol) in N-methylpyrrolidinone (800 µL, 0.008 mol) was microwave irradiated at 180° C. for 10 min. After cooling, it was purified by prep.-HPLC to afford 1.7 mg of the desired product. LC-MS: 398.3 (M+H)+.

Example 28

6-[2-(trans-4-Hydroxycyclohexyl)-1-oxo-2,7-diazaspiro[4.5]dec-7-yl]nicotinonitrile

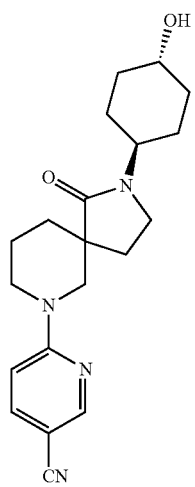 [SMILES: N#Cc1ccc(N2CCCC3(CCN([C@H]4CC[C@H](O)CC4)C3=O)C2)nc1]

This compound was prepared by using procedures analogous to those described for the synthesis of example 27. LC-MS: 355.3 (M+H)+.

Example 29

2-(trans-4-Hydroxycyclohexyl)-7-(6-methoxypyridin-2-yl)-2,7-diazaspiro[4.5]decan-1-one

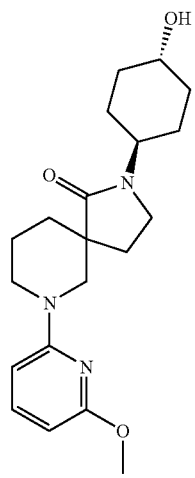 [SMILES: COc1cccc(N2CCCC3(CCN([C@H]4CC[C@H](O)CC4)C3=O)C2)n1]

This compound was prepared by using procedures that were analogous to those described for the synthesis of example 1, steps 1-5, and by the following microwave mediated amine/aryl coupling procedure:

A mixture of 2-(trans-4-hydroxycyclohexyl)-2,7-diazaspiro[4.5]decan-1-one hydrochloride (35 mg, 0.00012 mol), 2-bromo-6-methoxypyridine (34 mg, 0.00018 mol), triethylamine (200 µL, 0.001 mol), and copper(I) iodide (28 mg, 0.00014 mol) in N-methylpyrrolidinone (1.0 mL, 0.010 mol) was microwave irradiated at 180° C. for 20 min. After allowing the reaction mixture to cool to rt the crude mixture was purified by prep.-HPLC to afford 8.3 mg of the desired product. LC-MS: 360.3 (M+H)+.

Example 30

2-(trans-4-Hydroxycyclohexyl)-7-(6-methylpyridin-2-yl)-2,7-diazaspiro[4.5]decan-1-one

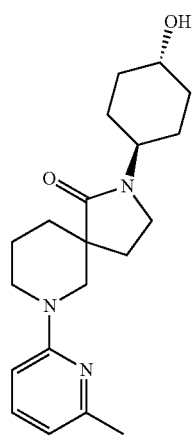 [SMILES: Cc1cccc(N2CCCC3(CCN([C@H]4CC[C@H](O)CC4)C3=O)C2)n1]

This compound was prepared by using procedures analogous to those described for the synthesis of example 29. LC-MS: 344.3 (M+H)+.

Example 31

2-(trans-4-Hydroxycyclohexyl)-7-(5-methylpyridin-2-yl)-2,7-diazaspiro[4.5]decan-1-one

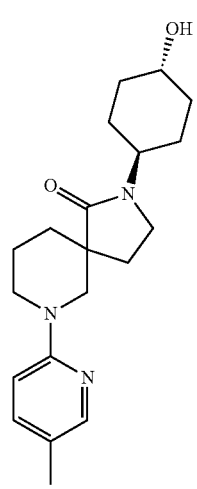 [SMILES: Cc1ccc(N2CCCC3(CCN([C@H]4CC[C@H](O)CC4)C3=O)C2)nc1]

This compound was prepared by using procedures analogous to those described for the synthesis of example 29. LC-MS: 344.3 (M+H)+.

Example 32

7-(5-Fluoropyridin-2-yl)-2-(trans-4-hydroxycyclohexyl)-2,7-diazaspiro[4.5]decan-1-one

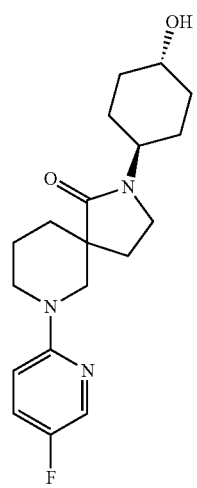 [SMILES: O=C1N([C@H]2CC[C@H](O)CC2)CCC12CCCN(c1ccc(F)cn1)C2]

This compound was prepared by using procedures analogous to those described for the synthesis of example 29. LC-MS: 348.3 (M+H)+.

Example 33

2-(trans-4-Hydroxycyclohexyl)-7-[6-(trifluoromethyl)pyridin-2-yl]-2,7-diazaspiro[4.5]decan-1-one

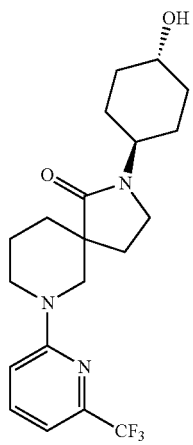 [SMILES: O=C1N([C@H]2CC[C@H](O)CC2)CCC12CCCN(c1cccc(C(F)(F)F)n1)C2]

This compound was prepared by using procedures analogous to those described for the synthesis of example 29. LC-MS: 398.3 (M+H)+.

Example 34

(5S)-2-(trans-4-Hydroxycyclohexyl)-7-[5-(trifluoromethyl)pyridin-2-yl]-2,7-diazaspiro[4.5]decan-1-one

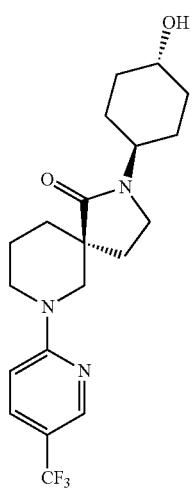 [SMILES: O=C1N([C@H]2CC[C@H](O)CC2)CC[C@]12CCCN(c1ccc(C(F)(F)F)cn1)C2]

This compound was prepared by chiral separation of example 27. Prep Chiral LC conditions: Column: ChiralPak IA, 20×250 mm, 5 µm (Chiral Technologies; Detection: 220 nm; Retention time: t=11.25 min for peak 1; t=19.21 min for peak 2). Example 34 corresponds to peak 2. LC-MS: 398.3 (M+H)+.

Example 35

(5R)-2-(trans-4-Hydroxycyclohexyl)-7-[5-(trifluoromethyl)pyridin-2-yl]-2,7-diazaspiro[4.5]decan-1-one

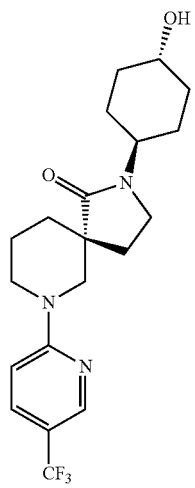 [SMILES: O=C1N([C@H]2CC[C@H](O)CC2)CC[C@@]12CCCN(c1ccc(C(F)(F)F)cn1)C2]

This compound was prepared by chiral separation of example 34. This compound corresponded to peak 1 of the chiral column. LC-MS: 398.3 (M+H)+.

Example 36

7-(6-Fluoropyridin-2-yl)-2-(trans-4-hydroxycyclohexyl)-2,7-diazaspiro[4.5]decan-1-one

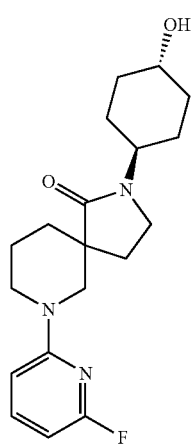 [SMILES: O=C1N([C@H]2CC[C@H](O)CC2)CCC12CCCN(c1cccc(F)n1)C2]

This compound was prepared by using procedures analogous to those described for the synthesis of example 29. LC-MS: 348.3 (M+H)+.

Example 37

2-(trans-4-Hydroxycyclohexyl)-7-(3-methylpyridin-2-yl)-2,7-diazaspiro[4.5]decan-1-one

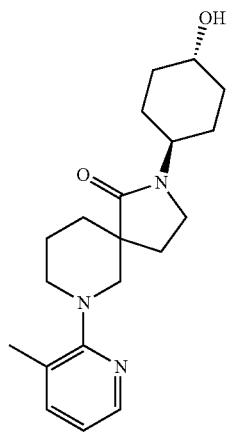 [SMILES: Cc1cccnc1N1CCCC2(CCN([C@H]3CC[C@H](O)CC3)C2=O)C1]

This compound was prepared by using procedures analogous to those described for the synthesis of example 29. LC-MS: 344.2 (M+H)+.

Example 38

2-(trans-4-Hydroxycyclohexyl)-7-(4-methoxypyridin-2-yl)-2,7-diazaspiro[4.5]decan-1-one

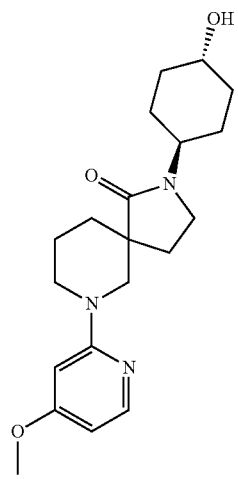 [SMILES: COc1ccnc(N2CCCC3(CCN([C@H]4CC[C@H](O)CC4)C3=O)C2)c1]

This compound was prepared by using procedures analogous to those described for the synthesis of example 29. LC-MS: 360.3 (M+H)+.

Example 39

2-(trans-4-Hydroxycyclohexyl)-7-pyridin-2-yl-2,7-diazaspiro[4.5]decan-1-one

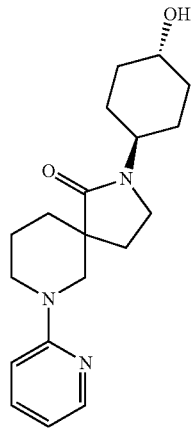 [SMILES: O=C1N([C@H]2CC[C@H](O)CC2)CCC12CCCN(c1ccccn1)C2]

This compound was prepared by using procedures analogous to those described for the synthesis of example 29. LC-MS: 330.3 (M+H)+.

Example 40

(5R)-2-Cyclohexyl-7-phenyl-2,7-diazaspiro[4.5]decan-1-one

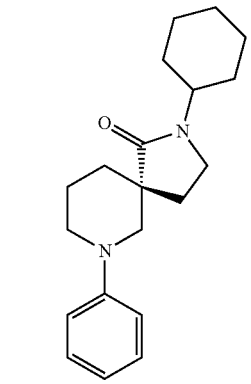 [SMILES: O=C1N(C2CCCCC2)CC[C@@]12CCCN(c1ccccc1)C2]

This compound was prepared by using procedures analogous to those described for the synthesis of example 17 followed by separation of the enantiomers using a chiral column. (Prep Chiral LC conditions:Column: ChiralCel OD-H, 20×250 mm, 5 μm (Chiral Technologies, Inc.); Mobile phase: 60% Ethanol/40% Hexanes; Flow rate: 8 mL/min.; Detection: 220 nm; Retention time: t=8.66 min for peak 1; t=11.40 min for peak 2). This compound corresponded to peak 1. LC-MS: 313.3 (M+H)+.

Example 41

(5S)-2-Cyclohexyl-7-phenyl-2,7-diazaspiro[4.5]decan-1-one

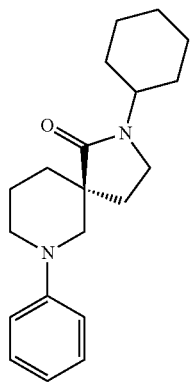 [SMILES: O=C1N(C2CCCCC2)CC[C@]12CCCN(c1ccccc1)C2]

This compound was prepared by using procedures analogous to those described for the synthesis of example 40. This compound corresponded to peak 2 of the chiral column. LC-MS: 313.3 (M+H)$^+$.

Example 42

7-[3-Chloro-5-(trifluoromethyl)pyridin-2-yl]-2-(trans-4-hydroxycyclohexyl)-2,7-diazaspiro[4.5]decan-1-one

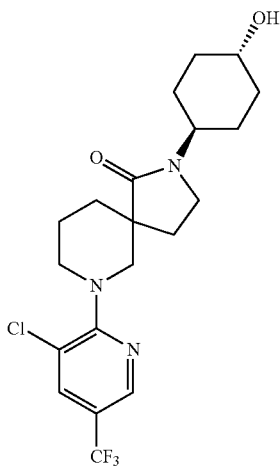 [SMILES: O=C1N([C@H]2CC[C@H](O)CC2)CCC12CCCN(c1ncc(C(F)(F)F)cc1Cl)C2]

This compound was prepared by using procedures analogous to those described for the synthesis of example 29. LC-MS: 432.2 (M+H)$^+$.

Example 43

4-[2-(trans-4-Hydroxycyclohexyl)-1-oxo-2,7-diazaspiro[4.5]dec-7-yl]benzonitrile

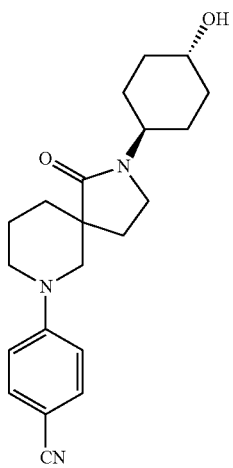

This compound was prepared by using procedures analogous to those described for the synthesis of example 17, with the exception that NaO-(t-Bu) was replaced by K$_2$CO$_3$. LC-MS: 354.2 (M+H)$^+$.

Example 44

2-(trans-4-Hydroxycyclohexyl)-7-[4-(trifluoromethyl)phenyl]-2,7-diazaspiro[4.5]decan-1-one

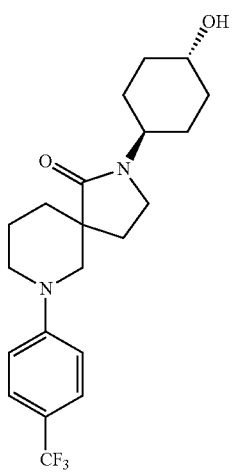 [SMILES: O=C1N([C@H]2CC[C@H](O)CC2)CCC12CCCN(c1ccc(C(F)(F)F)cc1)C2]

This compound was prepared by using procedures that were analogous to those described for the synthesis of example 1, steps 1-5, and by the following microwave mediated amine/aryl coupling procedure:

A mixture of 2-(trans-4-hydroxycyclohexyl)-2,7-diazaspiro[4.5]decan-1-one hydrochloride (25 mg, 0.000086 mol), 1-bromo-4-(trifluoromethyl)benzene (29 mg, 0.00013 mol), sodium tert-butoxide (28 mg, 0.00029 mol), palladium acetate (0.6 mg, 0.000002 mol), and 2-(di-tert-butylphosphino)biphenyl (0.8 mg, 0.000002 mol) in 1,4-dioxane (1.0 mL, 0.013 mol) was heated at 100° C. with stirring for 16 h. LCMS indicated that most of the desired product was oxidized to the ketone so the crude reaction mixture was cooled to −10° C. and 1.0 M of L-Selectride® in tetrahydrofuran (0.2 mL) was added and the mixture was stirred for 20 min. LCMS indicated that the ketone was converted to the alcohol. The crude mixture was purified by prep.-HPLC to afford 5.2 mg of the desired product. LC-MS: 397.2 (M+H)+.

Example 45

3-Fluoro-4-[2-(trans-4-hydroxycyclohexyl)-1-oxo-2,7-diazaspiro[4.5]dec-7-yl]benzonitrile

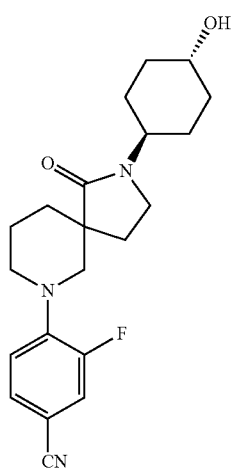 [SMILES: N#Cc1ccc(N2CCCC3(CCN([C@H]4CC[C@H](O)CC4)C3=O)C2)c(F)c1]

This compound was prepared by using procedures analogous to those described for the synthesis of example 43. LC-MS: 372.2 (M+H)+.

Example 46

4-(2-Cyclohexyl-1-oxo-2,7-diazaspiro[4.5]dec-7-yl)benzonitrile

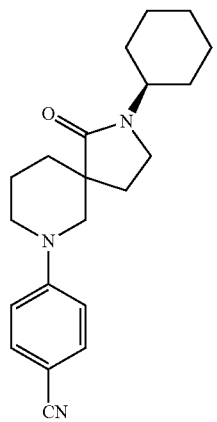

This compound was prepared by using procedures analogous to those described for the synthesis of example 43. LC-MS: 338.3 (M+H)+.

Example 47

4-(2-Cyclohexyl-1-oxo-2,7-diazaspiro[4.5]dec-7-yl)-3-fluorobenzonitrile

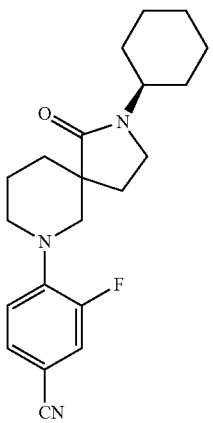

This compound was prepared by using procedures analogous to those described for the synthesis of example 43. LC-MS: 356.3 (M+H)+.

Example 48

2-(trans-4-Hydroxycyclohexyl)-7-(piperidin-1-ylcarbonyl)-2,7-diazaspiro[4.5]decan-1-one

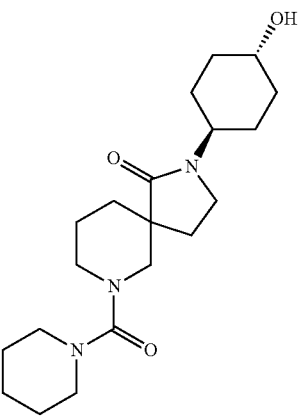 [SMILES: O=C(N1CCCCC1)N1CCCC2(CCN([C@H]3CC[C@H](O)CC3)C2=O)C1]

This compound was prepared by using procedures that were analogous to those described for the synthesis of example 1, steps 1-5, and by the following urea coupling procedure.

Step 1. 4-nitrophenyl 2-(trans-4-hydroxycyclohexyl)-1-oxo-2,7-diazaspiro[4.5]decane-7-carboxylate A mixture of 2-(trans-4-hydroxycyclohexyl)-2,7-diazaspiro[4.5]decan-1-one hydrochloride (0.30 g, 0.0010 mol), p-nitrophenyl chloroformate (0.25 g, 0.0012 mol), and N,N-diisopropylethylamine (540 μL, 0.0031 mol) in methylene chloride (4 mL, 0.06 mol) was stirred at rt for 16 h. The crude reaction mixture was purified by flash column chromatography to afford 120 mg of the desired product.

Step 2. 2-(trans-4-hydroxycyclohexyl)-7-(piperidin-1-ylcarbonyl)-2,7-diazaspiro[4.5]decan-1-one To a solution of 4-nitrophenyl 2-(trans-4-hydroxycyclohexyl)-1-oxo-2,7-diazaspiro[4.5]decane-7-carboxylate (30 mg, 0.00007 mol) in tetrahydrofuran (0.5 mL, 0.006 mol) was added N,N-diisopropylethylamine (25.0 µL, 0.000144 mol) and piperidine (10 µL, 0.0001 mol). After stirring at rt for 16 h, the crude reaction mixture was purified by prep.-HPLC to afford the desired product. LC-MS: 364.3 (M+H)⁺.

Example 49

2-(trans-4-Hydroxycyclohexyl)-7-(pyrrolidin-1-ylcarbonyl)-2,7-diazaspiro[4.5]decan-1-one

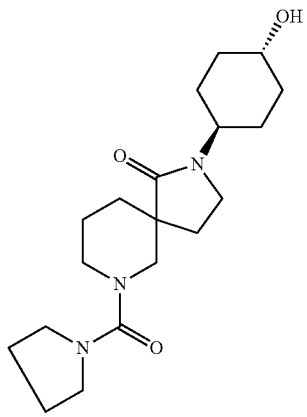 [SMILES: O=C(N1CCCC1)N1CCCC2(CCN([C@H]3CC[C@H](O)CC3)C2=O)C1]

This compound was prepared by using procedures analogous to those described for the synthesis of example 48. LC-MS: 350.3 (M+H)⁺.

Example 50

2-(trans-4-Hydroxycyclohexyl)-7-[(4-phenyl-3,6-dihydropyridin-1(2H)-yl)carbonyl]-2,7-diazaspiro[4.5]decan-1-one

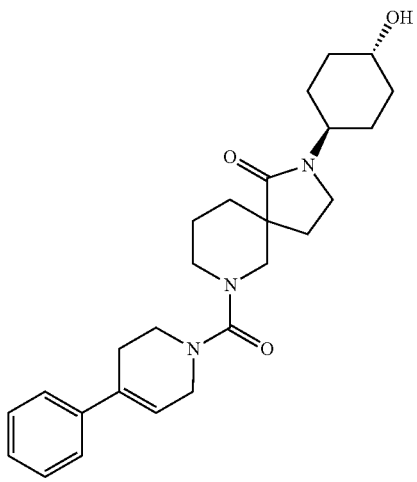 [SMILES: O=C(N1CC=C(c2ccccc2)CC1)N1CCCC2(CCN([C@H]3CC[C@H](O)CC3)C2=O)C1]

This compound was prepared by using procedures analogous to those described for the synthesis of example 48. LC-MS: 438.3 (M+H)⁺.

Example 51

2-(trans-4-Hydroxycyclohexyl)-7-[(4-phenylpiperidin-1-yl)carbonyl]-2,7-diazaspiro[4.5]decan-1-one

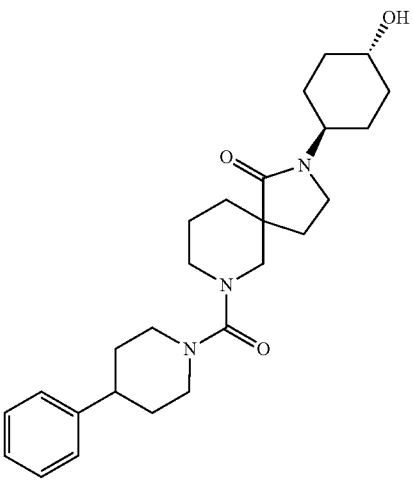 [SMILES: O=C(N1CCC(c2ccccc2)CC1)N1CCCC2(CCN([C@H]3CC[C@H](O)CC3)C2=O)C1]

This compound was prepared by using procedures analogous to those described for the synthesis of example 48. LC-MS: 440.3 (M+H)⁺.

Example 52

2-(trans-4-Hydroxycyclohexyl)-7-[(4-phenylpiperazin-1-yl)carbonyl]-2,7-diazaspiro[4.5]decan-1-one

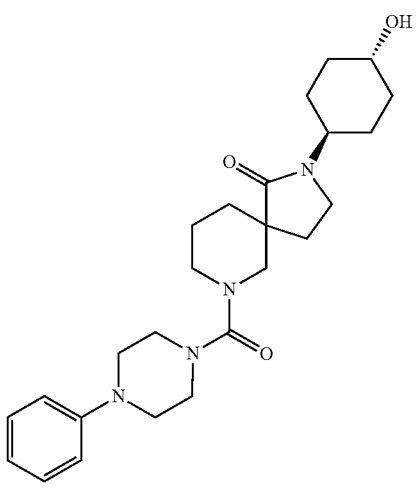 [SMILES: O=C(N1CCN(c2ccccc2)CC1)N1CCCC2(CCN([C@H]3CC[C@H](O)CC3)C2=O)C1]

This compound was prepared by using procedures analogous to those described for the synthesis of example 48. LC-MS: 441.2 (M+H)⁺.

Example 53

7-{[4-(2-Fluorophenyl)piperazin-1-yl]carbonyl}-2-(trans-4-hydroxycyclohexyl)-2,7-diazaspiro[4.5]decan-1-one

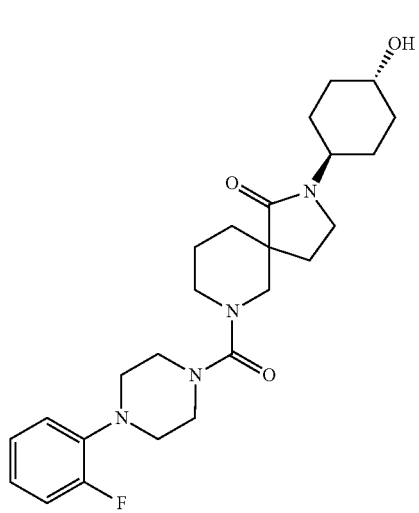 [SMILES: O=C(N1CCN(c2ccccc2F)CC1)N1CCCC2(CCN([C@H]3CC[C@H](O)CC3)C2=O)C1]

This compound was prepared by using procedures analogous to those described for the synthesis of example 48. LC-MS: 459.2 (M+H)+.

Example 54

2-(trans-4-Hydroxycyclohexyl)-7-({4-[2-(trifluoromethyl)phenyl]piperazin-1-yl}carbonyl)-2,7-diazaspiro[4.5]decan-1-one

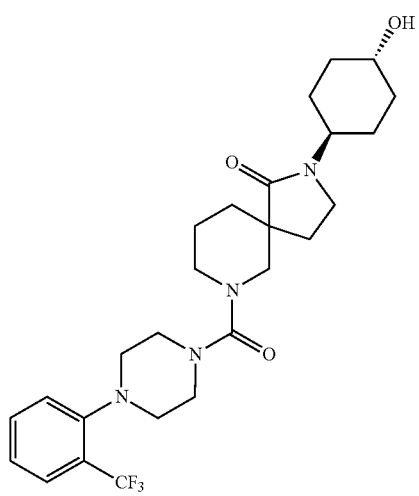 [SMILES: O=C(N1CCN(c2ccccc2C(F)(F)F)CC1)N1CCCC2(CCN([C@H]3CC[C@H](O)CC3)C2=O)C1]

This compound was prepared by using procedures analogous to those described for the synthesis of example 48. LC-MS: 509.2 (M+H)+.

Example 55

2-Cyclohexyl-7-isonicotinoyl-2,7-diazaspiro[4.5]decan-1-one

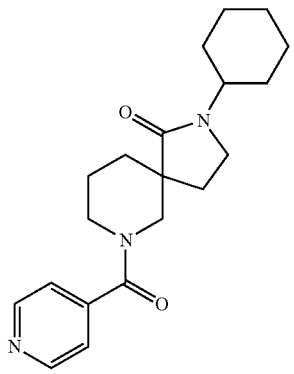 [SMILES: O=C(c1ccncc1)N1CCCC2(CCN(C3CCCCC3)C2=O)C1]

This compound was prepared by using procedures that were analogous to those described for the synthesis of example 1, steps 1-5, followed by the following acylation procedure:

A mixture of 2-cyclohexyl-2,7-diazaspiro[4.5]decan-1-one hydrochloride (15 mg, 0.000055 mol), isonicotinoyl chloride hydrochloride (12 mg, 0.000066 mol), and triethylamine (27 µL, 0.00019 mol) in acetonitrile (0.5 mL, 0.01 mol) was stirred at rt for 2 h. The crude reaction mixture was purified by prep.-HPLC to afford 18 mg of the desired product. LC-MS: 342.3 (M+H)+.

Example 56

7-Benzoyl-2-cyclohexyl-2,7-diazaspiro[4.5]decan-1-one

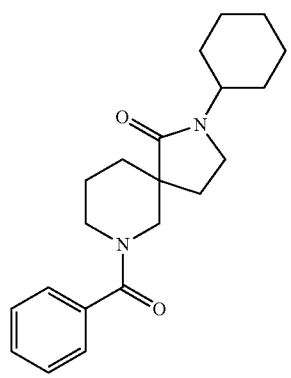 [SMILES: O=C(c1ccccc1)N1CCCC2(CCN(C3CCCCC3)C2=O)C1]

This compound was prepared by using procedures analogous to those described for the synthesis of example 55. LC-MS: 341.3 (M+H)+.

Example 57

2-Cyclohexyl-7-(pyridin-3-ylcarbonyl)-2,7-diaza-spiro[4.5]decan-1-one

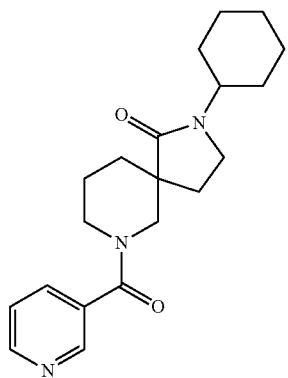 [SMILES: O=C(c1cccnc1)N1CCCC2(CCN(C3CCCCC3)C2=O)C1]

This compound was prepared by using procedures analogous to those described for the synthesis of example 55. LC-MS: 342.3 (M+H)+.

Example 59

7-Benzoyl-2-(trans-4-hydroxycyclohexyl)-2,7-diaza-spiro[4.5]decan-1-one

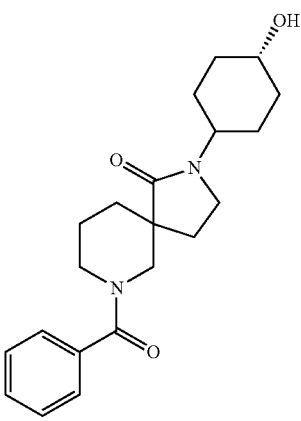

This compound was prepared by using procedures analogous to those described for the synthesis of example 55. LC-MS: 357.2 (M+H)+.

Example 61

Isopropyl {4-[2-(trans-4-hydroxycyclohexyl)-1-oxo-2,7-diazaspiro[4.5]dec-7-yl]phenyl}carbamate

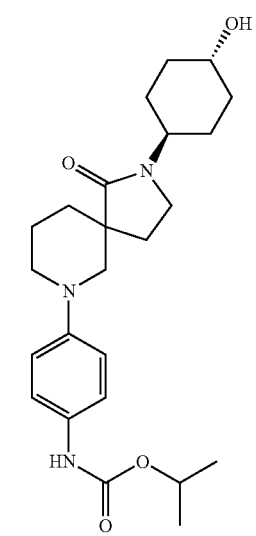 [SMILES: CC(C)OC(=O)Nc1ccc(N2CCCC3(CCN([C@H]4CC[C@H](O)CC4)C3=O)C2)cc1]

Step 1. 7-(4-Aminophenyl)-2-(trans-4-hydroxycyclohexyl)-2,7-diazaspiro[4.5]decan-1-one A mixture of 2-(trans-4-hydroxycyclohexyl)-7-(4-nitrophenyl)-2,7-diazaspiro[4.5]decan-1-one (0.13 g, 0.00028 mol, prepared by using a procedure that was analogous to that described for the synthesis of example 43), 10% Pd/C (activated) in methanol (5 mL, 0.1 mol) was stirred under a $H_2$ atmosphere (balloon) for 1.5 hour. The catalyst was filtered and the filtrate was concentrated in-vacuo to afford the desired product in quantitative yield. LC-MS: 344.3 (M+H)+.

Step 2. isopropyl {4-[2-(trans-4-hydroxycyclohexyl)-1-oxo-2,7-diazaspiro[4.5]dec-7-yl]phenyl}carbamate A mixture of 7-(4-aminophenyl)-2-(trans-4-hydroxycyclohexyl)-2,7-diazaspiro[4.5]decan-1-one (20 mg, 0.00006 mol), isopropyl chloroformate (11 mg, 0.000087 mol), and triethylamine (20 µL, 0.0002 mol) in methylene chloride (300 µL, 0.005 mol) was stirred at rt for 2 h. The crude reaction mixture was purified by prep.-HPLC to afford 17.4 mg of the desired product. LC-MS: 430.3 (M+H)+.

Example 62

Prop-2-yn-1-yl {4-[2-(trans-4-hydroxycyclohexyl)-1-oxo-2,7-diazaspiro[4.5]dec-7-yl]phenyl}carbamate

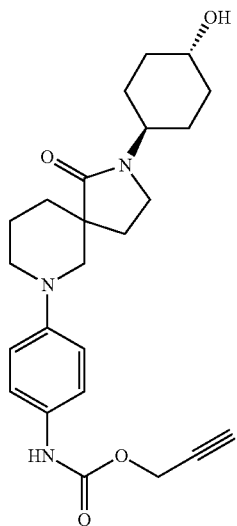 [SMILES: C#CCOC(=O)Nc1ccc(N2CCCC3(CCN([C@H]4CC[C@H](O)CC4)C3=O)C2)cc1]

This compound was prepared by using procedures analogous to those described for the synthesis of example 61. LC-MS: 426.3 (M+H)$^+$.

Example 63

Methyl {4-[2-(trans-4-hydroxycyclohexyl)-1-oxo-2,7-diazaspiro[4.5]dec-7-yl]phenyl}carbamate

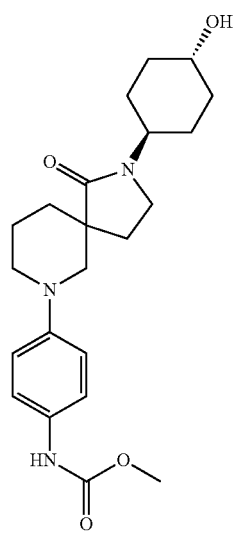 [SMILES: COC(=O)Nc1ccc(N2CCCC3(CCN([C@H]4CC[C@H](O)CC4)C3=O)C2)cc1]

This compound was prepared by using procedures analogous to those described for the synthesis of example 61. LC-MS: 402.2 (M+H)$^+$.

Example 64

N-{4-[2-(trans-4-Hydroxycyclohexyl)-1-oxo-2,7-diazaspiro[4.5]dec-7-yl]phenyl}acetamide

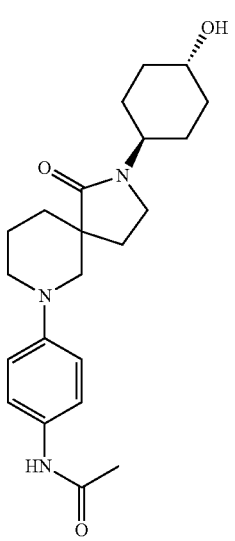 [SMILES: CC(=O)Nc1ccc(N2CCCC3(CCN([C@H]4CC[C@H](O)CC4)C3=O)C2)cc1]

This compound was prepared by using procedures analogous to those described for the synthesis of example 61. LC-MS: 386.3 (M+H)$^+$.

Example 65

N-{4-[2-(trans-4-Hydroxycyclohexyl)-1-oxo-2,7-diazaspiro[4.5]dec-7-yl]-phenyl}-cyclopropanecarboxamide

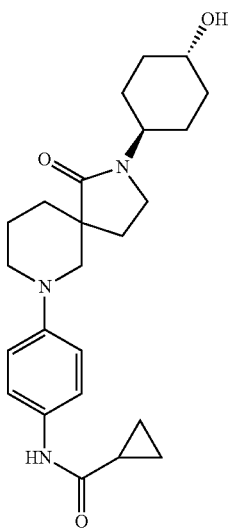 [SMILES: O=C(Nc1ccc(N2CCCC3(CCN([C@H]4CC[C@H](O)CC4)C3=O)C2)cc1)C1CC1]

This compound was prepared by using procedures analogous to those described for the synthesis of example 61. LC-MS: 412.3 (M+H)$^+$.

Example 66

Isopropyl {3-fluoro-4-[2-(trans-4-hydroxycyclohexyl)-1-oxo-2,7-diazaspiro[4.5]dec-7-yl]phenyl}carbamate

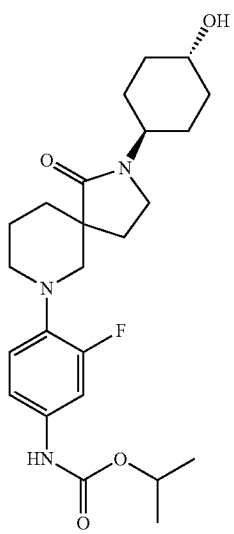 [SMILES: CC(C)OC(=O)Nc1ccc(N2CCCC3(CCN([C@H]4CC[C@H](O)CC4)C3=O)C2)c(F)c1]

This compound was prepared by using procedures analogous to those described for the synthesis of example 61. LC-MS: 448.3 (M+H)+.

Example 67

Prop-2-yn-1-yl {3-fluoro-4-[2-(trans-4-hydroxycyclohexyl)-1-oxo-2,7-diazaspiro[4.5]dec-7-yl]phenyl}carbamate

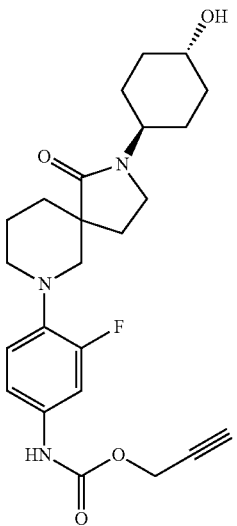 [SMILES: C#CCOC(=O)Nc1ccc(N2CCCC3(CCN([C@H]4CC[C@H](O)CC4)C3=O)C2)c(F)c1]

This compound was prepared by using procedures analogous to those described for the synthesis of example 61. LC-MS: 444.3 (M+H)+.

Example 68

Methyl {3-fluoro-4-[2-(trans-4-hydroxycyclohexyl)-1-oxo-2,7-diazaspiro[4.5]dec-7-yl]phenyl}carbamate

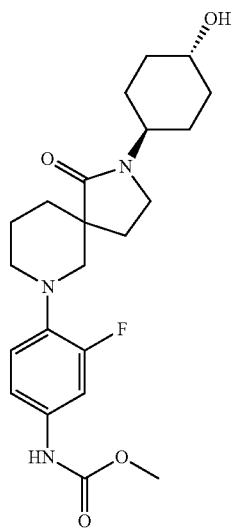 [SMILES: COC(=O)Nc1ccc(N2CCCC3(CCN([C@H]4CC[C@H](O)CC4)C3=O)C2)c(F)c1]

This compound was prepared by using procedures analogous to those described for the synthesis of example 61. LC-MS: 420.3 (M+H)+.

Example 69

N-{3-Fluoro-4-[2-(trans-4-hydroxycyclohexyl)-1-oxo-2,7-diazaspiro[4.5]dec-7-yl]phenyl}cyclopropanecarboxamide

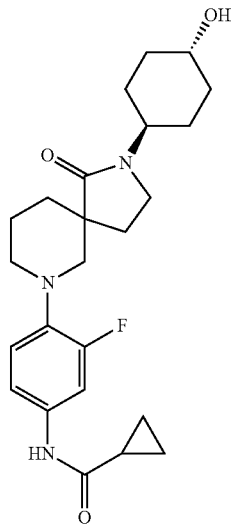 [SMILES: O=C(Nc1ccc(N2CCCC3(CCN([C@H]4CC[C@H](O)CC4)C3=O)C2)c(F)c1)C1CC1]

This compound was prepared by using procedures analogous to those described for the synthesis of example 61. LC-MS: 430.3 (M+H)+.

Example 70

7-(4-Chloropyrimidin-2-yl)-2-(trans-4-hydroxycyclohexyl)-2,7-diazaspiro[4.5]decan-1-one

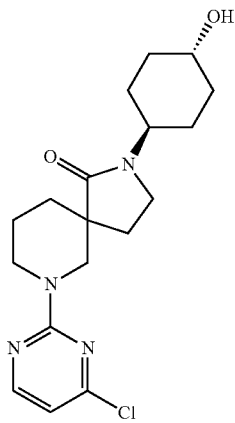 [SMILES: O=C1N([C@H]2CC[C@H](O)CC2)CCC12CCCN(c1nccc(Cl)n1)C2]

This compound was prepared by using procedures analogous to those described for the synthesis of example 29. LC-MS: 365.3 (M+H)$^+$.

Example 71

2-Cyclohexyl-7-[5-(trifluoromethyl)pyridin-2-yl]-2,7-diazaspiro[4.5]decan-1-one

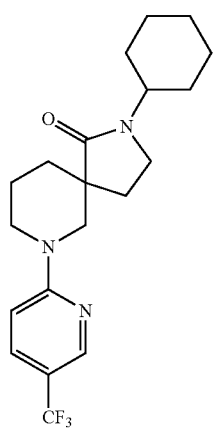 [SMILES: O=C1N(C2CCCCC2)CCC12CCCN(c1ccc(C(F)(F)F)cn1)C2]

This compound was prepared by using procedures analogous to those described for the synthesis of example 29. LC-MS: 382.2 (M+H)$^+$.

Example 72

2-Cyclohexyl-7-pyridin-2-yl-2,7-diazaspiro[4.5]decan-1-one

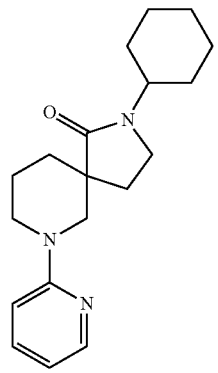

This compound was prepared by using procedures analogous to those described for the synthesis of example 29. LC-MS: 314.3 (M+H)$^+$.

Example 73

7-[3-Chloro-5-(trifluoromethyl)pyridin-2-yl]-2-cyclohexyl-2,7-diazaspiro[4.5]decan-1-one This compound was prepared by using procedures analogous to those described for the synthesis of example 29. LC-MS: 416.2 (M+H)$^+$.

Example 74

2-Cyclohexyl-7-(piperidin-1-ylcarbonyl)-2,7-diaza-spiro[4.5]decan-1-one

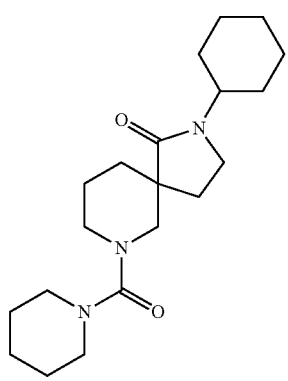 [SMILES: O=C(N1CCCCC1)N1CCCC2(CCN(C3CCCCC3)C2=O)C1]

This compound was prepared by using procedures that were analogous to those described for the synthesis of example 1, steps 1-5, and by the following urea coupling procedure:

To a solution of 2-cyclohexyl-2,7-diazaspiro[4.5]decan-1-one hydrochloride (20 mg, 0.00007 mol) in methylene chloride (0.5 mL, 0.008 mol) was added N,N-diisopropylethylamine (14.0 μL, 0.0000806 mol) and the solution was stirred at rt for 5 min. prior to the addition of N,N-carbonyldiimidazole (24 mg, 0.00015 mol). After stirring the reaction mixture at rt for 3 h, piperidine (6.2 mg, 0.00007 mol) was added and stirring was continued for 12 h. To drive the reaction to completion the mixture was heated at 170° C. under microwave irradiation for 1 h. The crude mixture was purified by prep.-HPLC to afford the desired product. LC-MS: 348.2 (M+H)$^+$.

Example 75

2-Cyclohexyl-7-(pyrrolidin-1-ylcarbonyl)-2,7-diaza-spiro[4.5]decan-1-one

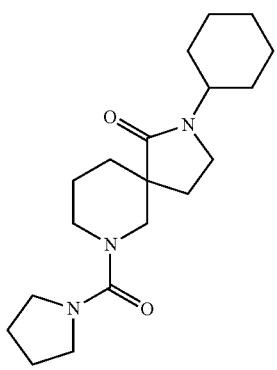 [SMILES: O=C(N1CCCC1)N1CCCC2(CCN(C3CCCCC3)C2=O)C1]

This compound was prepared by using procedures analogous to those described for the synthesis of example 74. LC-MS: 334.2 (M+H)$^+$.

Example 76

2-Cyclohexyl-7-[(4-phenyl-3,6-dihydropyridin-1(2H)-yl)carbonyl]-2,7-diazaspiro[4.5]decan-1-one

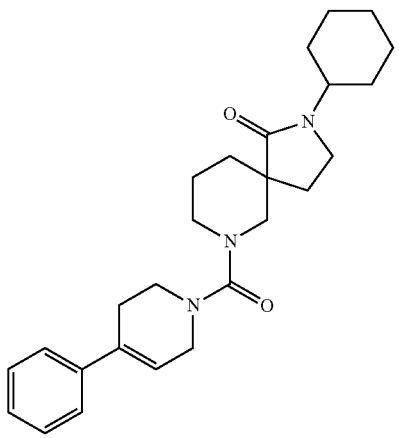 [SMILES: O=C(N1CC=C(c2ccccc2)CC1)N1CCCC2(CCN(C3CCCCC3)C2=O)C1]

This compound was prepared by using procedures analogous to those described for the synthesis of example 74. LC-MS: 422.2 (M+H)$^+$.

Example 77

2-Cyclohexyl-7-[(4-phenylpiperidin-1-yl)carbonyl]-2,7-diazaspiro[4.5]decan-1-one

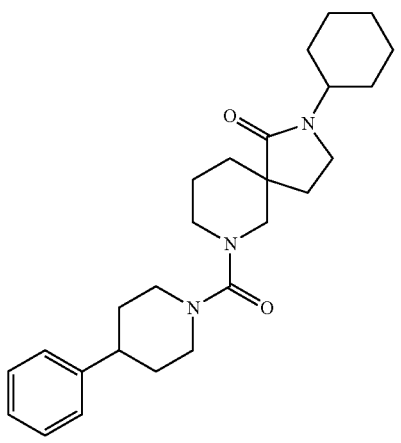 [SMILES: O=C(N1CCC(c2ccccc2)CC1)N1CCCC2(CCN(C3CCCCC3)C2=O)C1]

This compound was prepared by using procedures analogous to those described for the synthesis of example 74. LC-MS: 424.2 (M+H)$^+$.

Example 78

2-Cyclohexyl-7-[(4-phenylpiperazin-1-yl)carbonyl]-2,7-diazaspiro[4.5]decan-1-one

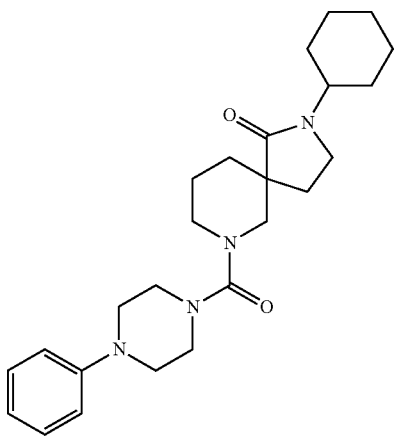 [SMILES: O=C(N1CCN(c2ccccc2)CC1)N1CCCC2(CCN(C3CCCCC3)C2=O)C1]

This compound was prepared by using procedures analogous to those described for the synthesis of example 74. LC-MS: 425.2 (M+H)+.

Example 79

2-Cyclohexyl-7-{[4-(2-fluorophenyl)piperazin-1-yl]carbonyl}-2,7-diazaspiro[4.5]decan-1-one

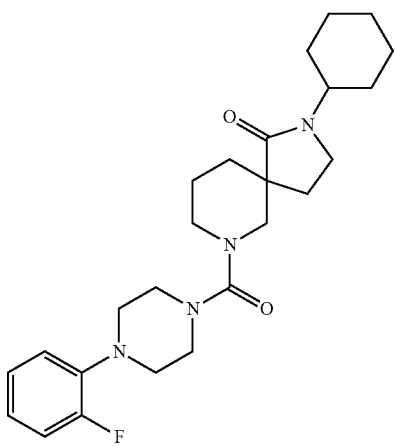 [SMILES: O=C(N1CCN(c2ccccc2F)CC1)N1CCCC2(CCN(C3CCCCC3)C2=O)C1]

This compound was prepared by using procedures analogous to those described for the synthesis of example 74. LC-MS: 443.2 (M+H)+.

Example 80

2-Cyclohexyl-7-({4-[2-(trifluoromethyl)phenyl]piperazin-1-yl}carbonyl)-2,7-diazaspiro[4.5]decan-1-one

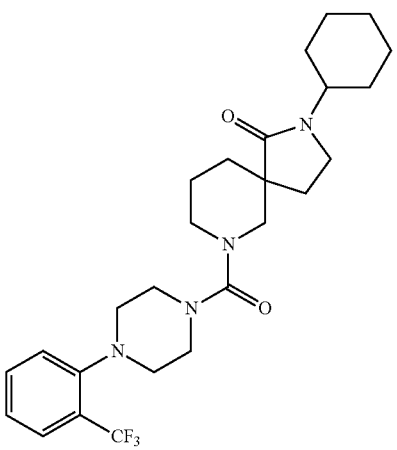 [SMILES: O=C(N1CCN(c2ccccc2C(F)(F)F)CC1)N1CCCC2(CCN(C3CCCCC3)C2=O)C1]

This compound was prepared by using procedures analogous to those described for the synthesis of example 74. LC-MS: 493.2 (M+H)+.

Example 83

2-[2-(trans-4-Hydroxycyclohexyl)-1-oxo-2,7-diazaspiro[4.5]dec-7-yl]nicotinonitrile

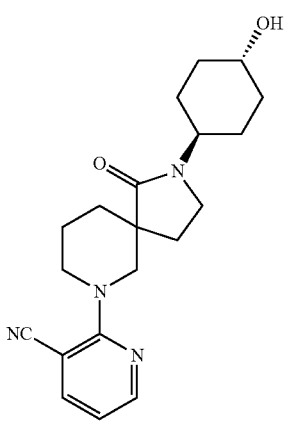 [SMILES: N#Cc1cccnc1N1CCCC2(CCN([C@H]3CC[C@H](O)CC3)C2=O)C1]

This compound was prepared by using procedures analogous to those described for the synthesis of example 27. LC-MS: 355.2 (M+H)+.

Example 84

7-(5-Chloropyridin-2-yl)-2-(trans-4-hydroxycyclohexyl)-2,7-diazaspiro[4.5]decan-1-one

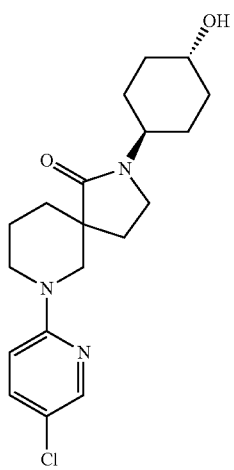 [SMILES: O=C1N([C@H]2CC[C@H](O)CC2)CCC12CCCN(c1ccc(Cl)cn1)C2]

This compound was prepared by using procedures analogous to those described for the synthesis of example 27. LC-MS: 364.2/366.2 (M+H)+.

Example 85

7-(3,5-Dichloropyridin-2-yl)-2-(trans-4-hydroxycyclohexyl)-2,7-diazaspiro[4.5]decan-1-one

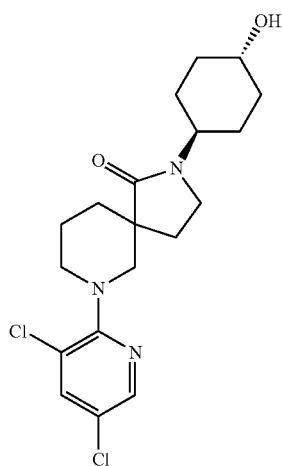 [SMILES: O=C1N([C@H]2CC[C@H](O)CC2)CCC12CCCN(c1ncc(Cl)cc1Cl)C2]

This compound was prepared by using procedures analogous to those described for the synthesis of example 27. LC-MS: 398.2/400.2/402.2 (M+H)+.

Example 86

2-(trans-4-Hydroxycyclohexyl)-7-[4-(trifluoromethyl)pyridin-2-yl]-2,7-diazaspiro[4.5]decan-1-one

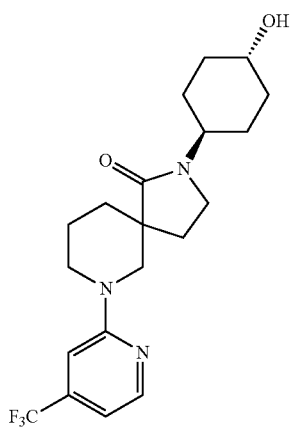 [SMILES: O=C1N([C@H]2CC[C@H](O)CC2)CCC12CCCN(c1cc(C(F)(F)F)ccn1)C2]

This compound was prepared by using procedures analogous to those described for the synthesis of example 27. LC-MS: 398.2 (M+H)+.

Example 87

2-(trans-4-Hydroxycyclohexyl)-7-[6-methyl-4-(trifluoromethyl)pyridin-2-yl]-2,7-diazaspiro[4.5]decan-1-one

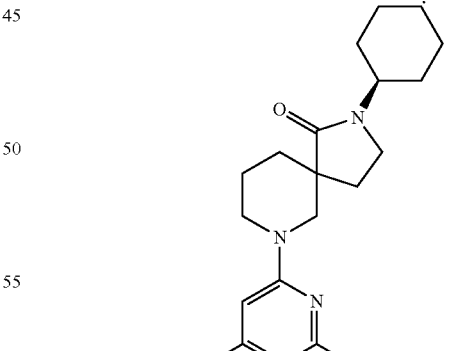

This compound was prepared by using procedures analogous to those described for the synthesis of example 27. LC-MS: 412.3 (M+H)+.

Example 88

Methyl 6-[2-(trans-4-hydroxycyclohexyl)-1-oxo-2,7-diazaspiro[4.5]dec-7-yl]nicotinate

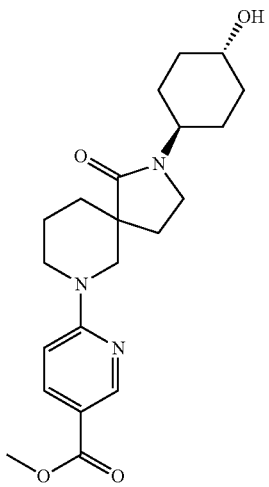 [SMILES: COC(=O)c1ccc(N2CCCC3(CCN([C@H]4CC[C@H](O)CC4)C3=O)C2)nc1]

This compound was prepared by using procedures analogous to those described for the synthesis of example 27. LC-MS: 388.2 (M+H)⁺.

Example 89

2-(trans-4-Hydroxycyclohexyl)-7-isoquinolin-1-yl-2,7-diazaspiro[4.5]decan-1-one

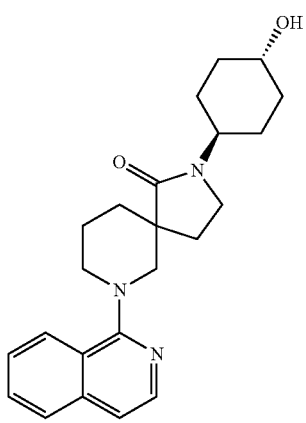 [SMILES: O=C1N([C@H]2CC[C@H](O)CC2)CCC12CCCN(c1nccc3ccccc13)C2]

This compound was prepared by using procedures analogous to those described for the synthesis of example 27. LC-MS: 380.3 (M+H)⁺.

Example 90

2-(trans-4-Hydroxycyclohexyl)-7-quinolin-2-yl-2,7-diazaspiro[4.5]decan-1-one

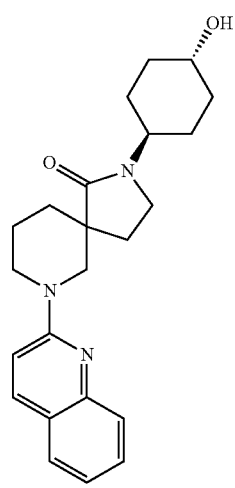 [SMILES: O=C1N([C@H]2CC[C@H](O)CC2)CCC12CCCN(c1ccc3ccccc3n1)C2]

This compound was prepared by using procedures analogous to those described for the synthesis of example 27. LC-MS: 380.2 (M+H)⁺.

Example 91

N-{3-Fluoro-4-[2-(trans-4-hydroxycyclohexyl)-1-oxo-2,7-diazaspiro[4.5]dec-7-yl]phenyl}acetamide

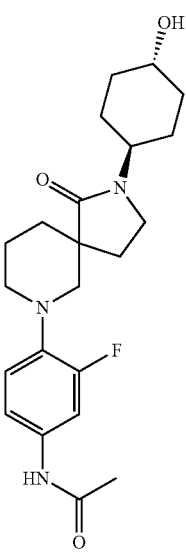 [SMILES: CC(=O)Nc1ccc(N2CCCC3(CCN([C@H]4CC[C@H](O)CC4)C3=O)C2)c(F)c1]

This compound was prepared by using procedures analogous to those described for the synthesis of example 61. LC-MS: 404.3 (M+H)⁺.

Example 92

(5S)-2-(2-Chlorophenyl)-7-(3,5-dichloropyridin-2-yl)-2,7-diazaspiro[4.5]decan-1-one

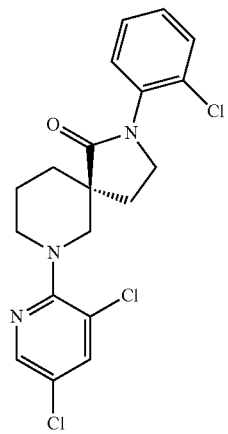 [SMILES: O=C1N(c2ccccc2Cl)CC[C@]12CCCN(c1ncc(Cl)cc1Cl)C2]

Step 1. 1-tert-butyl 3-ethyl 3-(2-chloroethyl)piperidine-1,3-dicarboxylate

Lithium diisopropylamide (1.8 M in THF, 3.9 mL) was slowly added to a solution of 1-tert-butyl 3-ethyl piperidine-1,3-dicarboxylate (1.50 g, 0.00583 mol) in tetrahydrofuran (20 mL, 0.2 mol) at −78° C. and the mixture was stirred for about 1 hour during which the temperature was allowed to rise to about −50° C. 1-Bromo-2-chloro-ethane (0.75 mL, 0.0082 mol) was slowly added to the mixture and then the resulting mixture was allowed to warm to rt (room temperature). After stirring for 2 h, the reaction mixture was quenched with saturated $NH_4Cl$ and extracted with ethyl ether twice. The combined organic layers were dried and concentrated in-vacuo to afford the crude product, which was purified by CombiFlash eluting with hexane/EtOAc (max. EA 20%).

Step 2. tert-butyl (5S)-2-(2-chlorophenyl)-1-oxo-2,7-diazaspiro[4.5]decane-7-carboxylate and tert-butyl (5S)-2-(2-chlorophenyl)-1-oxo-2,7-diazaspiro[4.5]decane-7-carboxylate Lithium hexamethyldisilazide (1.0 M in tetrahydrofuran, 2.5 mL) was slowly added to a solution of ϵ-chloroaniline (0.14 g, 0.0011 mol) in tetrahydrofuran (4.0 mL, 0.049 mol) at −78° C. and stirred for 30 min. To this mixture was added a solution of 1-tert-butyl 3-ethyl 3-(2-chloroethyl)piperidine-1,3-dicarboxylate (0.320 g, 0.00100 mol) in THF (0.5 mL) and the resultant mixture was stirred for additional 18 h. The reaction mixture was quenched by an addition of methanol (2 mL) and the solvent was removed in-vacuo to afford the racemic product, which was purified by CombiFlash (12 g column, eluting with hexane/EtOAc with max. EtOAc 30%) to afford the desired racemate (0.26 g, 72%). LC-MS: 309.1 (M+H−t-Bu (56)).[+] The pure enantiomers were separated by chiral HPLC (Chiralcel OD-H column, 30×250 mm, 5 micron particle size from Chiral Technologies, Inc. Item number 14475; Mobile phase: Isocratic, 30% ethanol, 70% hexanes; Flow Rate: 26 mL/min). The shorter retention time peak was found to be the R-enantiomer and the longer retention time peak was found to be the S-enantiomer (the S-enantiomer was found to be more active).

Step 3. (5S)-2-(2-chlorophenyl)-2,7-diazaspiro[4.5]decan-1-one hydrochloride Hydrogen chloride (4.0 M in 1,4-dioxane, 2.0 mL) was added to a solution of tert-butyl (5S)-2-(2-chlorophenyl)-1-oxo-2,7-diazaspiro[4.5]decane-7-carboxylate (0.103 g, 0.000283 mol) in ethyl acetate (0.5 mL) and the mixture was stirred for 2 h. Then the solvent was removed in-vacuo to afford the desired product. LC-MS: 265.2 (M+H).[+]

Step 4. (5S)-2-(2-chlorophenyl)-7-(3,5-dichloropyridin-2-yl)-2,7-diazaspiro[4.5]decan-1-one A mixture of (5S)-2-(2-chlorophenyl)-2,7-diazaspiro[4.5]decan-1-one hydrochloride (18.2 mg, 0.0000604 mol), 2,3,5-trichloropyridine (16 mg, 0.000091 mol) and triethylamine (0.025 mL, 0.00018 mol) in N,N-dimethylformamide (0.4 mL, 0.005 mol) was irradiated with microwaves to heat the mixture to 180° C. for 20 min. The crude product was purified by prep-HPLC to afford the desired product. LC-MS: 410.1/412.1/414.0 (M+H)[+].

Example 93

2-(2-Chlorophenyl)-7-[5-(trifluoromethyl)pyridin-2-yl]-2,7-diazaspiro[4.5]decan-1-one

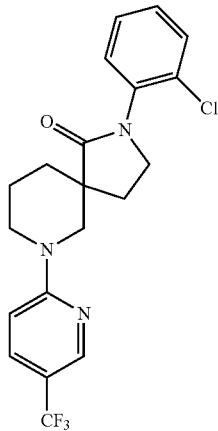 [SMILES: O=C1N(c2ccccc2Cl)CCC12CCCN(c1ccc(C(F)(F)F)cn1)C2]

A mixture of 2-(2-chlorophenyl)-2,7-diazaspiro[4.5]decan-1-one (16.0 mg, 0.0000604 mol, which was prepared by using a procedure that was analogous to that used for the synthesis of example 92, steps 1-4), 2-chloro-5-(trifluoromethyl)pyridine (13 mg, 0.000072 mol) and N,N-diisopropylethylamine (0.032 mL, 0.00018 mol) in N-methylpyrrolidinone (0.4 mL, 0.005 mol) was irradiated with microwaves to heat the reaction mixture to 180° C. for 20 min. The crude product was purified by prep-HPLC to afford the desired product. LC-MS: 410.2/412.2 (M+H)[+].

Example 94

2-(2-Chlorophenyl)-7-(3-chloropyrazin-2-yl)-2,7-diazaspiro[4.5]decan-1-one

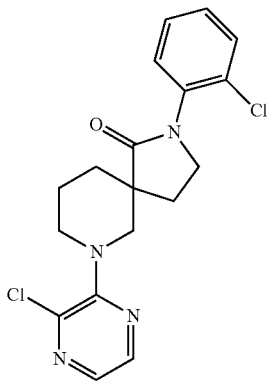 [SMILES: O=C1N(c2ccccc2Cl)CCC12CCCN(c1nccnc1Cl)C2]

This compound was prepared by using procedures analogous to those described for the synthesis of example 93. LC-MS: 377.1/379.1 (M+H)+.

Example 95

2-(2-Chlorophenyl)-7-(3-chloropyridin-2-yl)-2,7-diazaspiro[4.5]decan-1-one

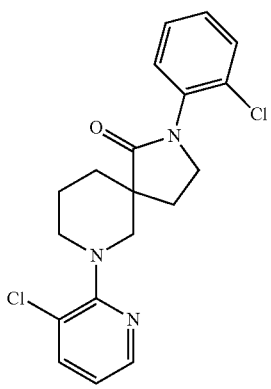 [SMILES: O=C1N(c2ccccc2Cl)CCC12CCCN(c1ncccc1Cl)C2]

This compound was prepared by using procedures analogous to those described for the synthesis of example 93. LC-MS: 376.1/378.1 (M+H)+.

Example 96

2-[(5S)-2-(2-Chlorophenyl)-1-oxo-2,7-diazaspiro[4.5]dec-7-yl]nicotinonitrile

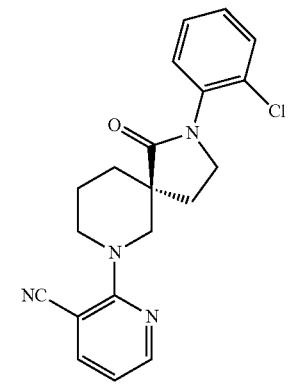 [SMILES: N#Cc1cccnc1N1CCC[C@]2(CCN(c3ccccc3Cl)C2=O)C1]

This compound was prepared by using procedures analogous to those described for the synthesis of example 92. LC-MS: 367.2/369.1 (M+H)+.

Example 97

(5S)-2-(2-Chlorophenyl)-7-[3-(trifluoromethyl)pyridin-2-yl]-2,7-diazaspiro[4.5]decan-1-one

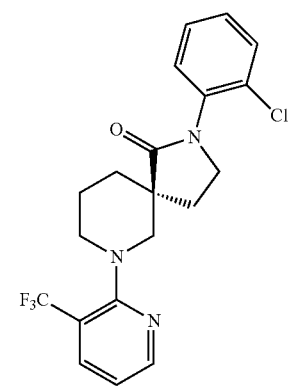 [SMILES: O=C1N(c2ccccc2Cl)CC[C@]12CCCN(c1ncccc1C(F)(F)F)C2]

This compound was prepared by using procedures analogous to those described for the synthesis of example 92. LC-MS: 410.1/412.1 (M+H)+.

Example 98

6-[(5S)-2-(2-Chlorophenyl)-1-oxo-2,7-diazaspiro[4.5]dec-7-yl]nicotinonitrile

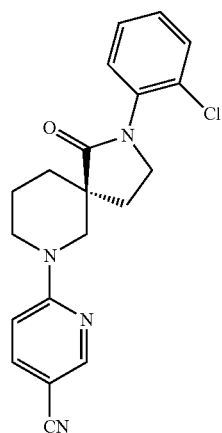 [SMILES: N#Cc1ccc(N2CCC[C@]3(CCN(c4ccccc4Cl)C3=O)C2)nc1]

This compound was prepared by using procedures analogous to those described for the synthesis of example 92. LC-MS: 367.2/369.1 (M+H)+.

Example 99

Methyl {6-[(5S)-2-(2-chlorophenyl)-1-oxo-2,7-diazaspiro[4.5]dec-7-yl]pyridin-3-yl}carbamate

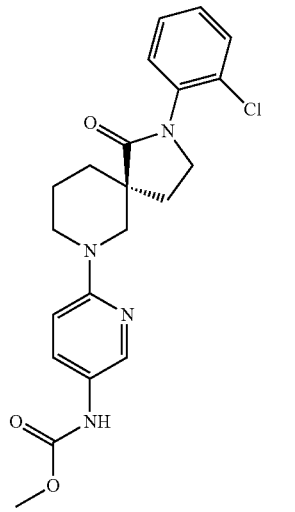 [SMILES: COC(=O)Nc1ccc(N2CCC[C@]3(CCN(c4ccccc4Cl)C3=O)C2)nc1]

Step 1. (5S)-7-(5-aminopyridin-2-yl)-2-(2-chlorophenyl)-2,7-diazaspiro[4.5]decan-1-one A mixture of (5S)-2-(2-chlorophenyl)-2,7-diazaspiro[4.5]decan-1-one hydrochloride (40.0 mg, 0.000133 mol, prepared by using a procedure analogous to that used for the synthesis of example 92, steps 1-3), 2-chloro-5-nitropyridine (23 mg, 0.00015 mol), and potassium carbonate (55 mg, 0.00040 mol) in N,N-dimethylformamide (1.0 mL, 0.013 mol) was stirred at 120° C. for 1.5 hours. After cooling the reaction mixture to ambient temperature the solid was filtered off and the filtrate was concentrated in-vacuo to afford the desired product. LC-MS: 387.1 (M+H)+. The resulting residue was dissolved in methanol and to this solution was added platinum [5 wt. % (dry basis) on activated carbon, wet, Degussa type F101, RA/W (Aldrich #330159), 15 mg] under an atmosphere of $H_2$ (g) at rt for 2 h. The catalyst was filtered off from the mixture and the filtrate was concentrated in-vacuo to afford the product in quantitative yield. LC-MS: 357.1 (M+H)+.

Step 2. Methyl {6-[(5S)-2-(2-chlorophenyl)-1-oxo-2,7-diazaspiro[4.5]dec-7-yl]pyridin-3-yl}carbamate Methyl chloroformate (4.4 μL, 0.000057 mol) was added to a solution of (5S)-7-(5-aminopyridin-2-yl)-2-(2-chlorophenyl)-2,7-diazaspiro[4.5]decan-1-one (18.5 mg, 0.0000478 mol) and pyridine (13 μL, 0.00016 mol) in methylene chloride (1.0 mL, 0.016 mol) and the mixture was stirred for 0.5 h at rt. The volatiles were removed in-vacuo and the crude product was purified by prep-HPLC. LC-MS: 415.1/417.1 (M+H)+.

Example 100

Ethyl {6-[(5S)-2-(2-chlorophenyl)-1-oxo-2,7-diazaspiro[4.5]dec-7-yl]pyridin-3-yl}carbamate

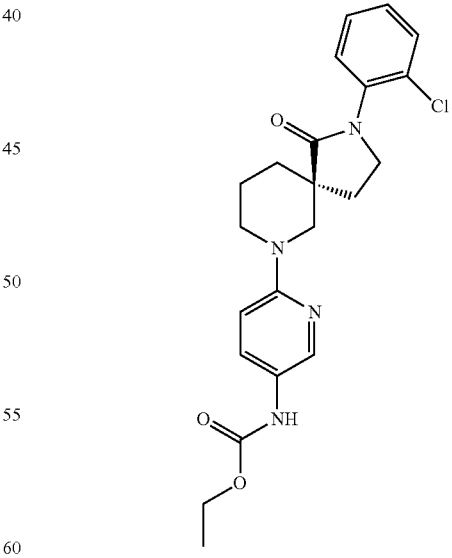

This compound was prepared by using procedures analogous to those described for the synthesis of example 99. LC-MS: 429.1 (M+H)+.

Example 101

Propyl {6-[(5S)-2-(2-chlorophenyl)-1-oxo-2,7-diaza-spiro[4.5]dec-7-yl]pyridin-3-yl}carbamate

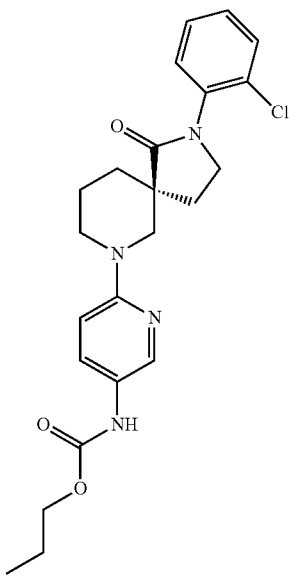 [SMILES: CCCOC(=O)Nc1ccc(N2CCC[C@]3(CCN(c4ccccc4Cl)C3=O)C2)nc1]

This compound was prepared by using procedures analogous to those described for the synthesis of example 99. LC-MS: 443.1 (M+H)⁺.

Example 102

6-[2-(2-Chlorophenyl)-1-oxo-2,7-diazaspiro[4.5]dec-7-yl]-N-methylnicotinamide

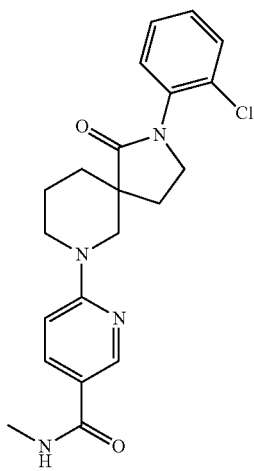 [SMILES: CNC(=O)c1ccc(N2CCCC3(CCN(c4ccccc4Cl)C3=O)C2)nc1]

This compound was prepared by using procedures analogous to those described for the synthesis of example 93. LC-MS: 399.2 (M+H)⁺.

Example 103

6-[2-(2-Chlorophenyl)-1-oxo-2,7-diazaspiro[4.5]dec-7-yl]-N-ethylnicotinamide

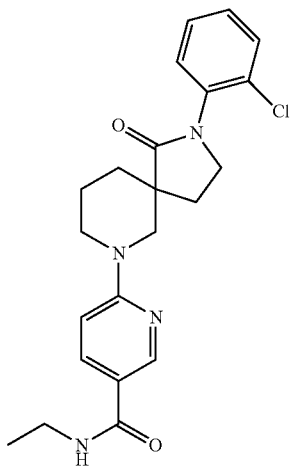 [SMILES: CCNC(=O)c1ccc(N2CCCC3(CCN(c4ccccc4Cl)C3=O)C2)nc1]

This compound was prepared by using procedures analogous to those described for the synthesis of example 93. LC-MS: 413.2 (M+H)⁺.

Example 104

(5R)-2-(Tetrahydro-2H-pyran-4-yl)-7-[5-(trifluoromethyl)pyridin-2-yl]-2,7-diazaspiro[4.5]decan-1-one and (5S)-2-(Tetrahydro-2H-pyran-4-yl)-7-[5-(trifluoromethyl)pyridin-2-yl]-2,7-diazaspiro[4.5]decan-1-one

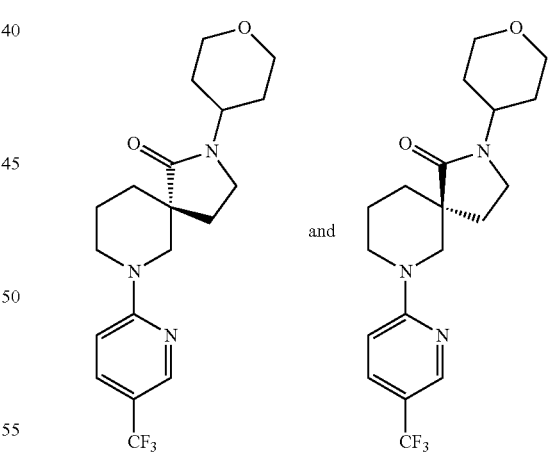

Racemic 2-(tetrahydro-2H-pyran-4-yl)-7-[5-(trifluoromethyl)pyridin-2-yl]-2,7-diazaspiro[4.5]decan-1-one (9.0 mg, 0.000023 mol, the racemic mixture was prepared by using procedures analogous to those described for the synthesis of example 93) was purified by chiral column (see Example 92 for column conditions) to give the pure two enantiomers. The shorter retention time peak was found to be the R-enantiomer and the longer retention time peak was found to be the S-enantiomer. The S-enantiomer was found to be more active. LC-MS: 384.2 (M+H)⁺.

Example 105

Methyl {6-[(5S)-1-oxo-2-(tetrahydro-2H-pyran-4-yl)-2,7-diazaspiro[4.5]dec-7-yl]pyridin-3-yl}carbamate

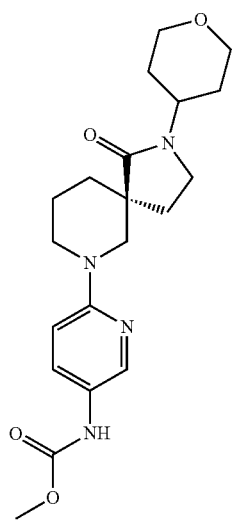 [SMILES: COC(=O)Nc1ccc(N2CCC[C@]3(CCN(C4CCOCC4)C3=O)C2)nc1]

Step 1. (5S)-7-(5-aminopyridin-2-yl)-2-(tetrahydro-2H-pyran-4-yl)-2,7-diazaspiro[4.5]decan-1-one A mixture of (5S)-2-(tetrahydro-2H-pyran-4-yl)-2,7-diazaspiro[4.5]decan-1-one [90 mg, 0.0004 mol, this compound was prepared by using procedures analogous to those described for the synthesis of example 92, steps 1-3], 2-chloro-5-nitropyridine (69 mg, 0.00044 mol), and potassium carbonate (160 mg, 0.0012 mol) in N,N-dimethylformamide (2 mL, 0.02 mol) was stirred at 120° C. for 1.5 hours. After cooling the reaction mixture to ambient temperature, the solid was filtered off and the filtrate was concentrated in-vacuo to afford the desired product. LC-MS: 361.2 $(M+H)^+$. The resulting residue was dissolved in methanol and to this solution was added 10% Pd on carbon and the reaction vessel was placed under a $H_2$ (g) atmosphere and stirred at rt for 1.5 h. The catalyst was filtered off from the mixture and the filtrate was concentrated to afford the desired product in quantitative yield and was used in the next step without further purification. LC-MS: 331.2 $(M+H)^+$.

Step 2. Methyl {6-[(5S)-1-oxo-2-(tetrahydro-2H-pyran-4-yl)-2,7-diazaspiro[4.5]dec-7-yl]pyridin-3-yl}carbamate Methyl chloroformate (4.4 µL, 0.000057 mol) was added to a solution of (5S)-7-(5-aminopyridin-2-yl)-2-(tetrahydro-2H-pyran-4-yl)-2,7-diazaspiro[4.5]decan-1-one (15.8 mg, 0.0000478 mol), N,N-diisopropylethylamine (27 µL, 0.00016 mol) and methylene chloride (1.0 mL, 0.016 mol); and the mixture was stirred for 1 h. The volatiles were removed in-vacuo and the crude product was purified by prep-HPLC. LC-MS: 389.2 $(M+H)^+$.

Example 106

Ethyl {6-[(5S)-1-oxo-2-(tetrahydro-2H-pyran-4-yl)-2,7-diazaspiro[4.5]dec-7-yl]pyridin-3-yl}carbamate

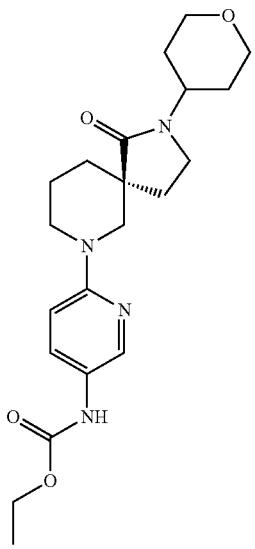 [SMILES: CCOC(=O)Nc1ccc(N2CCC[C@]3(CCN(C4CCOCC4)C3=O)C2)nc1]

This compound was prepared by using procedures analogous to those described for the synthesis of example 105. LC-MS: 403.3 $(M+H)^+$.

Example 107

Propyl {6-[(5S)-1-oxo-2-(tetrahydro-2H-pyran-4-yl)-2,7-diazaspiro[4.5]dec-7-yl]pyridin-3-yl}carbamate

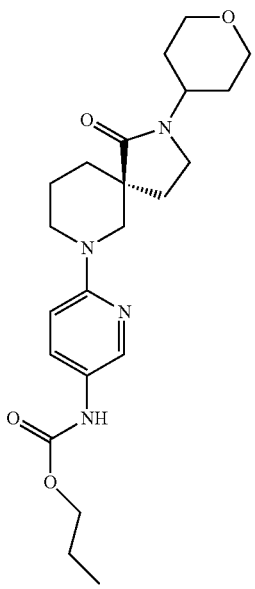 [SMILES: CCCOC(=O)Nc1ccc(N2CCC[C@]3(CCN(C4CCOCC4)C3=O)C2)nc1]

This compound was prepared by using procedures analogous to those described for the synthesis of example 105. LC-MS: 417.3 $(M+H)^+$.

Example 108

Isopropyl {6-[(5S)-1-oxo-2-(tetrahydro-2H-pyran-4-yl)-2,7-diazaspiro[4.5]dec-7-yl]pyridin-3-yl}carbamate

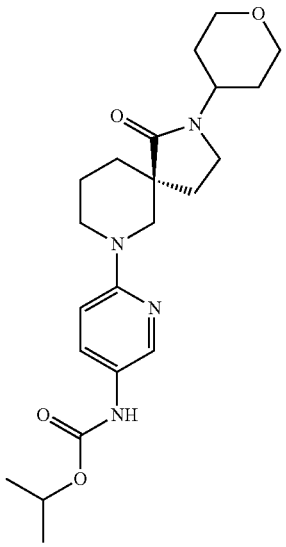 [SMILES: CC(C)OC(=O)Nc1ccc(N2CCC[C@]3(CCN(C4CCOCC4)C3=O)C2)nc1]

This compound was prepared by using procedures analogous to those described for the synthesis of example 105. LC-MS: 417.3 (M+H)⁺.

Example 109

Isobutyl {6-[(5S)-1-oxo-2-(tetrahydro-2H-pyran-4-yl)-2,7-diazaspiro[4.5]dec-7-yl]pyridin-3-yl}carbamate

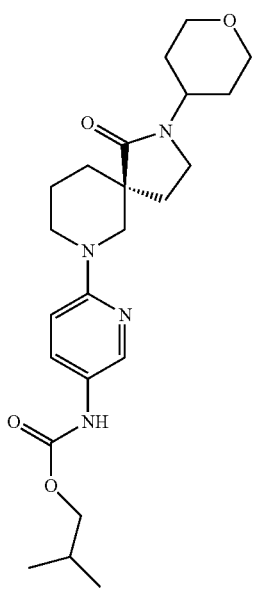 [SMILES: CC(C)COC(=O)Nc1ccc(N2CCC[C@]3(CCN(C4CCOCC4)C3=O)C2)nc1]

This compound was prepared by using procedures analogous to those described for the synthesis of example 105. LC-MS: 431.3 (M+H)⁺.

Example 110

(5S)-7-(3-Chloropyrazin-2-yl)-2-(tetrahydro-2H-pyran-4-yl)-2,7-diazaspiro[4.5]decan-1-one

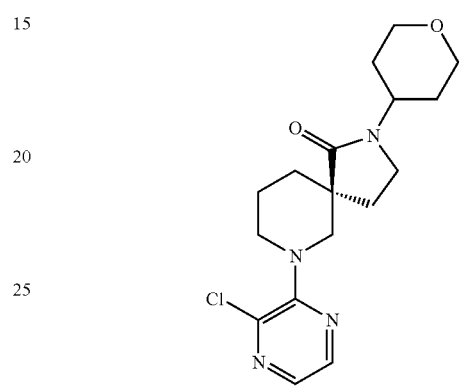

This compound was prepared by using procedures analogous to those described for the synthesis of example 93 starting from (5S)-2-(tetrahydro-2H-pyran-4-yl)-2,7-diazaspiro[4.5]decan-1-one as described in example 105. LC-MS: 351.1 (M+H)⁺.

Example 111

3-[(5S)-1-Oxo-2-(tetrahydro-2H-pyran-4-yl)-2,7-diazaspiro[4.5]dec-7-yl]pyrazine-2-carbonitrile

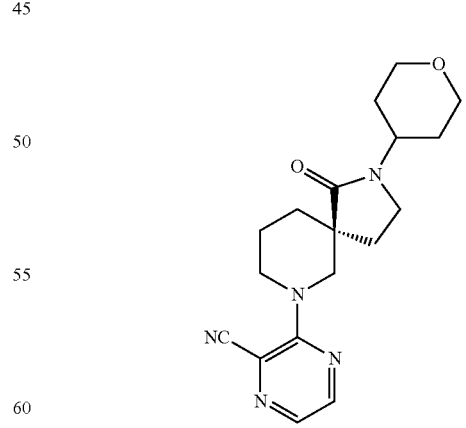

This compound was prepared by using procedures analogous to those described for the synthesis of example 93 starting from (5S)-2-(tetrahydro-2H-pyran-4-yl)-2,7-diazaspiro[4.5]decan-1-one as described in example 105. LC-MS: 342.2 (M+H)⁺.

Example 112

(5S)-7-(3-Chloropyridin-2-yl)-2-(tetrahydro-2H-pyran-4-yl)-2,7-diazaspiro[4.5]decan-1-one

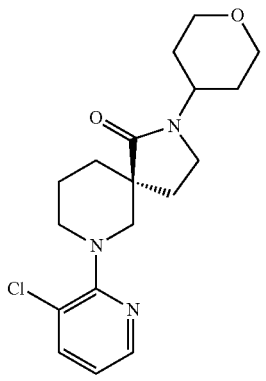 [SMILES: O=C1N(C2CCOCC2)CC[C@]12CCCN(c1ncccc1Cl)C2]

This compound was prepared by using procedures analogous to those described for the synthesis of example 93 starting from (5S)-2-(tetrahydro-2H-pyran-4-yl)-2,7-diazaspiro[4.5]decan-1-one as described in example 105. LC-MS: 350.2 (M+H)$^+$.

Example 113

2-[(5S)-1-Oxo-2-(tetrahydro-2H-pyran-4-yl)-2,7-diazaspiro[4.5]dec-7-yl]nicotinonitrile

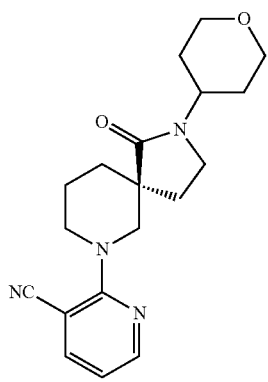 [SMILES: N#Cc1cccnc1N1CCC[C@]2(CCN(C3CCOCC3)C2=O)C1]

This compound was prepared by using procedures analogous to those described for the synthesis of example 93 starting from (5S)-2-(tetrahydro-2H-pyran-4-yl)-2,7-diazaspiro[4.5]decan-1-one as described in example 105. LC-MS: 341.2 (M+H)$^+$.

Example 114

(5S)-2-(Tetrahydro-2H-pyran-4-yl)-7-[3-(trifluoromethyl)pyridin-2-yl]-2,7-diazaspiro[4.5]decan-1-one

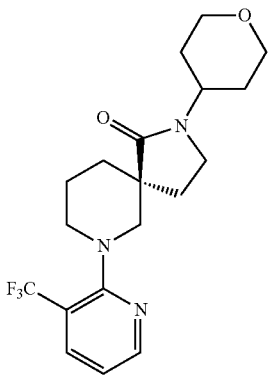 [SMILES: O=C1N(C2CCOCC2)CC[C@]12CCCN(c1ncccc1C(F)(F)F)C2]

This compound was prepared by using procedures analogous to those described for the synthesis of example 93 starting from (5S)-2-(tetrahydro-2H-pyran-4-yl)-2,7-diazaspiro[4.5]decan-1-one as described in example 105. LC-MS: 384.2 (M+H)$^+$.

Example 115

(5S)-7-(3,5-Dichloropyridin-2-yl)-2-(tetrahydro-2H-pyran-4-yl)-2,7-diazaspiro[4.5]decan-1-one This compound was prepared by using procedures analogous to those described for the synthesis of example 93 as described in example 105. LC-MS: 384.1 (M+H)$^+$.

Example 116

(5S)-7-(5-Chloropyridin-2-yl)-2-(tetrahydro-2H-pyran-4-yl)-2,7-diazaspiro[4.5]decan-1-one

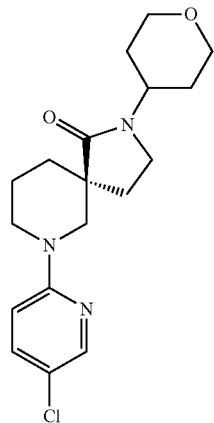 [SMILES: O=C1N(C2CCOCC2)CC[C@]12CCCN(c1ccc(Cl)cn1)C2]

A mixture of (5S)-2-(tetrahydro-2H-pyran-4-yl)-2,7-diazaspiro[4.5]decan-1-one hydrochloride (29.4 mg, 0.000107 mol, this compound was prepared by using procedures analogous to those described for the synthesis of example 92, steps 1-3), 5-chloro-2-fluoropyridine (17 mg, 0.00013 mol) and potassium carbonate (0.029 mL, 0.00032 mol) in N,N-dimethylformamide (0.6 mL, 0.008 mol) was heated at 120° C. for 5 h. The crude product was purified by prep-HPLC to afford the desired product. LC-MS: 350.2 (M+H)$^+$.

Example 117

Methyl {5-chloro-6-[(5S)-1-oxo-2-(tetrahydro-2H-pyran-4-yl)-2,7-diazaspiro[4.5]dec-7-yl]pyridin-3-yl}carbamate

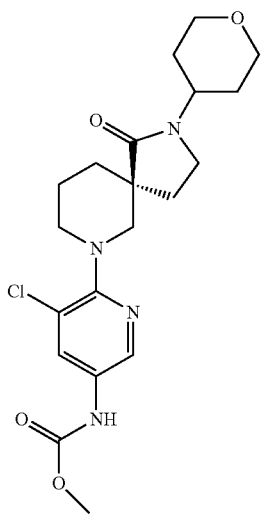 [SMILES: COC(=O)Nc1cnc(N2CCC[C@]3(CCN(C4CCOCC4)C3=O)C2)c(Cl)c1]

This compound was prepared by using procedures analogous to those described for the synthesis of example 105. LC-MS: 423.1 (M+H)$^+$.

Example 118

Ethyl {5-chloro-6-[(5S)-1-oxo-2-(tetrahydro-2H-pyran-4-yl)-2,7-diazaspiro[4.5]dec-7-yl]pyridin-3-yl}carbamate

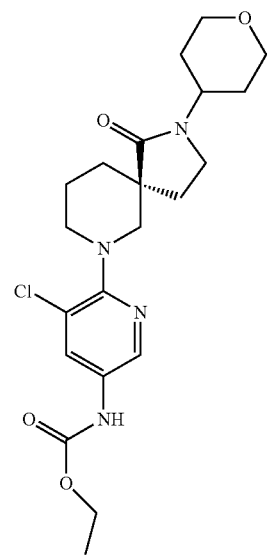 [SMILES: CCOC(=O)Nc1cnc(N2CCC[C@]3(CCN(C4CCOCC4)C3=O)C2)c(Cl)c1]

This compound was prepared by using procedures analogous to those described for the synthesis of example 105. LC-MS: 437.2 (M+H)$^+$.

Example 119

Propyl {5-chloro-6-[(5S)-1-oxo-2-(tetrahydro-2H-pyran-4-yl)-2,7-diazaspiro[4.5]dec-7-yl]pyridin-3-yl}carbamate

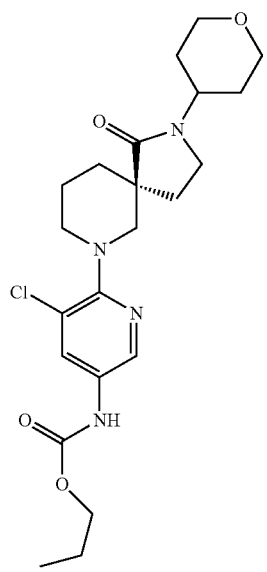 [SMILES: CCCOC(=O)Nc1cnc(N2CCC[C@]3(CCN(C4CCOCC4)C3=O)C2)c(Cl)c1]

This compound was prepared by using procedures analogous to those described for the synthesis of example 105. LC-MS: 451.2 (M+H)$^+$.

Example 120

Isopropyl {5-chloro-6-[(5S)-1-oxo-2-(tetrahydro-2H-pyran-4-yl)-2,7-diazaspiro[4.5]dec-7-yl]pyridin-3-yl}carbamate

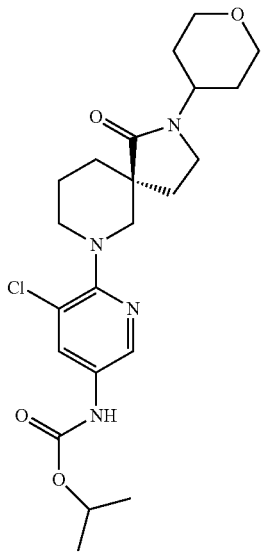 [SMILES: CC(C)OC(=O)Nc1cnc(N2CCC[C@]3(CCN(C4CCOCC4)C3=O)C2)c(Cl)c1]

This compound was prepared by using procedures analogous to those described for the synthesis of example 105. LC-MS: 451.2 (M+H)$^+$.

Example 121

Isobutyl {5-chloro-6-[(5S)-1-oxo-2-(tetrahydro-2H-pyran-4-yl)-2,7-diazaspiro[4.5]dec-7-yl]pyridin-3-yl}carbamate

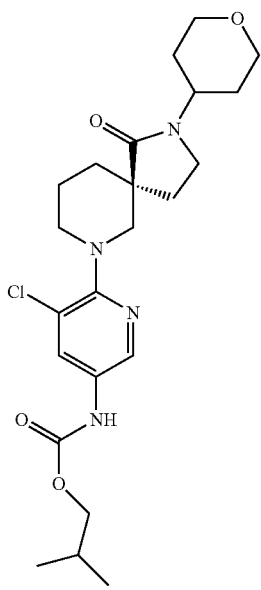 [SMILES: CC(C)COC(=O)Nc1cnc(N2CCC[C@]3(CCN(C4CCOCC4)C3=O)C2)c(Cl)c1]

This compound was prepared by using procedures analogous to those described for the synthesis of example 105. LC-MS: 465.2 (M+H)$^+$.

Example 122

3-Chloro-4-[(5S)-1-oxo-2-(tetrahydro-2H-pyran-4-yl)-2,7-diazaspiro[4.5]dec-7-yl]benzonitrile

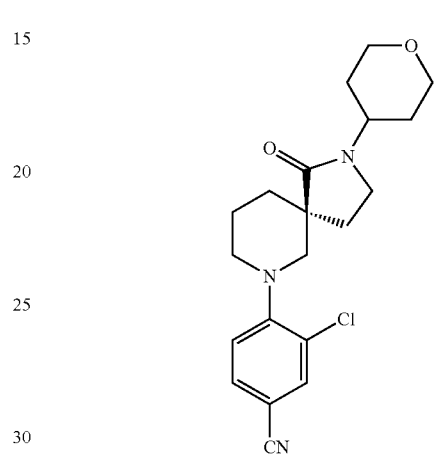

This compound was prepared by using procedures analogous to those described for the synthesis of example 116. LC-MS: 374.1 (M+H)$^+$.

Example 123

6-[(5S)-1-Oxo-2-(tetrahydro-2H-pyran-4-yl)-2,7-diazaspiro[4.5]dec-7-yl]nicotinonitrile

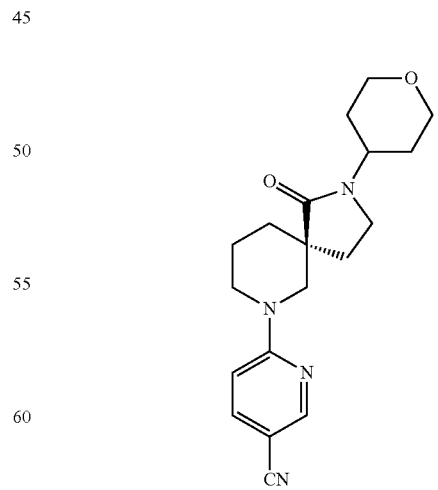

This compound was prepared by using procedures analogous to those described for the synthesis of example 116. LC-MS: 341.2 (M+H)$^+$.

Example 124

(5S)-7-(3,5-Difluoropyridin-2-yl)-2-(tetrahydro-2H-pyran-4-yl)-2,7-diazaspiro[4.5]decan-1-one

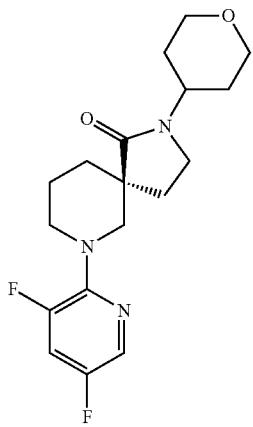 [SMILES: O=C1N(C2CCOCC2)CC[C@]12CCCN(c1ncc(F)cc1F)C2]

This compound was prepared by using procedures analogous to those described for the synthesis of example 116. LC-MS: 352.2 (M+H)+.

Example 125

(5S)-7-Isoquinolin-1-yl-2-(tetrahydro-2H-pyran-4-yl)-2,7-diazaspiro[4.5]decan-1-one

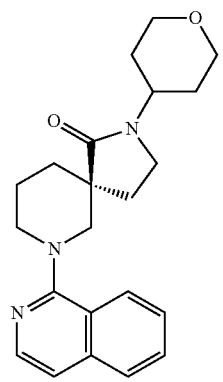 [SMILES: O=C1N(C2CCOCC2)CC[C@]12CCCN(c1nccc3ccccc13)C2]

This compound was prepared by using procedures analogous to those described for the synthesis of example 116. LC-MS: 366.3 (M+H)+.

Example 126

(5S)-7-quinolin-2-yl-2-(tetrahydro-2H-pyran-4-yl)-2,7-diazaspiro[4.5]decan-1-one

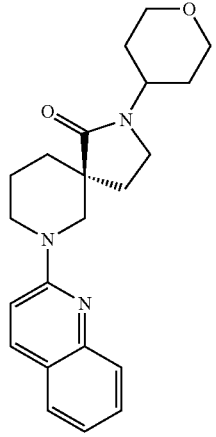 [SMILES: O=C1N(C2CCOCC2)CC[C@]12CCCN(c1ccc3ccccc3n1)C2]

This compound was prepared by using procedures analogous to those described for the synthesis of example 116. LC-MS: 366.2 (M+H)+.

Example 127

Methyl {5-methyl-6-[(5S)-1-oxo-2-(tetrahydro-2H-pyran-4-yl)-2,7-diazaspiro[4.5]dec-7-yl]pyridin-3-yl}carbamate

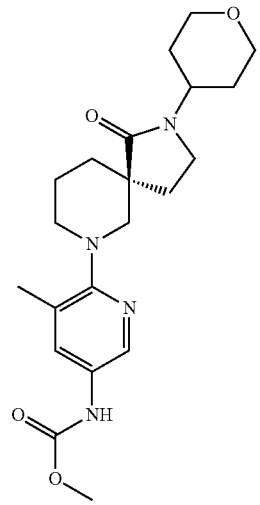 [SMILES: COC(=O)Nc1cnc(N2CCC[C@]3(CCN(C4CCOCC4)C3=O)C2)c(C)c1]

This compound was prepared by using procedures analogous to those described for the synthesis of example 105. LC-MS: 403.2 (M+H)+.

Example 128

Ethyl {5-methyl-6-[(5S)-1-oxo-2-(tetrahydro-2H-pyran-4-yl)-2,7-diazaspiro[4.5]dec-7-yl]pyridin-3-yl}carbamate

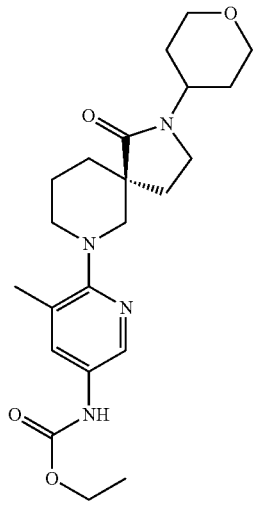 [SMILES: CCOC(=O)Nc1cnc(N2CCC[C@]3(CCN(C4CCOCC4)C3=O)C2)c(C)c1]

This compound was prepared by using procedures analogous to those described for the synthesis of example 105. LC-MS: 417.2 (M+H)+.

Example 129

Propyl {5-methyl-6-[(5S)-1-oxo-2-(tetrahydro-2H-pyran-4-yl)-2,7-diazaspiro[4.5]dec-7-yl]pyridin-3-yl}carbamate

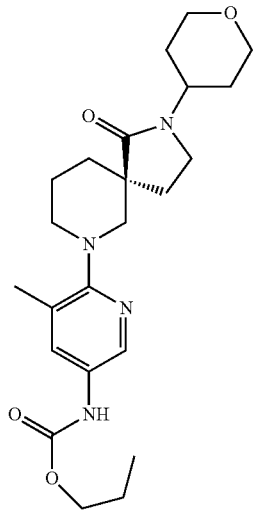 [SMILES: CCCOC(=O)Nc1cnc(N2CCC[C@]3(CCN(C4CCOCC4)C3=O)C2)c(C)c1]

This compound was prepared by using procedures analogous to those described for the synthesis of example 105. LC-MS: 431.2 (M+H)+.

Example 130

Methyl {3-fluoro-4-[(5S)-1-oxo-2-(tetrahydro-2H-pyran-4-yl)-2,7-diazaspiro[4,5]dec-7-yl]phenyl}carbamate

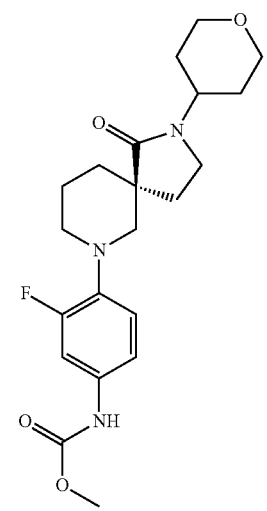 [SMILES: COC(=O)Nc1ccc(N2CCC[C@]3(CCN(C4CCOCC4)C3=O)C2)c(F)c1]

This compound was prepared by using procedures analogous to those described for the synthesis of example 105. LC-MS: 406.3 (M+H)+.

Example 131

Ethyl {3-fluoro-4-[(5S)-1-oxo-2-(tetrahydro-2H-pyran-4-yl)-2,7-diazaspiro[4.5]dec-7-yl]phenyl}carbamate

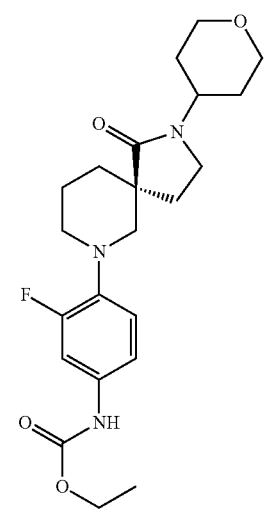 [SMILES: CCOC(=O)Nc1ccc(N2CCC[C@]3(CCN(C4CCOCC4)C3=O)C2)c(F)c1]

This compound was prepared by using procedures analogous to those described for the synthesis of example 105. LC-MS: 420.2 (M+H)+.

Example 132

Propyl {3-fluoro-4-[(5S)-1-oxo-2-(tetrahydro-2H-pyran-4-yl)-2,7-diazaspiro[4.5]dec-7-yl]phenyl}carbamate

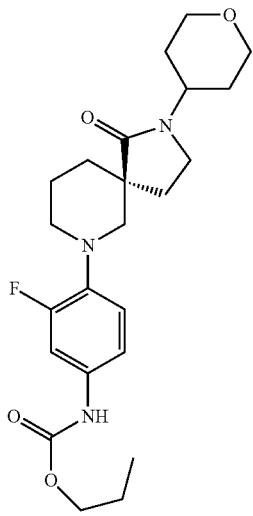 [SMILES: CCCOC(=O)Nc1ccc(N2CCC[C@]3(CCN(C4CCOCC4)C3=O)C2)c(F)c1]

This compound was prepared by using procedures analogous to those described for the synthesis of example 105. LC-MS: 434.2 (M+H)⁺.

Example 133

Isopropyl {3-fluoro-4-[(5S)-1-oxo-2-(tetrahydro-2H-pyran-4-yl)-2,7-diazaspiro[4.5]dec-7-yl]phenyl}carbamate

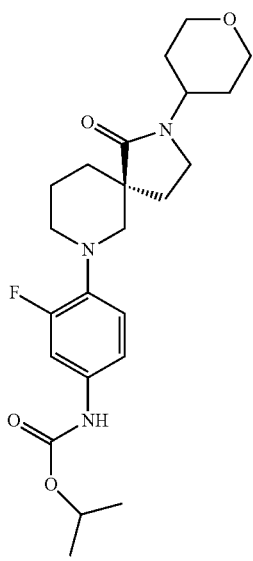 [SMILES: CC(C)OC(=O)Nc1ccc(N2CCC[C@]3(CCN(C4CCOCC4)C3=O)C2)c(F)c1]

This compound was prepared by using procedures analogous to those described for the synthesis of example 105. LC-MS: 434.3 (M+H)⁺.

Example 134

Isobutyl {3-fluoro-4-[(5S)-1-oxo-2-(tetrahydro-2H-pyran-4-yl)-2,7-diazaspiro[4.5]dec-7-yl]phenyl}carbamate

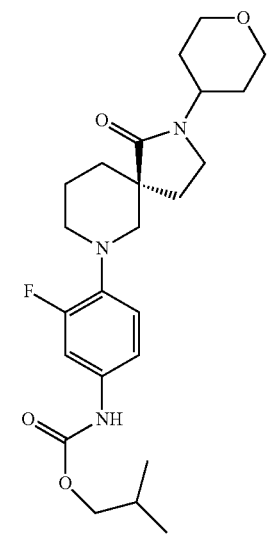 [SMILES: CC(C)COC(=O)Nc1ccc(N2CCC[C@]3(CCN(C4CCOCC4)C3=O)C2)c(F)c1]

This compound was prepared by using procedures analogous to those described for the synthesis of example 105. LC-MS: 448.3 (M+H)⁺.

Example 135

Methyl {4-[(5S)-1-oxo-2-(tetrahydro-2H-pyran-4-yl)-2,7-diazaspiro[4.5]dec-7-yl]phenyl}carbamate

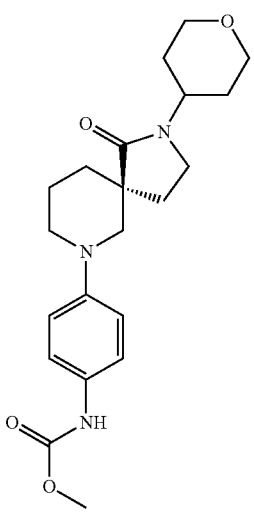 [SMILES: COC(=O)Nc1ccc(N2CCC[C@]3(CCN(C4CCOCC4)C3=O)C2)cc1]

This compound was prepared by using procedures analogous to those described for the synthesis of example 105. LC-MS: 388.3 (M+H)⁺.

Example 136

Ethyl {4-[(5S)-1-oxo-2-(tetrahydro-2H-pyran-4-yl)-2,7-diazaspiro[4.5]dec-7-yl]phenyl}carbamate

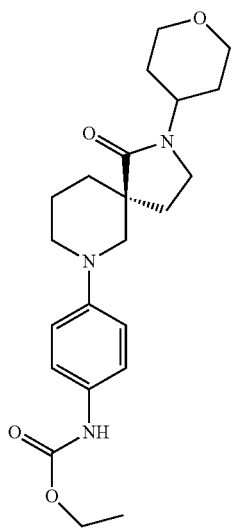 [SMILES: CCOC(=O)Nc1ccc(N2CCC[C@]3(CCN(C4CCOCC4)C3=O)C2)cc1]

This compound was prepared by using procedures analogous to those described for the synthesis of example 105. LC-MS: 402.2 (M+H)+.

Example 137

Propyl {4-[(5S)-1-oxo-2-(tetrahydro-2H-pyran-4-yl)-2,7-diazaspiro[4.5]dec-7-yl]phenyl}carbamate

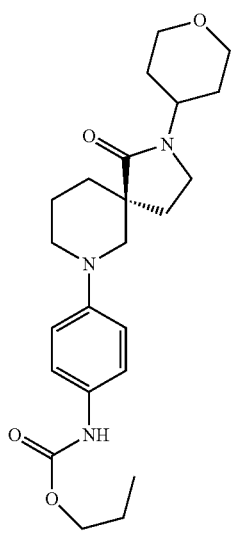 [SMILES: CCCOC(=O)Nc1ccc(N2CCC[C@]3(CCN(C4CCOCC4)C3=O)C2)cc1]

This compound was prepared by using procedures analogous to those described for the synthesis of example 105. LC-MS: 416.3 (M+H)+.

Example 138

Isopropyl {4-[(5S)-1-oxo-2-(tetrahydro-2H-pyran-4-yl)-2,7-diazaspiro[4.5]dec-7-yl]phenyl}carbamate

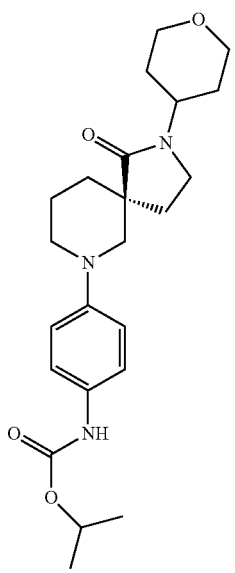 [SMILES: CC(C)OC(=O)Nc1ccc(N2CCC[C@]3(CCN(C4CCOCC4)C3=O)C2)cc1]

This compound was prepared by using procedures analogous to those described for the synthesis of example 105. LC-MS: 416.2 (M+H)+.

Example 139

Isobutyl {4-[(5S)-1-oxo-2-(tetrahydro-2H-pyran-4-yl)-2,7-diazaspiro[4.5]dec-7-yl]phenyl}carbamate

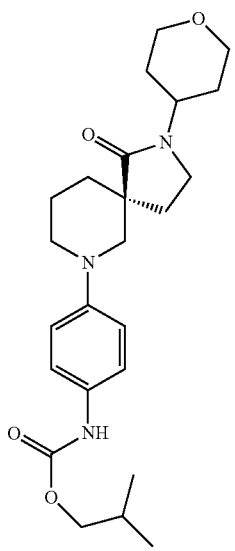 [SMILES: CC(C)COC(=O)Nc1ccc(N2CCC[C@]3(CCN(C4CCOCC4)C3=O)C2)cc1]

This compound was prepared by using procedures analogous to those described for the synthesis of example 105. LC-MS: 430.3 (M+H)+.

Example 140

Methyl methyl{4-[(5S)-1-oxo-2-(tetrahydro-2H-pyran-4-yl)-2,7-diazaspiro[4.5]dec-7-yl]phenyl}carbamate

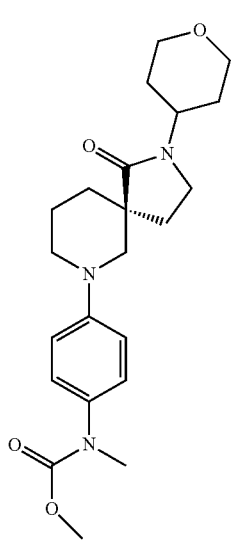 [SMILES: COC(=O)N(C)c1ccc(N2CCC[C@]3(CCN(C4CCOCC4)C3=O)C2)cc1]

Sodium hydride (1.6 mg, 0.000041 mol) was added to a solution of methyl {4-[(5S)-1-oxo-2-(tetrahydro-2H-pyran-4-yl)-2,7-diazaspiro[4.5]dec-7-yl]phenyl}carbamate (8.0 mg, 0.000021 mol) in tetrahydrofuran (1.0 mL, 0.012 mol) at rt. After stirring for 5 min., methyl iodide (2.6 μL, 0.000041 mol) was added and the reaction mixture was stirred for 1 h at rt. The crude product was purified by prep-HPLC. LC-MS: 402.3 (M+H)$^+$.

Example 141

3-Fluoro-4-[(5S)-1-oxo-2-(tetrahydro-2H-pyran-4-yl)-2,7-diazaspiro[4.5]dec-7-yl]benzonitrile

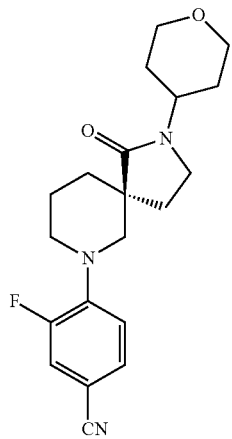 [SMILES: N#Cc1ccc(N2CCC[C@]3(CCN(C4CCOCC4)C3=O)C2)c(F)c1]

This compound was prepared by using procedures analogous to those described for the synthesis of example 116. LC-MS: 358.2 (M+H)$^+$.

Example 142

2-(1-Methylpiperidin-4-yl)-7-[5-(trifluoromethyl)pyridin-2-yl]-2,7-diazaspiro[4.5]decan-1-one

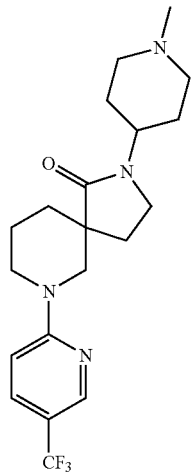 [SMILES: CN1CCC(N2CCC3(CCCN(c4ccc(C(F)(F)F)cn4)C3)C2=O)CC1]

This compound was prepared by using procedures analogous to those described for the synthesis of example 93. LC-MS: 397.2 (M+H)$^+$.

Example 143

Methyl 4-{1-oxo-7-[5-(trifluoromethyl)pyridin-2-yl]-2,7-diazaspiro[4.5]dec-2-yl}piperidine-1-carboxylate

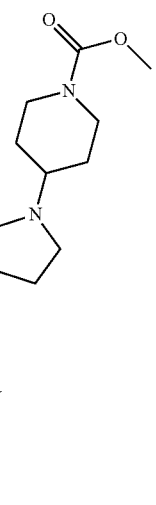

Step 1. 2-piperidin-4-yl-7-[5-(trifluoromethyl)pyridin-2-yl]-2,7-diazaspiro[4.5]decan-1-one A mixture of tert-butyl 4-(1-oxo-2,7-diazaspiro[4.5]dec-2-yl)piperidine-1-carboxylate (36.0 mg, 0.000107 mol, this compound was prepared by using a procedure that was analogous to that described for the synthesis of example 1, steps 1-4 followed by Pd catalyzed hydrogenation to remove the Cbz protecting group), 2-chloro-5-(trifluoromethyl)pyridine (23 mg, 0.00013 mol) and N,N-diisopropylethylamine (0.056 mL, 0.00032 mol) in N-methylpyrrolidinone (0.8 mL, 0.008 mol) was irradiated with microwaves to heat the mixture to 180° C. for 20 min. The mixture was diluted with ethyl acetate and washed with water and brine, dried over sodium sulfate, filtered and concentrated to afford the desired Boc-protected product. LC-MS: 483.2 (M+H)$^+$. The residue was treated with 4 N HCl in dioxane to afford the de-Boc product. LC-MS: 383.2 (M+H)$^+$.

Step 2. Methyl 4-{1-oxo-7-[5-(trifluoromethyl)pyridin-2-yl]-2,7-diazaspiro[4.5]dec-2-yl}piperidine-1-carboxylate Methyl chloroformate (4.4 µL, 0.000057 mol) was added to a solution of 2-piperidin-4-yl-7-[5-(trifluoromethyl)pyridin-2-yl]-2,7-diazaspiro[4.5]decan-1-one (18.3 mg, 0.0000478 mol) and N,N-diisopropylethylamine (27 µL, 0.00016 mol) in methylene chloride (1.0 mL, 0.016 mol); and the mixture was stirred for 0.5 h. The volatiles were removed in-vacuo and the product was purified by prep-HPLC. LC-MS: 441.2 (M+H)$^+$.

Example 144

N,N-Dimethyl-4-{1-oxo-7-[5-(trifluoromethyl)pyridin-2-yl]-2,7-diazaspiro[4.5]dec-2-yl}piperidine-1-carboxamide

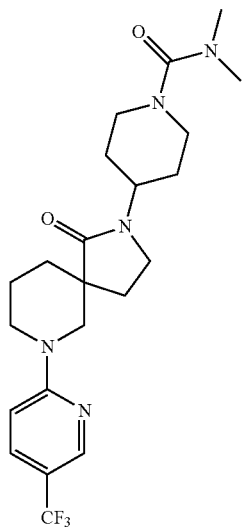 [SMILES: CN(C)C(=O)N1CCC(N2CCC3(CCCN(c4ccc(C(F)(F)F)cn4)C3)C2=O)CC1]

This compound was prepared by using procedures analogous to those described for the synthesis of example 143. LC-MS: 454.2 (M+H)$^+$.

Example 145

7-(3-Chloropyrazin-2-yl)-2-quinolin-5-yl-2,7-diazaspiro[4.5]decan-1-one

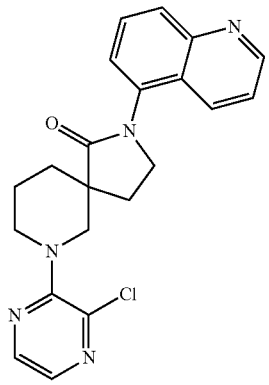 [SMILES: O=C1N(c2cccc3ncccc23)CCC12CCCN(c1nccnc1Cl)C2]

This compound was prepared by using procedures analogous to those described for the synthesis of example 93. LC-MS: 394.2 (M+H)$^+$.

Example 146

7-(3-Chloropyridin-2-yl)-2-quinolin-5-yl-2,7-diazaspiro[4.5]decan-1-one

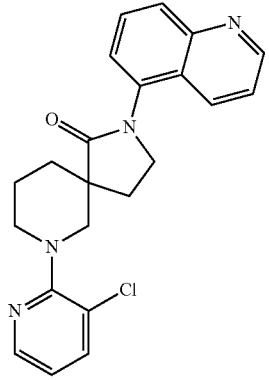 [SMILES: O=C1N(c2cccc3ncccc23)CCC12CCCN(c1ncccc1Cl)C2]

This compound was prepared by using procedures analogous to those described for the synthesis of example 93. LC-MS: 393.2 (M+H)$^+$.

Example 147

7-(3,5-Dichloropyridin-2-yl)-2-quinolin-5-yl-2,7-diazaspiro[4.5]decan-1-one

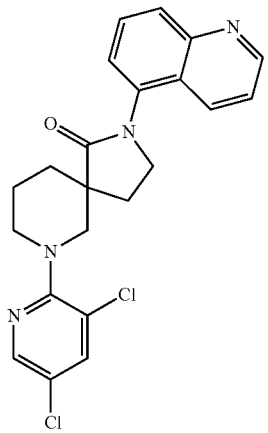 [SMILES: O=C1N(c2cccc3ncccc23)CCC12CCCN(c1ncc(Cl)cc1Cl)C2]

This compound was prepared by using procedures analogous to those described for the synthesis of example 93. LC-MS: 427.2 (M+H)$^+$.

Example 148

2-(2-Methylphenyl)-7-[4-(trifluoromethyl)pyrimidin-2-yl]-2,7-diazaspiro[4.5]decan-1-one

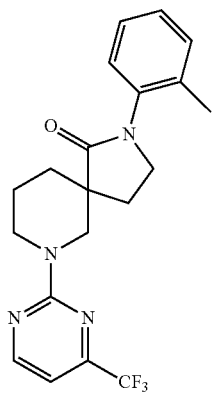 [SMILES: Cc1ccccc1N1CCC2(CCCN(c3nccc(C(F)(F)F)n3)C2)C1=O]

This compound was prepared by using procedures analogous to those described for the synthesis of example 93. LC-MS: 391.2 (M+H)$^+$.

Example 149

7-(4-Chloropyrimidin-2-yl)-2-(2-methylphenyl)-2,7-diazaspiro[4.5]decan-1-one

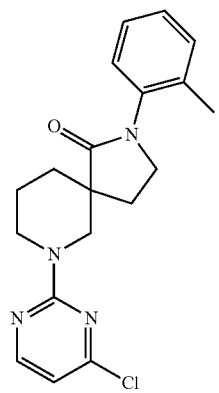 [SMILES: Cc1ccccc1N1CCC2(CCCN(c3nccc(Cl)n3)C2)C1=O]

This compound was prepared by using procedures analogous to those described for the synthesis of example 93. LC-MS: 357.2 (M+H)$^+$.

Example 150

7-(6-Chloro-7H-purin-2-yl)-2-(2-methylphenyl)-2,7-diazaspiro[4.5]decan-1-one

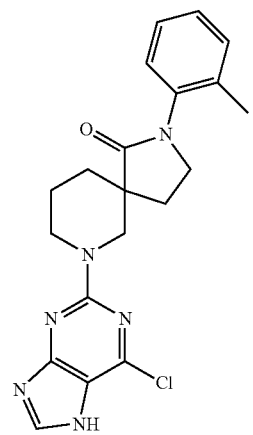 [SMILES: Cc1ccccc1N1CCC2(CCCN(c3nc(Cl)c4[nH]cnc4n3)C2)C1=O]

This compound was prepared by using procedures analogous to those described for the synthesis of example 93. LC-MS: 397.2 (M+H)$^+$.

Example 151

3-[2-(2-Methylphenyl)-1-oxo-2,7-diazaspiro[4.5]dec-7-yl]pyrazine-2-carbonitrile

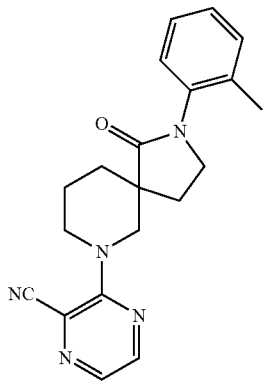 [SMILES: Cc1ccccc1N1CCC2(CCCN(c3nccnc3C#N)C2)C1=O]

This compound was prepared by using procedures analogous to those described for the synthesis of example 93. LC-MS: 348.2 (M+H)⁺.

Example 152

7-(6-Chloropyrazin-2-yl)-2-(2-methylphenyl)-2,7-diazaspiro[4.5]decan-1-one

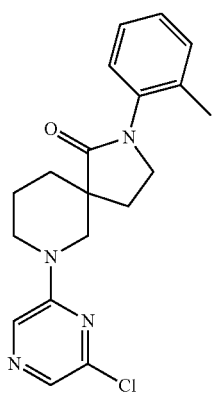 [SMILES: Cc1ccccc1N1CCC2(CCCN(c3cncc(Cl)n3)C2)C1=O]

This compound was prepared by using procedures analogous to those described for the synthesis of example 93. LC-MS: 357.2 (M+H)⁺.

Example 153

7-(3-Chloropyrazin-2-yl)-2-(2-methylphenyl)-2,7-diazaspiro[4.5]decan-1-one

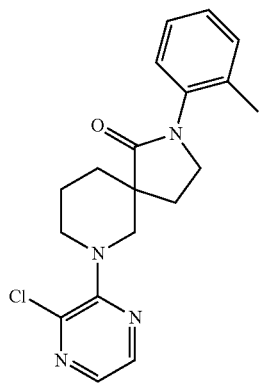 [SMILES: Cc1ccccc1N1CCC2(CCCN(c3nccnc3Cl)C2)C1=O]

This compound was prepared by using procedures analogous to those described for the synthesis of example 93. LC-MS: 357.2 (M+H)⁺.

Example 154

2-(2-Methylphenyl)-7-[5-(trifluoromethyl)pyridin-2-yl]-2,7-diazaspiro[4.5]decan-1-one

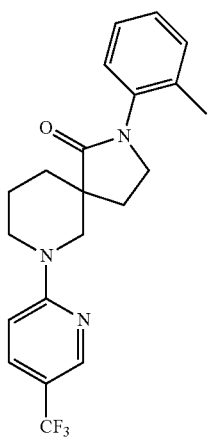 [SMILES: Cc1ccccc1N1CCC2(CCCN(c3ccc(C(F)(F)F)cn3)C2)C1=O]

This compound was prepared by using procedures analogous to those described for the synthesis of example 93. LC-MS: 390.2 (M+H)⁺.

Example 155

2-Quinolin-5-yl-7-[5-(trifluoromethyl)pyridin-2-yl]-2,7-diazaspiro[4.5]decan-1-one

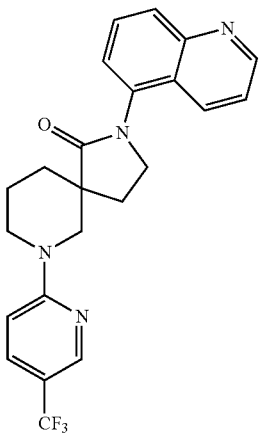 [SMILES: O=C1N(c2cccc3ncccc23)CCC12CCCN(c1ccc(C(F)(F)F)cn1)C2]

This compound was prepared by using procedures analogous to those described for the synthesis of example 93. LC-MS: 427.2 (M+H)$^+$.

Example 156

2-Isoquinolin-5-yl-7-[5-(trifluoromethyl)pyridin-2-yl]-2,7-diazaspiro[4.5]decan-1-one

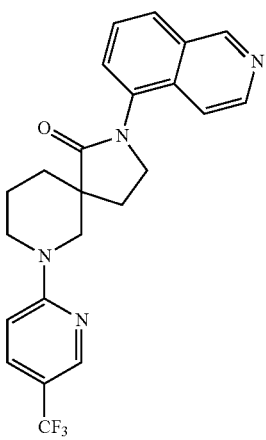 [SMILES: O=C1N(c2cccc3cnccc23)CCC12CCCN(c1ccc(C(F)(F)F)cn1)C2]

This compound was prepared by using procedures analogous to those described for the synthesis of example 93. LC-MS: 427.2 (M+H)$^+$.

Example 157

2-(4-Bromo-2-methylphenyl)-7-[5-(trifluoromethyl)pyridin-2-yl]-2,7-diazaspiro[4.5]decan-1-one

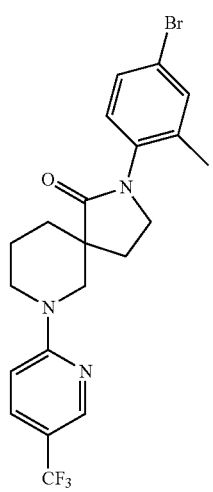 [SMILES: Cc1cc(Br)ccc1N1CCC2(CCCN(c3ccc(C(F)(F)F)cn3)C2)C1=O]

This compound was prepared by using procedures analogous to those described for the synthesis of example 93. LC-MS: 468.1/470.1 (M+H)$^+$.

Example 158

3-Methyl-4-{1-oxo-7-[5-(trifluoromethyl)pyridin-2-yl]-2,7-diazaspiro[4.5]dec-2-yl}benzonitrile

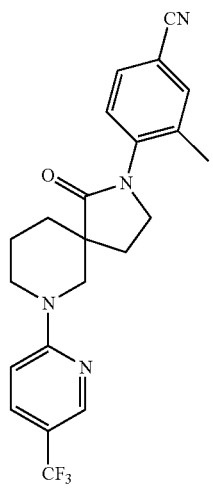 [SMILES: Cc1cc(C#N)ccc1N1CCC2(CCCN(c3ccc(C(F)(F)F)cn3)C2)C1=O]

A mixture of 2-(4-bromo-2-methylphenyl)-7-[5-(trifluoromethyl)pyridin-2-yl]-2,7-diazaspiro[4.5]decan-1-one (63.6 mg, 0.000136 mol), zinc cyanide (32 mg, 0.00027 mol), potassium carbonate (0.056 g, 0.00041 mol) and tetrakis(triphenylphosphine) palladium(0) (8 mg, 0.000007 mol) in N,N-dimethylformamide (0.5 mL, 0.006 mol) was stirred at 100° C. for 2 days. The reaction mixture was cooled to ambient temperature and purified by prep-HPLC (under pH ~10) to afford the desired product. LC-MS: 415.2 (M+H)$^+$.

Example 159

N-(3-Methyl-4-{1-oxo-7-[5-(trifluoromethyl)pyridin-2-yl]-2,7-diazaspiro[4.5]dec-2-yl}phenyl)acetamide

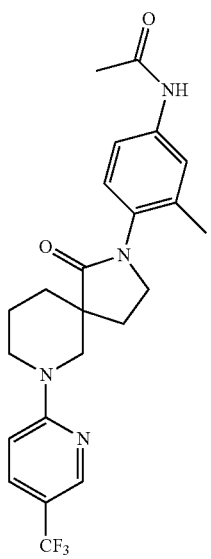 [SMILES: CC(=O)Nc1ccc(N2CCC3(CCCN(c4ccc(C(F)(F)F)cn4)C3)C2=O)c(C)c1]

To a solution of 2-(4-bromo-2-methylphenyl)-7-[5-(trifluoromethyl)pyridin-2-yl]-2,7-diazaspiro[4.5]decan-1-one (38.1 mg, 0.0000814 mol), in 1,4-dioxane (0.5 mL, 0.006 mol) was added (1S,2S)-N,N'-dimethylcyclohexane-1,2-diamine (2.3 mg, 0.000016 mol), copper(I) iodide (1.6 mg, 0.0000081 mol), acetamide (9.6 mg, 0.00016 mol), and potassium carbonate (23.6 mg, 0.000171 mol) and the mixture was stirred at 100° C. overnight. The product was purified by prep-HPLC. LC-MS: 447.2 (M+H)$^+$.

Example 160

N-(3-Methyl-4-{1-oxo-7-[5-(trifluoromethyl)pyridin-2-yl]-2,7-diazaspiro[4.5]dec-2-yl}phenyl)methanesulfonamide

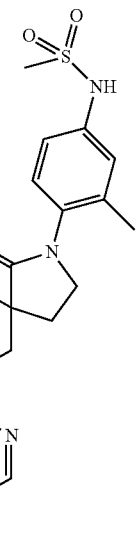

This compound was prepared by using procedures analogous to those described for the synthesis of example 159. LC-MS: 483.2 (M+H)$^+$.

Example 161

2-(3-Methylpyridin-4-yl)-7-[5-(trifluoromethyl)pyridin-2-yl]-2,7-diazaspiro[4.5]decan-1-one

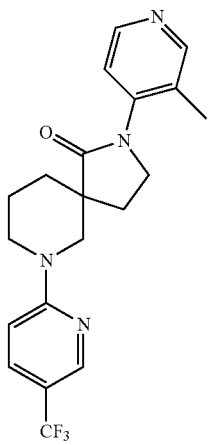 [SMILES: Cc1cnccc1N1CCC2(CCCN(c3ccc(C(F)(F)F)cn3)C2)C1=O]

Step 1. 1-tert-butyl 3-ethyl 3-[2-(tritylamino)ethyl]piperidine-1,3-dicarboxylate Tritylamine (180 mg, 0.00068 mol) was added to a solution of 1-tert-butyl 3-ethyl 3-(2-oxoethyl)piperidine-1,3-dicarboxylate (0.170 g, 0.000568 mol, this was prepared by using procedures analogous to that described for the synthesis of example 1, steps 1-2) in 1,2-dichloroethane (4.0 mL, 0.051 mol) and followed by sodium triacetoxyborohydride (0.36 g, 0.0017 mol) and the mixture was stirred overnight. The mixture was poured into pre-cooled water, and extracted with ethyl acetate. The organic layer was separated, dried (NaSO$_4$), and concentrated in-vacuo. The product was purified by CombiFlash eluting with hexane/EtOAc (max EtOAc 20%). LC-MS: 543.3 (M+H)$^+$; 243.2.

Step 2. 2,7-diazaspiro[4.5]decan-1-one

Trifluoroacetic acid (1.0 mL, 0.013 mol) was added to a solution of 1-tert-butyl 3-ethyl 3-[2-(tritylamino)ethyl]piperidine-1,3-dicarboxylate (0.10 g, 0.00018 mol) in methylene chloride (1.0 mL, 0.016 mol) and the mixture was stirred for 1 h at rt to remove the Boc and trityl groups. Then the solvent was removed under vacuum and to the resultant residue was added 1,4-dioxane (3.0 mL, 0.038 mol) followed by N,N-diisopropylethylamine (0.13 mL, 0.00074 mol) and the resultant mixture was stirred at 150° C. (microwave) for 1 h. The solvent from the mixture was removed under vacuum and the crude product was used in the next step without further purification. LC-MS: 155.2 (M+H)$^+$.

Step 3. 7-[5-(trifluoromethyl)pyridin-2-yl]-2,7-diazaspiro[4.5]decan-1-one

A mixture of 2,7-diazaspiro[4.5]decan-1-one (50.0 mg, 0.000324 mol), 2-chloro-5-(trifluoromethyl)pyridine (71 mg, 0.00039 mol) and N,N-diisopropylethylamine (0.17 mL, 0.00097 mol) in N-methylpyrrolidinone (2 mL, 0.02 mol) was irradiated with microwaves at 180° C. for 20 min. The product was purified by prep-HPLC. LC-MS: 300.2 (M+H)$^+$.

Step 4. 2-(3-methylpyridin-4-yl)-7-[5-(trifluoromethyl)pyridin-2-yl]-2,7-diazaspiro[4.5]decan-1-one To a solution of 7-[5-(trifluoromethyl)pyridin-2-yl]-2,7-diazaspiro[4.5]decan-1-one (24.4 mg, 0.0000814 mol) in 1,4-dioxane (0.5 mL, 0.006 mol) were added (1S,2S)-N,N'-dimethylcyclohexane-1,2-diamine (2.3 mg, 0.000016 mol), copper(I) iodide (1.6 mg, 0.0000081 mol), 4-bromo-3-methylpyridine (28 mg, 0.00016 mol) and potassium carbonate (23.6 mg, 0.000171 mol); and the mixture was stirred at 100° C. overnight. The product was purified by prep-HPLC. LC-MS: 391.2 (M+H)$^+$.

Example 162

2-(4-Methylpyridin-3-yl)-7-[5-(trifluoromethyl)pyridin-2-yl]-2,7-diazaspiro[4.5]decan-1-one

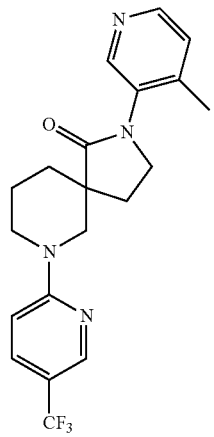 [SMILES: Cc1ccncc1N1CCC2(CCCN(c3ccc(C(F)(F)F)cn3)C2)C1=O]

Step 1. 1-tert-butyl 3-ethyl 3-{2-[(4-methylpyridin-3-yl)amino]ethyl}piperidine-1,3-dicarboxylate 4-Methylpyridin-3-amine (36.0 mg, 0.000333 mol) was added to a solution of 1-tert-butyl 3-ethyl 3-(2-oxoethyl)piperidine-1,3-dicarboxylate (0.095 g, 0.00032 mol) in 1,2-dichloroethane (1.9 mL, 0.025 mol) and followed by sodium triacetoxyborohydride (0.20 g, 0.00095 mol) and the mixture was stirred for 24 h. The mixture was poured into pre-cooled water, extracted with ethyl acetate. The organic layer was separated, dried and concentrated. The product was purified by CombiFlash using CH$_2$Cl$_2$/EtOAc (max EtOAc 50%). LC-MS: 392.3 (M+H)$^+$.

Step 2. ethyl 3-{2-[(4-methylpyridin-3-yl)amino]ethyl}piperidine-3-carboxylate trihydrochloride Hydrogen chloride in 1,4-dioxane (4.0 M, 2.0 mL) was added to a solution of 1-tert-butyl 3-ethyl 3-{2-[(4-methylpyridin-3-yl)amino]ethyl}piperidine-1,3-dicarboxylate (0.036 g, 0.000092 mol) in ethyl acetate (0.5 mL) and the mixture was stirred for 2 h. Then the solvent was removed in-vacuo to afford the product. LC-MS: 292.3 (M+H)$^+$.

Step 3. 2-(4-methylpyridin-3-yl)-7-[5-(trifluoromethyl)pyridin-2-yl]-2,7-diazaspiro[4.5]decan-1-one A mixture of ethyl 3-{2-[(4-methylpyridin-3-yl)amino]ethyl}piperidine-3-carboxylate trihydrochloride (42.8 mg, 0.000107 mol), 2-chloro-5-(trifluoromethyl)pyridine (23 mg, 0.00013 mol) and N,N-diisopropylethylamine (0.056 mL, 0.00032 mol) in N-methylpyrrolidinone (0.8 mL, 0.008 mol) was irradiated with microwaves to 180° C. for 20 min. Sodium hydride (30.0 mg) was then added to the above solution and the mixture was stirred overnight. The product was purified by prep-HPLC. LC-MS: 391.2 (M+H)$^+$.

Example 163

7-(3-Chloropyrazin-2-yl)-2-(1-methylpiperidin-4-yl)-2,7-diazaspiro[4.5]decan-1-one

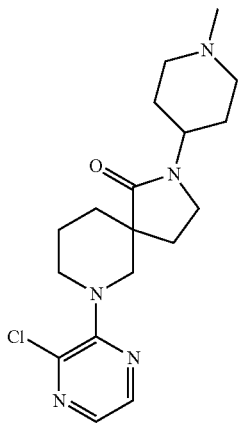 [SMILES: CN1CCC(N2CCC3(CCCN(c4nccnc4Cl)C3)C2=O)CC1]

This compound was prepared by using procedures analogous to those described for the synthesis of example 93. LC-MS: 364.1 (M+H)+.

Example 164

Methyl [4-[(5S)-2-cyclohexyl-1-oxo-2,7-diazaspiro[4.5]dec-7-yl]-3-(trifluoromethyl)phenyl]carbamate

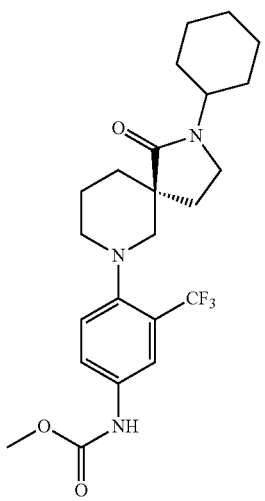 [SMILES: COC(=O)Nc1ccc(N2CCC[C@]3(CCN(C4CCCCC4)C3=O)C2)c(C(F)(F)F)c1]

This compound was prepared by using procedures analogous to those described for the synthesis of example 105. LC-MS: 454.2 (M+H)+.

Example 165

Ethyl [4-[(5S)-2-cyclohexyl-1-oxo-2,7-diazaspiro[4.5]dec-7-yl]-3-(trifluoromethyl)phenyl]carbamate

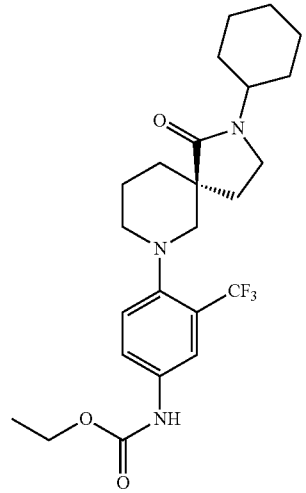 [SMILES: CCOC(=O)Nc1ccc(N2CCC[C@]3(CCN(C4CCCCC4)C3=O)C2)c(C(F)(F)F)c1]

This compound was prepared by using procedures analogous to those described for the synthesis of example 105. LC-MS: 468.2 (M+H)+.

Example 166

Prop-2-yn-1-yl [4-[(5S)-2-cyclohexyl-1-oxo-2,7-diazaspiro[4.5]dec-7-yl]-3-(trifluoromethyl)phenyl]carbamate

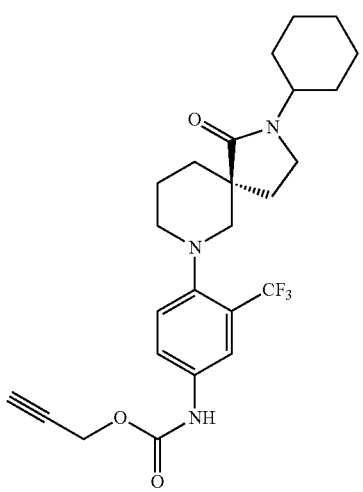 [SMILES: C#CCOC(=O)Nc1ccc(N2CCC[C@]3(CCN(C4CCCCC4)C3=O)C2)c(C(F)(F)F)c1]

This compound was prepared by using procedures analogous to those described for the synthesis of example 105. LC-MS: 478.1 (M+H)+.

Example 167

N-[4-[(5S)-2-Cyclohexyl-1-oxo-2,7-diazaspiro[4.5]
dec-7-yl]-3-(trifluoromethyl)phenyl]acetamide

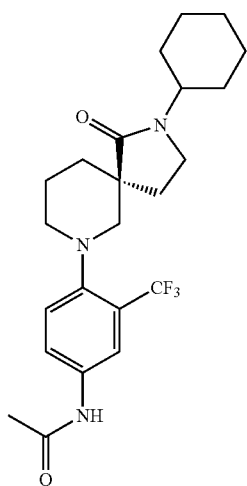 [SMILES: CC(=O)Nc1ccc(N2CCC[C@]3(CCN(C4CCCCC4)C3=O)C2)c(C(F)(F)F)c1]

This compound was prepared by using procedures analogous to those described for the synthesis of example 105. LC-MS: 438.1 (M+H)+.

Example 168

N-[4-[(5S)-2-Cyclohexyl-1-oxo-2,7-diazaspiro[4.5]
dec-7-yl]-3-(trifluoromethyl)phenyl]methanesulfonamide

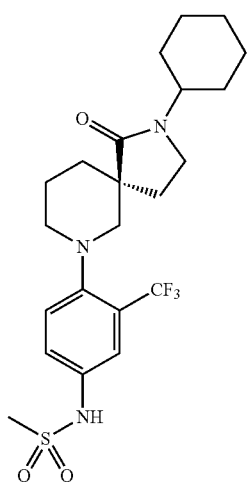 [SMILES: CS(=O)(=O)Nc1ccc(N2CCC[C@]3(CCN(C4CCCCC4)C3=O)C2)c(C(F)(F)F)c1]

This compound was prepared by using procedures analogous to those described for the synthesis of example 105. LC-MS: 474.1 (M+H)+.

Example 169

Methyl methyl[4-[(5S)-2-cyclohexyl-1-oxo-2,7-diazaspiro[4.5]dec-7-yl]-3-(trifluoromethyl)phenyl]
carbamate

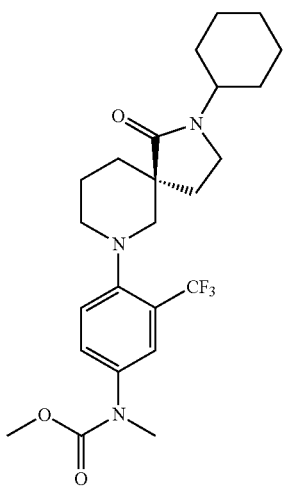 [SMILES: COC(=O)N(C)c1ccc(N2CCC[C@]3(CCN(C4CCCCC4)C3=O)C2)c(C(F)(F)F)c1]

This compound was prepared by using procedures analogous to those described for the synthesis of example 140. LC-MS: 468.1 (M+H)+.

Example 170

Prop-2-yn-1-yl {5-chloro-6-[(5S)-2-(trans-4-hydroxycyclohexyl)-1-oxo-2,7-diazaspiro[4.5]dec-7-yl]
pyridin-3-yl}carbamate

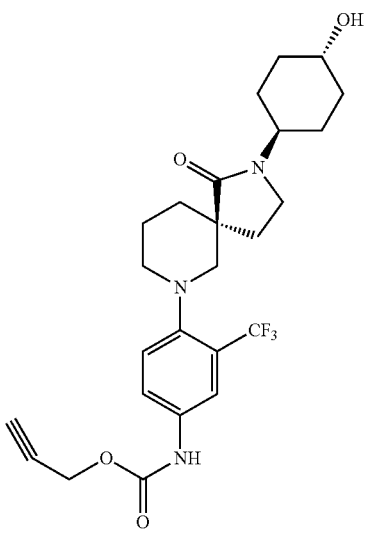 [SMILES: C#CCOC(=O)Nc1ccc(N2CCC[C@]3(CCN([C@H]4CC[C@H](O)CC4)C3=O)C2)c(C(F)(F)F)c1]

This compound was prepared by using procedures analogous to those described for the synthesis of example 105 starting from (S)-2-((trans)-4-hydroxycyclohexyl)-2,7-diazaspiro[4.5]decan-1-one which was prepared using procedures analogous to those described in the synthesis of example 472-a and followed by standard hydrogenation to remove the carbobenzyloxy (Cbz) protecting group. LC-MS: 461.1 (M+H)+.

Example 171

Methyl {5-chloro-6-[(5S)-2-(trans-4-hydroxycyclohexyl)-1-oxo-2,7-diazaspiro[4.5]dec-7-yl]pyridin-3-yl}carbamate

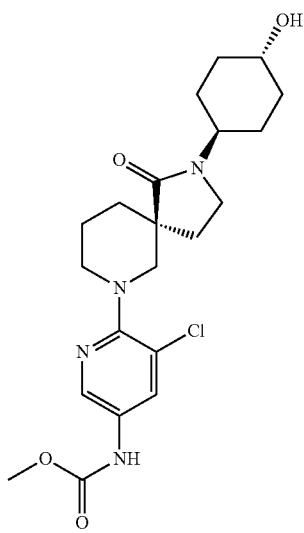 [SMILES: COC(=O)Nc1cnc(N2CCC[C@]3(CCN([C@H]4CC[C@H](O)CC4)C3=O)C2)c(Cl)c1]

This compound was prepared by using procedures analogous to those described for the synthesis of example 105 starting from (S)-2-((trans)-4-hydroxycyclohexyl)-2,7-diazaspiro[4.5]decan-1-one which was prepared using procedures analogous to those described in the synthesis of example 472-a and followed by standard hydrogenation to remove the carbobenzyloxy (Cbz) protecting group. LC-MS: 437.1 (M+H)+.

Example 172

Ethyl {5-chloro-6-[(5S)-2-(trans-4-hydroxycyclohexyl)-1-oxo-2,7-diazaspiro[4.5]dec-7-yl]pyridin-3-yl}carbamate

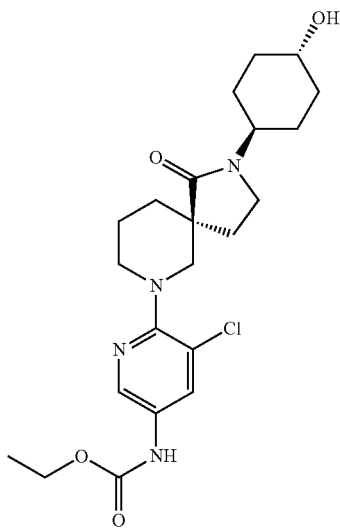 [SMILES: CCOC(=O)Nc1cnc(N2CCC[C@]3(CCN([C@H]4CC[C@H](O)CC4)C3=O)C2)c(Cl)c1]

This compound was prepared by using procedures analogous to those described for the synthesis of example 105 starting from (S)-2-((trans)-4-hydroxycyclohexyl)-2,7-diazaspiro[4.5]decan-1-one which was prepared using procedures analogous to those described in the synthesis of example 472-a and followed by standard hydrogenation to remove the carbobenzyloxy (Cbz) protecting group. LC-MS: 451.1 (M+H)+.

Example 173

N-{5-Chloro-6-[(5S)-2-(trans-4-hydroxycyclohexyl)-1-oxo-2,7-diazaspiro[4.5]dec-7-yl]pyridin-3-yl}acetamide

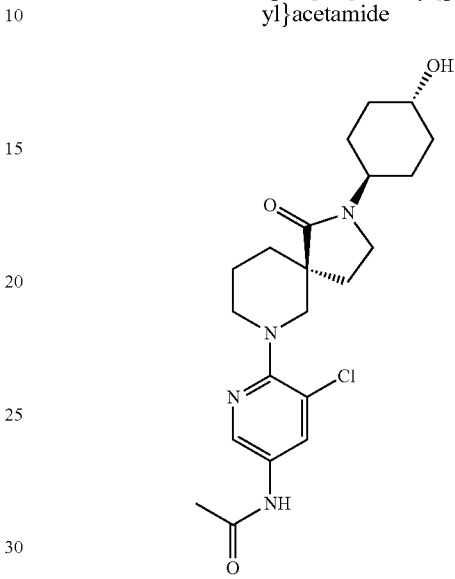

This compound was prepared by using procedures analogous to those described for the synthesis of example 105 starting from (S)-2-((trans)-4-hydroxycyclohexyl)-2,7-diazaspiro[4.5]decan-1-one which was prepared using procedures analogous to those described in the synthesis of example 472-a and followed by standard hydrogenation to remove the carbobenzyloxy (Cbz) protecting group. LC-MS: 421.1 (M+H)+.

Example 174

N-{5-Chloro-6-[(5S)-2-(trans-4-hydroxycyclohexyl)-1-oxo-2,7-diazaspiro[4.5]dec-7-yl]pyridin-3-yl}methanesulfonamide

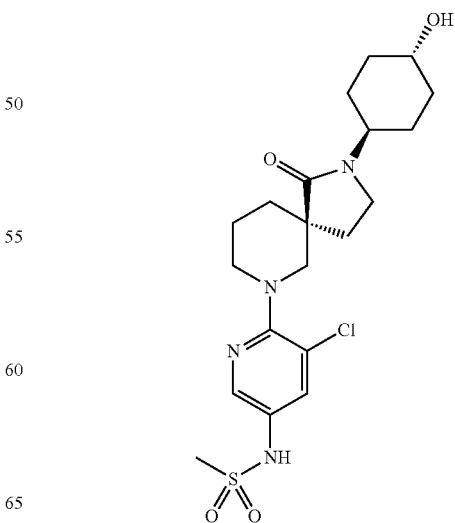

This compound was prepared by using procedures analogous to those described for the synthesis of example 105 starting from (S)-2-((trans)-4-hydroxycyclohexyl)-2,7-diazaspiro[4.5]decan-1-one which was prepared using procedures analogous to those described in the synthesis of example 472-a and followed by standard hydrogenation to remove the carbobenzyloxy (Cbz) protecting group. LC-MS: 457.2 (M+H)$^+$.

Example 175

4-{1-Oxo-7-[5-(trifluoromethyl)pyridin-2-yl]-2,7-diazaspiro[4.5]dec-2-yl}cyclohexanecarbonitrile

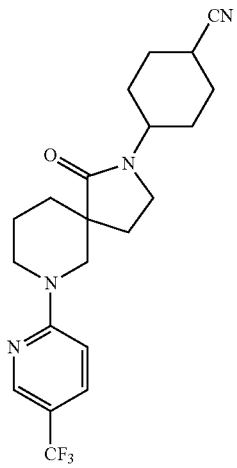 [SMILES: N#CC1CCC(N2CCC3(CCCN(c4ccc(C(F)(F)F)cn4)C3)C2=O)CC1]

This compound was prepared by using procedures analogous to those described for the synthesis of example 93. LC-MS: 407.2 (M+H)$^+$.

Example 176

4-{1-Oxo-7-[4-(trifluoromethyl)phenyl]-2,7-diazaspiro[4.5]dec-2-yl}cyclohexanecarbonitrile

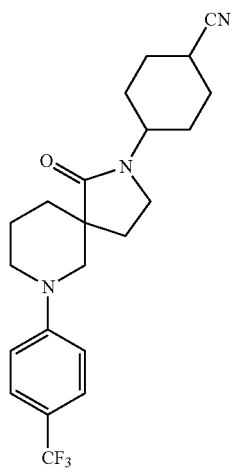 [SMILES: N#CC1CCC(N2CCC3(CCCN(c4ccc(C(F)(F)F)cc4)C3)C2=O)CC1]

This compound was prepared by using procedures analogous to those described for the synthesis of example 93. LC-MS: 406.2 (M+H)$^+$.

Example 177

4-{7-[3-Chloro-5-(trifluoromethyl)pyridin-2-yl]-1-oxo-2,7-diazaspiro[4.5]dec-2-yl}cyclohexanecarbonitrile

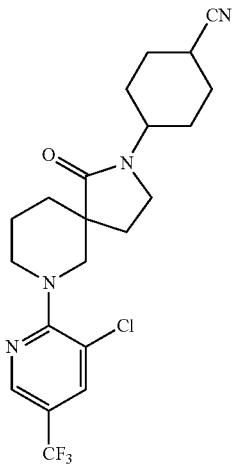 [SMILES: N#CC1CCC(N2CCC3(CCCN(c4ncc(C(F)(F)F)cc4Cl)C3)C2=O)CC1]

This compound was prepared by using procedures analogous to those described for the synthesis of example 93. LC-MS: 441.2 (M+H)$^+$.

Example 178

4-[7-(3,5-Dichloropyridin-2-yl)-1-oxo-2,7-diazaspiro[4.5]dec-2-yl]cyclohexanecarbonitrile

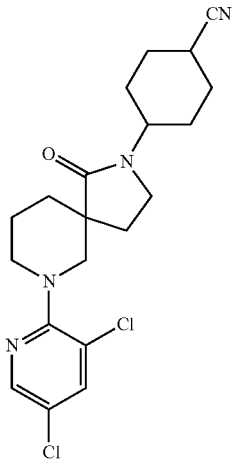 [SMILES: N#CC1CCC(N2CCC3(CCCN(c4ncc(Cl)cc4Cl)C3)C2=O)CC1]

This compound was prepared by using procedures analogous to those described for the synthesis of example 93. LC-MS: 407.2/409.2 (M+H)$^+$.

Example 179

4-[7-(6-Fluoropyridin-2-yl)-1-oxo-2,7-diazaspiro[4.5]dec-2-yl]cyclohexanecarbonitrile

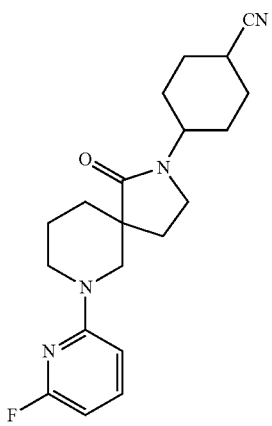 [SMILES: N#CC1CCC(N2CCC3(CCCN(c4cccc(F)n4)C3)C2=O)CC1]

This compound was prepared by using procedures analogous to those described for the synthesis of example 93. LC-MS: 357.1 (M+H)+.

Example 180

(5S)-7-(2-Fluoro-4-methylphenyl)-2-(trans-4-hydroxycyclohexyl)-2,7-diazaspiro[4.5]decan-1-one

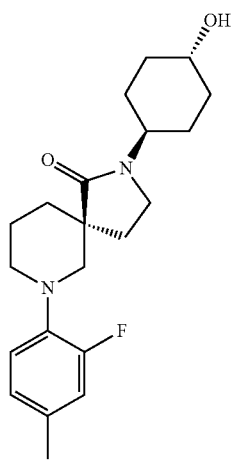 [SMILES: Cc1ccc(N2CCC[C@]3(CCN([C@H]4CC[C@H](O)CC4)C3=O)C2)c(F)c1]

A mixture of (5S)-2-(trans-4-hydroxycyclohexyl)-2,7-diazaspiro[4.5]decan-1-one (20 mg, 0.00007 mol) which was prepared using procedures analogous to those described in the synthesis of example 472-a and followed by standard hydrogenation to remove the carbobenzyloxy (Cbz) protecting and, 4-methyl-2-fluoro-1-iodobenzene (21 mg, 0.00009 mol), sodium tert-butoxide (9.98 mg, 0.000104 mol), 1,4,7,10,13,16-hexaoxacyclooctadecane (27.4 mg, 0.000104 mol), 2-(di-tert-butylphosphino)biphenyl (0.8 mg, 0.000003 mol), tris(dibenzylideneacetone)dipalladium(0) (1 mg, 0.000001 mol), in tert-butyl alcohol (1.0 mL, 0.010 mol) was stirred at rt for 18. The crude product was purified by prep-HPLC to afford the desired product. LC-MS: 361.1 (M+H)+.

Example 181

(5S)-2-(trans-4-Hydroxycyclohexyl)-7-(4-methoxyphenyl)-2,7-diazaspiro[4.5]decan-1-one

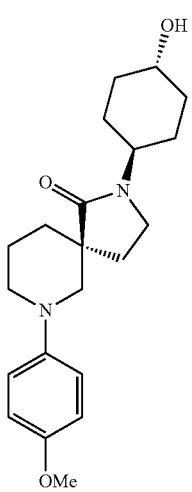 [SMILES: COc1ccc(N2CCC[C@]3(CCN([C@H]4CC[C@H](O)CC4)C3=O)C2)cc1]

This compound was prepared by using procedures analogous to those described for the synthesis of example 180. LC-MS: 359.1 (M+H)+.

Example 182

{4-[(5S)-2-(trans-4-Hydroxycyclohexyl)-1-oxo-2,7-diazaspiro[4.5]dec-7-yl]phenyl}acetonitrile

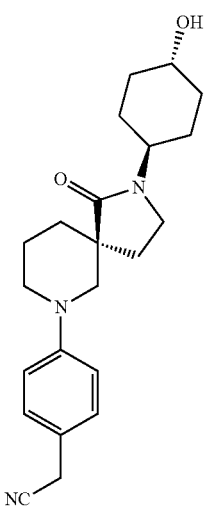 [SMILES: N#CCc1ccc(N2CCC[C@]3(CCN([C@H]4CC[C@H](O)CC4)C3=O)C2)cc1]

This compound was prepared by using procedures analogous to those described for the synthesis of example 180. LC-MS: 368.1 (M+H)+.

Example 183

(5S)-2-(trans-4-Hydroxycyclohexyl)-7-[3-(trifluoromethoxy)phenyl]-2,7-diazaspiro[4.5]decan-1-one

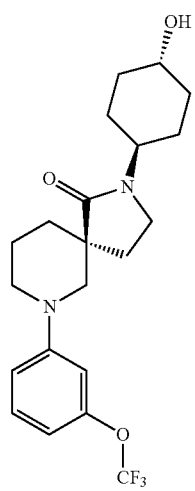 [SMILES: O=C1N([C@H]2CC[C@H](O)CC2)CC[C@]12CCCN(c1cccc(OC(F)(F)F)c1)C2]

This compound was prepared by using procedures analogous to those described for the synthesis of example 180. LC-MS: 413.1 (M+H)$^+$.

Example 184

(5S)-2-(trans-4-Hydroxycyclohexyl)-7-[3-(trifluoromethyl)phenyl]-2,7-diazaspiro[4.5]decan-1-one

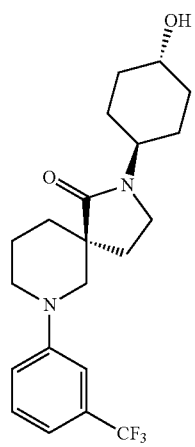 [SMILES: O=C1N([C@H]2CC[C@H](O)CC2)CC[C@]12CCCN(c1cccc(C(F)(F)F)c1)C2]

This compound was prepared by using procedures analogous to those described for the synthesis of example 180. LC-MS: 397.1 (M+H)$^+$.

Example 185

(5S)-2-(trans-4-Hydroxycyclohexyl)-7-[2-(trifluoromethoxy)phenyl]-2,7-diazaspiro[4.5]decan-1-one

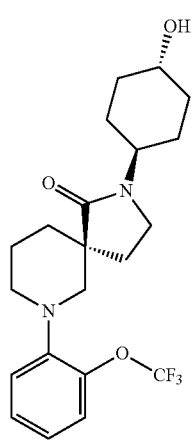 [SMILES: O=C1N([C@H]2CC[C@H](O)CC2)CC[C@]12CCCN(c1ccccc1OC(F)(F)F)C2]

This compound was prepared by using procedures analogous to those described for the synthesis of example 180. LC-MS: 413.1 (M+H)$^+$.

Example 186

(5S)-7-(4-Chloro-2-methylphenyl)-2-(trans-4-hydroxycyclohexyl)-2,7-diazaspiro[4.5]decan-1-one

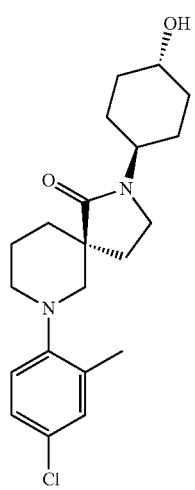

This compound was prepared by using procedures analogous to those described for the synthesis of example 180. LC-MS: 377.1 (M+H)$^+$.

Example 187

(5S)-7-(3-Chloro-2-methylphenyl)-2-(trans-4-hydroxycyclohexyl)-2,7-diazaspiro[4.5]decan-1

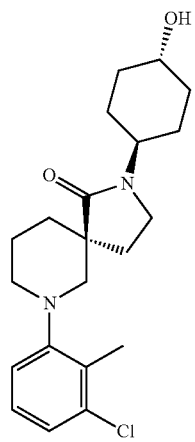 [SMILES: Cc1c(Cl)cccc1N1CCC[C@]2(CCN([C@H]3CC[C@H](O)CC3)C2=O)C1]

This compound was prepared by using procedures analogous to those described for the synthesis of example 180. LC-MS: 377.1 (M+H)$^+$.

Example 188

(5S)-7-(2-Chloro-4-methylphenyl)-2-(trans-4-hydroxycyclohexyl)-2,7-diazaspiro[4.5]decan-1-one

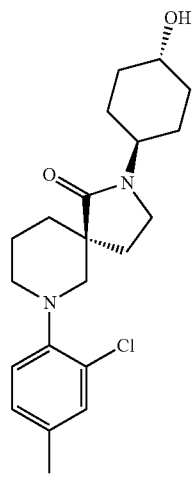 [SMILES: Cc1ccc(N2CCC[C@]3(CCN([C@H]4CC[C@H](O)CC4)C3=O)C2)c(Cl)c1]

A mixture of (5S)-2-(trans-4-hydroxycyclohexyl)-2,7-diazaspiro[4.5]decan-1-one (20 mg, 0.00007 mol) which was prepared using procedures analogous to those described in the synthesis of example 472-a and followed by standard hydrogenation to remove the carbobenzyloxy (Cbz) protecting group and 2-chloro-1-iodo-4-methylbenzene (22.7 mg, 0.0000831 mol), potassium carbonate (20.1 mg, 0.000145 mol), copper(I) iodide (0.6 mg, 0.000003 mol), and (1S,2S)-cyclohexane-1,2-diol (16.1 mg, 0.000138 mol) in tert-butyl alcohol (1.0 mL, 0.010 mol) was heated at 100° C. for 18 h. The crude product was purified by prep-HPLC to afford the desired product. LC-MS: 377.1 (M+H)$^+$.

Example 189

2-Fluoro-6-[(5S)-2-(trans-4-hydroxycyclohexyl)-1-oxo-2,7-diazaspiro[4.5]dec-7-yl]benzonitrile

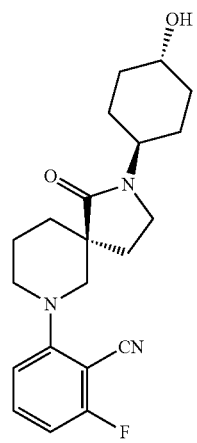

This compound was prepared by using procedures analogous to those described for the synthesis of example 188. LC-MS: 372.1 (M+H)$^+$.

Example 190

(5S)-7-(2,5-Dichlorophenyl)-2-(trans-4-hydroxycyclohexyl)-2,7-diazaspiro[4.5]decan-1-one

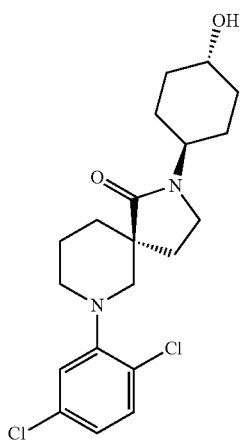 [SMILES: O=C1N([C@H]2CC[C@H](O)CC2)CC[C@]12CCCN(c1cc(Cl)ccc1Cl)C2]

This compound was prepared by using procedures analogous to those described for the synthesis of example 188. LC-MS: 397.2/399.2 (M+H)$^+$.

Example 191

(5S)-7-(2,3-Dichlorophenyl)-2-(trans-4-hydroxycyclohexyl)-2,7-diazaspiro[4.5]decan-1-one

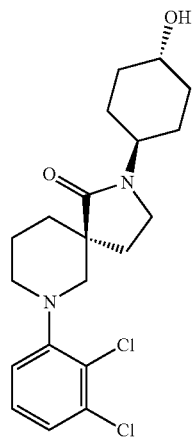 [SMILES: O=C1N([C@H]2CC[C@H](O)CC2)CC[C@]12CCCN(c1cccc(Cl)c1Cl)C2]

This compound was prepared by using procedures analogous to those described for the synthesis of example 188. LC-MS: 397.2/399.2 (M+H)+.

Example 192

(5S)-7-(3,5-Difluoro phenyl)-2-(trans-4-hydroxycyclohexyl)-2,7-diazaspiro[4.5]decan-1-one

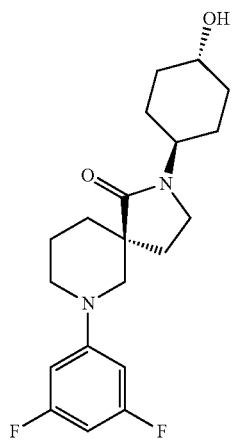 [SMILES: O=C1N([C@H]2CC[C@H](O)CC2)CC[C@]12CCCN(c1cc(F)cc(F)c1)C2]

This compound was prepared by using procedures analogous to those described for the synthesis of example 188. LC-MS: 365.1 (M+H)+.

Example 193

(5S)-7-(4-Chloro-2-methylphenyl)-2-(trans-4-hydroxycyclohexyl)-2,7-diazaspiro[4.5]decan-1-one

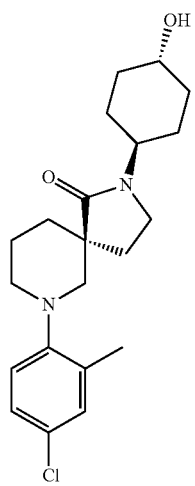

This compound was prepared by using procedures analogous to those described for the synthesis of example 188. LC-MS: 377.1 (M+H)+.

Example 194

(5S)-7-(3-Chloro-2-methylphenyl)-2-(trans-4-hydroxycyclohexyl)-2,7-diazaspiro[4.5]decan-1-one

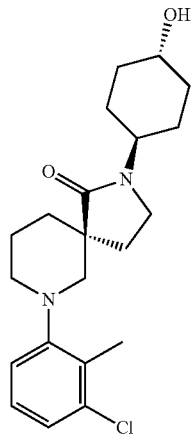 [SMILES: Cc1c(Cl)cccc1N1CCC[C@]2(CCN([C@H]3CC[C@H](O)CC3)C2=O)C1]

This compound was prepared by using procedures analogous to those described for the synthesis of example 188. LC-MS: 377.1 (M+H)+.

Example 195

(5S)-7-(2,6-Dichlorophenyl)-2-(trans-4-hydroxycyclohexyl)-2,7-diazaspiro[4.5]decan-1-one

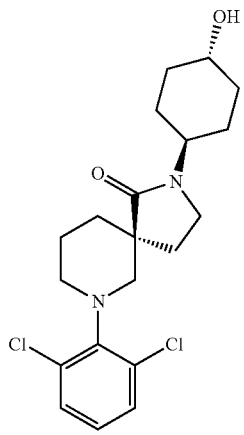 [SMILES: O=C1N([C@H]2CC[C@H](O)CC2)CC[C@]12CCCN(c1c(Cl)cccc1Cl)C2]

This compound was prepared by using procedures analogous to those described for the synthesis of example 188. LC-MS: 397.2/399.2 (M+H)$^+$.

Example 196

3-[(5S)-2-(trans-4-Hydroxycyclohexyl)-1-oxo-2,7-diazaspiro[4.5]dec-7-yl]benzonitrile

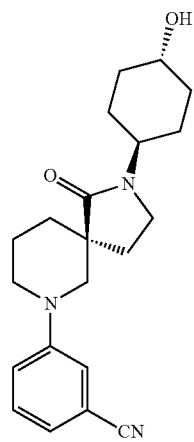

This compound was prepared by using procedures analogous to those described for the synthesis of example 188. LC-MS: 354.2 (M+H)$^+$.

Example 197

(5S)-7-(2-Fluorophenyl)-2-(trans-4-hydroxycyclohexyl)-2,7-diazaspiro[4.5]decan-1-one

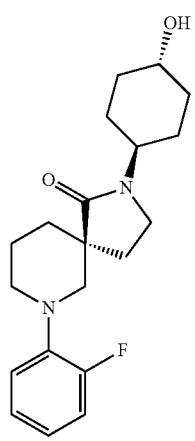 [SMILES: O=C1N([C@H]2CC[C@H](O)CC2)CC[C@]12CCCN(c1ccccc1F)C2]

This compound was prepared by using procedures analogous to those described for the synthesis of example 180. LC-MS: 347.1 (M+H)$^+$.

Example 198

(5S)-7-(2-Chlorophenyl)-2-(trans-4-hydroxycyclohexyl)-2,7-diazaspiro[4.5]decan-1-one This compound was prepared by using procedures analogous to those described for the synthesis of example 180. LC-MS: 363.1 (M+H)$^+$.

Example 199

(5S)-7-(4-Chloro-2-fluorophenyl)-2-(trans-4-hydroxycyclohexyl)-2,7-diazaspiro[4.5]decan-1-one

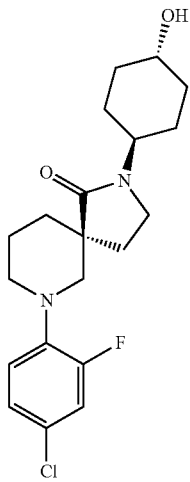 [SMILES: O=C1N([C@H]2CC[C@H](O)CC2)CC[C@]12CCCN(c1ccc(Cl)cc1F)C2]

This compound was prepared by using procedures analogous to those described for the synthesis of example 180. LC-MS: 381.1 (M+H)+.

Example 200

(5S)-7-(2,4-Difluorophenyl)-2-(trans-4-hydroxycyclohexyl)-2,7-diazaspiro[4.5]decan-1-one

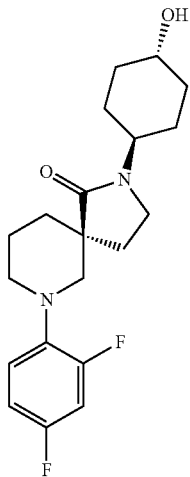 [SMILES: O=C1N([C@H]2CC[C@H](O)CC2)CC[C@]12CCCN(c1ccc(F)cc1F)C2]

This compound was prepared by using procedures analogous to those described for the synthesis of example 180. LC-MS: 365.1 (M+H)+.

Example 201

(5S)-7-(3-Chloro-2-fluorophenyl)-2-(trans-4-hydroxycyclohexyl)-2,7-diazaspiro[4.5]decan-1-one

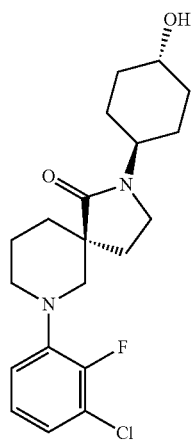

This compound was prepared by using procedures analogous to those described for the synthesis of example 180. LC-MS: 381.1 (M+H)+.

Example 202

(trans-4-{1-Oxo-7-[5-(trifluoromethyl)pyridin-2-yl]-2,7-diazaspiro[4.5]dec-2-yl}cyclohexyl)acetonitrile

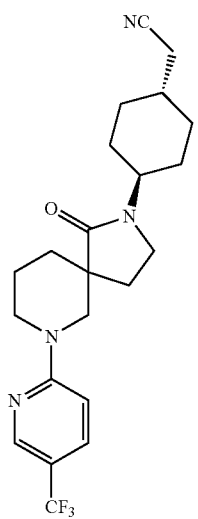 [SMILES: N#CC[C@H]1CC[C@H](N2CCC3(CCCN(c4ccc(C(F)(F)F)cn4)C3)C2=O)CC1]

This compound was prepared by using procedures analogous to those described for the synthesis of example 93. LC-MS: 421.1 (M+H)+.

Example 203

(trans-4-{1-Oxo-7-[4-(trifluoromethyl)phenyl]-2,7-diazaspiro[4.5]dec-2-yl}cyclohexyl)acetonitrile

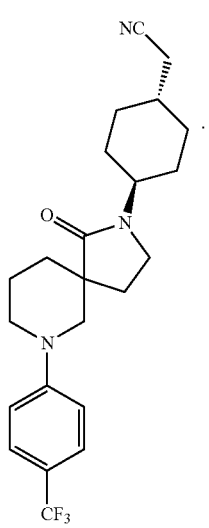 [SMILES: N#CC[C@H]1CC[C@H](N2CCC3(CCCN(c4ccc(C(F)(F)F)cc4)C3)C2=O)CC1]

This compound was prepared by using procedures analogous to those described for the synthesis of example 93. LC-MS: 420.1 (M+H)$^+$.

Example 204

(trans-4-{7-[3-Chloro-5-(trifluoromethyl)pyridin-2-yl]-1-oxo-2,7-diazaspiro[4.5]dec-2-yl}cyclohexyl)acetonitrile

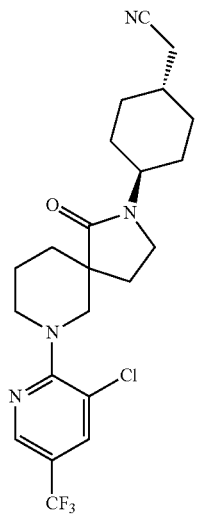

This compound was prepared by using procedures analogous to those described for the synthesis of example 93. LC-MS: 455.1 (M+H)$^+$.

Example 205

{trans-4-[7-(3,5-Dichloropyridin-2-yl)-1-oxo-2,7-diazaspiro[4.5]dec-2-yl]cyclohexyl}acetonitrile

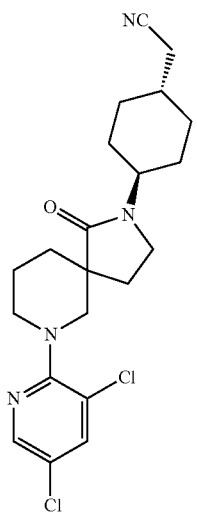 [SMILES: N#CC[C@H]1CC[C@H](N2CCC3(CCCN(c4ncc(Cl)cc4Cl)C3)C2=O)CC1]

This compound was prepared by using procedures analogous to those described for the synthesis of example 93. LC-MS: 421.1 (M+H)$^+$.

Example 206

{trans-4-[7-(6-Fluoropyridin-2-yl)-1-oxo-2,7-diazaspiro[4.5]dec-2-yl]cyclohexyl}acetonitrile

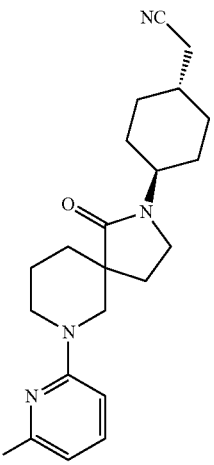

This compound was prepared by using procedures analogous to those described for the synthesis of example 93. LC-MS: 371.1 (M+H)$^+$.

Example 207

(5S)-2-(trans-4-Hydroxycyclohexyl)-7-(3,5,6-trifluoropyridin-2-yl)-2,7-diazaspiro[4.5]decan-1-one

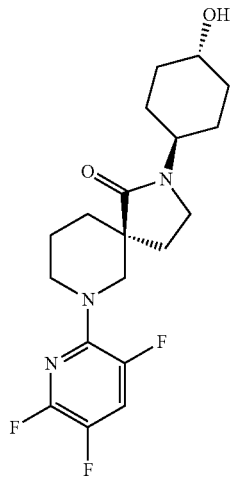 [SMILES: O=C1N([C@H]2CC[C@H](O)CC2)CC[C@]12CCCN(c1nc(F)c(F)cc1F)C2]

This compound was prepared by using procedures analogous to those described for the synthesis of example 93 starting from (5S)-2-(trans-4-hydroxycyclohexyl)-2,7-diazaspiro[4.5]decan-1-one. LC-MS: 384.1 (M+H)$^+$.

Example 208

(5S)-7-(4,6-Dimethoxypyrimidin-2-yl)-2-(trans-4-hydroxycyclohexyl)-2,7-diazaspiro[4.5]decan-1-one

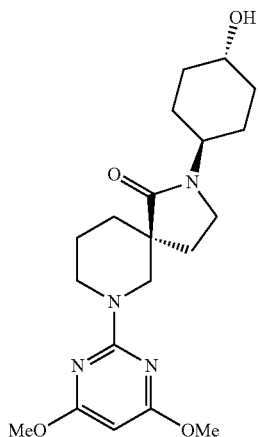 [SMILES: COc1cc(OC)nc(N2CCC[C@]3(CCN([C@H]4CC[C@H](O)CC4)C3=O)C2)n1]

This compound was prepared by using procedures analogous to those described for the synthesis of example 93 starting from (5S)-2-(trans-4-hydroxycyclohexyl)-2,7-diazaspiro[4.5]decan-1-one LC-MS: 391.1 (M+H)$^+$.

Example 209

(5S)-7-[4-Fluoro-5-(trifluoromethyl)pyrimidin-2-yl]-2-(trans-4-hydroxycyclohexyl)-2,7-diazaspiro[4.5]decan-1-one

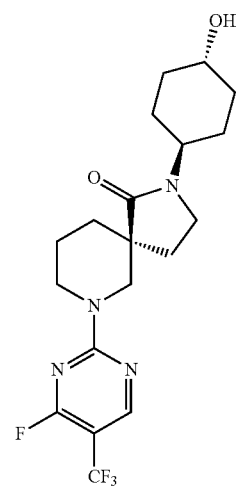 [SMILES: O=C1N([C@H]2CC[C@H](O)CC2)CC[C@]12CCCN(c1ncc(C(F)(F)F)c(F)n1)C2]

This compound was prepared by using procedures analogous to those described for the synthesis of example 93 starting from (5S)-2-(trans-4-hydroxycyclohexyl)-2,7-diazaspiro[4.5]decan-1-one. LC-MS: 417.1 (M+H)$^+$.

Example 210

(5S)-7-(2,5-Difluorophenyl)-2-(trans-4-hydroxycyclohexyl)-2,7-diazaspiro[4.5]decan-1-one

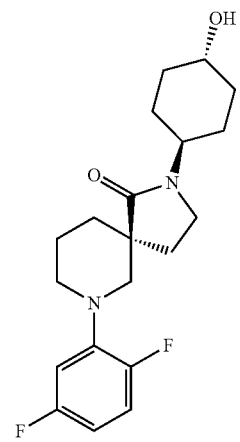 [SMILES: O=C1N([C@H]2CC[C@H](O)CC2)CC[C@]12CCCN(c1cc(F)ccc1F)C2]

This compound was prepared by using procedures analogous to those described for the synthesis of example 180. LC-MS: 365.1 (M+H)$^+$.

Example 211

(5S)-7-[2-(Difluoromethoxy)phenyl]-2-(trans-4-hydroxycyclohexyl)-2,7-diazaspiro[4.5]decan-1-one

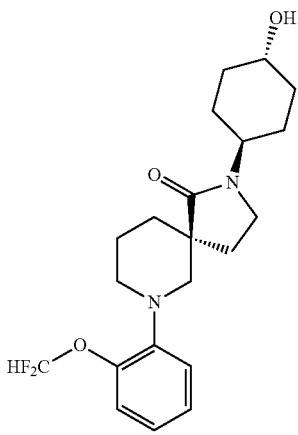

This compound was prepared by using procedures analogous to those described for the synthesis of example 180. LC-MS: 395.1 (M+H)$^+$.

Example 212

(5S)-7-(4-Fluoropyrimidin-2-yl)-2-(trans-4-hydroxycyclohexyl)-2,7-diazaspiro[4.5]decan-1-one

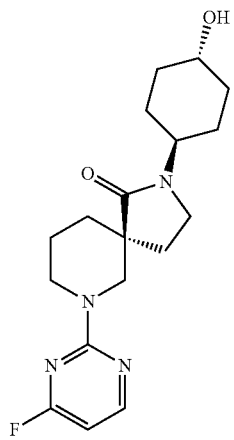 [SMILES: O=C1N([C@H]2CC[C@H](O)CC2)CC[C@]12CCCN(c1nccc(F)n1)C2]

This compound was prepared by using procedures analogous to those described for the synthesis of example 93 starting from (5S)-2-(trans-4-hydroxycyclohexyl)-2,7-diazaspiro[4.5]decan-1-one. LC-MS: 349.1 (M+H)$^+$.

Example 213

(5S)-7-[4-Chloro-5-(trifluoromethyl)pyrimidin-2-yl]-2-(trans-4-hydroxycyclohexyl)-2,7-diazaspiro[4.5]decan-1-one

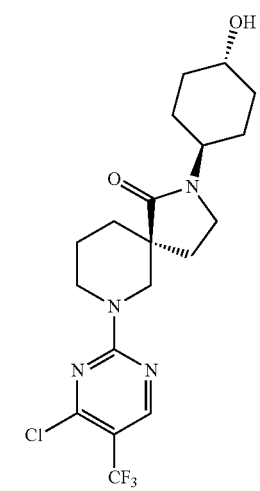 [SMILES: O=C1N([C@H]2CC[C@H](O)CC2)CC[C@]12CCCN(c1ncc(C(F)(F)F)c(Cl)n1)C2]

This compound was prepared by using procedures analogous to those described for the synthesis of example 93 starting from (5S)-2-(trans-4-hydroxycyclohexyl)-2,7-diazaspiro[4.5]decan-1-one. LC-MS: 433.1 (M+H)$^+$.

Example 214

(5S)-2-(trans-4-Hydroxycyclohexyl)-7-quinazoline-4-yl-2,7-diazaspiro[4.5]decan-1-one

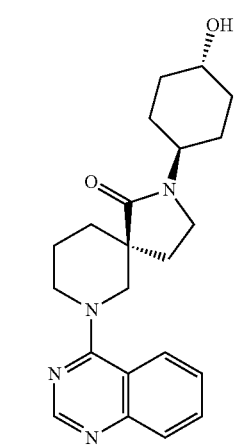 [SMILES: O=C1N([C@H]2CC[C@H](O)CC2)CC[C@]12CCCN(c1ncnc3ccccc13)C2]

This compound was prepared by using procedures analogous to those described for the synthesis of example 93 starting from (5S)-2-(trans-4-hydroxycyclohexyl)-2,7-diazaspiro[4.5]decan-1-one. LC-MS: 381.1 (M+H)$^+$.

Example 215

(5S)-2-(trans-4-Hydroxycyclohexyl)-7-(6-methoxy-pyridin-3-yl)-2,7-diazaspiro[4.5]decan-1-one

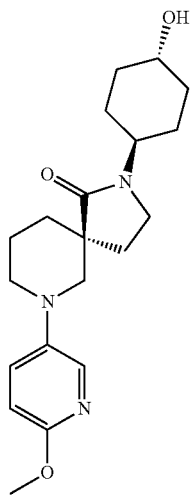 [SMILES: COc1ccc(N2CCC[C@]3(CCN([C@H]4CC[C@H](O)CC4)C3=O)C2)cn1]

This compound was prepared by using procedures analogous to those described for the synthesis of example 180. LC-MS: 360.1 (M+H)+.

Example 216

(5S)-2-(trans-4-Hydroxycyclohexyl)-7-[6-(methylamino)-9H-purin-2-yl]-2,7-diazaspiro[4.5]decan-1-one

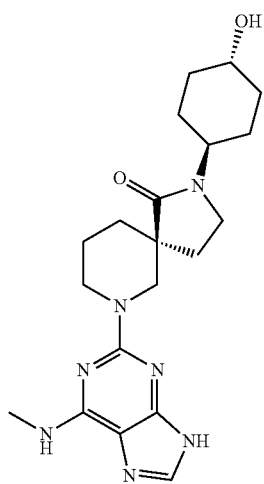 [SMILES: CNc1nc(N2CCC[C@]3(CCN([C@H]4CC[C@H](O)CC4)C3=O)C2)nc2[nH]cnc12]

This compound was prepared by using procedures analogous to those described for the synthesis of example 93 starting from (5S)-2-(trans-4-hydroxycyclohexyl)-2,7-diazaspiro[4.5]decan-1-one. LC-MS: 400.1 (M+H)+.

Example 218-a

7-{[4-(2-Chlorophenyl)piperazin-1-yl]carbonyl}-2-(trans-4-hydroxycyclohexyl)-2,7-diazaspiro[4.5]decan-1-one

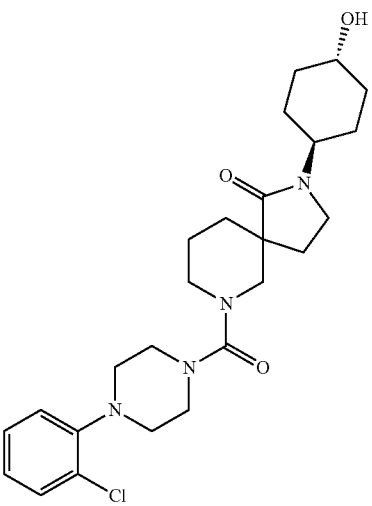 [SMILES: O=C(N1CCN(c2ccccc2Cl)CC1)N1CCCC2(CCN([C@H]3CC[C@H](O)CC3)C2=O)C1]

This compound was prepared by using procedures analogous to those described for the synthesis of example 48. LC-MS: 475.1 (M+H)+.

Example 218-b 2-(trans-4-Hydroxycyclohexyl)-7-({4-[2-(trifluoromethyl)quinolin-4-yl]piperazin-1-yl}carbonyl)-2,7-diazaspiro[4.5]decan-1-one

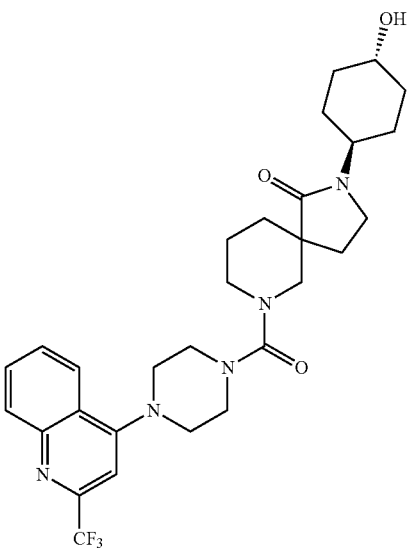 [SMILES: O=C(N1CCN(c2cc(C(F)(F)F)nc3ccccc23)CC1)N1CCCC2(CCN([C@H]3CC[C@H](O)CC3)C2=O)C1]

This compound was prepared by using procedures analogous to those described for the synthesis of example 48. LC-MS: 560.1 (M+H)+.

Example 219

2-(trans-4-Hydroxycyclohexyl)-7-({4-[3-(trifluoromethyl)pyridin-2-yl]piperazin-1-yl}carbonyl)-2,7-diazaspiro[4.5]decan-1-one

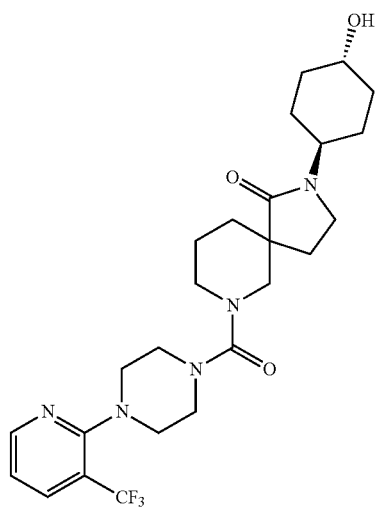 [SMILES: O=C(N1CCN(c2ncccc2C(F)(F)F)CC1)N1CCCC2(CCN([C@H]3CC[C@H](O)CC3)C2=O)C1]

This compound was prepared by using procedures analogous to those described for the synthesis of example 48. LC-MS: 510.1 (M+H)$^+$.

Example 220

2-(trans-4-Hydroxycyclohexyl)-7-{[4-(2-methylphenyl)piperazin-1-yl]carbonyl}-2,7-diazaspiro[4.5]decan-1-one

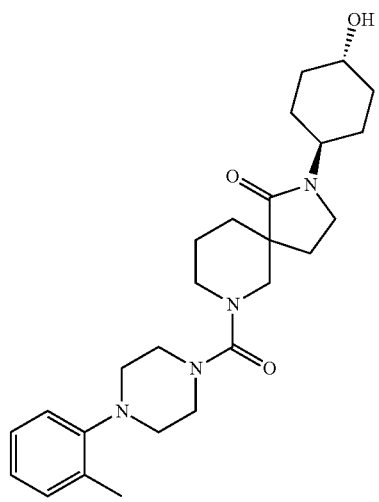 [SMILES: Cc1ccccc1N1CCN(C(=O)N2CCCC3(CCN([C@H]4CC[C@H](O)CC4)C3=O)C2)CC1]

This compound was prepared by using procedures analogous to those described for the synthesis of example 48. LC-MS: 455.1 (M+H)$^+$.

Example 221

7-{[4-(3,4-Dichlorophenyl)piperazin-1-yl]carbonyl}-2-(trans-4-hydroxycyclohexyl)-2,7-diazaspiro[4.5]decan-1-one

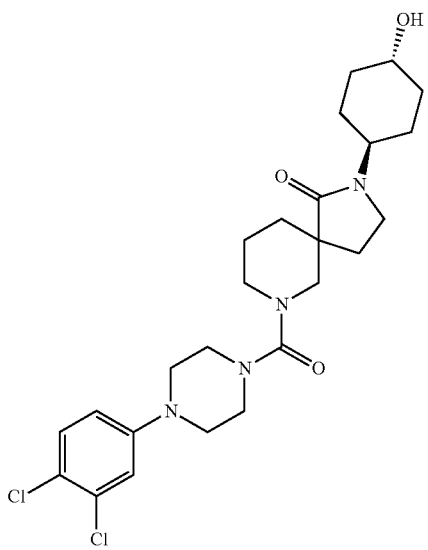 [SMILES: O=C(N1CCN(c2ccc(Cl)c(Cl)c2)CC1)N1CCCC2(CCN([C@H]3CC[C@H](O)CC3)C2=O)C1]

This compound was prepared by using procedures analogous to those described for the synthesis of example 48. LC-MS: 509.1 (M+H)$^+$.

Example 222

2-(trans-4-Hydroxycyclohexyl)-7-({4-[3-(trifluoromethyl)phenyl]piperazin-1-yl}carbonyl)-2,7-diazaspiro[4.5]decan-1-one

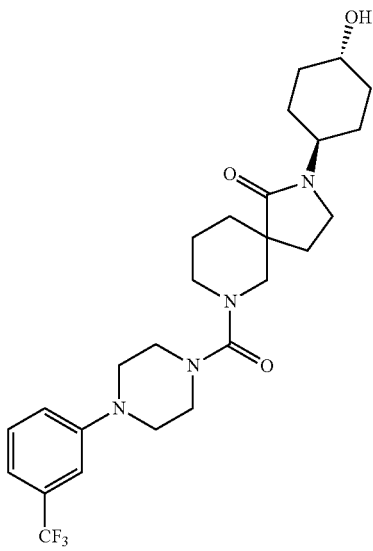 [SMILES: O=C(N1CCN(c2cccc(C(F)(F)F)c2)CC1)N1CCCC2(CCN([C@H]3CC[C@H](O)CC3)C2=O)C1]

This compound was prepared by using procedures analogous to those described for the synthesis of example 48. LC-MS: 509.1 (M+H)$^+$.

Example 223

7-[(4-Biphenyl-4-ylpiperazin-1-yl)carbonyl]-2-(trans-4-hydroxycyclohexyl)-2,7-diazaspiro[4.5]decan-1-one

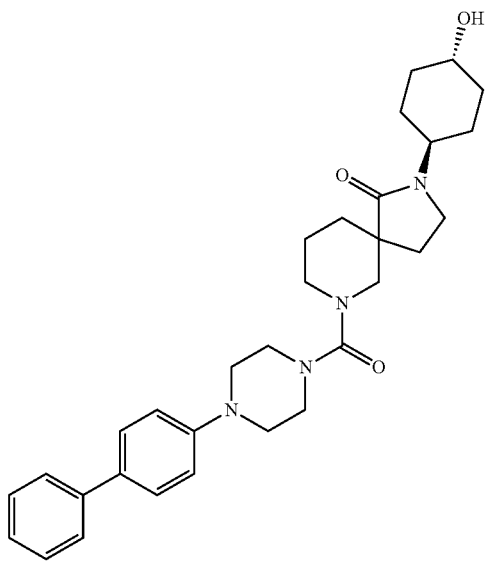 [SMILES: O=C(N1CCN(c2ccc(-c3ccccc3)cc2)CC1)N1CCCC2(CCN([C@H]3CC[C@H](O)CC3)C2=O)C1]

This compound was prepared by using procedures analogous to those described for the synthesis of example 48. LC-MS: 517.1 (M+H)+.

Example 224

2-(trans-4-Hydroxycyclohexyl)-7-({4-[5-(trifluoromethyl)pyridin-2-yl]piperazin-1-yl}carbonyl)-2,7-diazaspiro[4.5]decan-1-one

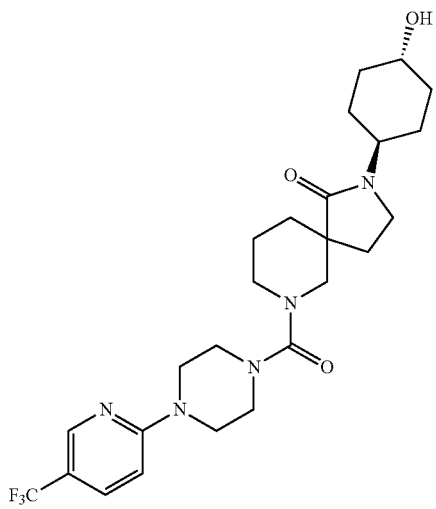 [SMILES: O=C(N1CCN(c2ccc(C(F)(F)F)cn2)CC1)N1CCCC2(CCN([C@H]3CC[C@H](O)CC3)C2=O)C1]

This compound was prepared by using procedures analogous to those described for the synthesis of example 48. LC-MS: 510.1 (M+H)+.

Example 225

2-(trans-4-Hydroxycyclohexyl)-7-{[4-(2-methoxyphenyl)piperazin-1-yl]carbonyl}-2,7-diazaspiro[4.5]decan-1-one

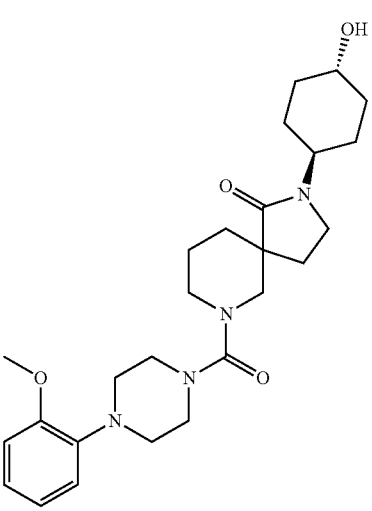 [SMILES: COc1ccccc1N1CCN(C(=O)N2CCCC3(CCN([C@H]4CC[C@H](O)CC4)C3=O)C2)CC1]

This compound was prepared by using procedures analogous to those described for the synthesis of example 48. LC-MS: 471.1 (M+H)+.

Example 226

2-(trans-4-Hydroxycyclohexyl)-7-[(4-pyridin-2-ylpiperazin-1-yl)carbonyl]-2,7-diazaspiro[4.5]decan-1-one

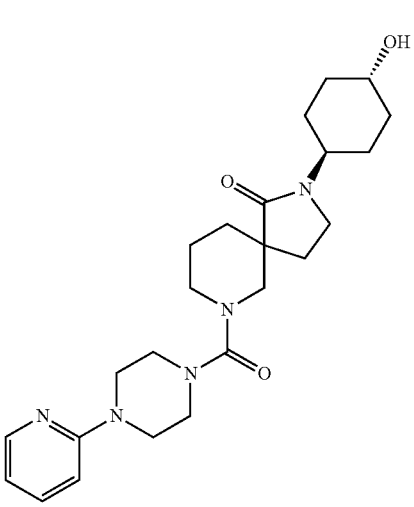

This compound was prepared by using procedures analogous to those described for the synthesis of example 48. LC-MS: 442.1 (M+H)+.

Example 227

7-{[4-(4-Chlorophenyl)piperazin-1-yl]carbonyl}-2-(trans-4-hydroxycyclohexyl)-2,7-diazaspiro[4.5]decan-1-one

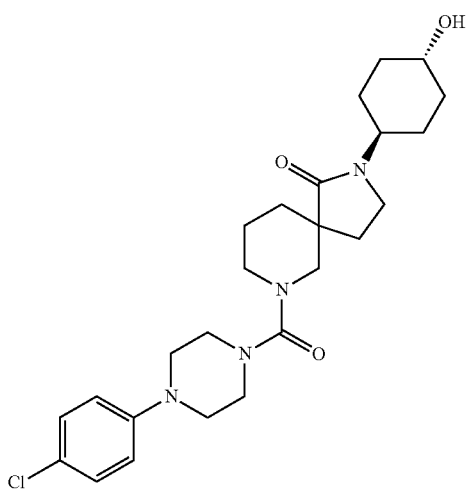 [SMILES: O=C(N1CCN(c2ccc(Cl)cc2)CC1)N1CCCC2(CCN([C@H]3CC[C@H](O)CC3)C2=O)C1]

This compound was prepared by using procedures analogous to those described for the synthesis of example 48. LC-MS: 475.1 (M+H)$^+$.

Example 228

7-{[4-(2-Ethoxyphenyl)piperazin-1-yl]carbonyl}-2-(trans-4-hydroxycyclohexyl)-2,7-diazaspiro[4.5]decan-1-one

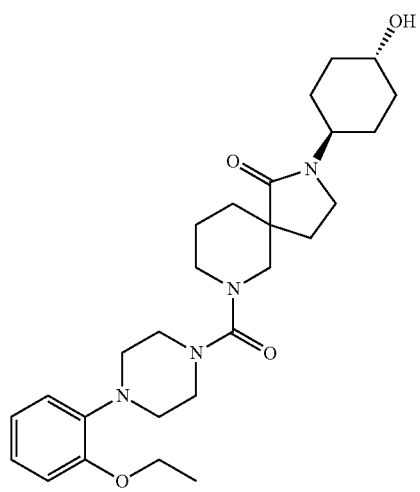 [SMILES: CCOc1ccccc1N1CCN(C(=O)N2CCCC3(CCN([C@H]4CC[C@H](O)CC4)C3=O)C2)CC1]

This compound was prepared by using procedures analogous to those described for the synthesis of example 48. LC-MS: 485.1 (M+H)$^+$.

Example 229

2-(trans-4-Hydroxycyclohexyl)-7-{[4-(3-methoxyphenyl)piperazin-1-yl]carbonyl}-2,7-diazaspiro[4.5]decan-1-one

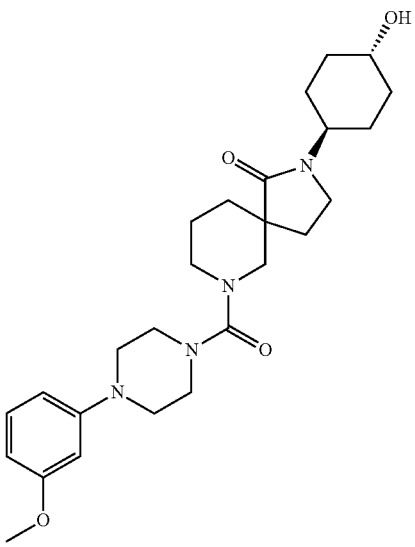 [SMILES: COc1cccc(N2CCN(C(=O)N3CCCC4(CCN([C@H]5CC[C@H](O)CC5)C4=O)C3)CC2)c1]

This compound was prepared by using procedures analogous to those described for the synthesis of example 48. LC-MS: 471.1 (M+H)$^+$.

Example 230

2-(trans-4-Hydroxycyclohexyl)-7-{[4-(3-methylphenyl)piperazin-1-yl]carbonyl}-2,7-diazaspiro[4.5]decan-1-one

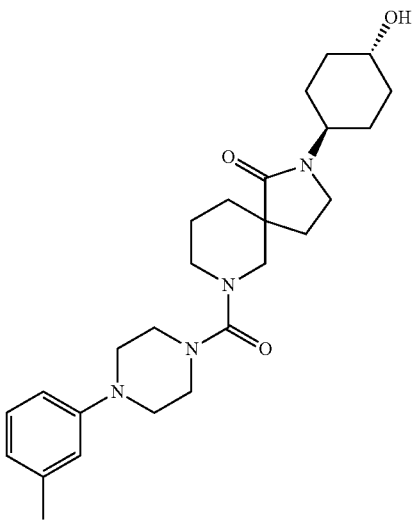 [SMILES: Cc1cccc(N2CCN(C(=O)N3CCCC4(CCN([C@H]5CC[C@H](O)CC5)C4=O)C3)CC2)c1]

This compound was prepared by using procedures analogous to those described for the synthesis of example 48. LC-MS: 455.1 (M+H)$^+$.

Example 231

7-{[4-(3-Chlorophenyl)piperazin-1-yl]carbonyl}-2-(trans-4-hydroxycyclohexyl)-2,7-diazaspiro[4.5]decan-1-one

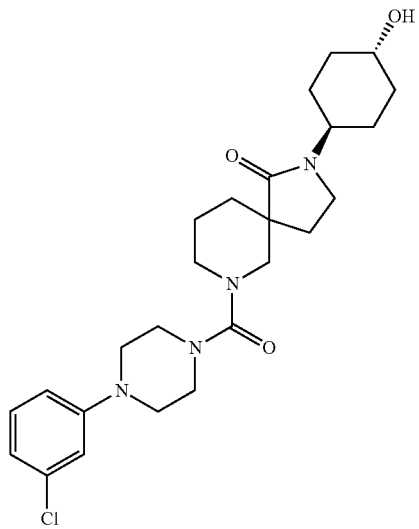 [SMILES: O=C(N1CCN(c2cccc(Cl)c2)CC1)N1CCCC2(CCN([C@H]3CC[C@H](O)CC3)C2=O)C1]

This compound was prepared by using procedures analogous to those described for the synthesis of example 48. LC-MS: 475.1 (M+H)$^+$.

Example 232

2-(trans-4-Hydroxycyclohexyl)-7-{[4-(4-methoxyphenyl)piperazin-1-yl]carbonyl}-2,7-diazaspiro[4.5]decan-1-one

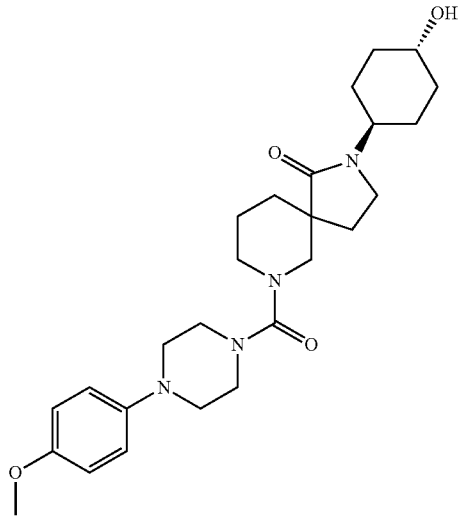 [SMILES: COc1ccc(N2CCN(C(=O)N3CCCC4(CCN([C@H]5CC[C@H](O)CC5)C4=O)C3)CC2)cc1]

This compound was prepared by using procedures analogous to those described for the synthesis of example 48. LC-MS: 471.1 (M+H)$^+$.

Example 233

4-(4-{[2-(trans-4-Hydroxycyclohexyl)-1-oxo-2,7-diazaspiro[4.5]dec-7-yl]carbonyl}piperazin-1-yl)benzonitrile

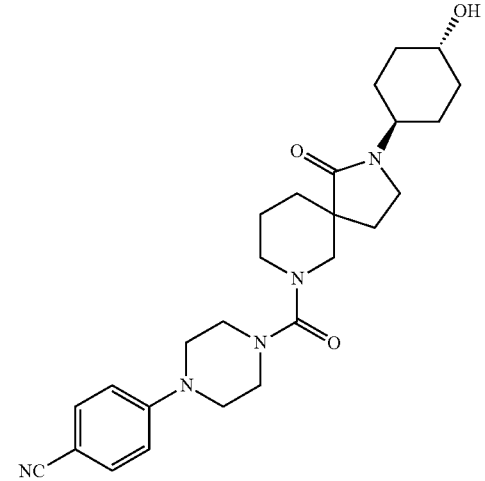 [SMILES: N#Cc1ccc(N2CCN(C(=O)N3CCCC4(CCN([C@H]5CC[C@H](O)CC5)C4=O)C3)CC2)cc1]

This compound was prepared by using procedures analogous to those described for the synthesis of example 48. LC-MS: 466.1 (M+H)$^+$.

Example 234

7-{[4-(3,5-Dichloropyridin-4-yl)piperazin-1-yl]carbonyl}-2-(trans-4-hydroxycyclohexyl)-2,7-diazaspiro[4.5]decan-1-one

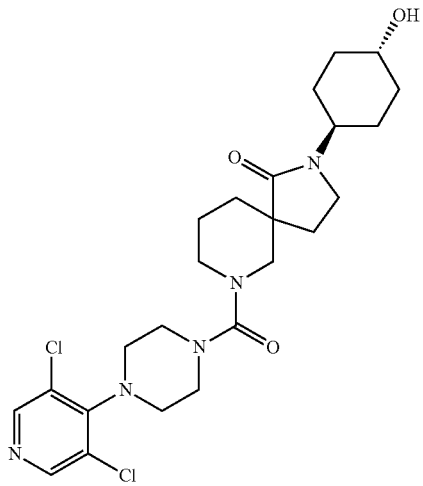 [SMILES: O=C(N1CCN(c2c(Cl)cncc2Cl)CC1)N1CCCC2(CCN([C@H]3CC[C@H](O)CC3)C2=O)C1]

This compound was prepared by using procedures analogous to those described for the synthesis of example 48. LC-MS: 510.1 (M+H)$^+$.

Example 235

(5S)-2-(trans-4-Hydroxycyclohexyl)-7-(1,3-thiazol-2-yl)-2,7-diazaspiro[4.5]decan-1-one

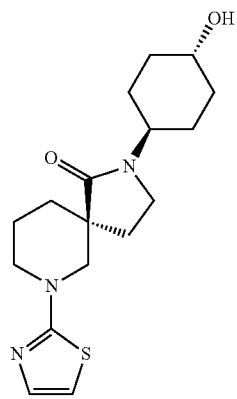 [SMILES: O=C1N([C@H]2CC[C@H](O)CC2)CC[C@]12CCCN(c1nccs1)C2]

This compound was prepared by using procedures analogous to those described for the synthesis of example 93 starting from (5S)-2-(trans-4-hydroxycyclohexyl)-2,7-diazaspiro[4.5]decan-1-one. LC-MS: 336.2 (M+H)⁺.

Example 236

2-(trans-4-Hydroxycyclohexyl)-7-({4-[4-(trifluoromethyl)phenyl]piperazin-1-yl}carbonyl)-2,7-diazaspiro[4.5]decan-1-one

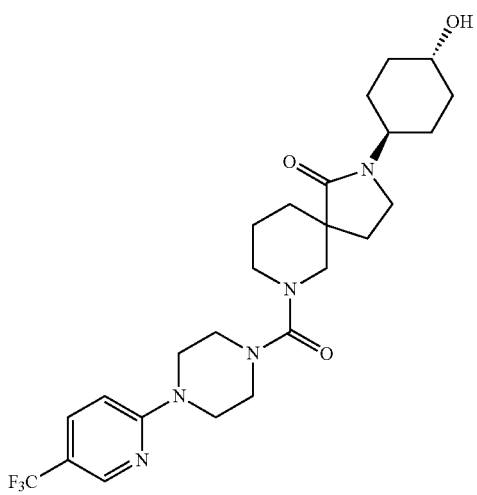 [SMILES: O=C(N1CCN(c2ccc(C(F)(F)F)cn2)CC1)N1CCCC2(CCN([C@H]3CC[C@H](O)CC3)C2=O)C1]

This compound was prepared by using procedures analogous to those described for the synthesis of example 48. LC-MS: 509.1 (M+H)⁺.

Example 237

7-(3,5-Dichloropyridin-2-yl)-2-(4-hydroxy-1-adamantyl)-2,7-diazaspiro[4.5]decan-1-one

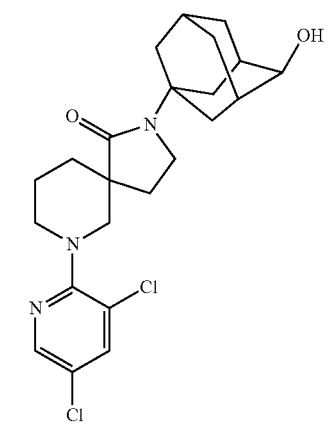

and

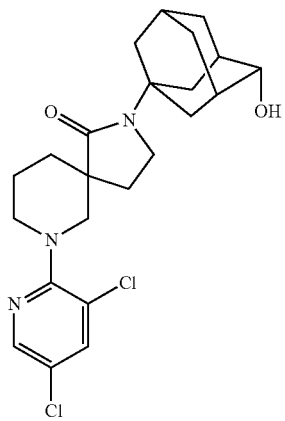

This compound was prepared by using procedures analogous to those described for the synthesis of example 93. LC-MS: 451.1 (M+H)⁺.

Example 238

Propyl {3-fluoro-4-[2-(4-hydroxy-1-adamantyl)-1-oxo-2,7-diazaspiro[4.5]dec-7-yl]phenyl}carbamate

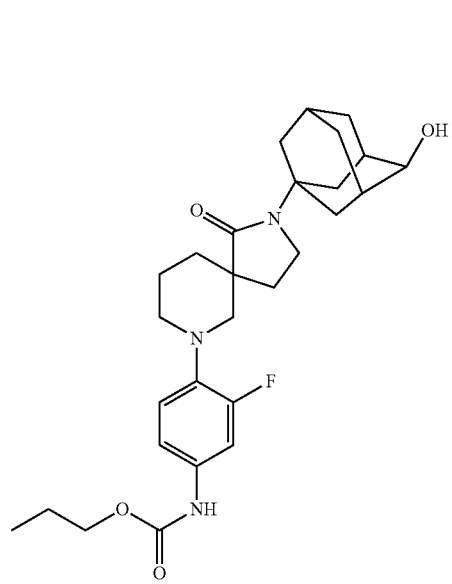

and

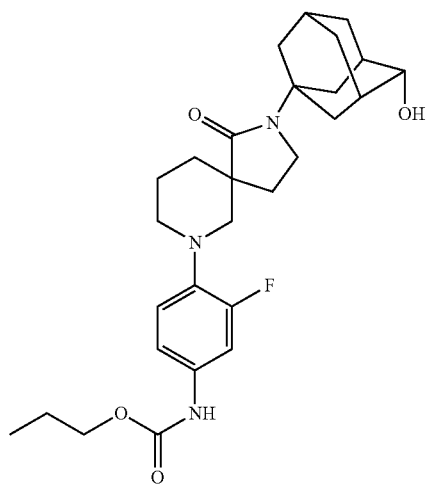

This compound was prepared by using procedures analogous to those described for the synthesis of example 105 starting from 2-(4-hydroxy-1-adamantyl)-2,7-diazaspiro[4.5]decan-1-one. LC-MS: 500.2 (M+H)+.

Example 239

2-(4-Hydroxy-1-adamantyl)-7-[3-(trifluoromethyl)pyridin-2-yl]-2,7-diazaspiro[4.5]decan-1-one

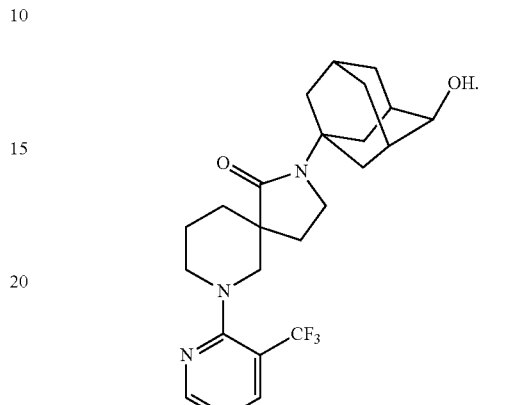

and

This compound was prepared by using procedures analogous to those described for the synthesis of example 93. LC-MS: 450.2 (M+H)+.

Example 240

Ethyl {3-fluoro-4-[2-(4-hydroxy-1-adamantyl)-1-oxo-2,7-diazaspiro[4.5]dec-7-yl]phenyl}carbamate

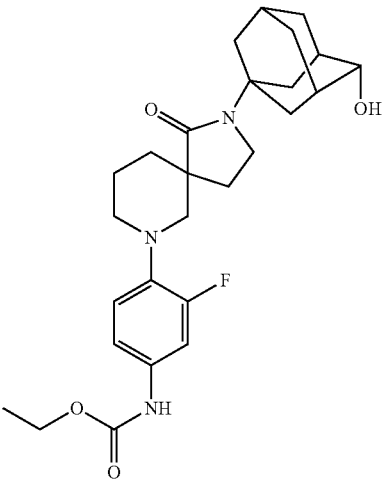

and

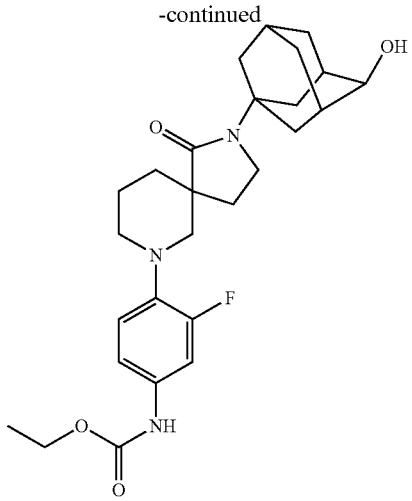

This compound was prepared by using procedures analogous to those described for the synthesis of example 105 starting from 2-(4-hydroxy-1-adamantyl)-2,7-diazaspiro[4.5]decan-1-one. LC-MS: 486.2 (M+H)⁺.

Example 241

7-(3,5-Difluoropyridin-2-yl)-2-(4-hydroxy-1-adamantyl)-2,7-diazaspiro[4.5]decan-1-one

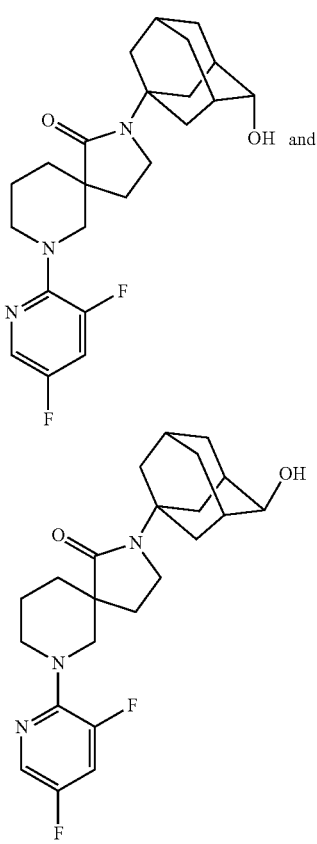

This compound was prepared by using procedures analogous to those described for the synthesis of example 93. LC-MS: 418.2 (M+H)⁺.

Example 242

3-Fluoro-4-[2-(4-hydroxy-1-adamantyl)-1-oxo-2,7-diazaspiro[4.5]dec-7-yl]benzonitrile

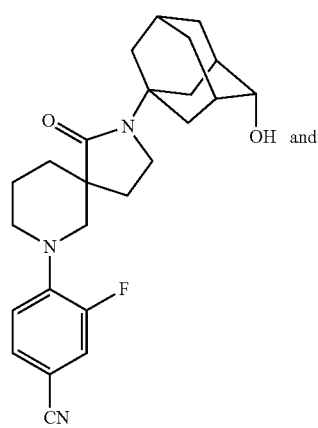

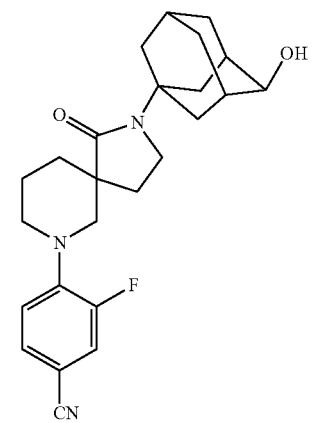

This compound was prepared by using procedures analogous to those described for the synthesis of example 93. LC-MS: 424.2 (M+H)⁺.

Example 243

2-[2-(4-Hydroxy-1-adamantyl)-1-oxo-2,7-diazaspiro[4.5]dec-7-yl]nicotinonitrile

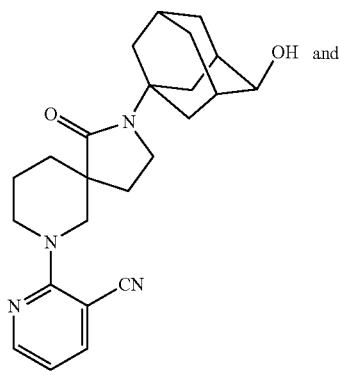

and

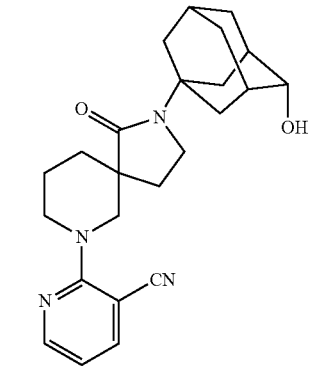

This compound was prepared by using procedures analogous to those described for the synthesis of example 93. LC-MS: 407.2 (M+H)⁺.

Example 244

4-[2-(4-Hydroxy-1-adamantyl)-1-oxo-2,7-diazaspiro[4.5]dec-7-yl]benzonitrile

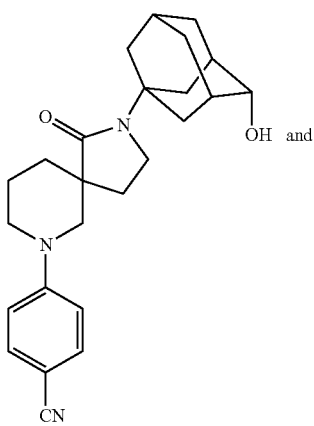

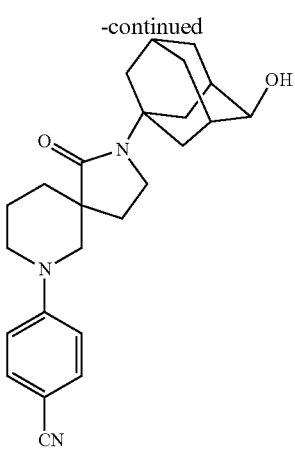

This compound was prepared by using procedures analogous to those described for the synthesis of example 93. LC-MS: 406.2 (M+H)⁺.

Example 245

N-{3-Fluoro-4-[2-(4-hydroxy-1-adamantyl)-1-oxo-2,7-diazaspiro[4.5]dec-7-yl]phenyl}cyclopropanecarboxamide

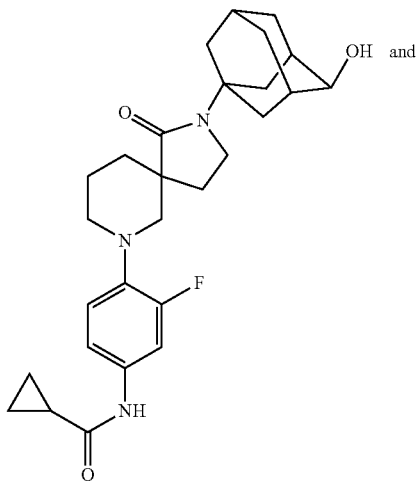

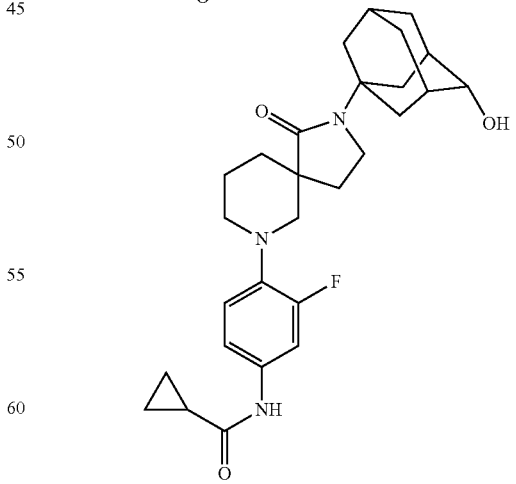

This compound was prepared by using procedures analogous to those described for the synthesis of example 105 starting from 2-(4-hydroxy-1-adamantyl)-2,7-diazaspiro[4.5]decan-1-one. LC-MS: 482.2 (M+H)⁺.

Example 246

2-(4-Hydroxy-1-adamantyl)-7-[5-(trifluoromethyl)pyridin-2-yl]-2,7-diazaspiro[4.5]decan-1-one

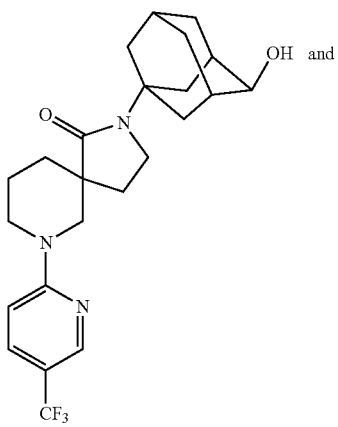

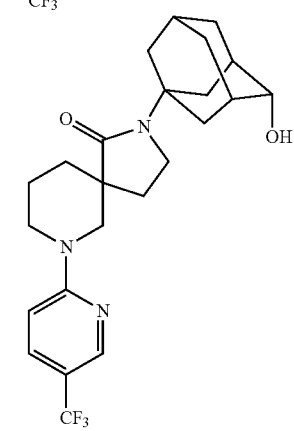

This compound was prepared by using procedures analogous to those described for the synthesis of example 93. LC-MS: 450.2 (M+H)⁺.

Example 247

7-(5-Ethylpyrimidin-2-yl)-2-(4-hydroxy-1-adamantyl)-2,7-diazaspiro[4.5]decan-1-one

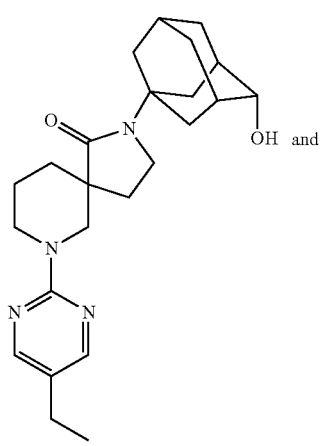

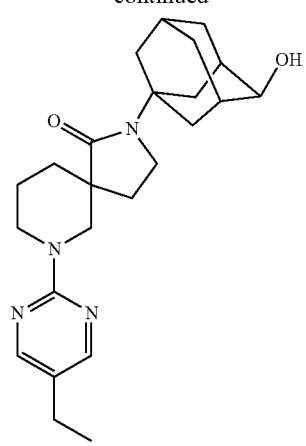

This compound was prepared by using procedures analogous to those described for the synthesis of example 93. LC-MS: 411.2 (M+H)⁺.

Example 248

7-(3-Fluoropyridin-2-yl)-2-(4-hydroxy-1-adamantyl)-2,7-diazaspiro[4.5]decan-1-one

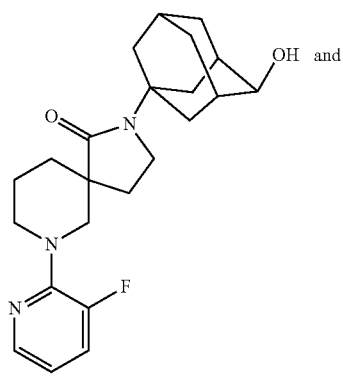

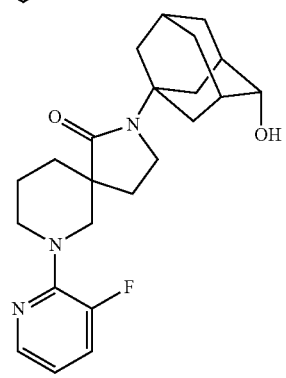

This compound was prepared by using procedures analogous to those described for the synthesis of example 93. LC-MS: 400.2 (M+H)⁺.

165
Example 249

N-{3-Fluoro-4-[2-(4-hydroxy-1-adamantyl)-1-oxo-2,7-diazaspiro[4.5]dec-7-yl]phenyl}acetamide

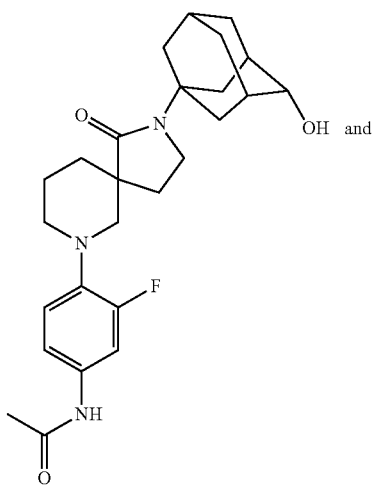

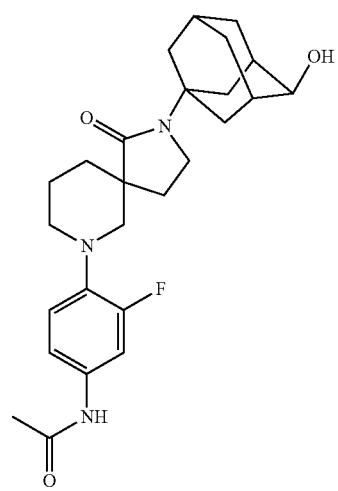

This compound was prepared by using procedures analogous to those described for the synthesis of example 105 starting from 2-(4-hydroxy-1-adamantyl)-2,7-diazaspiro[4.5]decan-1-one. LC-MS: 456.2 (M+H)⁺.

166
Example 250

N-{3-Fluoro-4-[2-(4-hydroxy-1-adamantyl)-1-oxo-2,7-diazaspiro[4.5]dec-7-yl]phenyl}propanamide

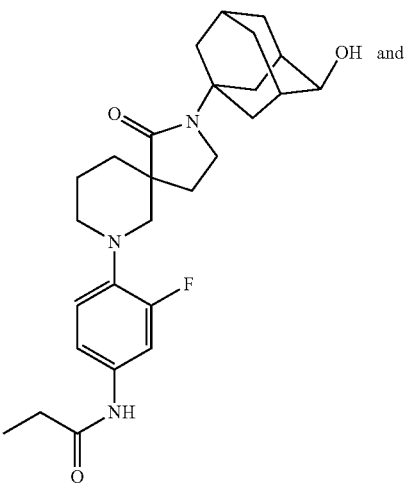

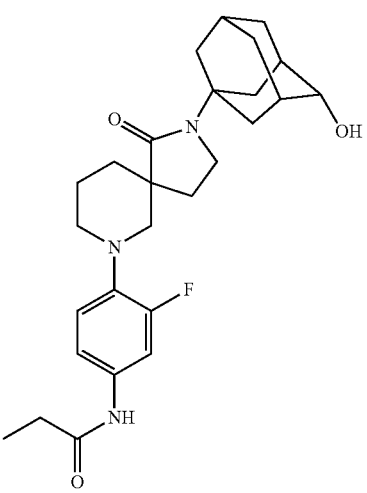

This compound was prepared by using procedures analogous to those described for the synthesis of example 105 starting from 2-(4-hydroxy-1-adamantyl)-2,7-diazaspiro[4.5]decan-1-one. LC-MS: 470.2 (M+H)⁺.

Example 251

N-{3-Fluoro-4-[2-(4-hydroxy-1-adamantyl)-1-oxo-2,7-diazaspiro[4.5]dec-7-yl]phenyl}methanesulfonamide

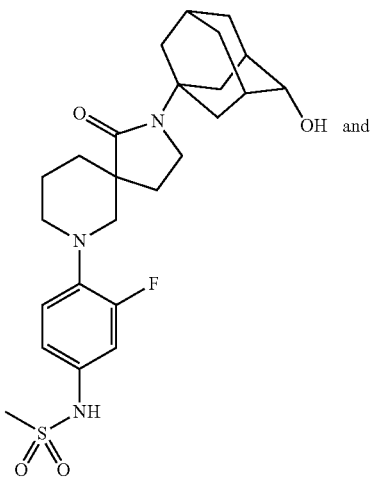

Example 252

(5S)-7-(2,3-Difluorophenyl)-2-(4-hydroxycyclohexyl)-2,7-diazaspiro[4.5]decan-1-one

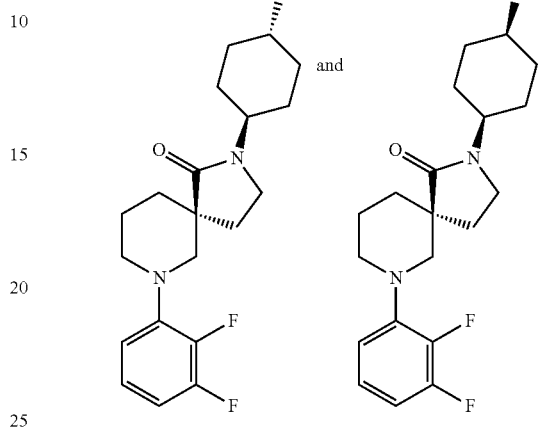

This compound was prepared by using procedures analogous to those described for the synthesis of example 44 starting from (5S)-2-(trans-4-hydroxycyclohexyl)-2,7-diazaspiro[4.5]decan-1-one. LC-MS: 365.2 (M+H)$^+$.

Example 253

(5S)-7-(3-Fluorophenyl)-2-(4-hydroxycyclohexyl)-2,7-diazaspiro[4.5]decan-1-one

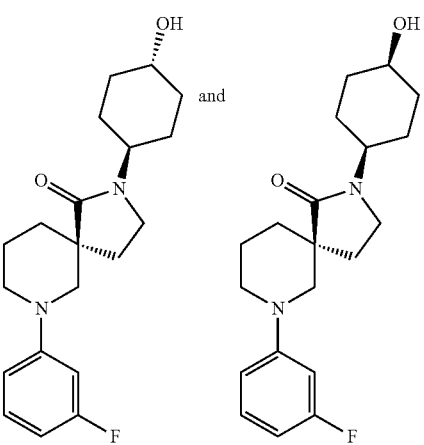 [SMILES: O=C1N([C@H]2CC[C@H](O)CC2)CC[C@]12CCCN(c1cccc(F)c1)C2 ; "and" ; O=C1N([C@H]2CC[C@@H](O)CC2)CC[C@]12CCCN(c1cccc(F)c1)C2]

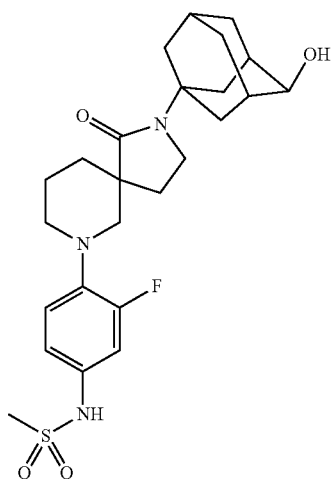

This compound was prepared by using procedures analogous to those described for the synthesis of example 105 starting from 2-(4-hydroxy-1-adamantyl)-2,7-diazaspiro[4.5]decan-1-one. LC-MS: 492.2 (M+H)$^+$.

This compound was prepared by using procedures analogous to those described for the synthesis of example 44 starting from (5S)-2-(trans-4-hydroxycyclohexyl)-2,7-diazaspiro[4.5]decan-1-one. LC-MS: 347.3 (M+H)$^+$.

Example 254

(5S)-7-(2-Chloro-3-fluorophenyl)-2-(4-hydroxycyclohexyl)-2,7-diazaspiro[4.5]decan-1-one

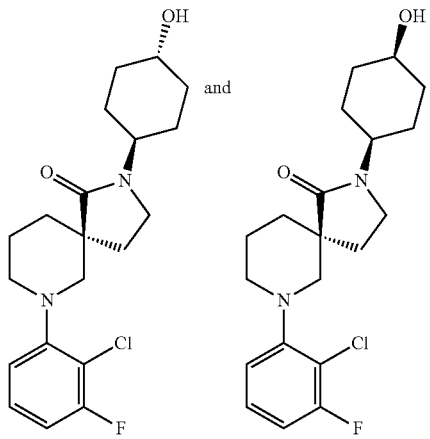 [SMILES: O=C1N([C@H]2CC[C@H](O)CC2)CC[C@]12CCCN(c1cccc(F)c1Cl)C2 ; "and" ; O=C1N([C@H]2CC[C@@H](O)CC2)CC[C@]12CCCN(c1cccc(F)c1Cl)C2]

This compound was prepared by using procedures analogous to those described for the synthesis of example 44 starting from (5S)-2-(trans-4-hydroxycyclohexyl)-2,7-diazaspiro[4.5]decan-1-one. LC-MS: 381.2 (M+H)$^+$.

Example 255

(5S)-7-(4-Fluorophenyl)-2-(4-hydroxycyclohexyl)-2,7-diazaspiro[4.5]decan-1-one

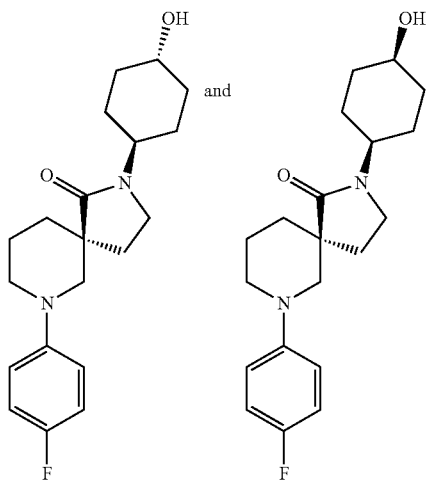 [SMILES: O=C1N([C@H]2CC[C@H](O)CC2)CC[C@]12CCCN(c1ccc(F)cc1)C2 ; "and" ; O=C1N([C@H]2CC[C@@H](O)CC2)CC[C@]12CCCN(c1ccc(F)cc1)C2]

This compound was prepared by using procedures analogous to those described for the synthesis of example 44 starting from (5S)-2-(trans-4-hydroxycyclohexyl)-2,7-diazaspiro[4.5]decan-1-one. LC-MS: 347.2 (M+H)$^+$.

Example 256

(5S)-7-[3-Chloro-5-(2-oxo-1,3-oxazinan-3-yl)pyridin-2-yl]-2-(trans-4-hydroxycyclohexyl)-2,7-diazaspiro[4.5]decan-1-one

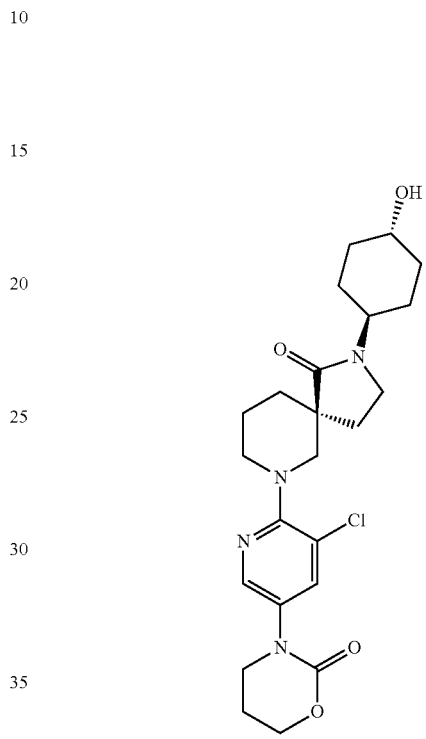

3-Chloropropyl chloridocarbonate (15.1 µL, 0.000125 mol) was added to a mixture of (5S)-7-(5-amino-3-chloropyridin-2-yl)-2-(trans-4-hydroxycyclohexyl)-2,7-diazaspiro[4.5]decan-1-one (37.89 mg, 0.0001000 mol, this compound was prepared by using procedures analogous to those described for the synthesis of example 105, step 1 starting from (5S)-2-(trans-4-hydroxycyclohexyl)-2,7-diazaspiro[4.5]decan-1-one) and 4-dimethylaminopyridine (18.3 mg, 0.000150 mol) in DMF (1.00 mL). After stirring the mixture for 1 h, 1.0000 M of potassium tert-butoxide in tetrahydrofuran (0.375 mL) was added and the resultant mixture was stirred at rt for 2 h. The mixture was diluted with methanol (0.8 mL) and was adjusted to pH=2.0 with TFA. The resulting solution was purified by prep.-HPLC to give the desired product. LC-MS: 463.1 (M+H)$^+$.

Example 257

(5S)-7-(3,4'-Bipyridin-6-yl)-2-(trans-4-hydroxycyclohexyl)-2,7-diazaspiro[4.5]decan-1-one

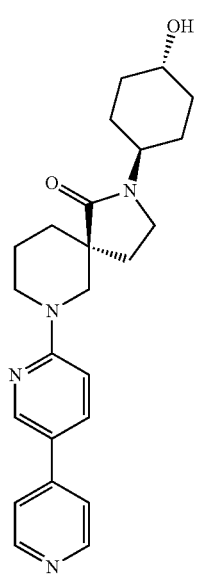

Sodium carbonate (10.6 mg, 0.000100 mol) in water (0.10 mL) was added to a mixture of (5S)-7-(5-bromopyridin-2-yl)-2-(trans-4-hydroxycyclohexyl)-2,7-diazaspiro[4.5]decan-1-one (20.4 mg, 0.0000500 mol) which was prepared by using a procedure that was analogous to the one described for the synthesis of example 93 starting from (5S)-2-(trans-4-hydroxycyclohexyl)-2,7-diazaspiro[4.5]decan-1-one in NMP (0.25 mL), 4-pyridinylboronic acid (9.22 mg, 0.0000750 mol) and tetrakis(triphenylphosphine) palladium (0) (1.7 mg, 0.0000015 mol) in toluene (200.0 μL, 0.001878 mol) and ethanol (100.000 μL, 1.71267E-3 mol). The resulting mixture was heated at 120° C. for 20 min. The mixture was filtered and the filtrate was diluted with methanol and adjusted to pH=2 with TFA. The resulting solution was purified by prep.-HPLC to give the desired product. LC-MS: 407.2 (M+H)$^+$.

Example 258

(5S)-2-(trans-4-Hydroxycyclohexyl)-7-(6'-methoxy-3,3'-bipyridin-6-yl)-2,7-diazaspiro[4.5]decan-1-one

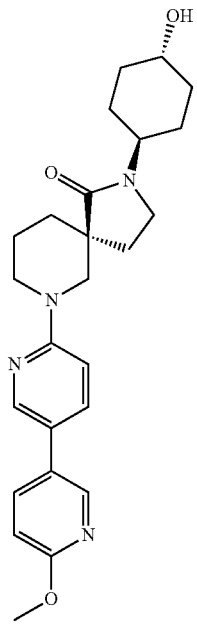 [SMILES: COc1ccc(-c2ccc(N3CCC[C@]4(CCN([C@H]5CC[C@H](O)CC5)C4=O)C3)nc2)cn1]

This compound was prepared by using procedures analogous to those described for the synthesis of example 257. LC-MS: 437.3 (M+H)$^+$.

Example 259

4-{6-[(5S)-2-(trans-4-Hydroxycyclohexyl)-1-oxo-2,7-diazaspiro[4.5]dec-7-yl]pyridin-3-yl}-N,N-dimethylbenzamide

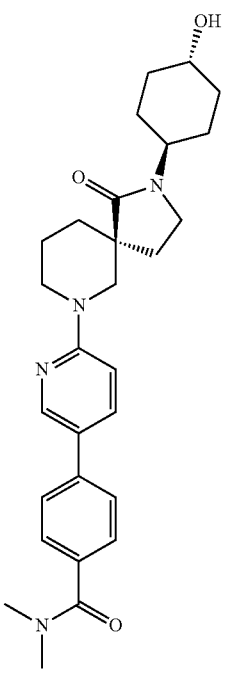 [SMILES: CN(C)C(=O)c1ccc(-c2ccc(N3CCC[C@]4(CCN([C@H]5CC[C@H](O)CC5)C4=O)C3)nc2)cc1]

This compound was prepared by using procedures analogous to those described for the synthesis of example 257. LC-MS: 477.3 (M+H)+.

Example 260

4-{6-[(5S)-2-(trans-4-Hydroxycyclohexyl)-1-oxo-2,7-diazaspiro[4.5]dec-7-yl]pyridin-3-yl}benzamide

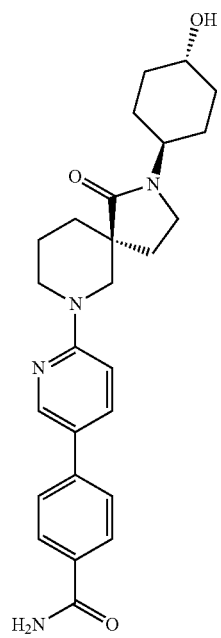 [SMILES: NC(=O)c1ccc(-c2ccc(N3CCC[C@]4(CCN([C@H]5CC[C@H](O)CC5)C4=O)C3)nc2)cc1]

This compound was prepared by using procedures analogous to those described for the synthesis of example 257. LC-MS: 449.3 (M+H)+.

Example 261

N-Cyclopropyl-4-{6-[(5S)-2-(trans-4-hydroxycyclohexyl)-1-oxo-2,7-diazaspiro[4.5]dec-7-yl]pyridin-3-yl}benzamide

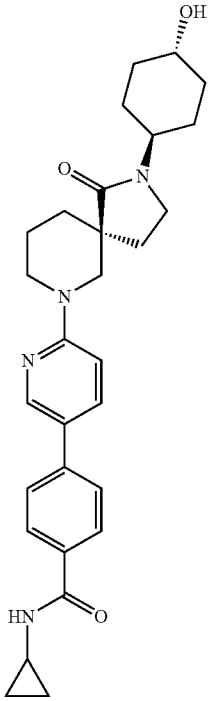 [SMILES: O=C(NC1CC1)c1ccc(-c2ccc(N3CCC[C@]4(CCN([C@H]5CC[C@H](O)CC5)C4=O)C3)nc2)cc1]

This compound was prepared by using procedures analogous to those described for the synthesis of example 257. LC-MS: 489.3 (M+H)+.

Example 262

N-(4-{6-[(5S)-2-(trans-4-Hydroxycyclohexyl)-1-oxo-2,7-diazaspiro[4.5]dec-7-yl]pyridin-3-yl}phenyl)acetamide

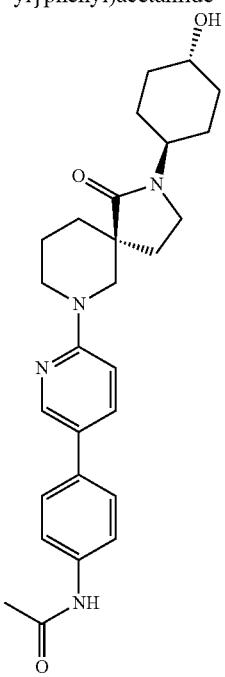

This compound was prepared by using procedures analogous to those described for the synthesis of example 257. LC-MS: 463.3 (M+H)+.

Example 263

(5S)-2-(trans-4-Hydroxycyclohexyl)-7-[5-(4-methoxyphenyl)pyridin-2-yl]-2,7-diazaspiro[4.5]decan-1-one

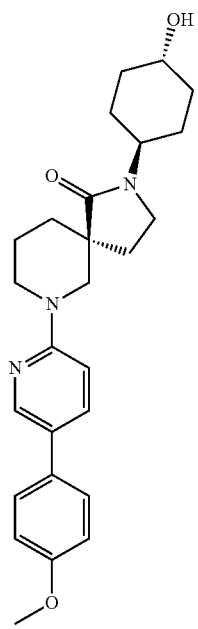 [SMILES: COc1ccc(-c2ccc(N3CCC[C@]4(CCN([C@H]5CC[C@H](O)CC5)C4=O)C3)nc2)cc1]

This compound was prepared by using procedures analogous to those described for the synthesis of example 257. LC-MS: 436.3 (M+H)+.

Example 264

(5S)-7-[5-(4-Fluorophenyl)pyridin-2-yl]-2-(trans-4-hydroxycyclohexyl)-2,7-diazaspiro[4.5]decan-1-one

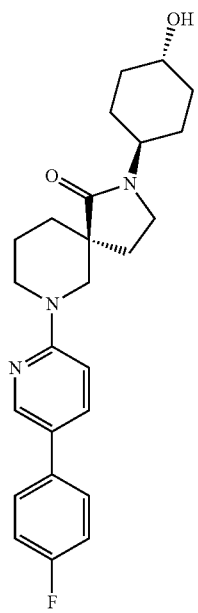 [SMILES: O=C1N([C@H]2CC[C@H](O)CC2)CC[C@]12CCCN(c1ccc(-c3ccc(F)cc3)cn1)C2]

This compound was prepared by using procedures analogous to those described for the synthesis of example 257. LC-MS: 424.2 (M+H)+.

Example 265

(5S)-7-(3,3'-Bipyridin-6-yl)-2-(trans-4-hydroxycyclohexyl)-2,7-diazaspiro[4.5]decan-1-one

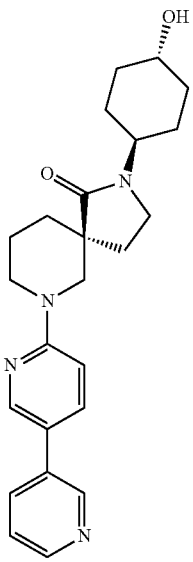 [SMILES: O=C1N([C@H]2CC[C@H](O)CC2)CC[C@]12CCCN(c1ccc(-c3cccnc3)cn1)C2]

This compound was prepared by using procedures analogous to those described for the synthesis of example 257. LC-MS: 407.3 (M+H)+.

Example 266

(5S)-7-(6'-Fluoro-3,3'-pyridin-6-yl)-2-(trans-4-hydroxycyclohexyl)-2,7-diazaspiro[4.5]decan-1-one

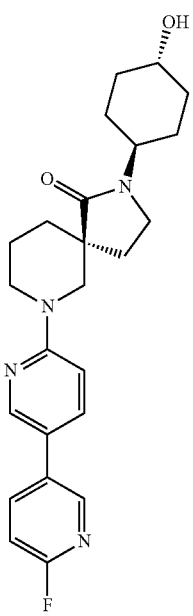 [SMILES: O=C1N([C@H]2CC[C@H](O)CC2)CC[C@]12CCCN(c1ccc(-c3ccc(F)nc3)cn1)C2]

This compound was prepared by using procedures analogous to those described for the synthesis of example 257. LC-MS: 425.3 (M+H)+.

Example 267

(5S)-2-(trans-4-Hydroxycyclohexyl)-7-(5-pyrimidin-5-ylpyridin-2-yl)-2,7-diazaspiro[4.5]decan-1-one

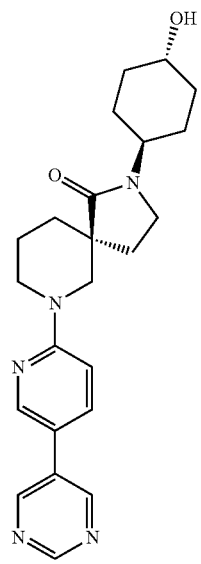 [SMILES: O=C1N([C@H]2CC[C@H](O)CC2)CC[C@]12CCCN(c1ccc(-c3cncnc3)cn1)C2]

This compound was prepared by using procedures analogous to those described for the synthesis of example 257. LC-MS: 408.3 (M+H)⁺.

Example 268

3-{6-[(5S)-2-(trans-4-Hydroxycyclohexyl)-1-oxo-2,7-diazaspiro[4.5]dec-7-yl]pyridin-3-yl}benzamide

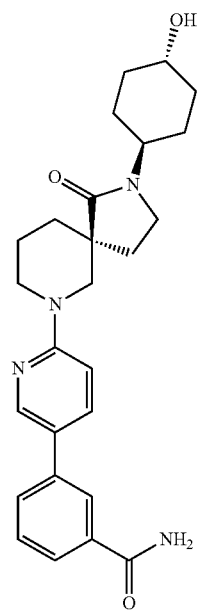 [SMILES: NC(=O)c1cccc(-c2ccc(N3CCC[C@]4(CCN([C@H]5CC[C@H](O)CC5)C4=O)C3)nc2)c1]

This compound was prepared by using procedures analogous to those described for the synthesis of example 257. LC-MS: 449.3 (M+H)⁺.

Example 269

N-(3-{6-[(5S)-2-(trans-4-Hydroxycyclohexyl)-1-oxo-2,7-diazaspiro[4.5]dec-7-yl]pyridin-3-yl}phenyl)acetamide

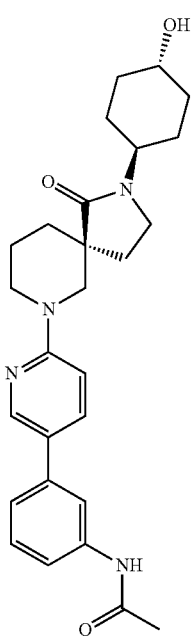 [SMILES: CC(=O)Nc1cccc(-c2ccc(N3CCC[C@]4(CCN([C@H]5CC[C@H](O)CC5)C4=O)C3)nc2)c1]

This compound was prepared by using procedures analogous to those described for the synthesis of example 257. LC-MS: 463.3 (M+H)⁺.

Example 270

(5S)-7-[5-(3,5-Dimethylisoxazol-4-yl)pyridin-2-yl]-2-(trans-4-hydroxycyclohexyl)-2,7-diazaspiro[4.5]decan-1-one

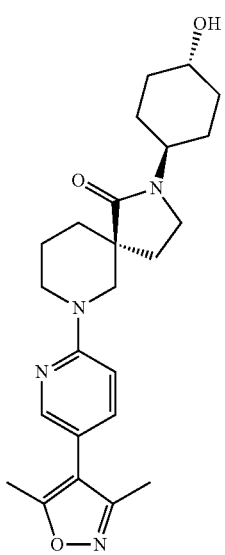 [SMILES: Cc1noc(C)c1-c1ccc(N2CCC[C@]3(CCN([C@H]4CC[C@H](O)CC4)C3=O)C2)nc1]

This compound was prepared by using procedures analogous to those described for the synthesis of example 257. LC-MS: 425.3 (M+H)+.

Example 271

(5S)-2-(trans-4-Hydroxycyclohexyl)-7-[5-(1-methyl-1H-pyrazol-4-yl)pyridin-2-yl]-2,7-diazaspiro[4.5]decan-1-one

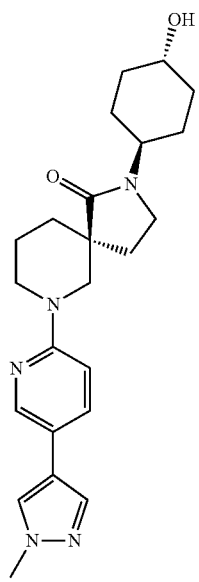 [SMILES: Cn1cc(-c2ccc(N3CCC[C@]4(CCN([C@H]5CC[C@H](O)CC5)C4=O)C3)nc2)cn1]

This compound was prepared by using procedures analogous to those described for the synthesis of example 257. LC-MS: 410.3 (M+H)+.

Example 272

4-{2-[(5S)-2-(trans-4-Hydroxycyclohexyl)-1-oxo-2,7-diazaspiro[4.5]dec-7-yl]pyrimidin-5-yl}-N,N-dimethylbenzamide

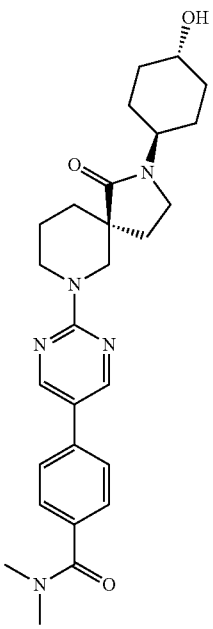 [SMILES: CN(C)C(=O)c1ccc(-c2cnc(N3CCC[C@]4(CCN([C@H]5CC[C@H](O)CC5)C4=O)C3)nc2)cc1]

This compound was prepared by using procedures analogous to those described for the synthesis of example 257. LC-MS: 478.2 (M+H)+.

Example 273

(5S)-2-(trans-4-Methoxycyclohexyl)-7-[3-(trifluoromethyl)pyridin-2-yl]-2,7-diazaspiro[4.5]decan-1-one

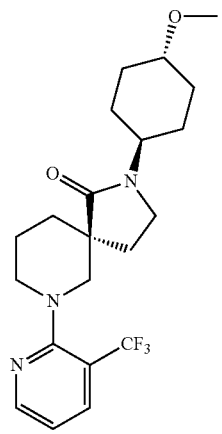 [SMILES: CO[C@H]1CC[C@H](N2CC[C@]3(CCCN(c4ncccc4C(F)(F)F)C3)C2=O)CC1]

This compound was prepared by using procedures analogous to those described for the synthesis of example 93 starting from (5S)-2-(trans-4-methoxycyclohexyl)-2,7-diazaspiro[4.5]decan-1-one which was prepared by treating of (S)-benzyl 2-(trans-4-hydroxycyclohexyl)-1-oxo-2,7-diazaspiro[4.5]decane-7-carboxylate with NaH and MeI in DMF, followed by Pd catalyzed Cbz deprotection. LC-MS: 412.2 (M+H)⁺.

Example 274

N-Cyclopropyl-4-{2-[(5S)-2-(trans-4-hydroxycyclohexyl)-1-oxo-2,7-diazaspiro[4.5]dec-7-yl]pyrimidin-5-yl}benzamide

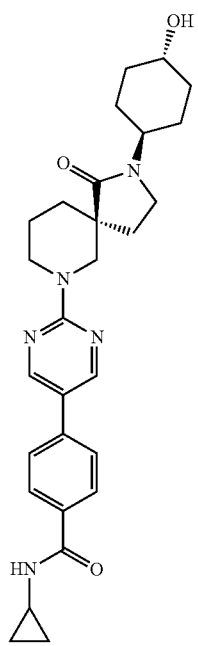 [SMILES: O=C(NC1CC1)c1ccc(-c2cnc(N3CCC[C@]4(CCN([C@H]5CC[C@H](O)CC5)C4=O)C3)nc2)cc1]

This compound was prepared by using procedures analogous to those described for the synthesis of example 257. LC-MS: 490.2 (M+H)⁺.

Example 275

(5S)-7-(5-Chloro-3,3'-bipyridin-6-yl)-2-(trans-4-hydroxycyclohexyl)-2,7-diazaspiro[4.5]decan-1-one

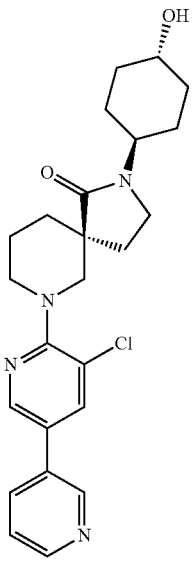 [SMILES: O=C1N([C@H]2CC[C@H](O)CC2)CC[C@]12CCCN(c1ncc(-c3cccnc3)cc1Cl)C2]

This compound was prepared by using procedures analogous to those described for the synthesis of example 257. LC-MS: 441.2 (M+H)⁺.

Example 276

(5S)-7-(5-Bromopyrimidin-2-yl)-2-(trans-4-hydroxycyclohexyl)-2,7-diazaspiro[4.5]decan-1-one

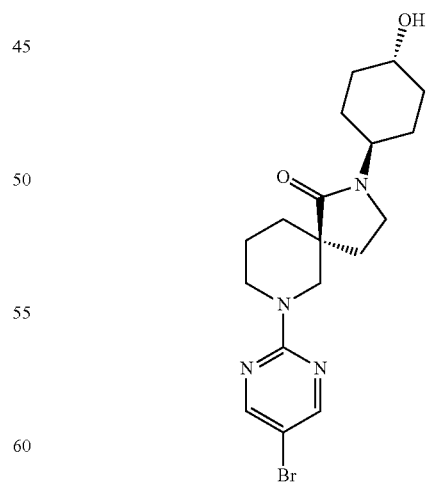

This compound was prepared by using procedures analogous to those described for the synthesis of example 93 starting from (5S)-2-(trans-4-hydroxycyclohexyl)-2,7-diazaspiro[4.5]decan-1-one. LC-MS: 409.1/411.1 (M+H)⁺.

Example 277

(5S)-7-[3-Chloro-5-(1-methyl-1H-pyrazol-4-yl)pyridin-2-yl]-2-(trans-4-hydroxycyclohexyl)-2,7-diazaspiro[4.5]decan-1-one

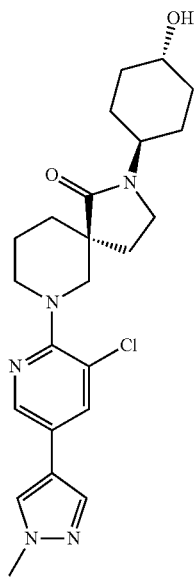 [SMILES: Cn1cc(-c2cnc(N3CCC[C@]4(CCN([C@H]5CC[C@H](O)CC5)C4=O)C3)c(Cl)c2)cn1]

This compound was prepared by using procedures analogous to those described for the synthesis of example 257. LC-MS: 444.2 (M+H)+.

Example 278

4-{2-[(5S)-2-(trans-4-Hydroxycyclohexyl)-1-oxo-2,7-diazaspiro[4.5]dec-7-yl]pyrimidin-5-yl}benzamide

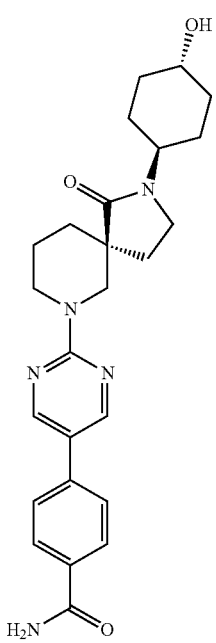 [SMILES: NC(=O)c1ccc(-c2cnc(N3CCC[C@]4(CCN([C@H]5CC[C@H](O)CC5)C4=O)C3)nc2)cc1]

This compound was prepared by using procedures analogous to those described for the synthesis of example 257. LC-MS: 450.2 (M+H)+.

Example 279

(5S)-7-(3,5-Difluoropyridin-2-yl)-2-(trans-4-methoxycyclohexyl)-2,7-diazaspiro[4.5]decan-1-one Error! Objects cannot be created from editing field codes.

This compound was prepared by using procedures analogous to those described for the synthesis of example 273. LC-MS: 380.2 (M+H)+.

Example 280

(5S)-7-(5-Chloro-3,4'-bipyridin-6-yl)-2-(trans-4-hydroxycyclohexyl)-2,7-diazaspiro[4.5]decan-1-one

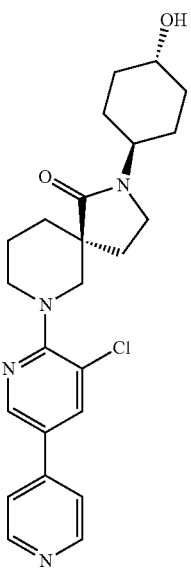 [SMILES: O=C1N([C@H]2CC[C@H](O)CC2)CC[C@]12CCCN(c1ncc(-c3ccncc3)cc1Cl)C2]

This compound was prepared by using procedures analogous to those described for the synthesis of example 257. LC-MS: 441.2 (M+H)+.

Example 281

(5S)-7-(5-Ethylpyrimidin-2-yl)-2-(trans-4-methoxycyclohexyl)-2,7-diazaspiro[4.5]decan-1-one Error! Objects cannot be created from editing field codes.

This compound was prepared by using procedures analogous to those described for the synthesis of example 273. LC-MS: 373.3 (M+H)+.

Example 282 tert-Butyl 5-chloro-6-[(5S)-2-(trans-4-hydroxycyclohexyl)-1-oxo-2,7-diazaspiro[4.5]dec-7-yl]-3',6'-dihydro-3,4'-bipyridine-1'(2'H)-carboxylate

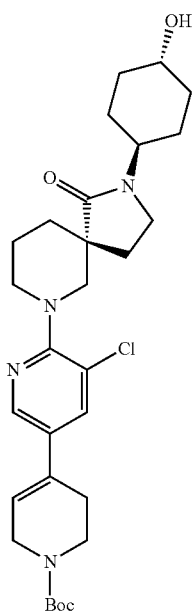 [SMILES: CC(C)(C)OC(=O)N1CC=C(c2cnc(N3CCC[C@@]4(CCN([C@H]5CC[C@H](O)CC5)C4=O)C3)c(Cl)c2)CC1]

This compound was prepared by using procedures analogous to those described for the synthesis of example 257. LC-MS: 545.3 (M+H)$^+$.

Example 283

(5S)-7-(5-Fluoropyrimidin-2-yl)-2-(trans-4-hydroxycyclohexyl)-2,7-diazaspiro[4.5]decan-1-one

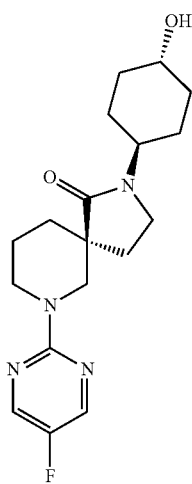 [SMILES: O=C1N([C@H]2CC[C@H](O)CC2)CC[C@]12CCCN(c1ncc(F)cn1)C2]

This compound was prepared by using procedures analogous to those described for the synthesis of example 93 starting from (5S)-2-(trans-4-hydroxycyclohexyl)-2,7-diazaspiro[4.5]decan-1-one. LC-MS: 349.2 (M+H)$^+$.

Example 284

(5S)-2-(trans-4-Hydroxycyclohexyl)-7-[4-(2-oxo-1,3-oxazolidin-3-yl)phenyl]-2,7-diazaspiro[4.5]decan-1-one

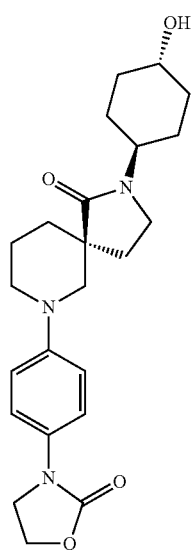 [SMILES: O=C1OCCN1c1ccc(N2CCC[C@]3(CCN([C@H]4CC[C@H](O)CC4)C3=O)C2)cc1]

This compound was prepared by using procedures analogous to those described for the synthesis of example 256. LC-MS: 414.3 (M+H)$^+$.

Example 285

(5S)-7-[2-Fluoro-4-(2-oxo-1,3-oxazolidin-3-yl)phenyl]-2-(trans-4-hydroxycyclohexyl)-2,7-diazaspiro[4.5]decan-1-one

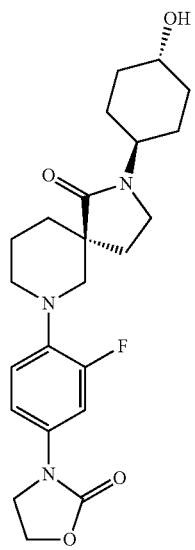

This compound was prepared by using procedures analogous to those described for the synthesis of example 256. LC-MS: 432.2 (M+H)$^+$.

Example 286

(5S)-7-[2-Fluoro-4-(2-oxopyrrolidin-1-yl)phenyl]-2-(trans-4-hydroxycyclohexyl)-2,7-diazaspiro[4.5]decan-1-one

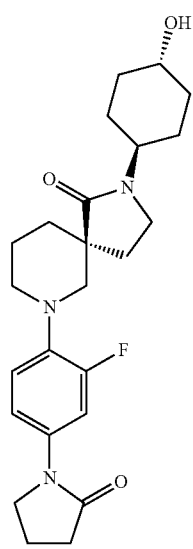 [SMILES: O=C1CCCN1c1ccc(N2CCC[C@]3(CCN([C@H]4CC[C@H](O)CC4)C3=O)C2)c(F)c1]

This compound was prepared by using procedures analogous to those described for the synthesis of example 256. LC-MS: 430.3 (M+H)+.

Example 287

(5S)-7-[3-Chloro-5-(2-oxopyrrolidin-1-yl)pyridin-2-yl]-2-(trans-4-hydroxycyclohexyl)-2,7-diazaspiro[4.5]decan-1-one

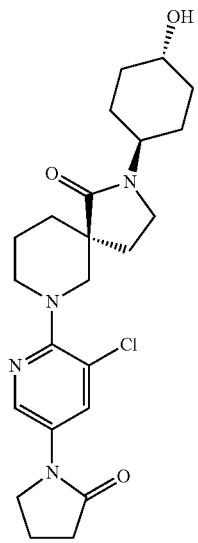 [SMILES: O=C1CCCN1c1cnc(N2CCC[C@]3(CCN([C@H]4CC[C@H](O)CC4)C3=O)C2)c(Cl)c1]

This compound was prepared by using procedures analogous to those described for the synthesis of example 256. LC-MS: 447.3 (M+H)+.

Example 288

(5S)-2-(trans-4-Hydroxycyclohexyl)-7-[4-(2-oxopyrrolidin-1-yl)phenyl]-2,7-diazaspiro[4.5]decan-1-one

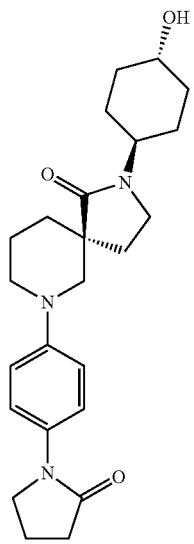 [SMILES: O=C1CCCN1c1ccc(N2CCC[C@]3(CCN([C@H]4CC[C@H](O)CC4)C3=O)C2)cc1]

This compound was prepared by using procedures analogous to those described for the synthesis of example 256. LC-MS: 412.2 (M+H)+.

Example 289

(5S)-7-[3-Chloro-5-(2-oxo-1,3-oxazolidin-3-yl)pyridin-2-yl]-2-(trans-4-hydroxycyclohexyl)-2,7-diazaspiro[4.5]decan-1-one

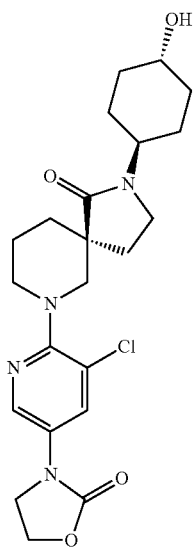 [SMILES: O=C1OCCN1c1cnc(N2CCC[C@]3(CCN([C@H]4CC[C@H](O)CC4)C3=O)C2)c(Cl)c1]

This compound was prepared by using procedures analogous to those described for the synthesis of example 256. LC-MS: 449.1 (M+H)+.

Example 290

(5S)-7-(2-Fluoro-4-pyrrolidin-1-ylphenyl)-2-(trans-4-hydroxycyclohexyl)-2,7-diazaspiro[4.5]decan-1-one

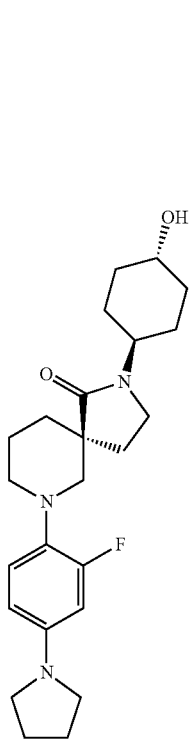 [SMILES: O=C1N([C@H]2CC[C@H](O)CC2)CC[C@]12CCCN(c1ccc(N3CCCC3)cc1F)C2]

A mixture of 1,4-diiodobutane (13.5 µL, 0.000100 mol), (5S)-7-(4-amino-2-fluorophenyl)-2-(trans-4-hydroxycyclohexyl)-2,7-diazaspiro[4.5]decan-1-one (28.9 mg, 0.0000800 mol, this compound was prepared by using procedures analogous to that described for the synthesis of example 105, step 1 starting from (5S)-2-(trans-4-hydroxycyclohexyl)-2,7-diazaspiro[4.5]decan-1-one) and 4-dimethylaminopyridine (14.7 mg, 0.000120 mol) in DMF (1.00 mL), and potassium iodide (1.5 mg, 0.0000090 mol) was heated at 110° C. by microwave for 15 min. The mixture was diluted with methanol (0.8 mL) and was adjusted to be acidic with TFA (the pH was about 2.0). The resulting solution was purified by prep-HPLC to give the desired product. LC-MS: 416.2 (M+H)+.

Example 291

(5S)-7-(3-Chloro-5-pyrrolidin-1-ylpyridin-2-yl)-2-(trans-4-hydroxycyclohexyl)-2,7-diazaspiro[4.5]decan-1-one

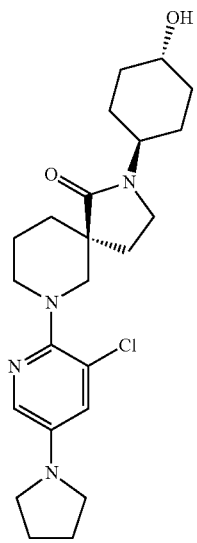 [SMILES: O=C1N([C@H]2CC[C@H](O)CC2)CC[C@]12CCCN(c1ncc(N3CCCC3)cc1Cl)C2]

This compound was prepared by using procedures analogous to those described for the synthesis of example 290. LC-MS: 433.2 (M+H)+.

Example 292

(5S)-2-(trans-4-Hydroxycyclohexyl)-7-(5-pyrrolidin-1-ylpyridin-2-yl)-2,7-diazaspiro[4.5]decan-1-one

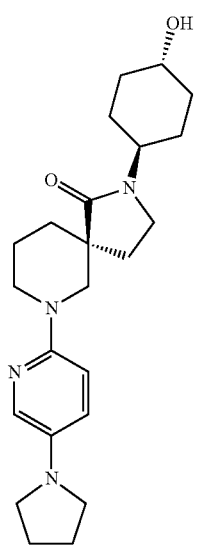 [SMILES: O=C1N([C@H]2CC[C@H](O)CC2)CC[C@]12CCCN(c1ccc(N3CCCC3)cn1)C2]

This compound was prepared by using procedures analogous to those described for the synthesis of example 290. LC-MS: 399.2 (M+H)+.

Example 293

(5S)-7-[2-Fluoro-4-(2-oxo-piperidin-1-yl)-phenyl]-2-(trans-4-hydroxy-cyclohexyl)-2,7-diazaspiro[4.5]decan-1-one

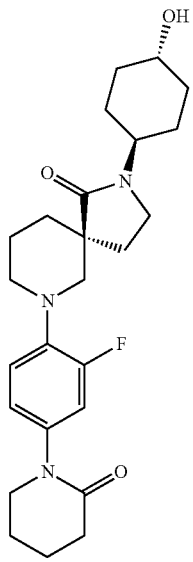 [SMILES: O=C1CCCCN1c1ccc(N2CCC[C@]3(CCN([C@H]4CC[C@H](O)CC4)C3=O)C2)c(F)c1]

This compound was prepared by using procedures analogous to those described for the synthesis of example 256. LC-MS: 444.3 (M+H)⁺.

Example 294

(5S)-7-[2-Fluoro-4-(2-oxo-1,3-oxazinan-3-yl)phenyl]-2-(trans-4-hydroxycyclohexyl)-2,7-diazaspiro[4.5]decan-1-one

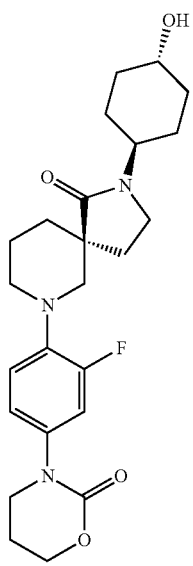 [SMILES: O=C1OCCCN1c1ccc(N2CCC[C@]3(CCN([C@H]4CC[C@H](O)CC4)C3=O)C2)c(F)c1]

This compound was prepared by using procedures analogous to those described for the synthesis of example 256. LC-MS: 446.3 (M+H)⁺.

Example 295

(5S)-2-(trans-4-hydroxycyclohexyl)-7-[4-(2-oxopiperidin-1-yl)phenyl]-2,7-diazaspiro[4.5]decan-1-one

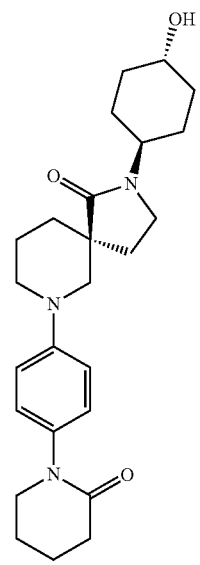 [SMILES: O=C1CCCCN1c1ccc(N2CCC[C@]3(CCN([C@H]4CC[C@H](O)CC4)C3=O)C2)cc1]

This compound was prepared by using procedures analogous to those described for the synthesis of example 256. LC-MS: 426.3 (M+H)⁺.

Example 296

(5S)-7-(1,3-Benzothiazol-2-yl)-2-(trans-4-hydroxycyclohexyl)-2,7-diazaspiro[4.5]decan-1-one

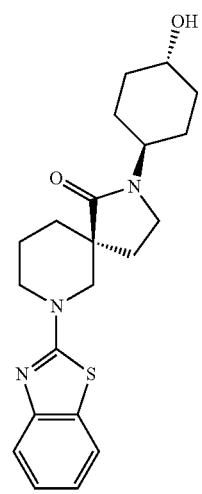 [SMILES: O=C1N([C@H]2CC[C@H](O)CC2)CC[C@]12CCCN(c1nc3ccccc3s1)C2]

This compound was prepared by using procedures analogous to those described for the synthesis of example 93 starting from (5S)-2-(trans-4-hydroxycyclohexyl)-2,7-diazaspiro[4.5]decan-1-one. LC-MS: 386.2 (M+H)⁺.

Example 297

2-[(5S)-2-(trans-4-Methoxycyclohexyl)-1-oxo-2,7-diazaspiro[4.5]dec-7-yl]nicotinonitrile

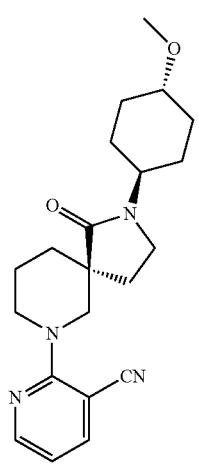 [SMILES: CO[C@H]1CC[C@H](N2CC[C@]3(CCCN(c4ncccc4C#N)C3)C2=O)CC1]

This compound was prepared by using procedures analogous to those described for the synthesis of example 273. LC-MS: 369.2 (M+H)⁺.

Example 298

(5S)-2-(trans-4-Methoxycyclohexyl)-7-[5-(trifluoromethyl)pyridin-2-yl]-2,7-diazaspiro[4.5]decan-1-one

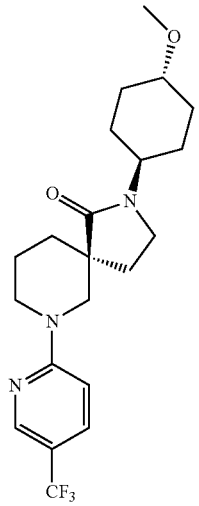 [SMILES: CO[C@H]1CC[C@H](N2CC[C@]3(CCCN(c4ccc(C(F)(F)F)cn4)C3)C2=O)CC1]

This compound was prepared by using procedures analogous to those described for the synthesis of example 273. LC-MS: 412.2 (M+H)⁺.

Example 299

(5S)-7-(5-Fluoropyrimidin-2-yl)-2-(trans-4-methoxycyclohexyl)-2,7-diazaspiro[4.5]decan-1-one

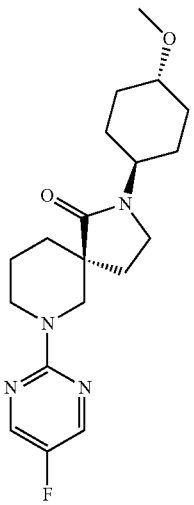 [SMILES: CO[C@H]1CC[C@H](N2CC[C@]3(CCCN(c4ncc(F)cn4)C3)C2=O)CC1]

This compound was prepared by using procedures analogous to those described for the synthesis of example 271. LC-MS: 363.2 (M+H)⁺.

Example 300

(5S)-7-{3-Chloro-5-[4-(trifluoromethoxy)phenyl]pyridin-2-yl}-2-(trans-4-hydroxycyclohexyl)-2,7-diazaspiro[4.5]decan-1-one

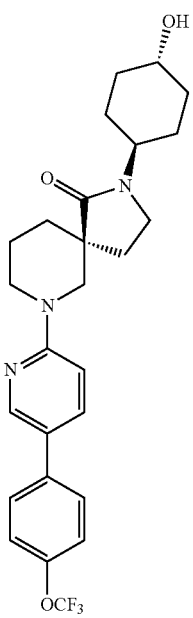 [SMILES: O=C1N([C@H]2CC[C@H](O)CC2)CC[C@]12CCCN(c1ccc(-c3ccc(OC(F)(F)F)cc3)cn1)C2]

This compound was prepared by using procedures analogous to those described for the synthesis of example 257. LC-MS: 524.2 (M+H)⁺.

Example 301

(5S)-7-(2-Chloro-9H-purin-6-yl)-2-(trans-4-hydroxycyclohexyl)-2,7-diazaspiro[4.5]decan-1-one

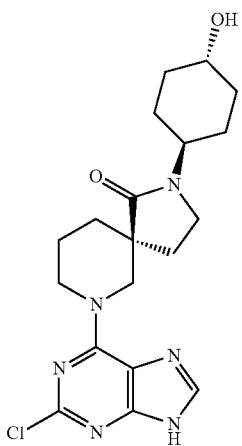 [SMILES: O=C1N([C@H]2CC[C@H](O)CC2)CC[C@]12CCCN(c1nc(Cl)nc3[nH]cnc13)C2]

This compound was prepared by using procedures analogous to those described for the synthesis of example 93 starting from (5S)-2-(trans-4-hydroxycyclohexyl)-2,7-diazaspiro[4.5]decan-1-one. LC-MS: 405.2 (M+H)$^+$.

Example 302

(5S)-7-(4-Amino-5-fluoropyrimidin-2-yl)-2-(trans-4-hydroxycyclohexyl)-2,7-diazaspiro[4.5]decan-1-one

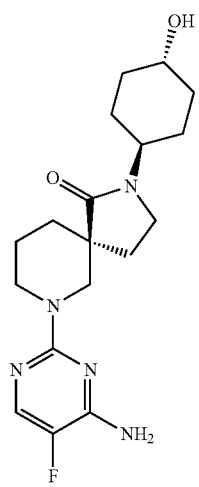

This compound was prepared by using procedures analogous to those described for the synthesis of example 93 starting from (5S)-2-(trans-4-hydroxycyclohexyl)-2,7-diazaspiro[4.5]decan-1-one. LC-MS: 364.2 (M+H)$^+$.

Example 303

N-{3-Fluoro-4-[(5S)-2-(trans-4-hydroxycyclohexyl)-1-oxo-2,7-diazaspiro[4.5]dec-7-yl]phenyl}cyclopropanecarboxamide

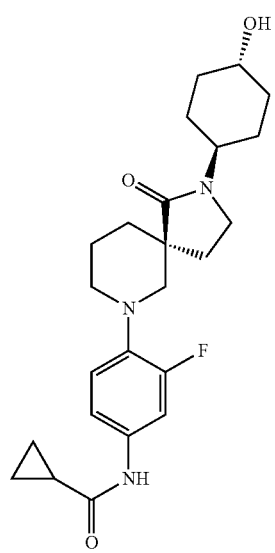 [SMILES: O=C(Nc1ccc(N2CCC[C@]3(CCN([C@H]4CC[C@H](O)CC4)C3=O)C2)c(F)c1)C1CC1]

This compound was prepared by using procedures analogous to those described for the synthesis of example 105. LC-MS: 430.3 (M+H)$^+$.

Example 304

N-{3-Fluoro-4-[(5S)-2-(trans-4-hydroxycyclohexyl)-1-oxo-2,7-diazaspiro[4.5]dec-7-yl]phenyl}cyclobutanecarboxamide

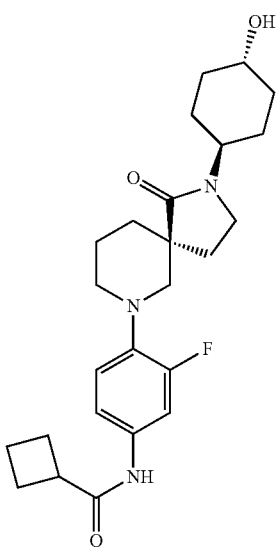 [SMILES: O=C(Nc1ccc(N2CCC[C@]3(CCN([C@H]4CC[C@H](O)CC4)C3=O)C2)c(F)c1)C1CCC1]

This compound was prepared by using procedures analogous to those described for the synthesis of example 105. LC-MS: 444.3 (M+H)$^+$.

Example 305

N-{3-Fluoro-4-[(5S)-2-(trans-4-hydroxycyclohexyl)-1-oxo-2,7-diazaspiro[4.5]dec-7-yl]phenyl}cyclopentanecarboxamide

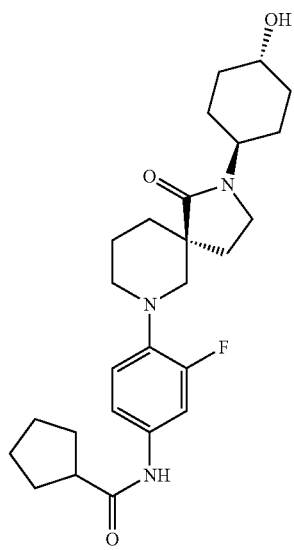 [SMILES: O=C(Nc1ccc(N2CCC[C@]3(CCN([C@H]4CC[C@H](O)CC4)C3=O)C2)c(F)c1)C1CCCC1]

This compound was prepared by using procedures analogous to those described for the synthesis of example 105. LC-MS: 458.3 (M+H)+.

Example 306

N-{3-Fluoro-4-[(5S)-2-(trans-4-hydroxycyclohexyl)-1-oxo-2,7-diazaspiro[4.5]dec-7-yl]phenyl}cyclohexanecarboxamide

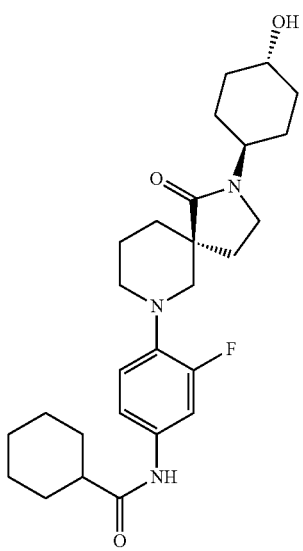 [SMILES: O=C(Nc1ccc(N2CCC[C@]3(CCN([C@H]4CC[C@H](O)CC4)C3=O)C2)c(F)c1)C1CCCCC1]

This compound was prepared by using procedures analogous to those described for the synthesis of example 105. LC-MS: 472.3 (M+H)+.

Example 307

Ethyl {3-fluoro-4-[(5S)-2-(trans-4-hydroxycyclohexyl)-1-oxo-2,7-diazaspiro[4.5]dec-7-yl]phenyl}carbamate

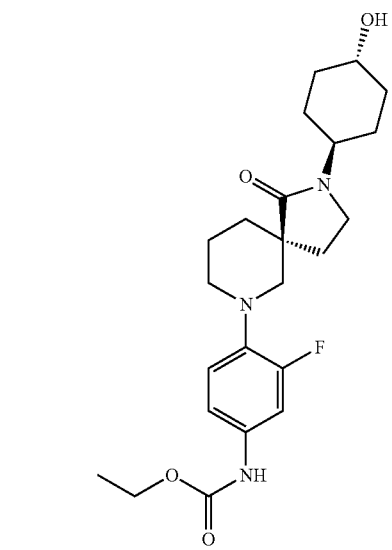 [SMILES: CCOC(=O)Nc1ccc(N2CCC[C@]3(CCN([C@H]4CC[C@H](O)CC4)C3=O)C2)c(F)c1]

This compound was prepared by using procedures analogous to those described for the synthesis of example 105. LC-MS: 434.3 (M+H)+.

Example 308

Propyl {3-fluoro-4-[(5S)-2-(trans-4-hydroxycyclohexyl)-1-oxo-2,7-diazaspiro[4.5]dec-7-yl]phenyl}carbamate

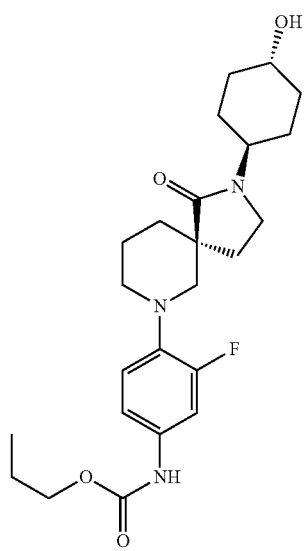 [SMILES: CCCOC(=O)Nc1ccc(N2CCC[C@]3(CCN([C@H]4CC[C@H](O)CC4)C3=O)C2)c(F)c1]

This compound was prepared by using procedures analogous to those described for the synthesis of example 105. LC-MS: 448.3 (M+H)+.

Example 309

Isobutyl {3-fluoro-4-[(5S)-2-(trans-4-hydroxycyclo-hexyl)-1-oxo-2,7-diazaspiro[4.5]dec-7-yl]phenyl}carbamate

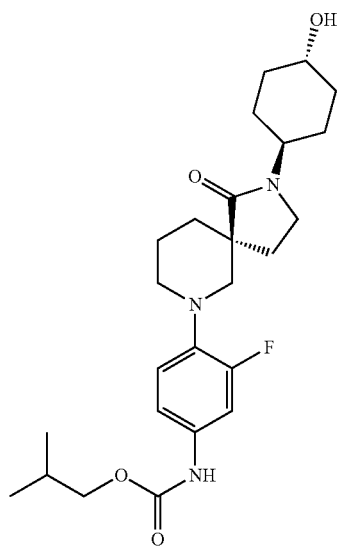 [SMILES: CC(C)COC(=O)Nc1ccc(N2CCC[C@]3(CCN([C@H]4CC[C@H](O)CC4)C3=O)C2)c(F)c1]

This compound was prepared by using procedures analogous to those described for the synthesis of example 105. LC-MS: 462.3 (M+H)$^+$.

Example 310

N-{3-Fluoro-4-[(5S)-2-(trans-4-hydroxycyclohexyl)-1-oxo-2,7-diazaspiro[4.5]dec-7-yl]phenyl}propanamide

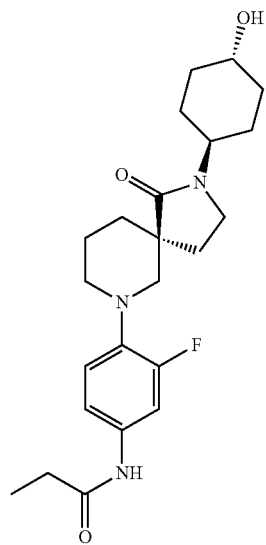 [SMILES: CCC(=O)Nc1ccc(N2CCC[C@]3(CCN([C@H]4CC[C@H](O)CC4)C3=O)C2)c(F)c1]

This compound was prepared by using procedures analogous to those described for the synthesis of example 105. LC-MS: 418.3 (M+H)$^+$.

Example 311

N-{3-Fluoro-4-[(5S)-2-(trans-4-hydroxycyclohexyl)-1-oxo-2,7-diazaspiro[4.5]dec-7-yl]phenyl}-2-methylpropanamide

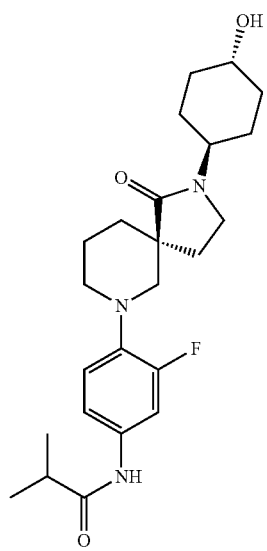 [SMILES: CC(C)C(=O)Nc1ccc(N2CCC[C@]3(CCN([C@H]4CC[C@H](O)CC4)C3=O)C2)c(F)c1]

This compound was prepared by using procedures analogous to those described for the synthesis of example 105. LC-MS: 432.3 (M+H)$^+$.

Example 312

N-{3-Fluoro-4-[(5S)-2-(trans-4-hydroxycyclohexyl)-1-oxo-2,7-diazaspiro[4.5]dec-7-yl]phenyl}methanesulfonamide

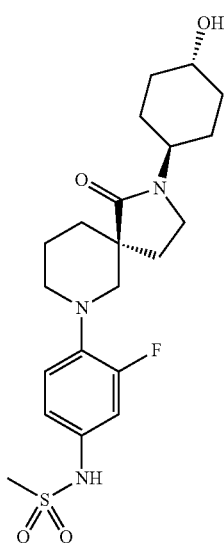 [SMILES: CS(=O)(=O)Nc1ccc(N2CCC[C@]3(CCN([C@H]4CC[C@H](O)CC4)C3=O)C2)c(F)c1]

This compound was prepared by using procedures analogous to those described for the synthesis of example 105. LC-MS: 440.2 (M+H)$^+$.

Example 313

N-{3-Fluoro-4-[(5S)-2-(trans-4-hydroxycyclohexyl)-1-oxo-2,7-diazaspiro[4.5]dec-7-yl]phenyl}ethanesulfonamide

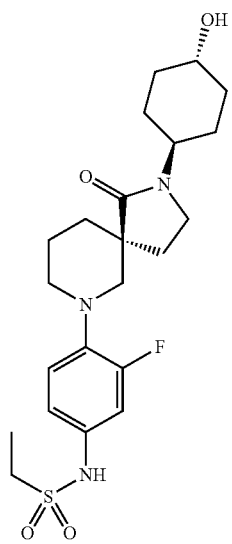 [SMILES: CCS(=O)(=O)Nc1ccc(N2CCC[C@]3(CCN([C@H]4CC[C@H](O)CC4)C3=O)C2)c(F)c1]

This compound was prepared by using procedures analogous to those described for the synthesis of example 105. LC-MS: 454.2 (M+H)$^+$.

Example 314

(5S)-2-(trans-4-Hydroxycyclohexyl)-7-[3-(trifluoromethyl)pyridin-2-yl]-2,7-diazaspiro[4.5]decan-1-one

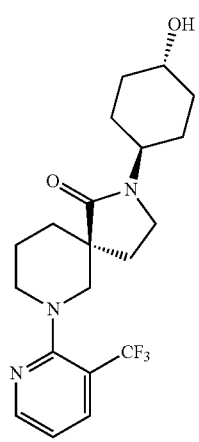 [SMILES: O=C1N([C@H]2CC[C@H](O)CC2)CC[C@]12CCCN(c1ncccc1C(F)(F)F)C2]

This compound was prepared by using procedures analogous to those described for the synthesis of example 93 starting from (5S)-2-(trans-4-hydroxycyclohexyl)-2,7-diazaspiro[4.5]decan-1-one. LC-MS: 398.2 (M+H)$^+$.

Example 315

Ethyl [4-[(5S)-2-(trans-4-hydroxycyclohexyl)-1-oxo-2,7-diazaspiro[4.5]dec-7-yl]-3-(trifluoromethyl)phenyl]carbamate

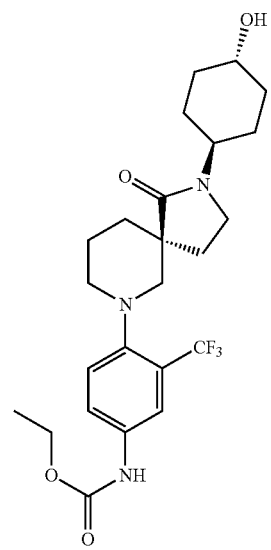 [SMILES: CCOC(=O)Nc1ccc(N2CCC[C@]3(CCN([C@H]4CC[C@H](O)CC4)C3=O)C2)c(C(F)(F)F)c1]

This compound was prepared by using procedures analogous to those described for the synthesis of example 105. LC-MS: 484.3 (M+H)$^+$.

Example 316

Methyl [4-[(5S)-2-(trans-4-hydroxycyclohexyl)-1-oxo-2,7-diazaspiro[4.5]dec-7-yl]-3-(trifluoromethyl)phenyl]carbamate

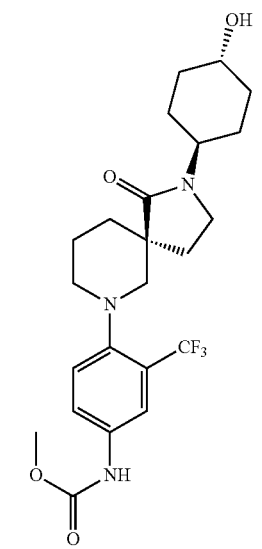 [SMILES: COC(=O)Nc1ccc(N2CCC[C@]3(CCN([C@H]4CC[C@H](O)CC4)C3=O)C2)c(C(F)(F)F)c1]

This compound was prepared by using procedures analogous to those described for the synthesis of example 105. LC-MS: 470.2 (M+H)$^+$.

Example 317

Propyl [4-[(5S)-2-(trans-4-hydroxycyclohexyl)-1-oxo-2,7-diazaspiro[4.5]dec-7-yl]-3-(trifluoromethyl)phenyl]carbamate

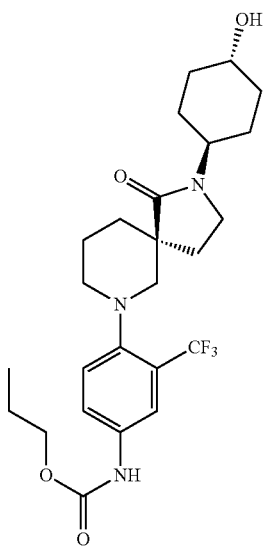 [SMILES: CCCOC(=O)Nc1ccc(N2CCC[C@]3(CCN([C@H]4CC[C@H](O)CC4)C3=O)C2)c(C(F)(F)F)c1]

This compound was prepared by using procedures analogous to those described for the synthesis of example 105. LC-MS: 498.3 (M+H)$^+$.

Example 318

Isobutyl [4-[(5S)-2-(trans-4-hydroxycyclohexyl)-1-oxo-2,7-diazaspiro[4.5]dec-7-yl]-3-(trifluoromethyl)phenyl]carbamate

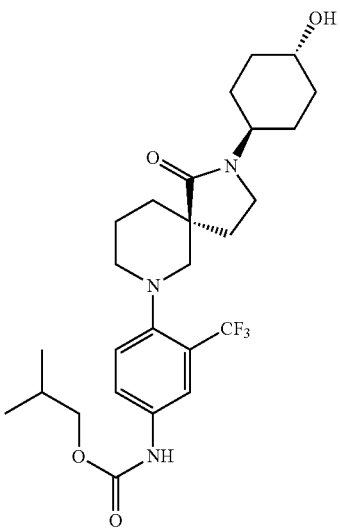 [SMILES: CC(C)COC(=O)Nc1ccc(N2CCC[C@]3(CCN([C@H]4CC[C@H](O)CC4)C3=O)C2)c(C(F)(F)F)c1]

This compound was prepared by using procedures analogous to those described for the synthesis of example 105. LC-MS: 512.3 (M+H)$^+$.

Example 319

Isopropyl [4-[(5S)-2-(trans-4-hydroxycyclohexyl)-1-oxo-2,7-diazaspiro[4.5]dec-7-yl]-3-(trifluoromethyl)phenyl]carbamate

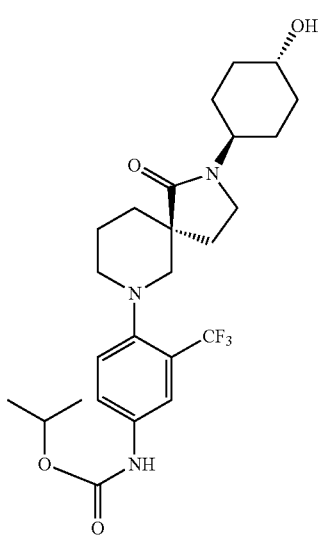 [SMILES: CC(C)OC(=O)Nc1ccc(N2CCC[C@]3(CCN([C@H]4CC[C@H](O)CC4)C3=O)C2)c(C(F)(F)F)c1]

This compound was prepared by using procedures analogous to those described for the synthesis of example 105. LC-MS: 498.3 (M+H)$^+$.

Example 320

N-[4-[(5S)-2-(trans-4-Hydroxycyclohexyl)-1-oxo-2,7-diazaspiro[4.5]dec-7-yl]-3-(trifluoromethyl)phenyl]cyclopropanecarboxamide

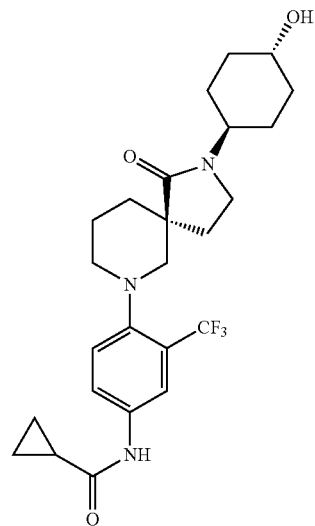 [SMILES: O=C(Nc1ccc(N2CCC[C@]3(CCN([C@H]4CC[C@H](O)CC4)C3=O)C2)c(C(F)(F)F)c1)C1CC1]

This compound was prepared by using procedures analogous to those described for the synthesis of example 105. LC-MS: 480.3 (M+H)$^+$.

Example 321

N-[4-[(5S)-2-(trans-4-Hydroxycyclohexyl)-1-oxo-2,7-diazaspiro[4.5]dec-7-yl]-3-(trifluoromethyl)phenyl]cyclobutanecarboxamide

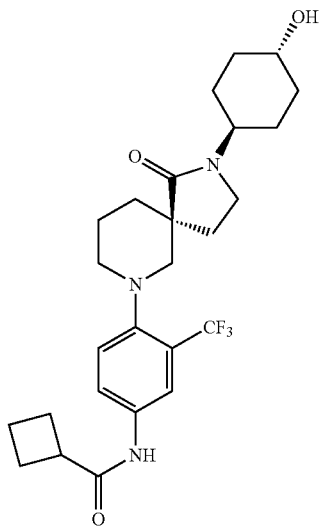 [SMILES: O=C(Nc1ccc(N2CCC[C@]3(CCN([C@H]4CC[C@H](O)CC4)C3=O)C2)c(C(F)(F)F)c1)C1CCC1]

This compound was prepared by using procedures analogous to those described for the synthesis of example 105. LC-MS: 494.3 (M+H)$^+$.

Example 322

N-[4-[(5S)-2-(trans-4-Hydroxycyclohexyl)-1-oxo-2,7-diazaspiro[4.5]dec-7-yl]-3-(trifluoromethyl)phenyl]cyclopentanecarboxamide

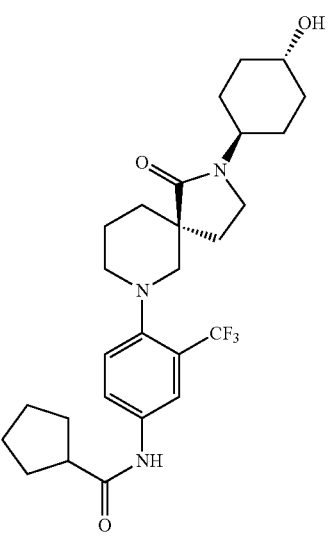 [SMILES: O=C(Nc1ccc(N2CCC[C@]3(CCN([C@H]4CC[C@H](O)CC4)C3=O)C2)c(C(F)(F)F)c1)C1CCCC1]

This compound was prepared by using procedures analogous to those described for the synthesis of example 105. LC-MS: 508.3 (M+H)$^+$.

Example 323

N-[4-[(5S)-2-(trans-4-Hydroxycyclohexyl)-1-oxo-2,7-diazaspiro[4.5]dec-7-yl]-3-(trifluoromethyl)phenyl]methanesulfonamide

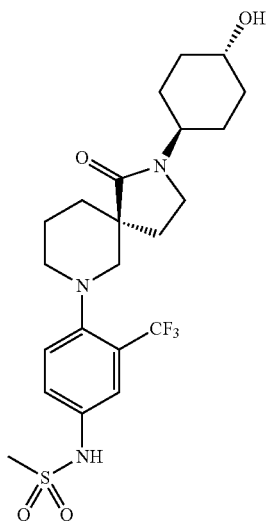 [SMILES: CS(=O)(=O)Nc1ccc(N2CCC[C@]3(CCN([C@H]4CC[C@H](O)CC4)C3=O)C2)c(C(F)(F)F)c1]

This compound was prepared by using procedures analogous to those described for the synthesis of example 105. LC-MS: 490.2 (M+H)$^+$.

Example 324

N-[4-[(5S)-2-(trans-4-Hydroxycyclohexyl)-1-oxo-2,7-diazaspiro[4.5]dec-7-yl]-3-(trifluoromethyl)phenyl]acetamide

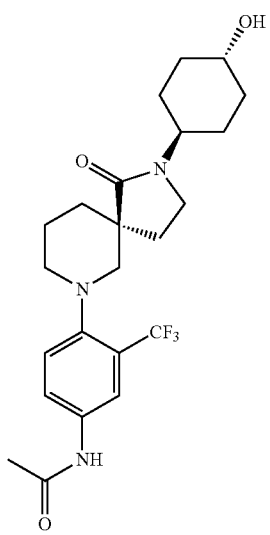

This compound was prepared by using procedures analogous to those described for the synthesis of example 105. LC-MS: 454.3 (M+H)$^+$.

Example 325

N-[4-[(5S)-2-(trans-4-Hydroxycyclohexyl)-1-oxo-2,7-diazaspiro[4.5]dec-7-yl]-3-(trifluoromethyl)phenyl]propanamide

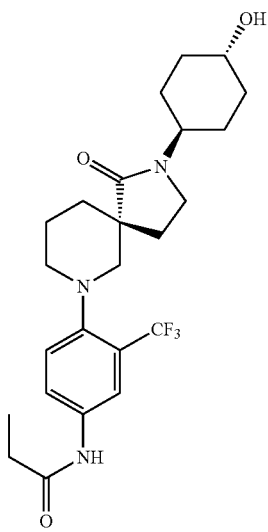 [SMILES: CCC(=O)Nc1ccc(N2CCC[C@@]3(CCN([C@H]4CC[C@H](O)CC4)C3=O)C2)c(C(F)(F)F)c1]

This compound was prepared by using procedures analogous to those described for the synthesis of example 105. LC-MS: 468.3 (M+H)+.

Example 326

N-[4-[(5S)-2-(trans-4-Hydroxycyclohexyl)-1-oxo-2,7-diazaspiro[4.5]dec-7-yl]-3-(trifluoromethyl)phenyl]-2-methylpropanamide

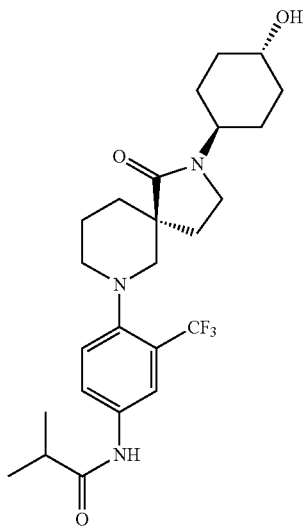 [SMILES: CC(C)C(=O)Nc1ccc(N2CCC[C@]3(CCN([C@H]4CC[C@H](O)CC4)C3=O)C2)c(C(F)(F)F)c1]

This compound was prepared by using procedures analogous to those described for the synthesis of example 105. LC-MS: 482.3 (M+H)+.

Example 327

(5S)-7-[2-Fluoro-4-(pyridin-2-yloxy)phenyl]-2-(trans-4-hydroxycyclohexyl)-2,7-diazaspiro[4.5]decan-1-one

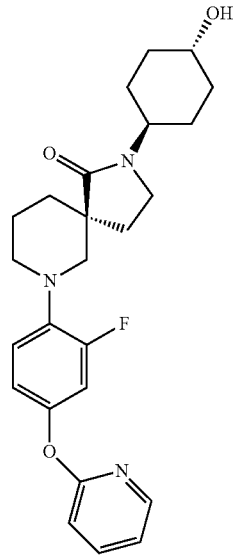 [SMILES: O=C1N([C@H]2CC[C@H](O)CC2)CC[C@]12CCCN(c1ccc(Oc3ccccn3)cc1F)C2]

This compound was prepared by using procedures analogous to those described for the synthesis of example 180. LC-MS: 440.3 (M+H)+.

Example 328

Methyl {6-[(5S)-2-(trans-4-hydroxycyclohexyl)-1-oxo-2,7-diazaspiro[4.5]dec-7-yl]pyridin-3-yl}carbamate

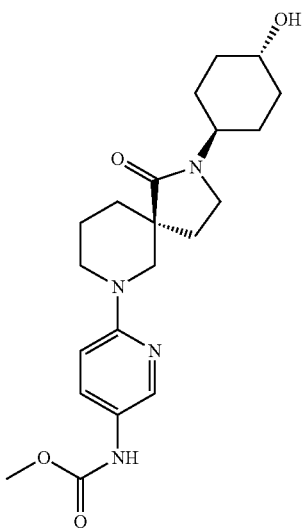

This compound was prepared by using procedures analogous to those described for the synthesis of example 105. LC-MS: 403.3 (M+H)+.

Example 329

Ethyl {6-[(5S)-2-(trans-4-hydroxycyclohexyl)-1-oxo-2,7-diazaspiro[4.5]dec-7-yl]pyridin-3-yl}carbamate

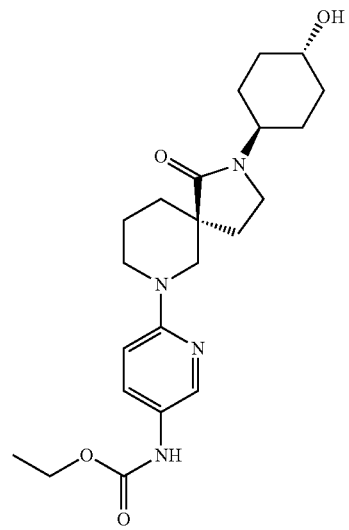

This compound was prepared by using procedures analogous to those described for the synthesis of example 105. LC-MS: 417.3 (M+H)+.

Example 330

Propyl {6-[(5S)-2-(trans-4-hydroxycyclohexyl)-1-oxo-2,7-diazaspiro[4.5]dec-7-yl]pyridin-3-yl}carbamate

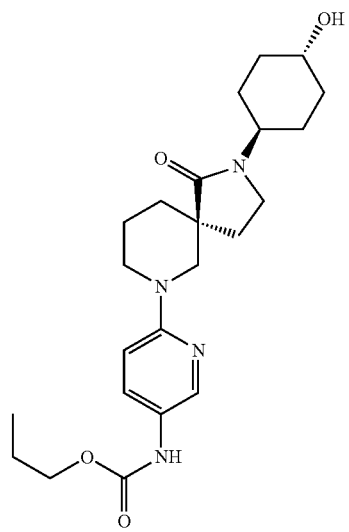

This compound was prepared by using procedures analogous to those described for the synthesis of example 105. LC-MS: 431.3 (M+H)+.

Example 331

Isobutyl {6-[(5S)-2-(trans-4-hydroxycyclohexyl)-1-oxo-2,7-diazaspiro[4.5]dec-7-yl]pyridin-3-yl}carbamate

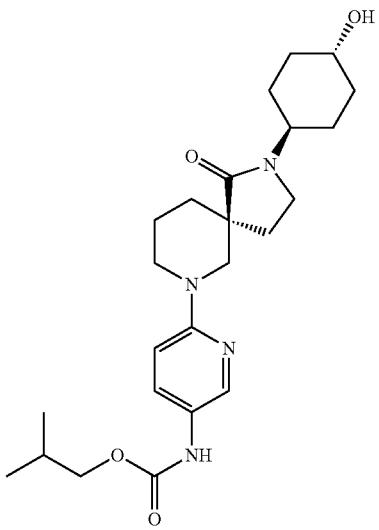 [SMILES: CC(C)COC(=O)Nc1ccc(N2CCC[C@]3(CCN([C@H]4CC[C@H](O)CC4)C3=O)C2)nc1]

This compound was prepared by using procedures analogous to those described for the synthesis of example 105. LC-MS: 445.3 (M+H)+.

Example 332

Isopropyl {6-[(5S)-2-(trans-4-hydroxycyclohexyl)-1-oxo-2,7-diazaspiro[4.5]dec-7-yl]pyridin-3-yl}carbamate

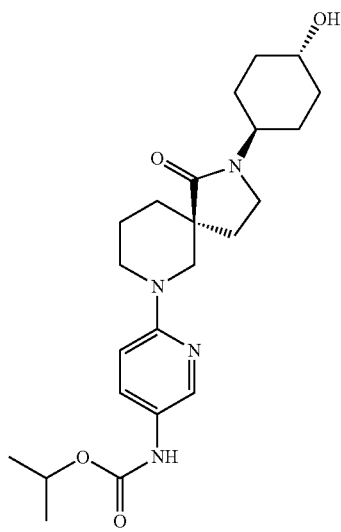 [SMILES: CC(C)OC(=O)Nc1ccc(N2CCC[C@]3(CCN([C@H]4CC[C@H](O)CC4)C3=O)C2)nc1]

This compound was prepared by using procedures analogous to those described for the synthesis of example 105. LC-MS: 431.3 (M+H)+.

Example 333

N-{6-[(5S)-2-(trans-4-Hydroxycyclohexyl)-1-oxo-2,7-diazaspiro[4.5]dec-7-yl]pyridin-3-yl}cyclopropanecarboxamide

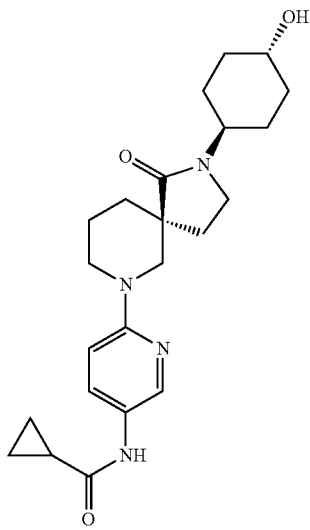 [SMILES: O=C(Nc1ccc(N2CCC[C@]3(CCN([C@H]4CC[C@H](O)CC4)C3=O)C2)nc1)C1CC1]

This compound was prepared by using procedures analogous to those described for the synthesis of example 105. LC-MS: 413.3 (M+H)⁺.

Example 334

N-{6-[(5S)-2-(trans-4-Hydroxycyclohexyl)-1-oxo-2,7-diazaspiro[4.5]dec-7-yl]pyridin-3-yl}cyclobutanecarboxamide

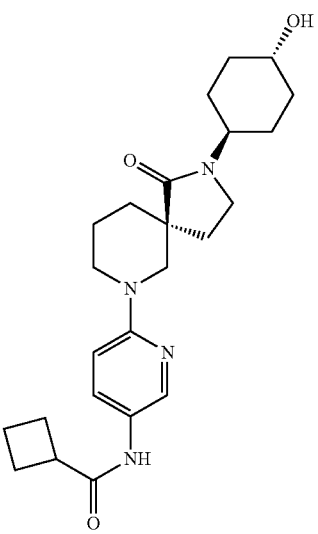 [SMILES: O=C(Nc1ccc(N2CCC[C@]3(CCN([C@H]4CC[C@H](O)CC4)C3=O)C2)nc1)C1CCC1]

This compound was prepared by using procedures analogous to those described for the synthesis of example 105. LC-MS: 427.3 (M+H)⁺.

Example 335

N-{6-[(5S)-2-(trans-4-Hydroxycyclohexyl)-1-oxo-2,7-diazaspiro[4.5]dec-7-yl]pyridin-3-yl}cyclopentanecarboxamide

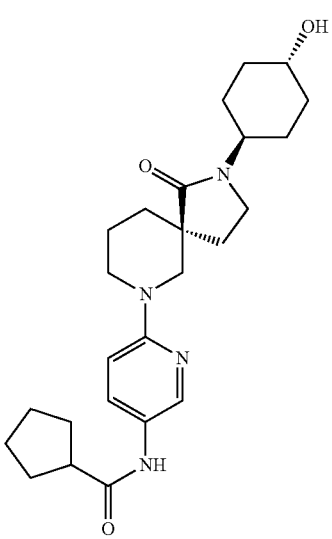 [SMILES: O=C(Nc1ccc(N2CCC[C@]3(CCN([C@H]4CC[C@H](O)CC4)C3=O)C2)nc1)C1CCCC1]

This compound was prepared by using procedures analogous to those described for the synthesis of example 105. LC-MS: 441.3 (M+H)⁺.

Example 336

N-{6-[(5S)-2-(trans-4-Hydroxycyclohexyl)-1-oxo-2,7-diazaspiro[4.5]dec-7-yl]pyridin-3-yl}acetamide

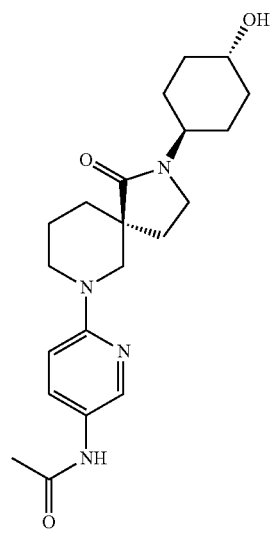 [SMILES: CC(=O)Nc1ccc(N2CCC[C@]3(CCN([C@H]4CC[C@H](O)CC4)C3=O)C2)nc1]

This compound was prepared by using procedures analogous to those described for the synthesis of example 105. LC-MS: 387.3 (M+H)⁺.

Example 337

N-{6-[(5S)-2-(trans-4-Hydroxycyclohexyl)-1-oxo-2,7-diazaspiro[4.5]dec-7-yl]pyridin-3-yl}propanamide

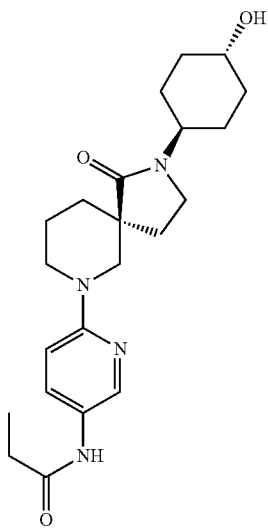 [SMILES: CCC(=O)Nc1ccc(N2CCC[C@]3(CCN([C@H]4CC[C@H](O)CC4)C3=O)C2)nc1]

This compound was prepared by using procedures analogous to those described for the synthesis of example 105. LC-MS: 401.3 (M+H)+.

Example 338

N-{6-[(5S)-2-(trans-4-Hydroxycyclohexyl)-1-oxo-2,7-diazaspiro[4.5]dec-7-yl]pyridin-3-yl}-2-methyl-propanamide

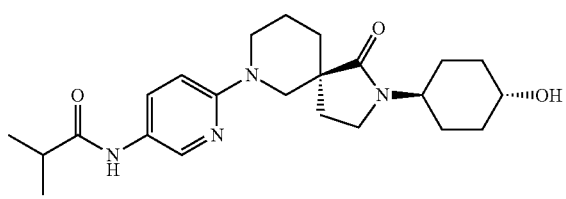 [SMILES: CC(C)C(=O)Nc1ccc(N2CCC[C@]3(CCN([C@H]4CC[C@H](O)CC4)C3=O)C2)nc1]

This compound was prepared by using procedures analogous to those described for the synthesis of example 105. LC-MS: 415.3 (M+H)+.

Example 339

N-{6-[(5S)-2-(trans-4-Hydroxycyclohexyl)-1-oxo-2,7-diazaspiro[4.5]dec-7-yl]pyridin-3-yl}cyclohexanecarboxamide

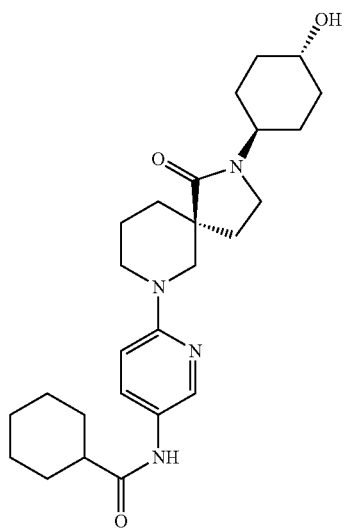 [SMILES: O=C(Nc1ccc(N2CCC[C@]3(CCN([C@H]4CC[C@H](O)CC4)C3=O)C2)nc1)C1CCCCC1]

This compound was prepared by using procedures analogous to those described for the synthesis of example 105. LC-MS: 455.3 (M+H)+.

Example 340

Methyl {6-[(5S)-2-(trans-4-hydroxycyclohexyl)-1-oxo-2,7-diazaspiro[4.5]dec-7-yl]-5-methylpyridin-3-yl}carbamate

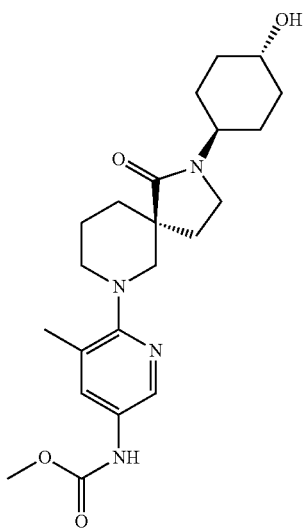 [SMILES: COC(=O)Nc1cnc(N2CCC[C@]3(CCN([C@H]4CC[C@H](O)CC4)C3=O)C2)c(C)c1]

This compound was prepared by using procedures analogous to those described for the synthesis of example 105. LC-MS: 417.1 (M+H)+.

Example 341

Ethyl {6-[(5S)-2-(trans-4-hydroxycyclohexyl)-1-oxo-2,7-diazaspiro[4.5]dec-7-yl]-5-methylpyridin-3-yl}carbamate

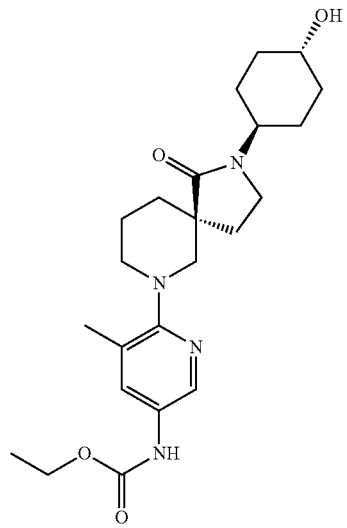 [SMILES: CCOC(=O)Nc1cnc(N2CCC[C@]3(CCN([C@H]4CC[C@H](O)CC4)C3=O)C2)c(C)c1]

This compound was prepared by using procedures analogous to those described for the synthesis of example 105. LC-MS: 431.2 (M+H)$^+$.

Example 342

Propyl {6-[(5S)-2-(trans-4-hydroxycyclohexyl)-1-oxo-2,7-diazaspiro[4.5]dec-7-yl]-5-methylpyridin-3-yl}carbamate

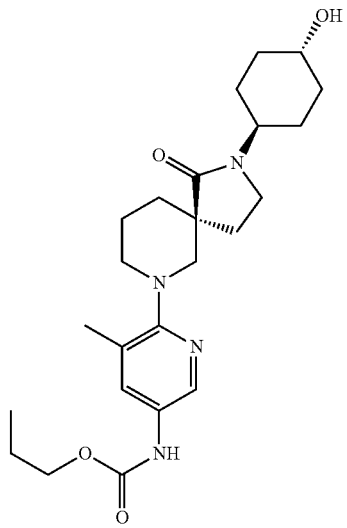 [SMILES: CCCOC(=O)Nc1cnc(N2CCC[C@]3(CCN([C@H]4CC[C@H](O)CC4)C3=O)C2)c(C)c1]

This compound was prepared by using procedures analogous to those described for the synthesis of example 105. LC-MS: 445.1 (M+H)$^+$.

Example 343

Methyl {3-cyano-4-[(5S)-2-(trans-4-hydroxycyclohexyl)-1-oxo-2,7-diazaspiro[4.5]dec-7-yl]phenyl}carbamate

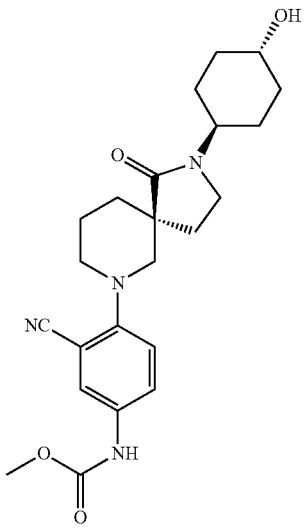 [SMILES: COC(=O)Nc1ccc(N2CCC[C@]3(CCN([C@H]4CC[C@H](O)CC4)C3=O)C2)c(C#N)c1]

This compound was prepared by using procedures analogous to those described for the synthesis of example 105. LC-MS: 427.2 (M+H)$^+$.

Example 344

Ethyl {3-cyano-4-[(5S)-2-(trans-4-hydroxycyclohexyl)-1-oxo-2,7-diazaspiro[4.5]dec-7-yl]phenyl}carbamate

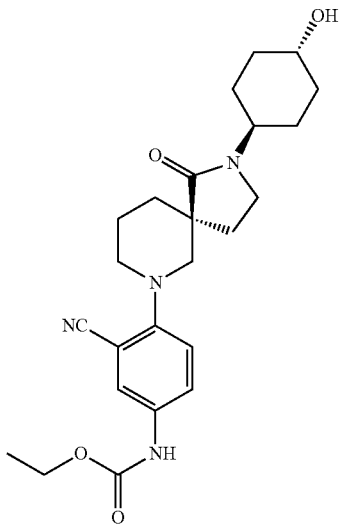 [SMILES: CCOC(=O)Nc1ccc(N2CCC[C@]3(CCN([C@H]4CC[C@H](O)CC4)C3=O)C2)c(C#N)c1]

This compound was prepared by using procedures analogous to those described for the synthesis of example 105. LC-MS: 441.3 (M+H)$^+$.

217

Example 345

Propyl {3-cyano-4-[(5S)-2-(trans-4-hydroxycyclohexyl)-1-oxo-2,7-diazaspiro[4.5]dec-7-yl]phenyl}carbamate

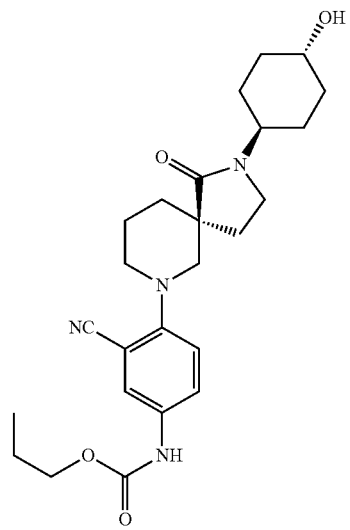 [SMILES: CCCOC(=O)Nc1ccc(N2CCC[C@]3(CCN([C@H]4CC[C@H](O)CC4)C3=O)C2)c(C#N)c1]

This compound was prepared by using procedures analogous to those described for the synthesis of example 105. LC-MS: 455.3 (M+H)$^+$.

Example 346

Isobutyl {3-cyano-4-[(5S)-2-(trans-4-hydroxycyclohexyl)-1-oxo-2,7-diazaspiro[4.5]dec-7-yl]phenyl}carbamate

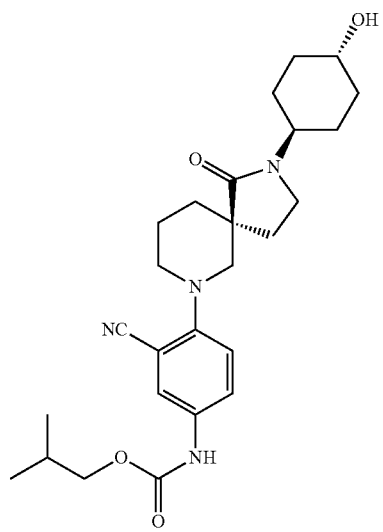 [SMILES: CC(C)COC(=O)Nc1ccc(N2CCC[C@]3(CCN([C@H]4CC[C@H](O)CC4)C3=O)C2)c(C#N)c1]

This compound was prepared by using procedures analogous to those described for the synthesis of example 105. LC-MS: 469.3 (M+H)$^+$.

218

Example 347

Isopropyl {3-cyano-4-[(5S)-2-(trans-4-hydroxycyclohexyl)-1-oxo-2,7-diazaspiro[4.5]dec-7-yl]phenyl}carbamate

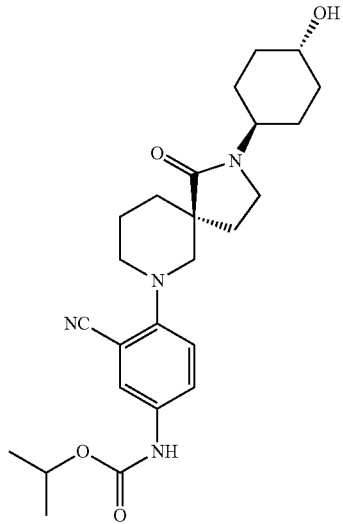 [SMILES: CC(C)OC(=O)Nc1ccc(N2CCC[C@]3(CCN([C@H]4CC[C@H](O)CC4)C3=O)C2)c(C#N)c1]

This compound was prepared by using procedures analogous to those described for the synthesis of example 105. LC-MS: 455.3 (M+H)$^+$.

Example 348

N-{3-Cyano-4-[(5S)-2-(trans-4-hydroxycyclohexyl)-1-oxo-2,7-diazaspiro[4.5]dec-7-yl]phenyl}cyclopropanecarboxamide

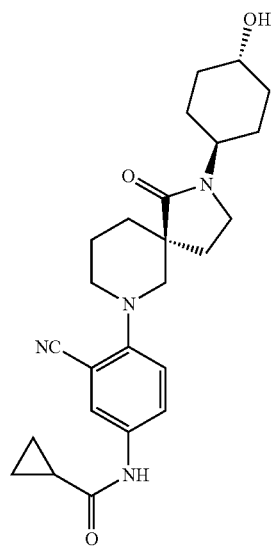 [SMILES: N#Cc1cc(NC(=O)C2CC2)ccc1N1CCC[C@]2(CCN([C@H]3CC[C@H](O)CC3)C2=O)C1]

This compound was prepared by using procedures analogous to those described for the synthesis of example 105. LC-MS: 437.3 (M+H)$^+$.

Example 349

N-{3-Cyano-4-[(5S)-2-(trans-4-hydroxycyclohexyl)-1-oxo-2,7-diazaspiro[4.5]dec-7-yl]phenyl}cyclobutanecarboxamide

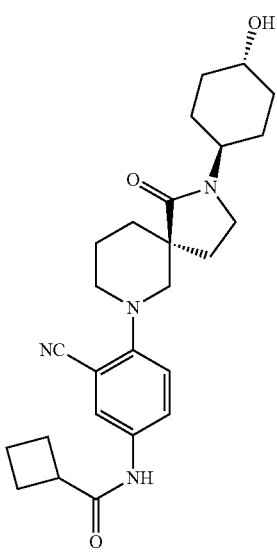 [SMILES: N#Cc1cc(NC(=O)C2CCC2)ccc1N1CCC[C@]2(CCN([C@H]3CC[C@H](O)CC3)C2=O)C1]

This compound was prepared by using procedures analogous to those described for the synthesis of example 105. LC-MS: 451.3 (M+H)$^+$.

Example 350

N-{3-Cyano-4-[(5S)-2-(trans-4-hydroxycyclohexyl)-1-oxo-2,7-diazaspiro[4.5]dec-7-yl]phenyl}cyclopentanecarboxamide

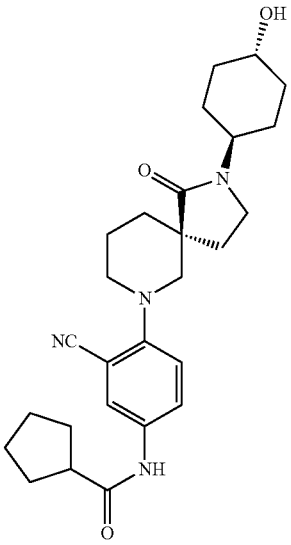 [SMILES: N#Cc1cc(NC(=O)C2CCCC2)ccc1N1CCC[C@]2(CCN([C@H]3CC[C@H](O)CC3)C2=O)C1]

This compound was prepared by using procedures analogous to those described for the synthesis of example 105. LC-MS: 465.3 (M+H)$^+$.

Example 351

N-{3-Cyano-4-[(5S)-2-(trans-4-hydroxycyclohexyl)-1-oxo-2,7-diazaspiro[4.5]dec-7-yl]phenyl}acetamide

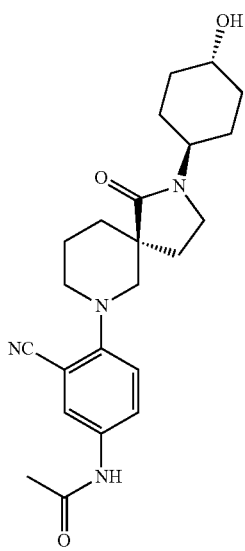 [SMILES: CC(=O)Nc1ccc(N2CCC[C@]3(CCN([C@H]4CC[C@H](O)CC4)C3=O)C2)c(C#N)c1]

This compound was prepared by using procedures analogous to those described for the synthesis of example 105. LC-MS: 411.3 (M+H)$^+$.

Example 352

N-{3-Cyano-4-[(5S)-2-(trans-4-hydroxycyclohexyl)-1-oxo-2,7-diazaspiro[4.5]dec-7-yl]phenyl}propanamide

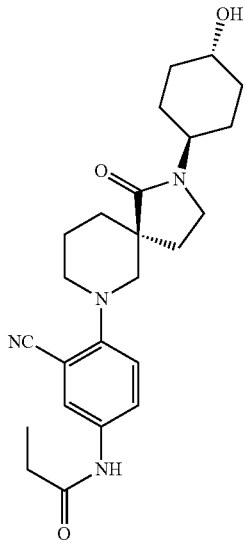 [SMILES: CCC(=O)Nc1ccc(N2CCC[C@]3(CCN([C@H]4CC[C@H](O)CC4)C3=O)C2)c(C#N)c1]

This compound was prepared by using procedures analogous to those described for the synthesis of example 105. LC-MS: 425.3 (M+H)$^+$.

Example 353

N-{3-Cyano-4-[(5S)-2-(trans-4-hydroxycyclohexyl)-1-oxo-2,7-diazaspiro[4.5]dec-7-yl]phenyl}-2-methylpropanamide

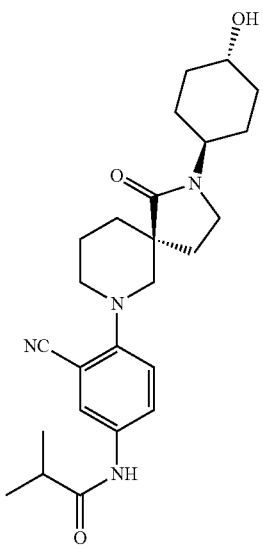 [SMILES: CC(C)C(=O)Nc1ccc(N2CCC[C@]3(CCN([C@H]4CC[C@H](O)CC4)C3=O)C2)c(C#N)c1]

This compound was prepared by using procedures analogous to those described for the synthesis of example 105. LC-MS: 439.3 (M+H)+.

Example 354

N-{3-Cyano-4-[(5S)-2-(trans-4-hydroxycyclohexyl)-1-oxo-2,7-diazaspiro[4.5]dec-7-yl]phenyl}cyclohexanecarboxamide

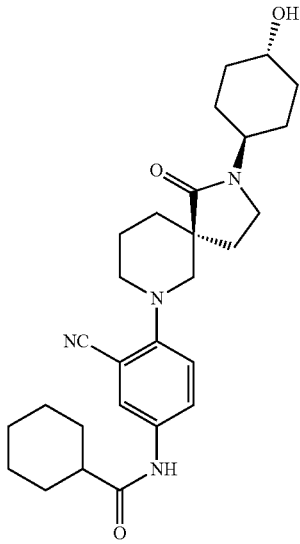 [SMILES: N#Cc1cc(NC(=O)C2CCCCC2)ccc1N1CCC[C@]2(CCN([C@H]3CC[C@H](O)CC3)C2=O)C1]

This compound was prepared by using procedures analogous to those described for the synthesis of example 105. LC-MS: 479.3 (M+H)+.

Example 355

Methyl {4-[(5S)-2-(trans-4-hydroxycyclohexyl)-1-oxo-2,7-diazaspiro[4.5]dec-7-yl]-3-methylphenyl}carbamate

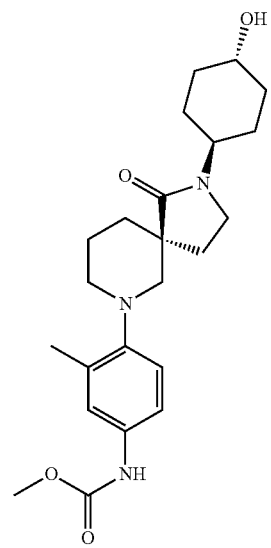 [SMILES: COC(=O)Nc1ccc(N2CCC[C@]3(CCN([C@H]4CC[C@H](O)CC4)C3=O)C2)c(C)c1]

This compound was prepared by using procedures analogous to those described for the synthesis of example 105. LC-MS: 416.3 (M+H)+.

Example 356

Ethyl {4-[(5S)-2-(trans-4-hydroxycyclohexyl)-1-oxo-2,7-diazaspiro[4.5]dec-7-yl]-3-methylphenyl}carbamate

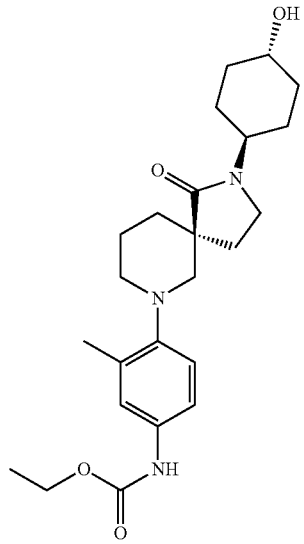 [SMILES: CCOC(=O)Nc1ccc(N2CCC[C@]3(CCN([C@H]4CC[C@H](O)CC4)C3=O)C2)c(C)c1]

This compound was prepared by using procedures analogous to those described for the synthesis of example 105. LC-MS: 430.3 (M+H)+.

Example 357

Propyl {4-[(5S)-2-(trans-4-hydroxycyclohexyl)-1-oxo-2,7-diazaspiro[4.5]dec-7-yl]-3-methylphenyl}carbamate

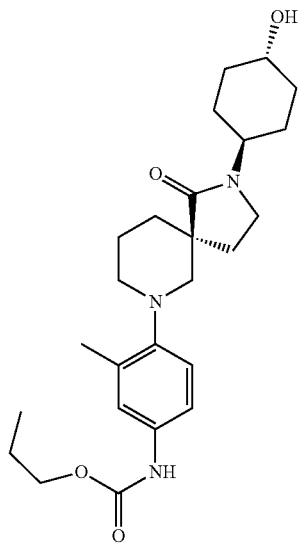 [SMILES: CCCOC(=O)Nc1ccc(N2CCC[C@]3(CCN([C@H]4CC[C@H](O)CC4)C3=O)C2)c(C)c1]

This compound was prepared by using procedures analogous to those described for the synthesis of example 105. LC-MS: 444.3 (M+H)⁺.

Example 358

Isobutyl {4-[(5S)-2-(trans-4-hydroxycyclohexyl)-1-oxo-2,7-diazaspiro[4.5]dec-7-yl]-3-methylphenyl}carbamate

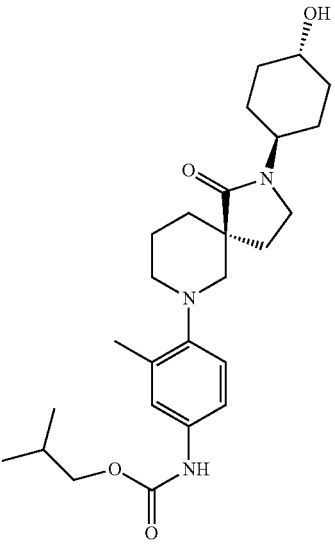 [SMILES: Cc1cc(NC(=O)OCC(C)C)ccc1N1CCC[C@]2(CCN([C@H]3CC[C@H](O)CC3)C2=O)C1]

This compound was prepared by using procedures analogous to those described for the synthesis of example 105. LC-MS: 458.3 (M+H)⁺.

Example 359

Isopropyl {4-[(5S)-2-(trans-4-hydroxycyclohexyl)-1-oxo-2,7-diazaspiro[4.5]dec-7-yl]-3-methylphenyl}carbamate

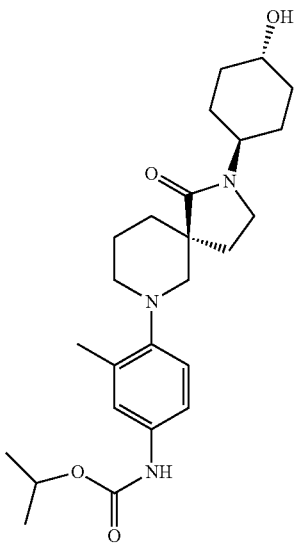 [SMILES: Cc1cc(NC(=O)OC(C)C)ccc1N1CCC[C@]2(CCN([C@H]3CC[C@H](O)CC3)C2=O)C1]

This compound was prepared by using procedures analogous to those described for the synthesis of example 105. LC-MS: 444.3 (M+H)⁺.

Example 360

N-{4-[(5S)-2-(trans-4-Hydroxycyclohexyl)-1-oxo-2,7-diazaspiro[4.5]dec-7-yl]-3-methylphenyl}cyclopropanecarboxamide

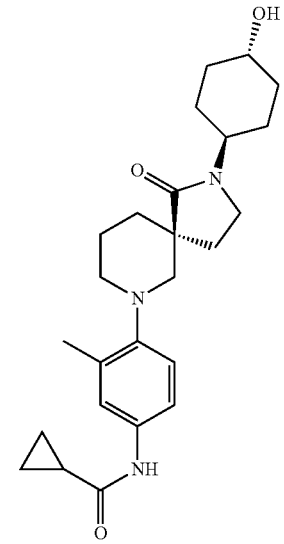 [SMILES: Cc1cc(NC(=O)C2CC2)ccc1N1CCC[C@]2(CCN([C@H]3CC[C@H](O)CC3)C2=O)C1]

This compound was prepared by using procedures analogous to those described for the synthesis of example 105. LC-MS: 426.3 (M+H)⁺.

Example 361

N-{4-[(5S)-2-(trans-4-Hydroxycyclohexyl)-1-oxo-2,
7-diazaspiro[4.5]dec-7-yl]-3-
methylphenyl}cyclobutanecarboxamide

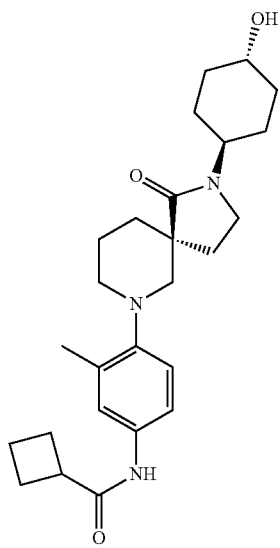 [SMILES: Cc1cc(NC(=O)C2CCC2)ccc1N1CCC[C@]2(CCN([C@H]3CC[C@H](O)CC3)C2=O)C1]

This compound was prepared by using procedures analogous to those described for the synthesis of example 105. LC-MS: 440.3 (M+H)⁺.

Example 362

N-{4-[(5S)-2-(trans-4-Hydroxycyclohexyl)-1-oxo-2,
7-diazaspiro[4.5]dec-7-yl]-3-
methylphenyl}cyclopentanecarboxamide

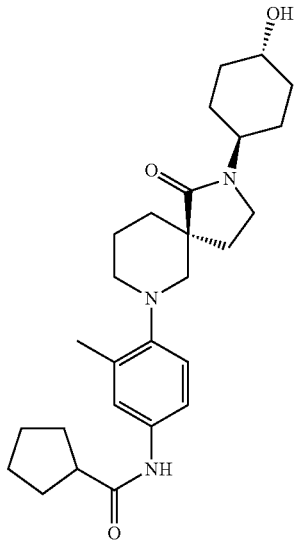 [SMILES: Cc1cc(NC(=O)C2CCCC2)ccc1N1CCC[C@]2(CCN([C@H]3CC[C@H](O)CC3)C2=O)C1]

This compound was prepared by using procedures analogous to those described for the synthesis of example 105. LC-MS: 454.4 (M+H)⁺.

Example 363

N-{4-[(5S)-2-(trans-4-Hydroxycyclohexyl)-1-oxo-2,
7-diazaspiro[4.5]dec-7-yl]-3-
methylphenyl}cyclohexanecarboxamide

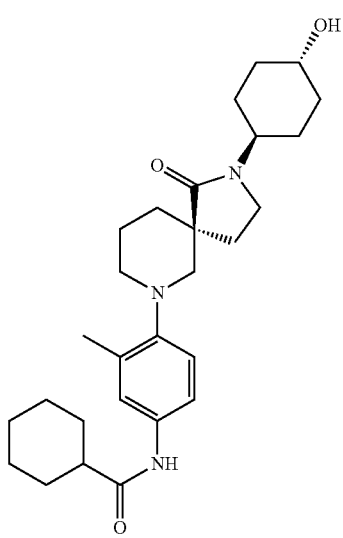 [SMILES: Cc1cc(NC(=O)C2CCCCC2)ccc1N1CCC[C@]2(CCN([C@H]3CC[C@H](O)CC3)C2=O)C1]

This compound was prepared by using procedures analogous to those described for the synthesis of example 105. LC-MS: 468.3 (M+H)⁺.

Example 364

N-{4-[(5S)-2-(trans-4-Hydroxycyclohexyl)-1-oxo-2,
7-diazaspiro[4.5]dec-7-yl]-3-
methylphenyl}acetamide

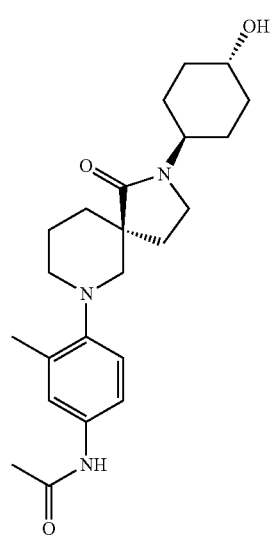

This compound was prepared by using procedures analogous to those described for the synthesis of example 105. LC-MS: 400.3 (M+H)⁺.

Example 365

N-{4-[(5S)-2-(trans-4-Hydroxycyclohexyl)-1-oxo-2,7-diazaspiro[4.5]dec-7-yl]-3-methylphenyl}propanamide

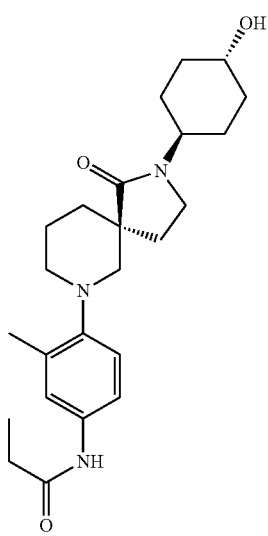 [SMILES: CCC(=O)Nc1ccc(N2CCC[C@]3(CCN([C@H]4CC[C@H](O)CC4)C3=O)C2)c(C)c1]

This compound was prepared by using procedures analogous to those described for the synthesis of example 105. LC-MS: 414.3 (M+H)$^+$.

Example 366

N-{4-[(5S)-2-(trans-4-Hydroxycyclohexyl)-1-oxo-2,7-diazaspiro[4.5]dec-7-yl]-3-methylphenyl}-2-methylpropanamide

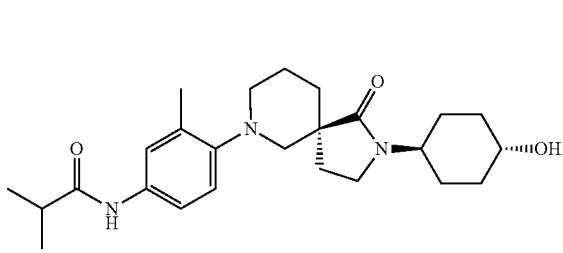 [SMILES: Cc1cc(NC(=O)C(C)C)ccc1N1CCC[C@]2(CCN([C@H]3CC[C@H](O)CC3)C2=O)C1]

This compound was prepared by using procedures analogous to those described for the synthesis of example 105. LC-MS: 428.3 (M+H)$^+$.

Example 367

(5S)-2-(trans-4-Hydroxycyclohexyl)-7-[4-(trifluoromethyl)quinolin-2-yl]-2,7-diazaspiro[4.5]decan-1-one

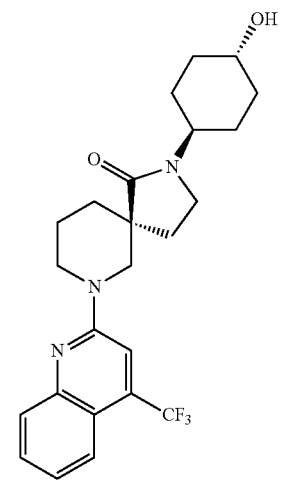 [SMILES: O=C1N([C@H]2CC[C@H](O)CC2)CC[C@]12CCCN(c1cc(C(F)(F)F)c3ccccc3n1)C2]

This compound was prepared by using procedures analogous to those described for the synthesis of example 93 starting from (5S)-2-(trans-4-hydroxycyclohexyl)-2,7-diazaspiro[4.5]decan-1-one. LC-MS: 448.3 (M+H)$^+$.

Example 368

(5S)-7-(3-Chloropyridin-2-yl)-2-(trans-4-hydroxycyclohexyl)-2,7-diazaspiro[4.5]decan-1-one

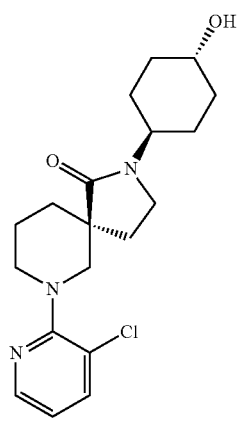 [SMILES: O=C1N([C@H]2CC[C@H](O)CC2)CC[C@]12CCCN(c1ncccc1Cl)C2]

This compound was prepared by using procedures analogous to those described for the synthesis of example 93 starting from (5S)-2-(trans-4-hydroxycyclohexyl)-2,7-diazaspiro[4.5]decan-1-one. LC-MS: 364.2 (M+H)$^+$.

Example 369

(5S)-7-[3-Fluoro-4-(trifluoromethyl)pyridin-2-yl]-2-(trans-4-hydroxycyclohexyl)-2,7-diazaspiro[4.5]decan-1-one

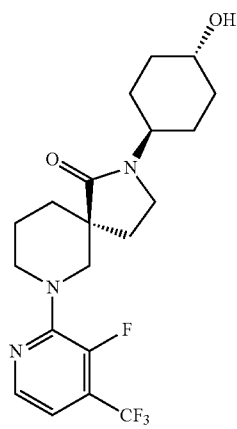 [SMILES: O=C1N([C@H]2CC[C@H](O)CC2)CC[C@]12CCCN(c1nccc(C(F)(F)F)c1F)C2]

This compound was prepared by using procedures analogous to those described for the synthesis of example 93 starting from (5S)-2-(trans-4-hydroxycyclohexyl)-2,7-diazaspiro[4.5]decan-1-one. LC-MS: 416.2 (M+H)$^+$.

Example 370

(5S)-2-(trans-4-Hydroxycyclohexyl)-7-(3,5,6-trifluoro-4-methylpyridin-2-yl)-2,7-diazaspiro[4.5]decan-1-one

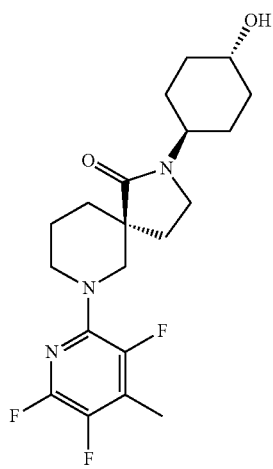 [SMILES: Cc1c(F)c(F)nc(N2CCC[C@]3(CCN([C@H]4CC[C@H](O)CC4)C3=O)C2)c1F]

This compound was prepared by using procedures analogous to those described for the synthesis of example 93 starting from (5S)-2-(trans-4-hydroxycyclohexyl)-2,7-diazaspiro[4.5]decan-1-one. LC-MS: 398.2 (M+H)$^+$.

Example 371

2,3,5-Trifluoro-6-[(5S)-2-(trans-4-hydroxycyclohexyl)-1-oxo-2,7-diazaspiro[4.5]dec-7-yl]isonicotinonitrile

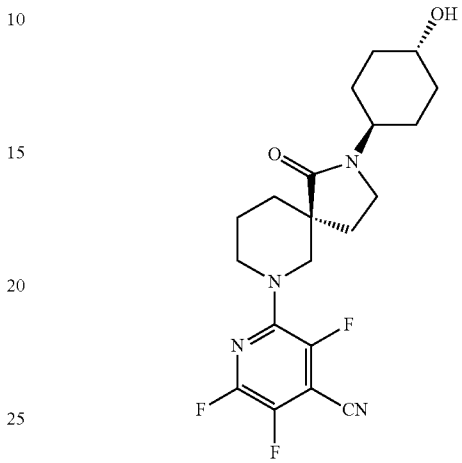

This compound was prepared by using procedures analogous to those described for the synthesis of example 93 starting from (5S)-2-(trans-4-hydroxycyclohexyl)-2,7-diazaspiro[4.5]decan-1-one. LC-MS: 409.2 (M+H)$^+$.

Example 372

(5S)-7-(3,5-Difluoropyridin-2-yl)-2-(trans-4-hydroxycyclohexyl)-2,7-diazaspiro[4.5]decan-1-one

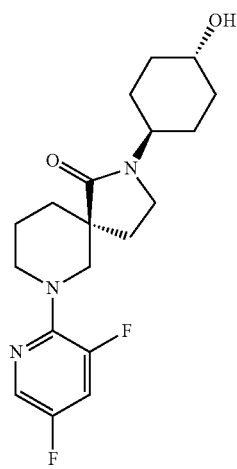 [SMILES: O=C1N([C@H]2CC[C@H](O)CC2)CC[C@]12CCCN(c1ncc(F)cc1F)C2]

This compound was prepared by using procedures analogous to those described for the synthesis of example 93 starting from (5S)-2-(trans-4-hydroxycyclohexyl)-2,7-diazaspiro[4.5]decan-1-one. LC-MS: 366.2 (M+H)$^+$.

Example 373

(5S)-2-(trans-4-hydroxycyclohexyl)-7-[4-(trifluoromethyl)pyridin-2-yl]-2,7-diazaspiro[4.5]decan-1-one

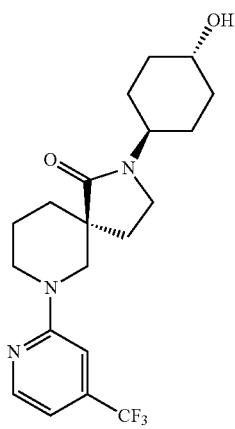 [SMILES: O=C1N([C@H]2CC[C@H](O)CC2)CC[C@]12CCCN(c1cc(C(F)(F)F)ccn1)C2]

This compound was prepared by using procedures analogous to those described for the synthesis of example 93 starting from (5S)-2-(trans-4-hydroxycyclohexyl)-2,7-diazaspiro[4.5]decan-1-one. LC-MS: 398.2 (M+H)⁺.

Example 374

(5S)-7-(3-Fluoropyridin-2-yl)-2-(trans-4-hydroxycyclohexyl)-2,7-diazaspiro[4.5]decan-1-one

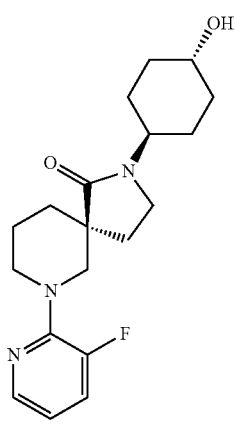 [SMILES: O=C1N([C@H]2CC[C@H](O)CC2)CC[C@]12CCCN(c1ncccc1F)C2]

This compound was prepared by using procedures analogous to those described for the synthesis of example 29. LC-MS: 348.2 (M+H)⁺.

Example 375

(5S)-7-(5-Chloro-3-fluoropyridin-2-yl)-2-(trans-4-hydroxycyclohexyl)-2,7-diazaspiro[4.5]decan-1-one

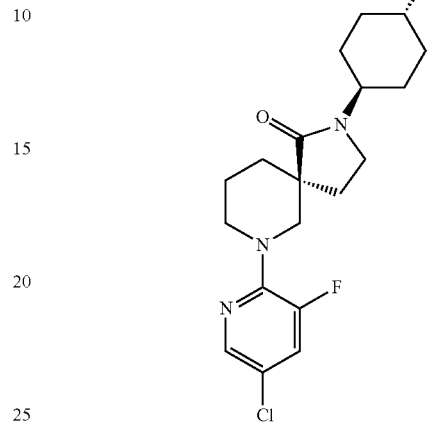

This compound was prepared by using procedures analogous to those described for the synthesis of example 93 starting from (5S)-2-(trans-4-hydroxycyclohexyl)-2,7-diazaspiro[4.5]decan-1-one. LC-MS: 382.1 (M+H)⁺.

Example 376

(5S)-7-(3-Ethynylpyridin-2-yl)-2-(trans-4-hydroxycyclohexyl)-2,7-diazaspiro[4.5]decan-1-one

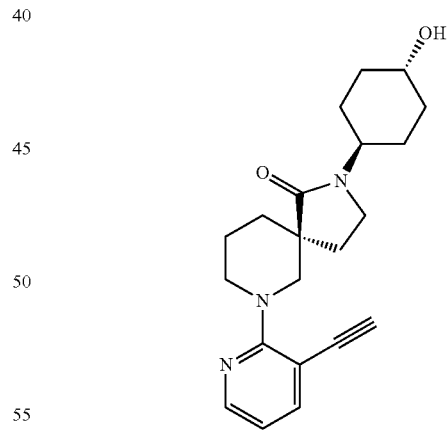

A mixture of (5S)-2-(trans-4-hydroxycyclohexyl)-7-{3-[(trimethylsilyl)ethynyl]pyridin-2-yl}-2,7-diazaspiro[4.5]decan-1-one (10 mg, 0.00002 mol, this compound was prepared by using procedures analogous to those described for the synthesis of example 93), lithium hydroxide monohydrate (1.1 mg, 0.000026 mol) in tetrahydrofuran (0.5 mL, 0.006 mol) and a couple of drops of water was stirred at rt for 30 min. The crude reaction mixture was purified by prep-HPLC to afford 7.2 mg of the desired product. LC-MS: 354.2 (M+H)⁺.

Example 377

7-(2-Fluoro-4-nitrophenyl)-2-(trans-4-hydroxycyclohexyl)-2,7-diazaspiro[4.5]decan-1-one

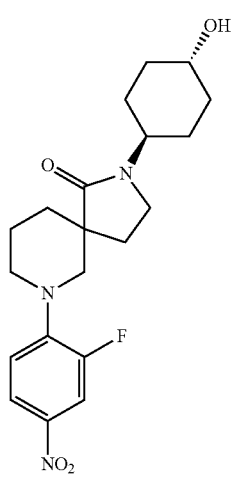 [SMILES: O=C1N([C@H]2CC[C@H](O)CC2)CCC12CCCN(c1ccc([N+](=O)[O-])cc1F)C2]

This compound was prepared by using procedures analogous to those described for the synthesis of example 43. LC-MS: 392.2 (M+H)$^+$.

Example 378

2-[(5S)-2-(trans-4-Hydroxycyclohexyl)-1-oxo-2,7-diazaspiro[4.5]dec-7-yl]-6-methylnicotinonitrile

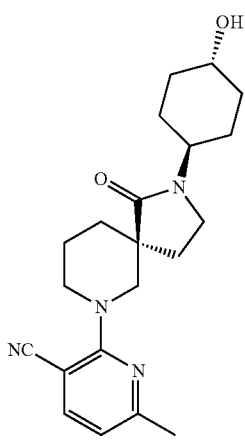 [SMILES: Cc1ccc(C#N)c(N2CCC[C@]3(CCN([C@H]4CC[C@H](O)CC4)C3=O)C2)n1]

This compound was prepared by using procedures analogous to those described for the synthesis of example 93 starting from (5S)-2-(trans-4-hydroxycyclohexyl)-2,7-diazaspiro[4.5]decan-1-one. LC-MS: 369.2 (M+H)$^+$.

Example 379

(5S)-2-(trans-4-Hydroxycyclohexyl)-7-quinolin-2-yl-2,7-diazaspiro[4.5]decan-1-one

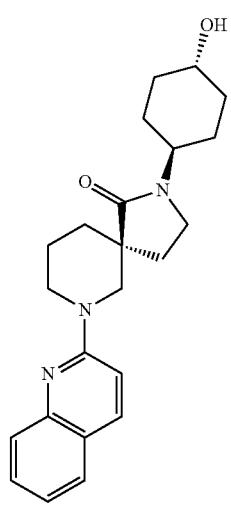 [SMILES: O=C1N([C@H]2CC[C@H](O)CC2)CC[C@]12CCCN(c1ccc3ccccc3n1)C2]

This compound was prepared by using procedures analogous to those described for the synthesis of example 93 starting from (5S)-2-(trans-4-hydroxycyclohexyl)-2,7-diazaspiro[4.5]decan-1-one. LC-MS: 380.3 (M+H)$^+$.

Example 380

2-(trans-4-Hydroxycyclohexyl)-7-[6-methyl-4-(trifluoromethyl)pyridin-2-yl]-2,7-diazaspiro[4.5]decan-1-one

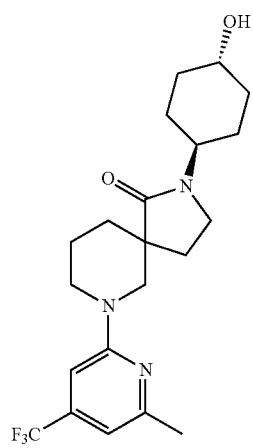 [SMILES: Cc1cc(C(F)(F)F)cc(N2CCCC3(CCN([C@H]4CC[C@H](O)CC4)C3=O)C2)n1]

This compound was prepared by using procedures analogous to those described for the synthesis of example 93. LC-MS: 412.3 (M+H)$^+$.

Example 381

(5S)-7-(3-Fluoropyridin-2-yl)-2-(trans-4-hydroxycyclohexyl)-2,7-diazaspiro[4.5]decan-1-one

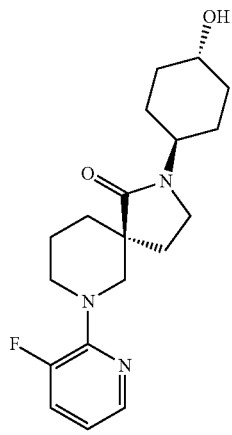 [SMILES: O=C1N([C@H]2CC[C@H](O)CC2)CC[C@]12CCCN(c1ncccc1F)C2]

This compound was prepared by using procedures analogous to those described for the synthesis of example 93 starting from (5S)-2-(trans-4-hydroxycyclohexyl)-2,7-diazaspiro[4.5]decan-1-one. LC-MS: 348.2 (M+H)$^+$.

Example 382

7-(5-Ethylpyrimidin-2-yl)-2-(trans-4-hydroxycyclohexyl)-2,7-diazaspiro[4.5]decan-1-one

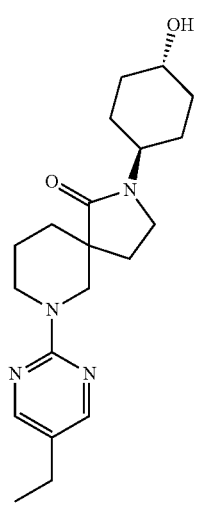 [SMILES: CCc1cnc(N2CCCC3(CCN([C@H]4CC[C@H](O)CC4)C3=O)C2)nc1]

This compound was prepared by using procedures analogous to those described for the synthesis of example 29. LC-MS: 359.3 (M+H)$^+$.

Example 383

(5S)-2-(trans-4-Hydroxycyclohexyl)-7-(3-methylquinolin-2-yl)-2,7-diazaspiro[4.5]decan-1-one

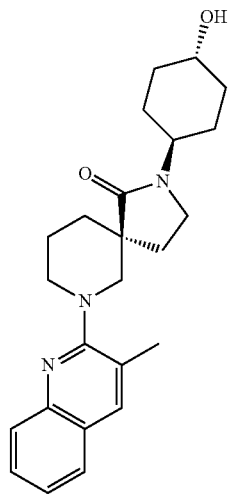 [SMILES: Cc1cc2ccccc2nc1N1CCC[C@]2(CCN([C@H]3CC[C@H](O)CC3)C2=O)C1]

This compound was prepared by using procedures analogous to those described for the synthesis of example 93 starting from (5S)-2-(trans-4-hydroxycyclohexyl)-2,7-diazaspiro[4.5]decan-1-one. LC-MS: 394.3 (M+H)$^+$.

Example 384

N-{4-[(5S)-2-(trans-4-Hydroxycyclohexyl)-1-oxo-2,7-diazaspiro[4.5]dec-7-yl]phenyl}methanesulfonamide

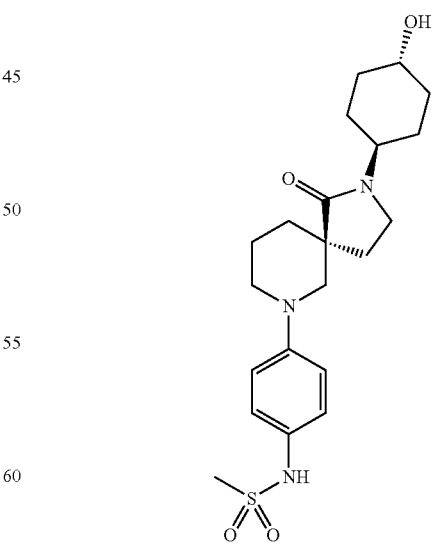

This compound was prepared by using procedures analogous to those described for the synthesis of example 105. LC-MS: 422.2 (M+H)$^+$.

Example 385

(5S)-7-[2-Fluoro-4-(pyridin-4-yloxy)phenyl]-2-(trans-4-hydroxycyclohexyl)-2,7-diazaspiro[4.5]decan-1-one

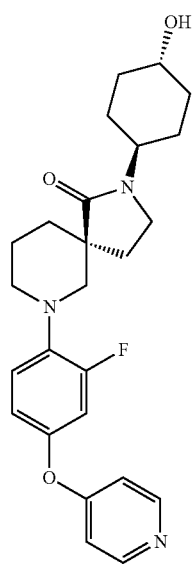 [SMILES: O=C1N([C@H]2CC[C@H](O)CC2)CC[C@]12CCCN(c1ccc(Oc3ccncc3)cc1F)C2]

This compound was prepared by using procedures analogous to those described for the synthesis of example 180. LC-MS: 440.2 (M+H)$^+$.

Example 386

(5S)-2-(trans-4-Hydroxycyclohexyl)-7-[5-(hydroxymethyl)pyridin-2-yl]-2,7-diazaspiro[4.5]decan-1-one

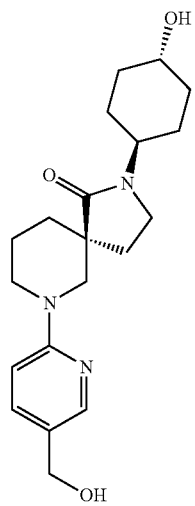 [SMILES: O=C1N([C@H]2CC[C@H](O)CC2)CC[C@]12CCCN(c1ccc(CO)cn1)C2]

This compound was prepared by using procedures analogous to those described for the synthesis of example 180. LC-MS: 360.2 (M+H)$^+$.

Example 387

6-[(5S)-2-(trans-4-Hydroxycyclohexyl)-1-oxo-2,7-diazaspiro[4.5]dec-7-yl]-N-methylnicotinamide

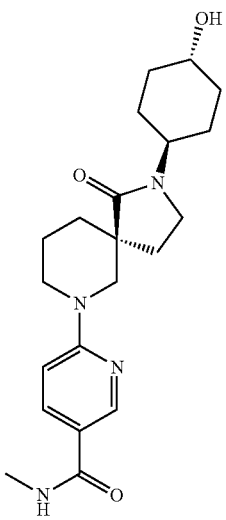 [SMILES: CNC(=O)c1ccc(N2CCC[C@]3(CCN([C@H]4CC[C@H](O)CC4)C3=O)C2)nc1]

This compound was prepared by using procedures analogous to those described for the synthesis of example 93 starting from (5S)-2-(trans-4-hydroxycyclohexyl)-2,7-diazaspiro[4.5]decan-1-one. LC-MS: 387.3 (M+H)$^+$.

Example 388

(5S)-7-(3-Fluoropyridin-4-yl)-2-(trans-4-hydroxycyclohexyl)-2,7-diazaspiro[4.5]decan-1-one

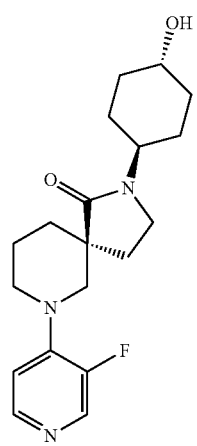 [SMILES: O=C1N([C@H]2CC[C@H](O)CC2)CC[C@]12CCCN(c1ccncc1F)C2]

This compound was prepared by using procedures analogous to those described for the synthesis of example 93 starting from (5S)-2-(trans-4-hydroxycyclohexyl)-2,7-diazaspiro[4.5]decan-1-one. LC-MS: 348.3 (M+H)$^+$.

Example 389

(5S)-7-(2-Chloropyridin-4-yl)-2-(trans-4-hydroxycyclohexyl)-2,7-diazaspiro[4.5]decan-1-one

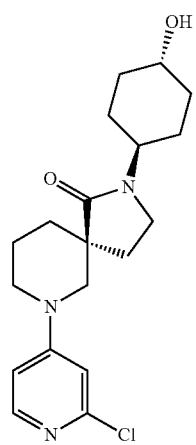 [SMILES: O=C1N([C@H]2CC[C@H](O)CC2)CC[C@]12CCCN(c1ccnc(Cl)c1)C2]

This compound was prepared by using procedures analogous to those described for the synthesis of example 93 starting from (5S)-2-(trans-4-hydroxycyclohexyl)-2,7-diazaspiro[4.5]decan-1-one. LC-MS: 364.2 (M+H)$^+$.

Example 390

N-{3-Fluoro-4-[(5S)-2-(trans-4-hydroxycyclohexyl)-1-oxo-2,7-diazaspiro[4.5]dec-7-yl]phenyl}-N-methylmethanesulfonamide

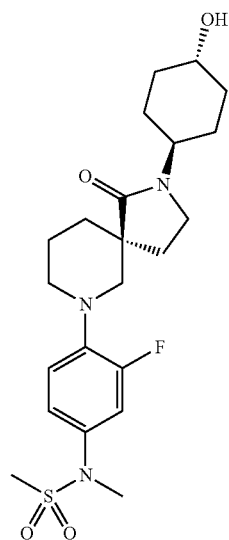 [SMILES: CN(c1ccc(N2CCC[C@]3(CCN([C@H]4CC[C@H](O)CC4)C3=O)C2)c(F)c1)S(C)(=O)=O]

A mixture of N-{3-fluoro-4-[(5S)-2-(trans-4-hydroxycyclohexyl)-1-oxo-2,7-diazaspiro[4.5]dec-7-yl]phenyl}methanesulfonamide (20 mg, 0.00006 mol, example 312), methyl iodide (4.1 µL, 0.000066 mol), and potassium carbonate (10 mg, in excess) in acetone (2 mL, 0.03 mol) was stirred at rt for 2 h and then heated to 40° C. for 2 h. The reaction mixture was allowed to cool to rt and was purified by prep-HPLC to afford the desired product. LC-MS: 454.2 (M+H)$^+$.

Example 391

N-{6-[(5S)-2-(trans-4-Hydroxycyclohexyl)-1-oxo-2,7-diazaspiro[4.5]dec-7-yl]pyridin-3-yl}-2-methylpropanamide

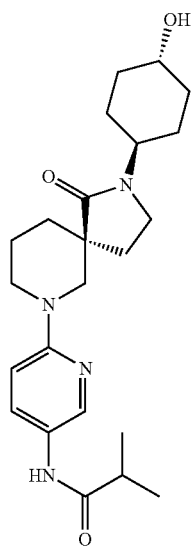 [SMILES: CC(C)C(=O)Nc1ccc(N2CCC[C@]3(CCN([C@H]4CC[C@H](O)CC4)C3=O)C2)nc1]

This compound was prepared by using procedures analogous to those described for the synthesis of example 105. LC-MS: 415.3 (M+H)$^+$.

Example 392

7-(2-Chloropyrimidin-4-yl)-2-(trans-4-hydroxycyclohexyl)-2,7-diazaspiro[4.5]decan-1-one

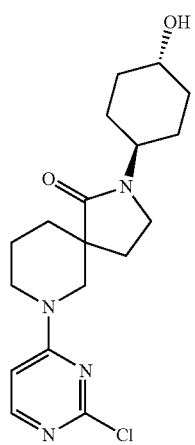 [SMILES: O=C1N([C@H]2CC[C@H](O)CC2)CCC12CCCN(c1ccnc(Cl)n1)C2]

This compound was prepared by using procedures analogous to those described for the synthesis of example 29. LC-MS: 365.2 (M+H)$^+$.

Example 393

6-[2-(trans-4-Hydroxycyclohexyl)-1-oxo-2,7-diaza-spiro[4.5]dec-7-yl]-N,N-dimethylnicotinamide

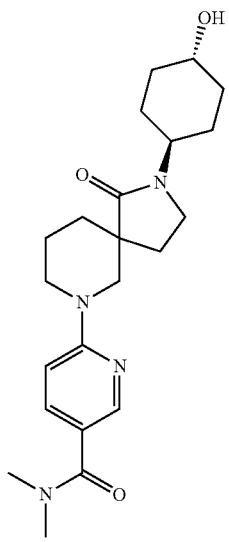 [SMILES: CN(C)C(=O)c1ccc(N2CCCC3(CCN([C@H]4CC[C@H](O)CC4)C3=O)C2)nc1]

This compound was prepared by using procedures analogous to those described for the synthesis of example 29. LC-MS: 401.2 (M+H)$^+$.

Example 394

Ethyl {2-[(5S)-2-(trans-4-hydroxycyclohexyl)-1-oxo-2,7-diazaspiro[4.5]dec-7-yl]-6-methoxypyridin-3-yl}carbamate

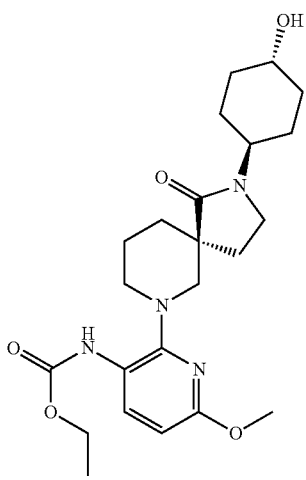 [SMILES: CCOC(=O)Nc1ccc(OC)nc1N1CCC[C@]2(CCN([C@H]3CC[C@H](O)CC3)C2=O)C1]

This compound was prepared by using procedures analogous to those described for the synthesis of example 105. LC-MS: 447.2 (M+H)$^+$.

Example 395

Methyl {2-[(5S)-2-(trans-4-hydroxycyclohexyl)-1-oxo-2,7-diazaspiro[4.5]dec-7-yl]-6-methoxypyridin-3-yl}carbamate

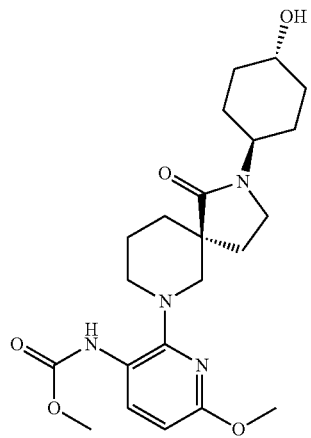 [SMILES: COC(=O)Nc1ccc(OC)nc1N1CCC[C@]2(CCN([C@H]3CC[C@H](O)CC3)C2=O)C1]

This compound was prepared by using procedures analogous to those described for the synthesis of example 105. LC-MS: 433.2 (M+H)$^+$.

Example 396

N-{2-[(5S)-2-(trans-4-Hydroxycyclohexyl)-1-oxo-2,7-diazaspiro[4.5]dec-7-yl]-6-methoxypyridin-3-yl}acetamide

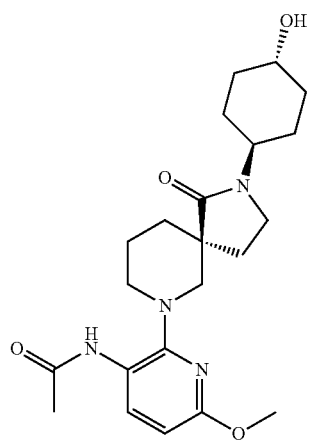 [SMILES: COc1ccc(NC(C)=O)c(N2CCC[C@]3(CCN([C@H]4CC[C@H](O)CC4)C3=O)C2)n1]

This compound was prepared by using procedures analogous to those described for the synthesis of example 105. LC-MS: 417.2 (M+H)$^+$.

Example 397

5-[(5S)-2-(trans-4-Hydroxycyclohexyl)-1-oxo-2,7-diazaspiro[4.5]dec-7-yl]-N-methylpyridine-2-carboxamide

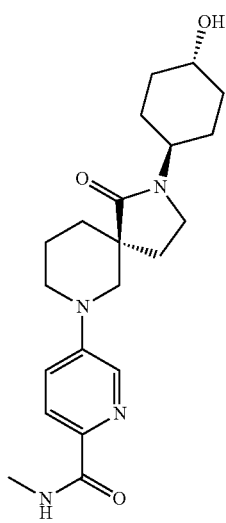 [SMILES: CNC(=O)c1ccc(N2CCC[C@]3(CCN([C@H]4CC[C@H](O)CC4)C3=O)C2)cn1]

This compound was prepared by using procedures analogous to those described for the synthesis of example 180. LC-MS: 387.2 (M+H)$^+$.

Example 398

(5S)-2-(trans-4-Hydroxycyclohexyl)-7-(3-methoxypyridin-2-yl)-2,7-diazaspiro[4.5]decan-1-one

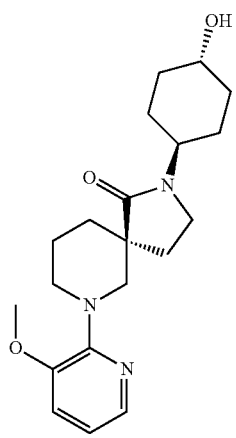

This compound was prepared by using procedures analogous to those described for the synthesis of example 93 starting from (5S)-2-(trans-4-hydroxycyclohexyl)-2,7-diazaspiro[4.5]decan-1-one. Additionally, NaH was used instead of N,N-diisopropylethylamine as the base. LC-MS: 360.2 (M+H)$^+$.

Example 399

2-[8-(trans-4-Hydroxycyclohexyl)-7-oxo-2,8-diazaspiro[5.5]undec-2-yl]nicotinonitrile

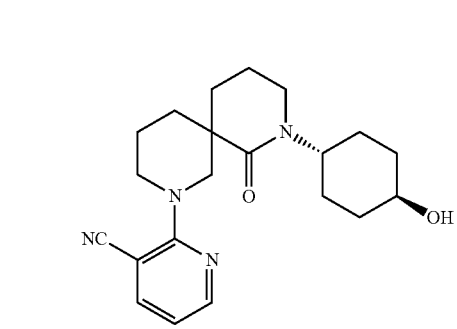 [SMILES: N#Cc1cccnc1N1CCCC2(CCCN([C@H]3CC[C@H](O)CC3)C2=O)C1]

This compound was prepared by using procedures analogous to those described for the synthesis of example 1. LC-MS: 369.2 (M+H)$^+$.

Example 400

2-(trans-4-Hydroxycyclohexyl)-8-[3-(trifluoromethyl)pyridin-2-yl]-2,8-diazaspiro[5.5]undecan-1-one

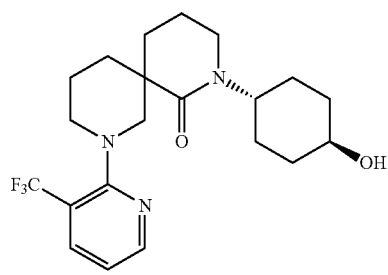 [SMILES: O=C1N([C@H]2CC[C@H](O)CC2)CCCC12CCCN(c1ncccc1C(F)(F)F)C2]

This compound was prepared by using procedures analogous to those described for the synthesis of example 1. LC-MS: 412.2 (M+H)$^+$.

Example 401

3-Cyclohexyl-7-[5-(trifluoromethyl)pyridin-2-yl]-1,3,7-triazaspiro[4.5]decane-2,4-dione

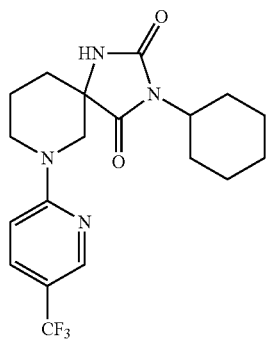 [SMILES: O=C1NC2(CCCN(c3ccc(C(F)(F)F)cn3)C2)C(=O)N1C1CCCCC1]

Step 1. tert-butyl 3-oxopiperidine-1-carboxylate

To a solution of pyridinium chlorochromate (3.21 g, 0.0149 mol) in methylene chloride (18 mL) was added another solution of tert-butyl 3-hydroxypiperidine-1-carboxylate (1.00 g, 0.00497 mol) in 7 mL methylene chloride at rt. After stirring for 18 h, the reaction mixture was diluted with diethyl ether, filtered through a bed of celite, concentrated in-vacuo, and then purified by Combiflash to afford the desired product verified by NMR.

Step 2. tert-butyl 2,4-dioxo-1,3,7-triazaspiro[4.5]decane-7-carboxylate

A mixture of tert-butyl 3-oxopiperidine-1-carboxylate (0.20 g, 0.0010 mol), potassium cyanide (0.13 g, 0.0020 mol) and ammonium carbonate (0.77 g, 0.0080 mol) in ethanol (4.0 mL, 0.068 mol) and water (2.0 mL) was stirred at 70° C. for 4 h. The mixture was then diluted with ethyl acetate and washed with water, brine, dried and concentrated to give the desired product. LC-MS: 292.0 (M+Na)$^+$.

Step 3. tert-butyl 3-cyclohexyl-2,4-dioxo-1,3,7-triazaspiro[4.5]decane-7-carboxylate Diethyl azodicarboxylate (0.315 mL, 0.00200 mol) was added to a mixture of tert-butyl 2,4-dioxo-1,3,7-triazaspiro[4.5]decane-7-carboxylate (269.3 mg, 0.001000 mol), cyclohexanol (0.156 mL, 0.00150 mol), and triphenylphosphine (524 mg, 0.00200 mol) in tetrahydrofuran (6 mL, 0.08 mol). The reaction mixture was stirred at room temperature overnight. The mixture was concentrated and the residue was purified by Combiflash with ethyl acetate/hexane. LC-MS: 296.2 (M−Bu+2H)$^+$.

Step 4. 3-cyclohexyl-7-[5-(trifluoromethyl)pyridin-2-yl]-1,3,7-triazaspiro[4.5]decane-2,4-dione This compound was prepared by using procedures analogous to those described for the synthesis of example 92, steps 3 and 4. LC-MS: 397.2 (M+H)$^+$.

Example 402

6-(3-cyclohexyl-2,4-dioxo-1,3,7-triazaspiro[4.5]dec-7-yl)nicotinonitrile

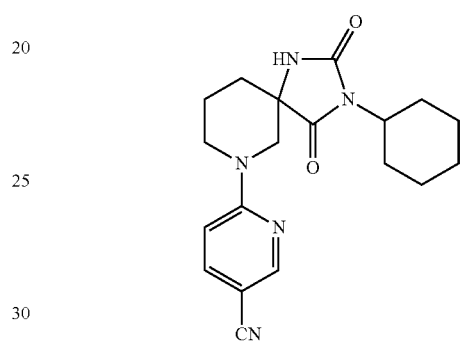

This compound was prepared by using procedures analogous to those described for the synthesis of example 401. LC-MS: 354.2 (M+H)$^+$.

Example 403

4-(3-Cyclohexyl-2,4-dioxo-1,3,7-triazaspiro[4.5]dec-7-yl)-3-fluorobenzonitrile

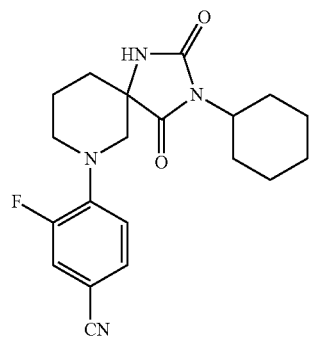 [SMILES: N#Cc1ccc(N2CCCC3(C2)NC(=O)N(C2CCCCC2)C3=O)c(F)c1]

This compound was prepared by using procedures analogous to those described for the synthesis of example 401. LC-MS: 393.1 (M+Na)$^+$, 371.1 (M+H)$^+$.

Example 404

3-Cyclohexyl-7-(5-ethylpyrimidin-2-yl)-1,3,7-triaza-spiro[4.5]decane-2,4-dione

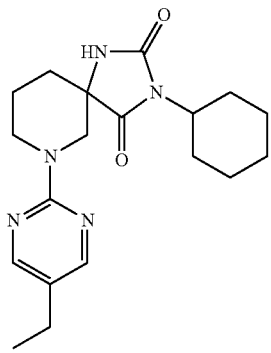 [SMILES: CCc1cnc(N2CCCC3(C2)NC(=O)N(C2CCCCC2)C3=O)nc1]

This compound was prepared by using procedures analogous to those described for the synthesis of example 401. LC-MS: 358.1 (M+H)$^+$.

Example 405

3-Cyclohexyl-7-(3-fluoropyridin-2-yl)-1,3,7-triaza-spiro[4.5]decane-2,4-dione

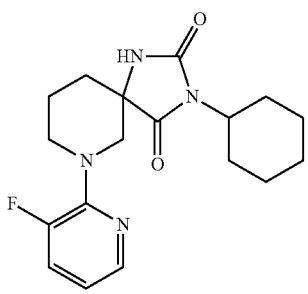 [SMILES: O=C1NC2(CCCN(c3ncccc3F)C2)C(=O)N1C1CCCCC1]

This compound was prepared by using procedures analogous to those described for the synthesis of example 401. LC-MS: 347.1 (M+H)$^+$.

Example 406

3-Cyclohexyl-7-(3,5-difluoropyridin-2-yl)-1,3,7-triazaspiro[4.5]decane-2,4-dione

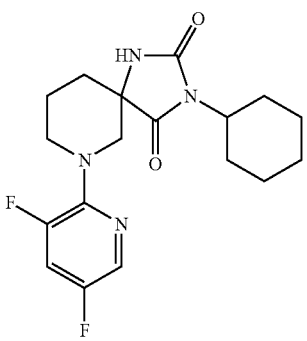 [SMILES: O=C1NC2(CCCN(c3ncc(F)cc3F)C2)C(=O)N1C1CCCCC1]

This compound was prepared by using procedures analogous to those described for the synthesis of example 401. LC-MS: 365.2 (M+H)$^+$.

Example 407

3-Cyclohexyl-7-(3,5-dichloropyridin-2-yl)-1,3,7-triazaspiro[4.5]decane-2,4-dione

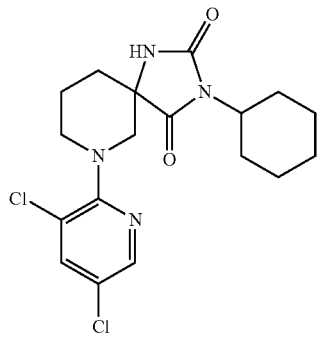 [SMILES: O=C1NC2(CCCN(c3ncc(Cl)cc3Cl)C2)C(=O)N1C1CCCCC1]

This compound was prepared by using procedures analogous to those described for the synthesis of example 401. LC-MS: 397.1/399.1 (M+H)$^+$.

Example 408

2-(3-Methylpyridin-2-yl)-7-[5-(trifluoromethyl)pyridin-2-yl]-2,7-diazaspiro[4.5]decan-1-one

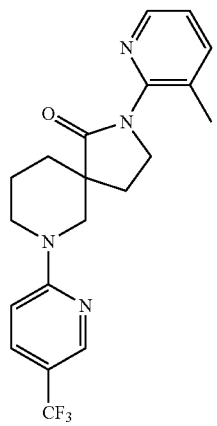 [SMILES: Cc1cccnc1N1CCC2(CCCN(c3ccc(C(F)(F)F)cn3)C2)C1=O]

This compound was prepared by using procedures analogous to those described for the synthesis of example 92 starting from 3-methylpyridin-2-amine and prepared as a racemic compound. LC-MS: 391.2 (M+H)$^+$.

Example 409

N,N-Dimethyl-5-[(5S)-1-oxo-2-(tetrahydro-2H-pyran-4-yl)-2,7-diazaspiro[4.5]dec-7-yl]pyridine-2-carboxamide

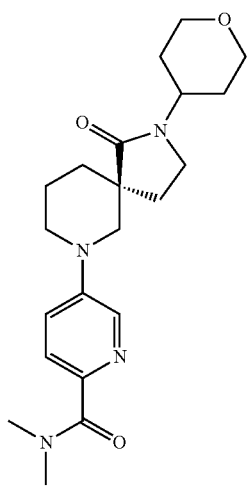 [SMILES: CN(C)C(=O)c1ccc(N2CCC[C@]3(CCN(C4CCOCC4)C3=O)C2)cn1]

This compound was prepared by using procedures analogous to those described for the synthesis of example 180. LC-MS: 387.2 (M+H)$^+$.

Example 410

3-Fluoro-4-[(5S)-1-oxo-2-(tetrahydro-2H-pyran-4-yl)-2,7-diazaspiro[4.5]dec-7-yl]benzonitrile

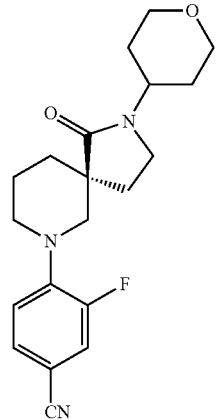

This compound was prepared by using procedures analogous to those described for the synthesis of example 43 starting from (5S)-2-(tetrahydro-2H-pyran-4-yl)-2,7-diazaspiro[4.5]decan-1-one prepared as described in Example 105. LC-MS: 358.2 (M+H)$^+$.

Example 411

(5S)-2-(trans-4-Hydroxycyclohexyl)-7-(6-methoxy-2-methylpyridin-3-yl)-2,7-diazaspiro[4.5]decan-1-one

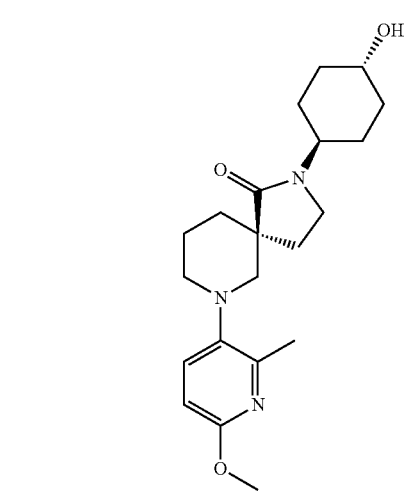 [SMILES: COc1ccc(N2CCC[C@]3(CCN([C@H]4CC[C@H](O)CC4)C3=O)C2)c(C)n1]

This compound was prepared by using procedures analogous to those described for the synthesis of example 180. LC-MS: 374.2 (M+H)$^+$.

Example 412

(5S)-2-(4-Hydroxycyclohexyl)-7-(6-methoxy-4-methylpyridin-3-yl)-2,7-diazaspiro[4.5]decan-1-one

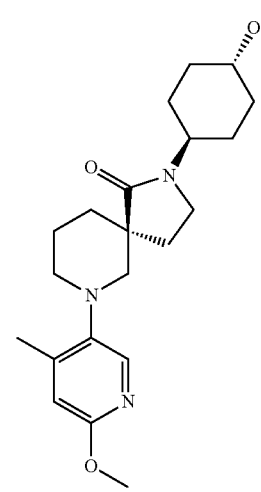

and

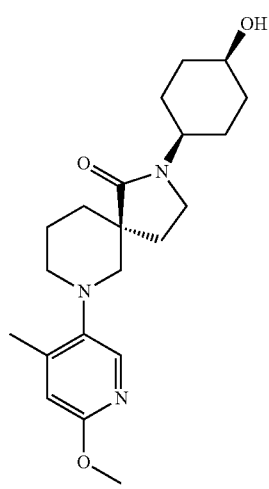

This compound was prepared by using procedures analogous to those described for the synthesis of example 180. LC-MS: 374.2 (M+H)+.

Example 413

(5S)-7-(2,6-Difluorophenyl)-2-(4-hydroxycyclohexyl)-2,7-diazaspiro[4.5]decan-1-one

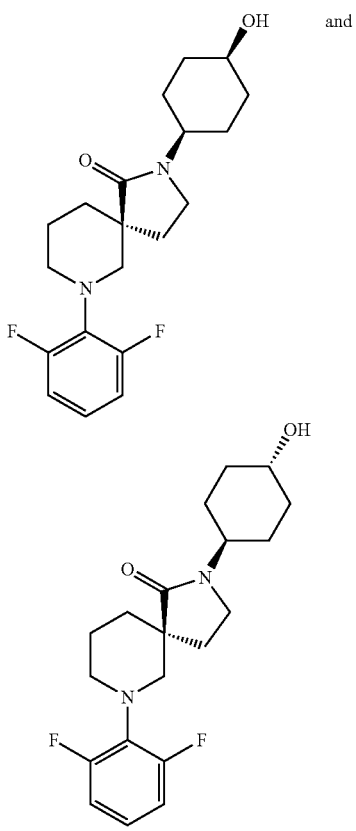

This compound was prepared by using procedures analogous to those described for the synthesis of example 180. LC-MS: 365.2 (M+H)+.

Example 414

7-(5-Chloropyridin-2-yl)-2-(4-hydroxy-1-adamantyl)-2,7-diazaspiro[4.5]decan-1-one

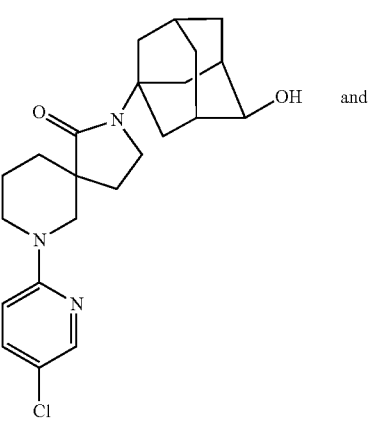

and

-continued

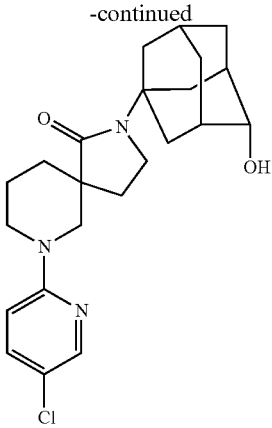

This compound was prepared by using procedures analogous to those described for the synthesis of example 93. LC-MS: 416.2 (M+H)+.

Example 415

7-(3-Fluoropyridin-4-yl)-2-(4-hydroxy-1-adamantyl)-2,7-diazaspiro[4.5]decan-1-one

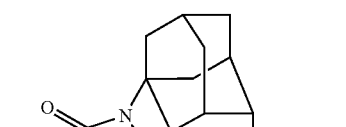

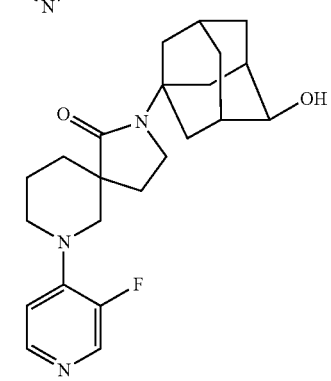

This compound was prepared by using procedures analogous to those described for the synthesis of example 93. LC-MS: 400.1 (M+H)+.

Example 416

N-{3-Fluoro-4-[2-(4-hydroxy-1-adamantyl)-1-oxo-2,7-diazaspiro[4.5]dec-7-yl]phenyl}propanamide

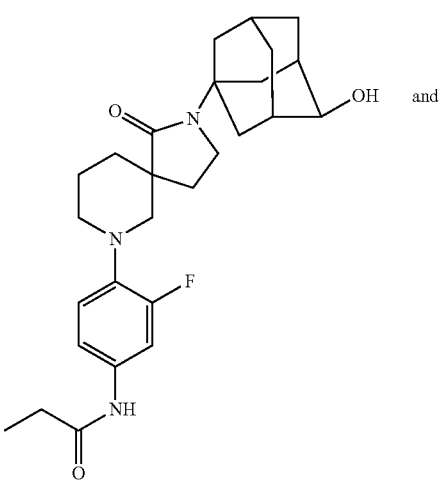

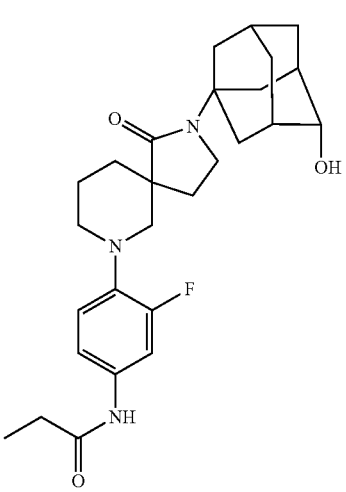

This compound was prepared by using procedures analogous to those described for the synthesis of example 105 starting from N-{3-fluoro-4-[2-(4-hydroxy-1-adamantyl)-1-oxo-2,7-diazaspiro[4.5]dec-7-yl]phenyl}amine and prepared as a racemic compound. LC-MS: 470.1 (M+H)+.

Example 417

Methyl {3-fluoro-4-[2-(4-hydroxy-1-adamantyl)-1-oxo-2,7-diazaspiro[4.5]dec-7-yl]phenyl}carbamate

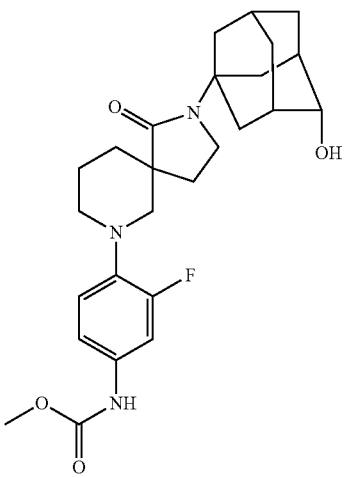

Example 418

Propyl {3-fluoro-4-[2-(4-hydroxy-1-adamantyl)-1-oxo-2,7-diazaspiro[4.5]dec-7-yl]phenyl}carbamate

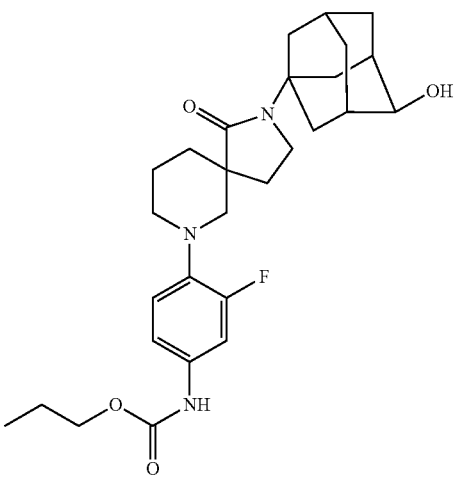 [SMILES: CCCOC(=O)Nc1ccc(N2CCCC3(CCN(C45CC6CC(C4)C(O)C(C6)C5)C3=O)C2)c(F)c1]

This compound was prepared by using procedures analogous to those described for the synthesis of example 105 starting from N-{3-fluoro-4-[2-(4-hydroxy-1-adamantyl)-1-oxo-2,7-diazaspiro[4.5]dec-7-yl]phenyl}amine and prepared as a racemic compound. LC-MS: 500.1 (M+H)$^+$.

Example 419

N-{3-Fluoro-4-[2-(4-hydroxy-1-adamantyl)-1-oxo-2,7-diazaspiro[4.5]dec-7-yl]phenyl}ethanesulfonamide

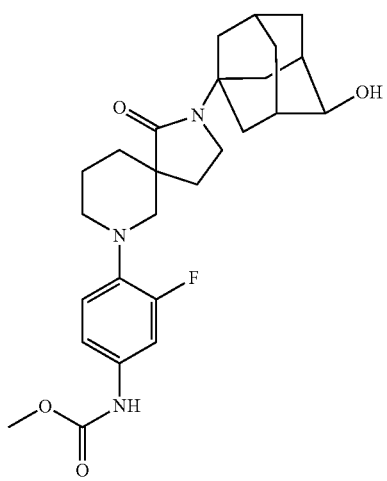

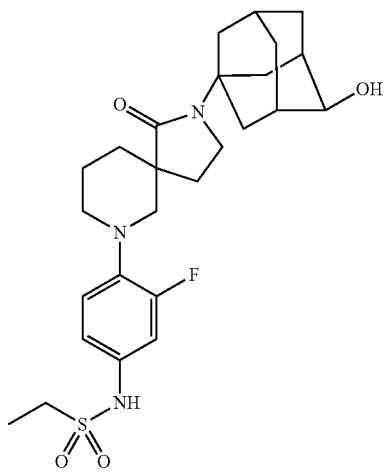 [SMILES: CCS(=O)(=O)Nc1ccc(N2CCCC3(CCN(C45CC6CC(C4)C(O)C(C6)C5)C3=O)C2)c(F)c1]

This compound was prepared by using procedures analogous to those described for the synthesis of example 105 starting from N-{3-fluoro-4-[2-(4-hydroxy-1-adamantyl)-1-oxo-2,7-diazaspiro[4.5]dec-7-yl]phenyl}amine, and prepared as a racemic compound. LC-MS: 472.1 (M+H)$^+$.

This compound was prepared by using procedures analogous to those described for the synthesis of example 105 starting from N-{3-fluoro-4-[2-(4-hydroxy-1-adamantyl)-1-oxo-2,7-diazaspiro[4.5]dec-7-yl]phenyl}amine and prepared as a racemic compound. LC-MS: 506.1 (M+H)$^+$.

Example 420

2-[(5S)-2-(cis-4-Hydroxycyclohexyl)-1-oxo-2,7-diazaspiro[4.5]dec-7-yl]nicotinonitrile

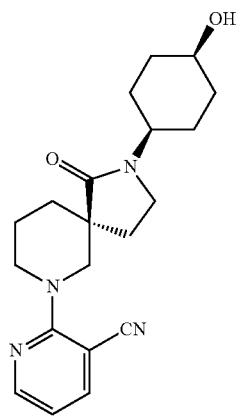

Step 1. benzyl (5S)-2-[cis-4-(benzoyloxy)cyclohexyl]-1-oxo-2,7-diazaspiro[4.5]decane-7-carboxylate Diethyl azodicarboxylate (163.0 µL, 0.001035 mol) was added to a mixture of benzyl (5S)-2-(trans-4-hydroxycyclohexyl)-1-oxo-2,7-diazaspiro[4.5]decane-7-carboxylate (200.0 mg, 0.0005175 mol, this compound was prepared by using the procedures of example 472-a, step 1), and triphenylphosphine (271.4 mg, 0.001035 mol) in tetrahydrofuran (3.0 mL, 0.037 mol) at rt. The mixture was stirred at rt for 5 minutes, then benzoic acid (66.36 mg, 0.0005434 mol) was added. After stirring for an additional 2 h, the volatiles in the mixture were removed in-vacuo and the residue was purified by flash chromatography to afford the desired product.

Step 2. cis-4-[(5S)-1-oxo-2,7-diazaspiro[4.5]dec-2-yl]cyclohexyl benzoate

Benzyl (5S)-2-[cis-4-(benzoyloxy)cyclohexyl]-1-oxo-2,7-diazaspiro[4.5]decane-7-carboxylate (0.16 g, 0.00033 mol) in methanol (5 mL, 0.1 mol) was stirred with palladium (20 mg, 0.00002 mol) under an atmosphere of hydrogen for 2 h. The mixture was filtered and the filtrate was concentrated to afford the desired product. LC-MS: 357.2 (M+H)$^+$.

Step 3. 2-[(5S)-2-(cis-4-hydroxycyclohexyl)-1-oxo-2,7-diazaspiro[4.5]dec-7-yl]nicotinonitrile A mixture of cis-4-[(5S)-1-oxo-2,7-diazaspiro[4.5]dec-2-yl]cyclohexyl benzoate (19.0 mg, 0.0000533 mol), 2-chloronicotinonitrile (8.12 mg, 0.0000586 mol) and N,N-diisopropylethylamine (20.0 µL, 0.000115 mol) in N-methylpyrrolidinone (0.6 mL, 0.006 mol) was irradiated by microwave at 180° C. for 20 min. After cooling to rt, lithium hydroxide aqueous solution (1.0 M, 0.150 mL) was added, followed by methanol (0.2 mL). The mixture was heated at 100° C. for 5 h. The crude reaction mixture was then purified by prep-HPLC under basic conditions to afford the desired product. LC-MS: 355.2 (M+H)$^+$.

Example 421

(5S)-2-(cis-4-Hydroxycyclohexyl)-7-[3-(trifluoromethyl)pyridin-2-yl]-2,7-diazaspiro[4.5]decan-1-one

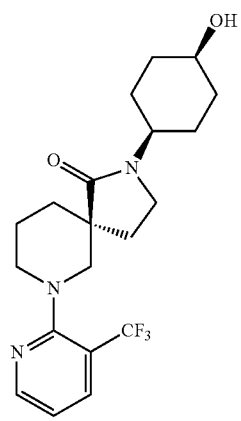 [SMILES: O=C1N([C@H]2CC[C@@H](O)CC2)CC[C@]12CCCN(c1ncccc1C(F)(F)F)C2]

This compound was prepared by using procedures analogous to those described for the synthesis of example 420. LC-MS: 398.2 (M+H)$^+$.

Example 422

(5S)-7-(3-Fluoropyridin-2-yl)-2-(cis-4-hydroxycyclohexyl)-2,7-diazaspiro[4.5]decan-1-one

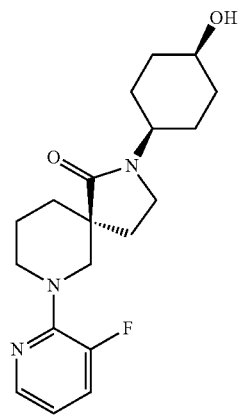 [SMILES: O=C1N([C@H]2CC[C@@H](O)CC2)CC[C@]12CCCN(c1ncccc1F)C2]

This compound was prepared by using procedures analogous to those described for the synthesis of example 420. LC-MS: 348.2 (M+H)$^+$.

Example 423

(5S)-7-(3,5-Dichloropyridin-2-yl)-2-(cis-4-hydroxy-cyclohexyl)-2,7-diazaspiro[4.5]decan-1-one

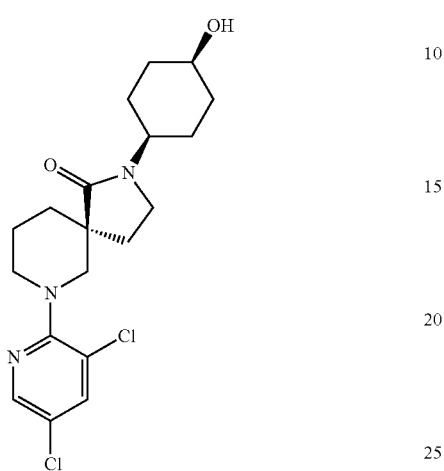

This compound was prepared by using procedures analogous to those described for the synthesis of example 420. LC-MS: 398.1/400.2 (M+H)⁺.

Example 424

(5S)-7-(5-Chloro-3-fluoropyridin-2-yl)-2-(cis-4-hydroxycyclohexyl)-2,7-diazaspiro[4.5]decan-1-one

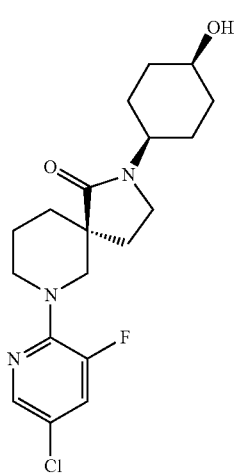

This compound was prepared by using procedures analogous to those described for the synthesis of example 420. LC-MS: 382.2 (M+H)⁺.

Example 425

(5S)-7-(3-Chloropyridin-2-yl)-2-(cis-4-hydroxycyclohexyl)-2,7-diazaspiro[4.5]decan-1-one

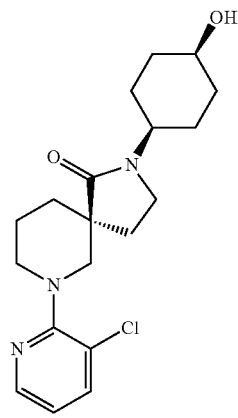

This compound was prepared by using procedures analogous to those described for the synthesis of example 420. LC-MS: 364.2 (M+H)⁺.

Example 426

Methyl {4-[(5S)-2-(trans-4-hydroxycyclohexyl)-1-oxo-2,7-diazaspiro[4.5]dec-7-yl]-2-methylphenyl}carbamate

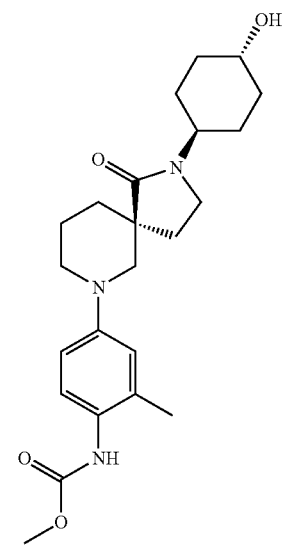 [SMILES: COC(=O)Nc1ccc(N2CCC[C@]3(CCN([C@H]4CC[C@H](O)CC4)C3=O)C2)cc1C]

This compound was prepared by using procedures analogous to those described for the synthesis of example 105. LC-MS: 416.2 (M+H)⁺.

Example 427

Ethyl {4-[(5S)-2-(trans-4-hydroxycyclohexyl)-1-oxo-2,7-diazaspiro[4.5]dec-7-yl]-2-methylphenyl}carbamate

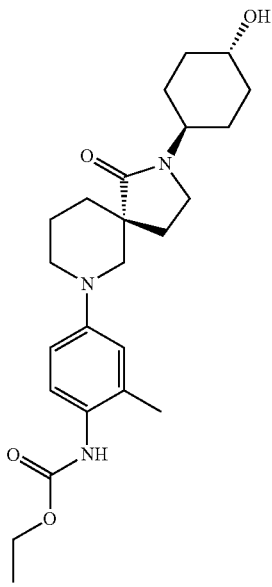 [SMILES: CCOC(=O)Nc1ccc(N2CCC[C@@]3(CCN([C@H]4CC[C@H](O)CC4)C3=O)C2)cc1C]

This compound was prepared by using procedures analogous to those described for the synthesis of example 105. LC-MS: 430.3 (M+H)⁺.

Example 428

Prop-2-yn-1-yl {4-[(5S)-2-(trans-4-hydroxycyclohexyl)-1-oxo-2,7-diazaspiro[4.5]dec-7-yl]-2-methylphenyl}carbamate

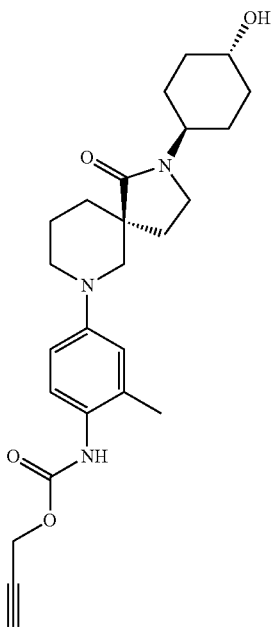 [SMILES: C#CCOC(=O)Nc1ccc(N2CCC[C@]3(CCN([C@H]4CC[C@H](O)CC4)C3=O)C2)cc1C]

This compound was prepared by using procedures analogous to those described for the synthesis of example 105. LC-MS: 440.3 (M+H)⁺.

Example 429

Methyl {6-[(5S)-2-(trans-4-hydroxycyclohexyl)-1-oxo-2,7-diazaspiro[4.5]dec-7-yl]-4-methylpyridin-3-yl}carbamate

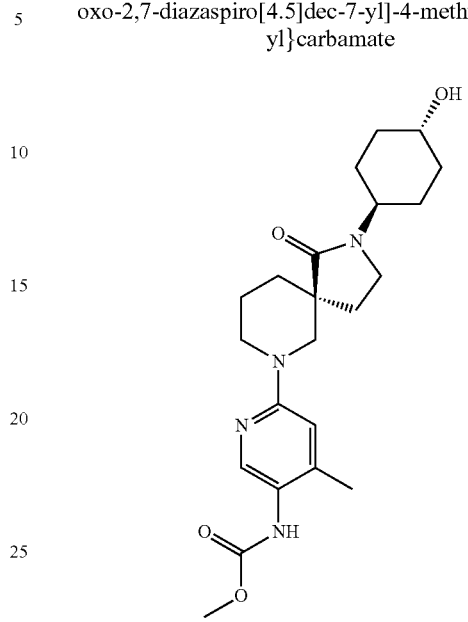

This compound was prepared by using procedures analogous to those described for the synthesis of example 105. LC-MS: 417.2 (M+H)⁺.

Example 430

Ethyl {6-[(5S)-2-(trans-4-hydroxycyclohexyl)-1-oxo-2,7-diazaspiro[4.5]dec-7-yl]-4-methylpyridin-3-yl}carbamate

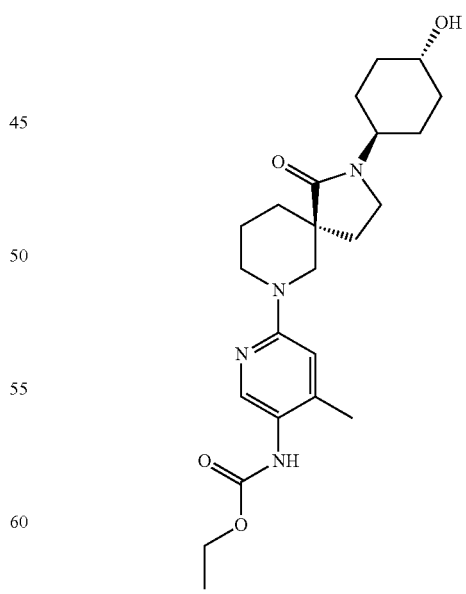

This compound was prepared by using procedures analogous to those described for the synthesis of example 105. LC-MS: 431.3 (M+H)⁺.

Example 431

Prop-2-yn-1-yl {6-[(5S)-2-(trans-4-hydroxycyclohexyl)-1-oxo-2,7-diazaspiro[4.5]dec-7-yl]-4-methylpyridin-3-yl}carbamate

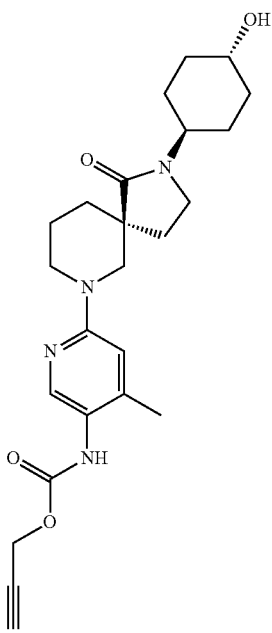 [SMILES: C#CCOC(=O)Nc1cnc(N2CCC[C@]3(CCN([C@H]4CC[C@H](O)CC4)C3=O)C2)cc1C]

This compound was prepared by using procedures analogous to those described for the synthesis of example 105. LC-MS: 441.2 (M+H)⁺.

Example 432

Methyl {6-[(5S)-2-(trans-4-hydroxycyclohexyl)-1-oxo-2,7-diazaspiro[4.5]dec-7-yl]-5-methoxypyridin-3-yl}carbamate

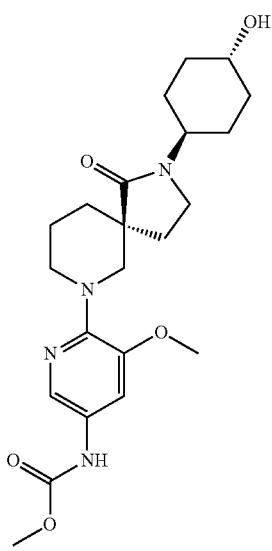 [SMILES: COC(=O)Nc1cnc(N2CCC[C@]3(CCN([C@H]4CC[C@H](O)CC4)C3=O)C2)c(OC)c1]

This compound was prepared by using procedures analogous to those described for the synthesis of example 105. LC-MS: 433.3 (M+H)⁺.

Example 433

Ethyl {6-[(5S)-2-(trans-4-hydroxycyclohexyl)-1-oxo-2,7-diazaspiro[4.5]dec-7-yl]-5-methoxypyridin-3-yl}carbamate

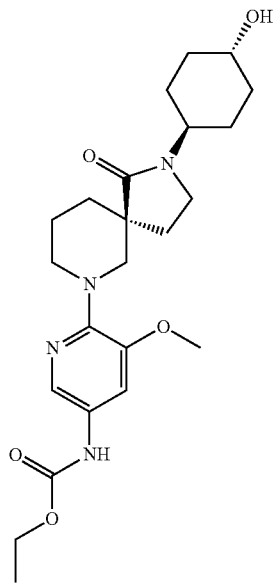 [SMILES: CCOC(=O)Nc1cnc(N2CCC[C@]3(CCN([C@H]4CC[C@H](O)CC4)C3=O)C2)c(OC)c1]

This compound was prepared by using procedures analogous to those described for the synthesis of example 105. LC-MS: 447.3 (M+H)⁺.

Example 434

Prop-2-yn-1-yl {6-[(5S)-2-(trans-4-hydroxycyclohexyl)-1-oxo-2,7-diazaspiro[4.5]dec-7-yl]-5-methoxypyridin-3-yl}carbamate

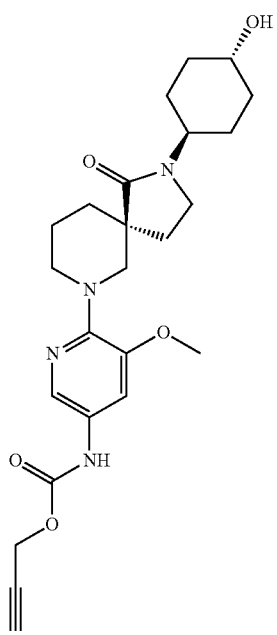 [SMILES: C#CCOC(=O)Nc1cnc(N2CCC[C@]3(CCN([C@H]4CC[C@H](O)CC4)C3=O)C2)c(OC)c1]

This compound was prepared by using procedures analogous to those described for the synthesis of example 105. LC-MS: 457.2 (M+H)⁺.

Example 435

Methyl {5-fluoro-2-[(5S)-2-(trans-4-hydroxycyclohexyl)-1-oxo-2,7-diazaspiro[4.5]dec-7-yl]pyrimidin-4-yl}carbamate

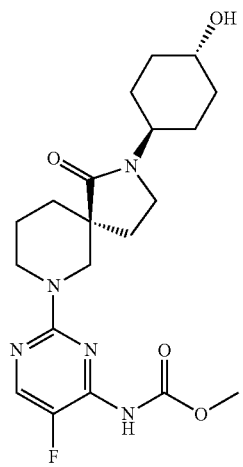 [SMILES: COC(=O)Nc1nc(N2CCC[C@]3(CCN([C@H]4CC[C@H](O)CC4)C3=O)C2)ncc1F]

This compound was prepared by using procedures analogous to those described for the synthesis of example 105. LC-MS: 422.2 (M+H)⁺.

Example 436

Isopropyl {3-fluoro-4-[(5S)-2-(trans-4-hydroxycyclohexyl)-1-oxo-2,7-diazaspiro[4.5]dec-7-yl]phenyl}methylcarbamate

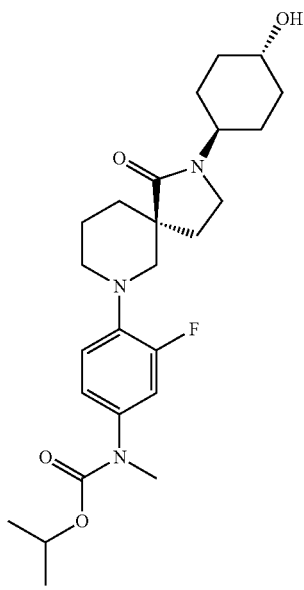 [SMILES: CC(C)OC(=O)N(C)c1ccc(N2CCC[C@]3(CCN([C@H]4CC[C@H](O)CC4)C3=O)C2)c(F)c1]

A mixture of isopropyl {3-fluoro-4-[(5S)-2-(trans-4-hydroxycyclohexyl)-1-oxo-2,7-diazaspiro[4.5]dec-7-yl]phenyl}carbamate (6 mg, 0.00001 mol, this compound was prepared by using procedures analogous to those described for the synthesis of example 105), methyl iodide (0.5 mL, 0.008 mol), and potassium carbonate (6 mg, 0.00004 mol) was stirred at rt for 24 h at 60° C. After cooling, the reaction mixture was purified by prep.-HPLC to afford the desired product. LC-MS: 462.3 (M+H)⁺.

Example 437

(5S)-7-(3-Bromo-5-methylpyridin-2-yl)-2-(trans-4-hydroxycyclohexyl)-2,7-diazaspiro[4.5]decan-1-one

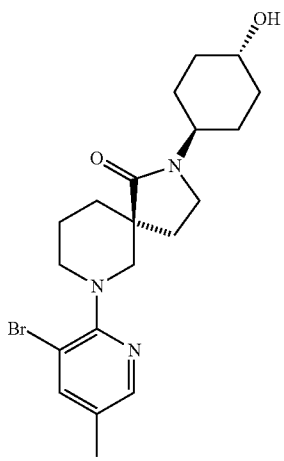 [SMILES: Cc1cnc(N2CCC[C@]3(CCN([C@H]4CC[C@H](O)CC4)C3=O)C2)c(Br)c1]

This compound was prepared by using procedures analogous to those described for the synthesis of example 93 starting from (S)-2-((trans)-4-hydroxycyclohexyl)-2,7-diazaspiro[4.5]decan-1-one (which was prepared using procedures analogous to those described in the synthesis of Example 472-a). LC-MS: 422.2/424 (M+H)⁺.

Example 438

2-[(5S)-2-Cyclohexyl-1-oxo-2,7-diazaspiro[4.5]dec-7-yl]nicotinonitrile

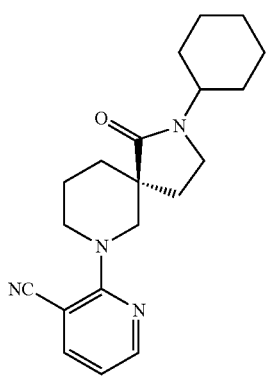 [SMILES: N#Cc1cccnc1N1CCC[C@]2(CCN(C3CCCCC3)C2=O)C1]

This compound was prepared by using procedures analogous to those described for the synthesis of example 93 starting from (S)-2-cyclohexyl-2,7-diazaspiro[4.5]decan-1-one (which was prepared using procedures analogous to those described for the synthesis of Example 92). LC-MS: 339.2 (M+H)⁺.

Example 439

2-[(5S)-2-(trans-4-Hydroxycyclohexyl)-1-oxo-2,7-diazaspiro[4.5]dec-7-yl]isonicotinonitrile

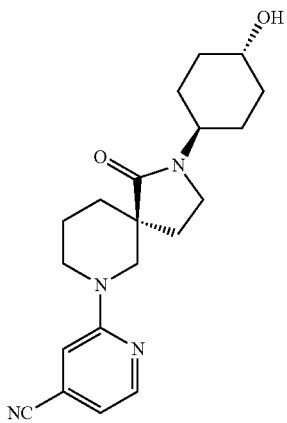 [SMILES: N#Cc1ccnc(N2CCC[C@]3(CCN([C@H]4CC[C@H](O)CC4)C3=O)C2)c1]

This compound was prepared by using procedures analogous to those described for the synthesis of example 93 starting from (S)-2-((trans)-4-hydroxycyclohexyl)-2,7-diazaspiro[4.5]decan-1-one (which was prepared using procedures analogous to those described in the synthesis of example 472-a). LC-MS: 355.2 (M+H)⁺.

Example 440

(5S)-7-(3-Fluoro-6-methylpyridin-2-yl)-2-(trans-4-hydroxycyclohexyl)-2,7-diazaspiro[4.5]decan-1-one

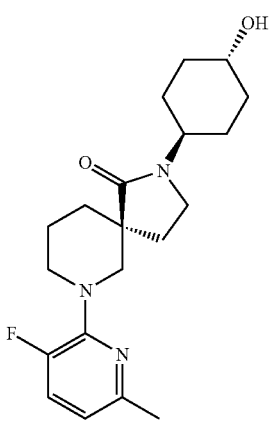 [SMILES: Cc1ccc(F)c(N2CCC[C@]3(CCN([C@H]4CC[C@H](O)CC4)C3=O)C2)n1]

This compound was prepared by using procedures analogous to those described for the synthesis of example 93 starting from (S)-2-((trans)-4-hydroxycyclohexyl)-2,7-diazaspiro[4.5]decan-1-one (which was prepared using procedures analogous to those described in the synthesis of example 472-a). LC-MS: 362.2 (M+H)⁺.

Example 441

6-[(5S)-2-(trans-4-Hydroxycyclohexyl)-1-oxo-2,7-diazaspiro[4.5]dec-7-yl]-2-methylnicotinonitrile

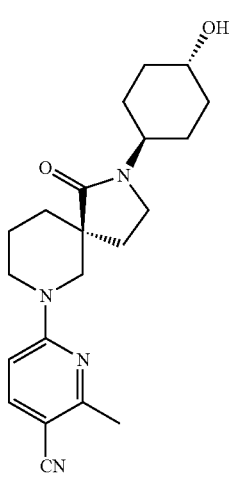 [SMILES: Cc1nc(N2CCC[C@]3(CCN([C@H]4CC[C@H](O)CC4)C3=O)C2)ccc1C#N]

This compound was prepared by using procedures analogous to those described for the synthesis of example 93 starting from (S)-2-((trans)-4-hydroxycyclohexyl)-2,7-diazaspiro[4.5]decan-1-one (which was prepared using procedures analogous to those described in the synthesis of example 472-a). LC-MS: 369.2 (M+H)⁺.

Example 442

2-[(5S)-2-(trans-4-Hydroxycyclohexyl)-1-oxo-2,7-diazaspiro[4.5]dec-7-yl]-4,6-dimethylnicotinonitrile

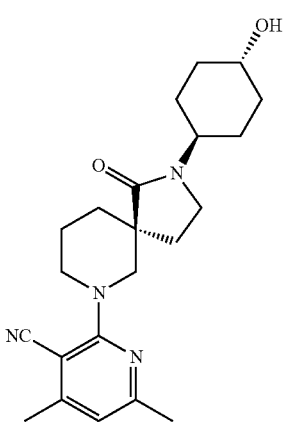 [SMILES: Cc1cc(C)c(C#N)c(N2CCC[C@]3(CCN([C@H]4CC[C@H](O)CC4)C3=O)C2)n1]

This compound was prepared by using procedures analogous to those described for the synthesis of example 93 starting from (S)-2-((trans)-4-hydroxycyclohexyl)-2,7-diazaspiro[4.5]decan-1-one (which was prepared using procedures analogous to those described in the synthesis of example 472-a). LC-MS: 383.2 (M+H)⁺.

Example 443

(5S)-2-(trans-4-Hydroxycyclohexyl)-7-[2-(trifluoromethyl)quinazolin-4-yl]-2,7-diazaspiro[4.5]decan-1-one

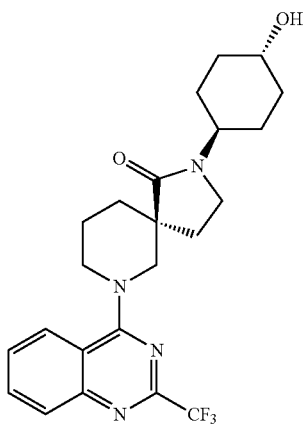 [SMILES: O=C1N([C@H]2CC[C@H](O)CC2)CC[C@]12CCCN(c1nc(C(F)(F)F)nc3ccccc13)C2]

This compound was prepared by using procedures analogous to those described for the synthesis of example 93 starting from (S)-2-((trans)-4-hydroxycyclohexyl)-2,7-diazaspiro[4.5]decan-1-one (which was prepared using procedures analogous to those described in the synthesis of example 472-a). LC-MS: 449.1 (M+H)+.

Example 444

(5S)-2-Cyclohexyl-7-[2-fluoro-4-(2-oxo-1,3-oxazolidin-3-yl)phenyl]-2,7-diazaspiro[4.5]decan-1-one

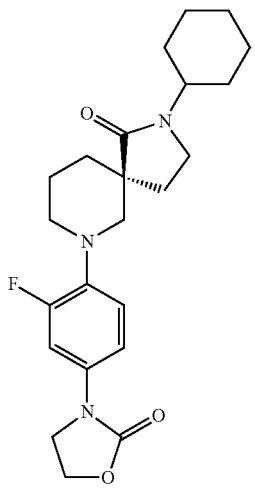 [SMILES: O=C1OCCN1c1ccc(N2CCC[C@]3(CCN(C4CCCCC4)C3=O)C2)c(F)c1]

This compound was prepared by using procedures analogous to those described for the synthesis of example 256. LC-MS: 416.1 (M+H)+.

Example 445

(5S)-2-Cyclohexyl-7-[2-fluoro-4-(2-oxopyrrolidin-1-yl)phenyl]-2,7-diazaspiro[4.5]decan-1-one

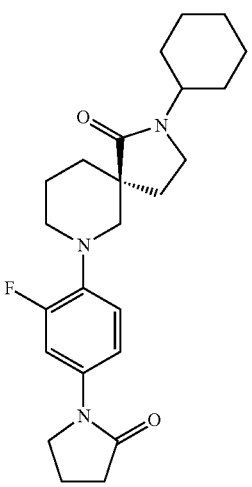 [SMILES: O=C1CCCN1c1ccc(N2CCC[C@]3(CCN(C4CCCCC4)C3=O)C2)c(F)c1]

This compound was prepared by using procedures analogous to those described for the synthesis of example 256. LC-MS: 414.1 (M+H)+.

Example 446

(5S)-7-(3-Fluoropyridin-2-yl)-2-(tetrahydro-2H-pyran-4-yl)-2,7-diazaspiro[4.5]decan-1-one

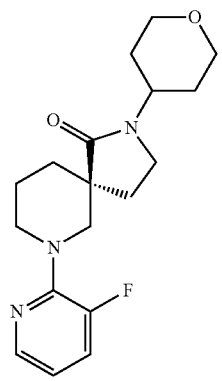 [SMILES: O=C1N(C2CCOCC2)CC[C@]12CCCN(c1ncccc1F)C2]

This compound was prepared by using procedures analogous to those described for the synthesis of example 116. LC-MS: 334.1 (M+H)+.

Example 447

(5S)-7-[2-Fluoro-4-(2-oxo-1,3-oxazolidin-3-yl)phenyl]-2-(tetrahydro-2H-pyran-4-yl)-2,7-diazaspiro[4.5]decan-1-one

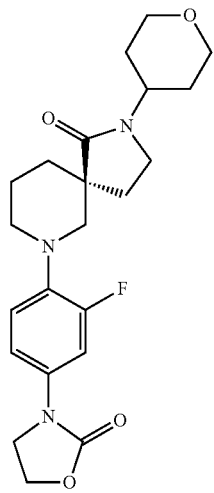 [SMILES: O=C1OCCN1c1ccc(N2CCC[C@]3(CCN(C4CCOCC4)C3=O)C2)c(F)c1]

This compound was prepared by using procedures analogous to those described for the synthesis of example 256. LC-MS: 418.1 (M+H)$^+$.

Example 448

(5S)-7-[2-Fluoro-4-(2-oxo-1,3-oxazinan-3-yl)phenyl]-2-(tetrahydro-2H-pyran-4-yl)-2,7-diazaspiro[4.5]decan-1-one

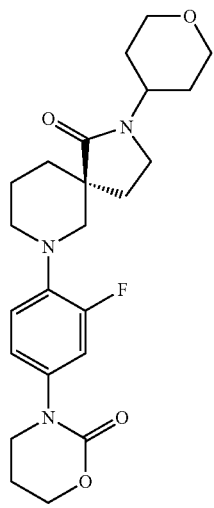 [SMILES: O=C1OCCCN1c1ccc(N2CCC[C@]3(CCN(C4CCOCC4)C3=O)C2)c(F)c1]

This compound was prepared by using procedures analogous to those described for the synthesis of example 256. LC-MS: 432.2 (M+H)$^+$.

Example 449

(5S)-7-[2-Fluoro-4-(2-oxopiperidin-1-yl)phenyl]-2-(tetrahydro-2H-pyran-4-yl)-2,7-diazaspiro[4.5]decan-1-one

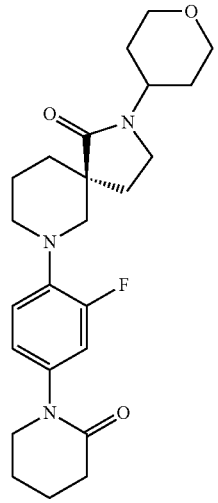 [SMILES: O=C1CCCCN1c1ccc(N2CCC[C@]3(CCN(C4CCOCC4)C3=O)C2)c(F)c1]

This compound was prepared by using procedures analogous to those described for the synthesis of example 256. LC-MS: 430.2 (M+H)$^+$.

Example 450

(5S)-7-[2-Fluoro-4-(2-oxopyrrolidin-1-yl)phenyl]-2-(tetrahydro-2H-pyran-4-yl)-2,7-diazaspiro[4.5]decan-1-one

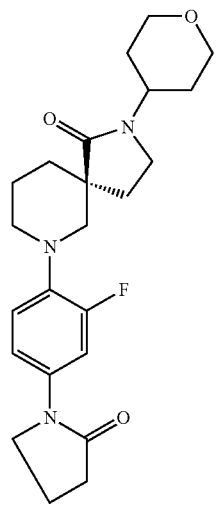 [SMILES: O=C1CCCN1c1ccc(N2CCC[C@]3(CCN(C4CCOCC4)C3=O)C2)c(F)c1]

This compound was prepared by using procedures analogous to those described for the synthesis of example 256. LC-MS: 416.2 (M+H)$^+$.

Example 451

3-Fluoro-N-methyl-4-[(5S)-1-oxo-2-(tetrahydro-2H-pyran-4-yl)-2,7-diazaspiro[4.5]dec-7-yl]benzamide

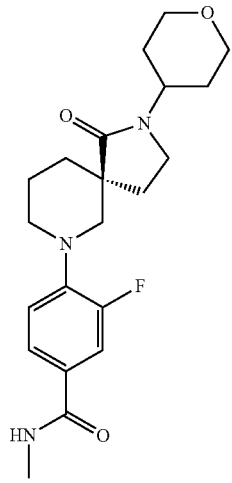 [SMILES: CNC(=O)c1ccc(N2CCC[C@]3(CCN(C4CCOCC4)C3=O)C2)c(F)c1]

This compound was prepared by using procedures analogous to those described for the synthesis of example 116. LC-MS: 390.2 (M+H)+.

Example 452

3-Fluoro-N,N-dimethyl-4-[(5S)-1-oxo-2-(tetrahydro-2H-pyran-4-yl)-2,7-diazaspiro[4.5]dec-7-yl]benzamide

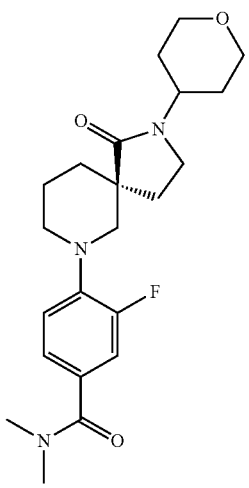 [SMILES: CN(C)C(=O)c1ccc(N2CCC[C@]3(CCN(C4CCOCC4)C3=O)C2)c(F)c1]

This compound was prepared by using procedures analogous to those described for the synthesis of example 116. LC-MS: 404.2 (M+H)+.

Example 453

2-[(5S)-1-Oxo-2-(tetrahydro-2H-pyran-4-yl)-2,7-diazaspiro[4.5]dec-7-yl]benzonitrile

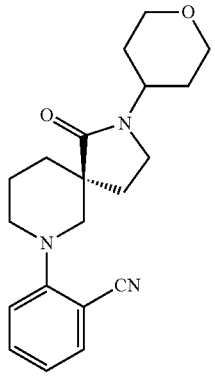 [SMILES: N#Cc1ccccc1N1CCC[C@]2(CCN(C3CCOCC3)C2=O)C1]

This compound was prepared by using procedures analogous to those described for the synthesis of example 116. LC-MS: 340.2 (M+H)+.

Example 454

(5S)-7-(3,5-Dichloropyridin-2-yl)-2-(3-methylpyridin-2-yl)-2,7-diazaspiro[4.5]decan-1-one

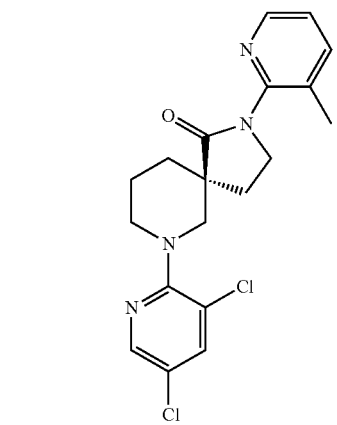 [SMILES: Cc1cccnc1N1CC[C@]2(CCCN(c3ncc(Cl)cc3Cl)C2)C1=O]

This compound was prepared by using procedures analogous to those described for the synthesis of example 116 starting from (S)-2-(3-methylpyridin-2-yl)-2,7-diazaspiro[4.5]decan-1-one (which was prepared using procedures analogous to those described for the synthesis of example 92). LC-MS: 391.1 (M+H)+.

Example 455

3-Bromo-4-[(5S)-2-(trans-4-hydroxycyclohexyl)-1-oxo-2,7-diazaspiro[4.5]dec-7-yl]benzonitrile

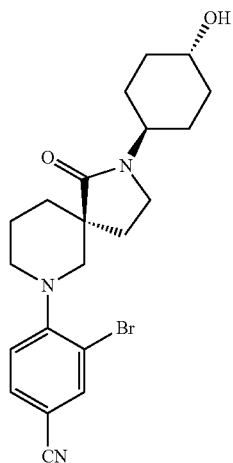 [SMILES: N#Cc1ccc(N2CCC[C@]3(CCN([C@H]4CC[C@H](O)CC4)C3=O)C2)c(Br)c1]

This compound was prepared by using procedures analogous to those described for the synthesis of example 44 starting from (S)-2-((trans)-4-hydroxycyclohexyl)-2,7-diazaspiro[4.5]decan-1-one (which was prepared using procedures analogous to those described in the synthesis of example 472-a followed by Pd catalyzed hydrogenation to remove the Cbz protecting group). LC-MS: 432.1/434.1 (M+H)$^+$.

Example 456

(5S)-7-(2,5-difluorophenyl)-2-(4-hydroxycyclohexyl)-2,7-diazaspiro[4.5]decan-1-one

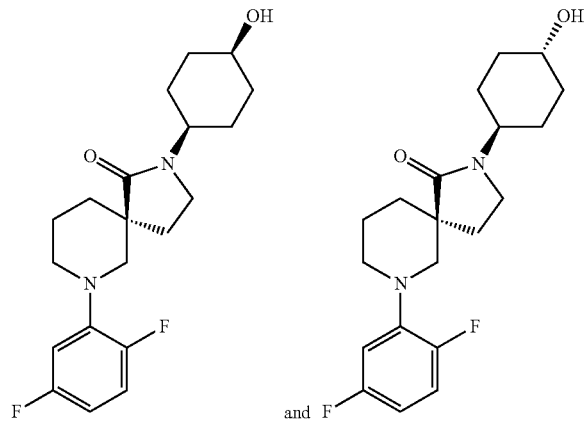 [SMILES: O=C1N([C@H]2CC[C@@H](O)CC2)CC[C@]12CCCN(c1cc(F)ccc1F)C2 ; O=C1N([C@H]2CC[C@H](O)CC2)CC[C@]12CCCN(c1cc(F)ccc1F)C2]

This compound was prepared by using procedures analogous to those described for the synthesis of example 44 starting from (S)-2-((trans)-4-hydroxycyclohexyl)-2,7-diazaspiro[4.5]decan-1-one (which was prepared using procedures analogous to those described in the synthesis of example 472-a followed by Pd catalyzed hydrogenation to remove the Cbz protecting group). LC-MS: 365.2 (M+H)$^+$.

Example 457

(5S)-7-(2-Bromo-3-fluorophenyl)-2-(trans-4-hydroxycyclohexyl)-2,7-diazaspiro[4.5]decan-1-one

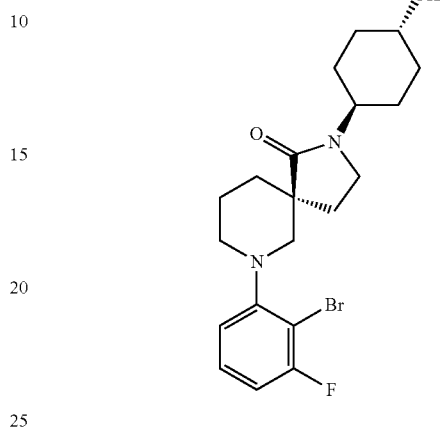

This compound was prepared by using procedures analogous to those described for the synthesis of example 44 starting from (S)-2-((trans)-4-hydroxycyclohexyl)-2,7-diazaspiro[4.5]decan-1-one (which was prepared using procedures analogous to those described in the synthesis of example 472-a followed by Pd catalyzed hydrogenation to remove the Cbz protecting group). LC-MS: 425.1/427.1 (M+H)$^+$.

Example 458

(5S)-7-(5-Fluoro-2-methylphenyl)-2-(4-hydroxycyclohexyl)-2,7-diazaspiro[4.5]decan-1-one

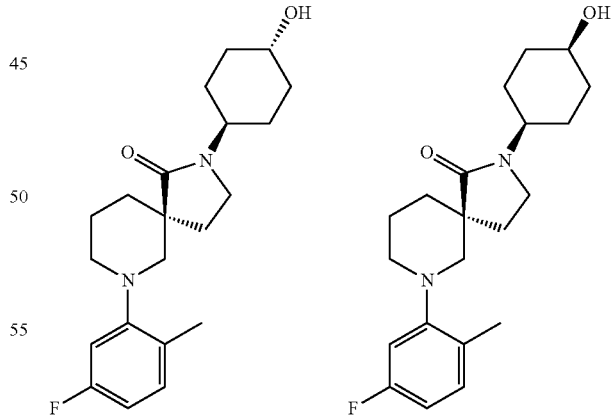

This compound was prepared by using procedures analogous to those described for the synthesis of example 44 starting from (S)-2-((trans)-4-hydroxycyclohexyl)-2,7-diazaspiro[4.5]decan-1-one (which was prepared using procedures analogous to those described in the synthesis of example 472-a followed by Pd catalyzed hydrogenation to remove the Cbz protecting group). LC-MS: 361.2 (M+H)$^+$.

Example 459

(5S)-7-(2,3-Dichlorophenyl)-2-(4-hydroxycyclohexyl)-2,7-diazaspiro[4.5]decan-1-one

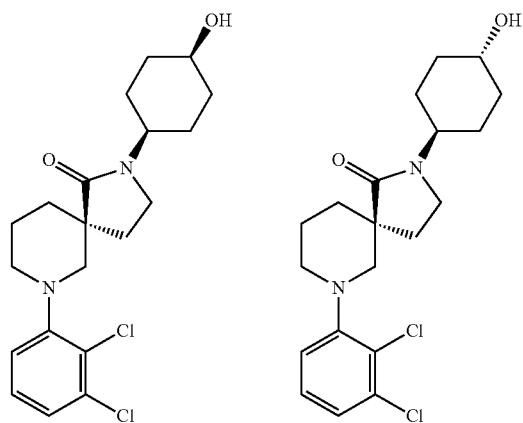 [SMILES: O=C1N([C@H]2CC[C@@H](O)CC2)CC[C@]12CCCN(c1cccc(Cl)c1Cl)C2 ; O=C1N([C@H]2CC[C@H](O)CC2)CC[C@]12CCCN(c1cccc(Cl)c1Cl)C2]

This compound was prepared by using procedures analogous to those described for the synthesis of example 44 starting from (S)-2-((trans)-4-hydroxycyclohexyl)-2,7-diazaspiro[4.5]decan-1-one (which was prepared using procedures analogous to those described in the synthesis of example 472-a followed by Pd catalyzed hydrogenation to remove the Cbz protecting group). LC-MS: 397.1/399.1 (M+H)$^+$.

Example 460

(5S)-7-(2,6-Dichlorophenyl)-2-(trans-4-hydroxycyclohexyl)-2,7-diazaspiro[4.5]decan-1-one

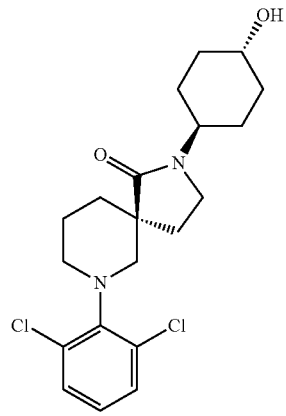 [SMILES: O=C1N([C@H]2CC[C@H](O)CC2)CC[C@]12CCCN(c1c(Cl)cccc1Cl)C2]

This compound was prepared by using procedures analogous to those described for the synthesis of example 44 starting from (S)-2-((trans)-4-hydroxycyclohexyl)-2,7-diazaspiro[4.5]decan-1-one (which was prepared using procedures analogous to those described in the synthesis of example 472-a followed by Pd catalyzed hydrogenation to remove the Cbz protecting group). LC-MS: 397.1/399.1 (M+H)$^+$.

Example 461

4-Bromo-2-[(5S)-2-(cis-4-hydroxycyclohexyl)-1-oxo-2,7-diazaspiro[4.5]dec-7-yl]benzonitrile

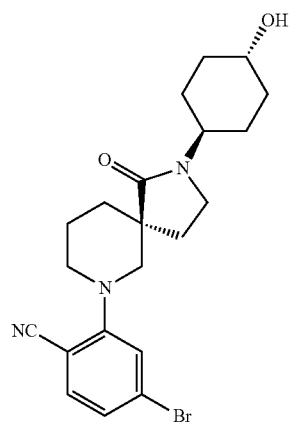 [SMILES: N#Cc1ccc(Br)cc1N1CCC[C@]2(CCN([C@H]3CC[C@H](O)CC3)C2=O)C1]

This compound was prepared by using procedures analogous to those described for the synthesis of example 93 starting from (S)-2-((trans)-4-hydroxycyclohexyl)-2,7-diazaspiro[4.5]decan-1-one (which was prepared using procedures analogous to those described in the synthesis of example 472-a followed by Pd catalyzed hydrogenation to remove the Cbz protecting group). LC-MS: 432.1 (M+H)$^+$.

Example 462

2-[(5S)-2-(trans-4-Hydroxycyclohexyl)-1-oxo-2,7-diazaspiro[4.5]dec-7-yl]benzonitrile

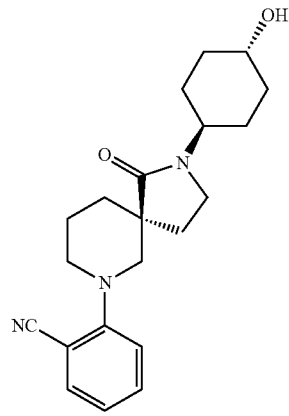 [SMILES: N#Cc1ccccc1N1CCC[C@]2(CCN([C@H]3CC[C@H](O)CC3)C2=O)C1]

This compound was prepared by using procedures analogous to those described for the synthesis of example 44 starting from (S)-2-((trans)-4-hydroxycyclohexyl)-2,7-diazaspiro[4.5]decan-1-one (which was prepared using procedures analogous to those described in the synthesis of example 472-a followed by Pd catalyzed hydrogenation to remove the Cbz protecting group). LC-MS: 354.2 (M+H)$^+$.

Example 463

(5S)-7-(2-Fluorophenyl)-2-(4-hydroxycyclohexyl)-2,7-diazaspiro[4.5]decan-1-one

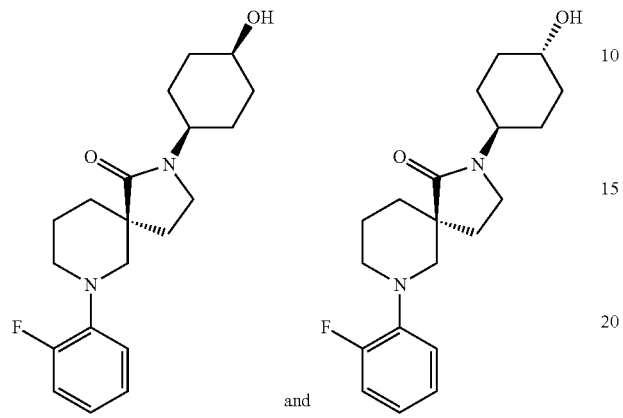

and

This compound was prepared by using procedures analogous to those described for the synthesis of example 44 starting from (S)-2-((trans)-4-hydroxycyclohexyl)-2,7-diazaspiro[4.5]decan-1-one (which was prepared using procedures analogous to those described in the synthesis of example 472-a followed by Pd catalyzed hydrogenation to remove the Cbz protecting group). LC-MS: 347.2 (M+H)$^+$.

Example 464

2-[(5S)-2-(cis-4-Hydroxycyclohexyl)-1-oxo-2,7-diazaspiro[4.5]dec-7-yl]isonicotinonitrile

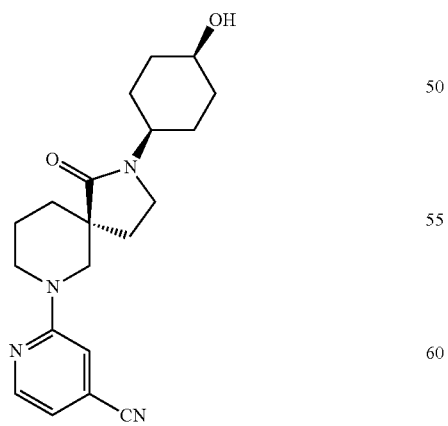

This compound was prepared by using procedures analogous to those described for the synthesis of example 420. LC-MS: 355.2 (M+H)$^+$.

Example 465

(5S)-7-(3-Bromo-5-fluoropyridin-2-yl)-2-(cis-4-hydroxycyclohexyl)-2,7-diazaspiro[4.5]decan-1-one

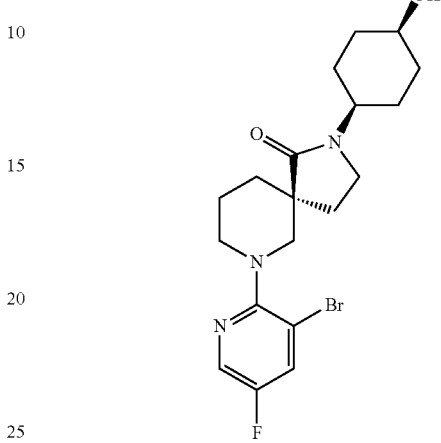

This compound was prepared by using procedures analogous to those described for the synthesis of example 420. LC-MS: 426.1/428.1 (M+H)$^+$.

Example 466

(5S)-7-(3-Fluoro-4-methylpyridin-2-yl)-2-(cis-4-hydroxycyclohexyl)-2,7-diazaspiro[4.5]decan-1-one

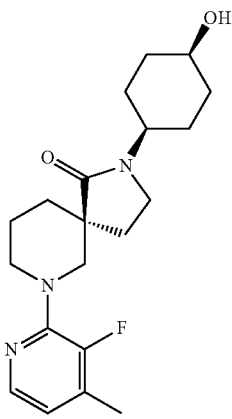 [SMILES: Cc1ccnc(N2CCC[C@]3(CCN([C@H]4CC[C@@H](O)CC4)C3=O)C2)c1F]

This compound was prepared by using procedures analogous to those described for the synthesis of example 420. LC-MS: 362.2 (M+H)$^+$.

Example 467

6-[(5S)-2-(cis-4-Hydroxycyclohexyl)-1-oxo-2,7-diazaspiro[4.5]dec-7-yl]-2-methylnicotinonitrile

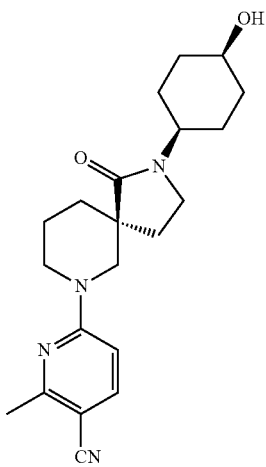 [SMILES: Cc1nc(N2CCC[C@]3(CCN([C@H]4CC[C@@H](O)CC4)C3=O)C2)ccc1C#N]

This compound was prepared by using procedures analogous to those described for the synthesis of example 420. LC-MS: 369.2 (M+H)+.

Example 468

(5S)-7-(5-Chloro-3-methylpyridin-2-yl)-2-(cis-4-hydroxycyclohexyl)-2,7-diazaspiro[4.5]decan-1-one

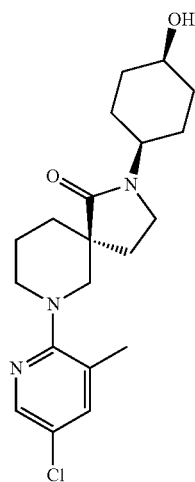 [SMILES: Cc1cc(Cl)cnc1N1CCC[C@]2(CCN([C@H]3CC[C@@H](O)CC3)C2=O)C1]

This compound was prepared by using procedures analogous to those described for the synthesis of example 420. LC-MS: 378.1 (M+H)+.

Example 469

4-Chloro-2-[(5S)-2-(cis-4-hydroxycyclohexyl)-1-oxo-2,7-diazaspiro[4.5]dec-7-yl]benzonitrile

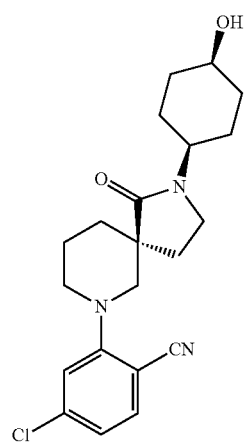 [SMILES: N#Cc1ccc(Cl)cc1N1CCC[C@]2(CCN([C@H]3CC[C@@H](O)CC3)C2=O)C1]

This compound was prepared by using procedures analogous to those described for the synthesis of example 420. LC-MS: 388.1 (M+H)+.

Example 470

2-Fluoro-4-[(5S)-2-(cis-4-hydroxycyclohexyl)-1-oxo-2,7-diazaspiro[4.5]dec-7-yl]benzonitrile

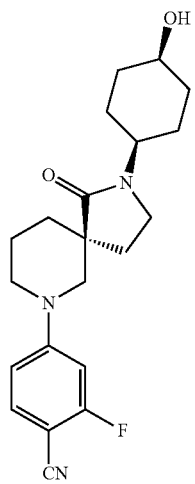 [SMILES: N#Cc1ccc(N2CCC[C@]3(CCN([C@H]4CC[C@@H](O)CC4)C3=O)C2)cc1F]

This compound was prepared by using procedures analogous to those described for the synthesis of example 420. LC-MS: 372.1 (M+H)+.

Example 471

4-Bromo-2-[(5S)-2-(cis-4-hydroxycyclohexyl)-1-oxo-2,7-diazaspiro[4.5]dec-7-yl]benzonitrile

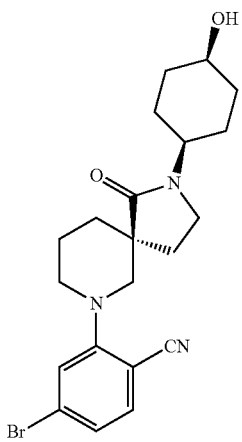

This compound was prepared by using procedures analogous to those described for the synthesis of example 420. LC-MS: 432.1 (M+H)+.

Example 472

7-[(3-Chloro-2-methylphenyl)sulfonyl]-2-(trans-4-hydroxycyclohexyl)-2,7-diazaspiro[4.5]decan-1-one

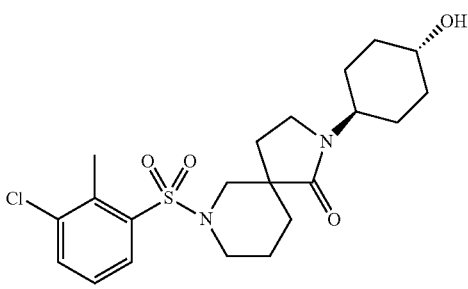

This compound was prepared by using procedures analogous to those described for the synthesis of example 1. LC-MS: 441.2/443.2 (M+H)+.

Example 472-a (5S)-7-[2-Chloro-5-(trifluoromethyl)phenyl]-2-(trans-4-hydroxycyclohexyl)-2,7-diazaspiro[4.5]decan-1-one

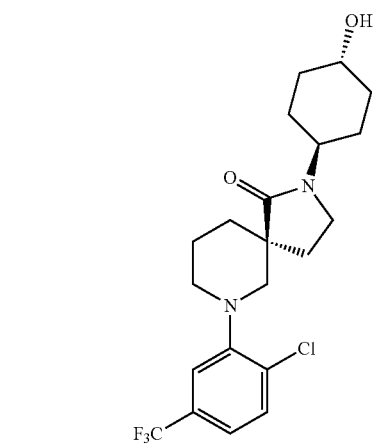 [SMILES: O=C1N([C@H]2CC[C@H](O)CC2)CC[C@]12CCCN(c1cc(C(F)(F)F)ccc1Cl)C2]

Step 1. Benzyl (5S)-2-(trans-4-hydroxycyclohexyl)-1-oxo-2,7-diazaspiro[4.5]decane-7-carboxylate A mixture of 1-benzyl 3-ethyl 3-(2-oxoethyl)piperidine-1,3-dicarboxylate (1.0 g, 0.0030 mol, prepared by using procedures analogous to those described for the synthesis of example 1, steps 1 and 2), trans-4-aminocyclohexanol hydrochloride (0.50 g, 0.0033 mol), and triethylamine (0.48 g, 0.0048 mol) in 1,2-dichloroethane (8 mL, 0.1 mol) was stirred at rt for 30 min. To the mixture was added sodium triacetoxyborohydride (1.6 g, 0.0075 mol) and the resulting mixture was stirred at rt for 1 h. The reaction mixture then was warmed to 80° C. with stirring for 16 h. After cooling to ambient temperature, the reaction mixture was diluted with dichloromethane and the solution was washed with 1N HCl, water, brine, and dried over MgSO4. After filtration, the filtrate was concentrated in-vacuo and the resulting residue was purified by flash column chromatography to afford 1.04 g of the desired product. Further purification by chiral HPLC was carried out (Chiralcel OD-H column (3.0×25 cm, 5 micron particle size, Chiral Technologies; Item number 14475) eluting with 15% ethanol/hexanes (isocratic, 26 mL/min.); Detection: 220 nm; retention time: 10.0 minute for peak 1, 12.5 minute for peak 2). The first peak to elute was found to be the R configuration and the second peak was found to be the S configuration and used for analog synthesis. LC-MS: 387.3 (M+H)+.

Step 2. Benzyl (5S)-1-oxo-2-{trans-4-[(triethylsilyl)oxy]cyclohexyl}-2,7-diazaspiro[4.5]decane-7-carboxylate To a solution of benzyl (5S)-2-(trans-4-hydroxycyclohexyl)-1-oxo-2,7-diazaspiro[4.5]decane-7-carboxylate (2.0 g, 0.0052 mol) in N,N-dimethylformamide (5 mL, 0.06 mol) were added 1H-imidazole (0.986 g, 0.0145 mol) and chlorotriethylsilane (1.13 mL, 0.00673 mol) at rt. After stirring for 2 h ice-water was added and the resulting mixture was stirred at room temperature for 30 minutes and extracted three times with AcOEt. The combined extracts were washed with brine, dried over sodium sulfate, and concentrated. The residual oil was purified by column chromatography using 30% by volume AcOEt in hexanes.

Step 3. (5S)-2-{trans-4-[(triethylsilyl)oxy]cyclohexyl}-2,7-diazaspiro[4.5]decan-1-one To a solution of benzyl (5S)-1-oxo-2-{trans-4-[(triethylsilyl)oxy]cyclohexyl}-2,7-diazaspiro[4.5]decane-7-carboxylate (2.4 g, 0.0048 mol) in methanol (10 mL, 0.2 mol) was added Pd/C, and the suspension was stirred at rt under a H$_2$ balloon for 1.5 h. The inorganics were filtered and the filtrate was concentrated to afford the desired product.

Step 4. (5S)-7-[2-chloro-5-(trifluoromethyl)phenyl]-2-(trans-4-hydroxycyclohexyl)-2,7-diazaspiro[4.5]decan-1-one A mixture of 2-bromo-1-chloro-4-(trifluoromethyl)benzene (26 mg, 0.0001 mol), tris(dibenzylideneacetone)dipalladium(0) (2 mg, 0.000002 mol), 2'-(dicyclohexylphosphino)-N,N-dimethylbiphenyl-2-amine (5 mg, 0.00001 mol) in 1,4-dioxane (0.5 mL, 0.006 mol) was stirred under N$_2$ (g) for 20 min. To this mixture were added (5S)-2-{trans-4-[(triethylsilyl)oxy]cyclohexyl}-2,7-diazaspiro[4.5]decan-1-one (30 mg, 0.00008 mol) and sodium tert-butoxide (11.8 mg, 0.000123 mol), and the resulting mixture was degassed and stirred at 100° C. for 16 h. At this time 1M TBAF (tetra-n-butylammonium fluoride) in THF (0.3 mL) was added dropwise to the reaction mixture and the solution was stirred at rt for 1 h. The volatiles were removed in-vacuo and the residue was purified by prep-HPLC to afford the desired product. LC-MS: 431.1 (M+H)$^+$.

Example 473

(5S)-7-[3-Fluoro-5-(trifluoromethyl)phenyl]-2-(trans-4-hydroxycyclohexyl)-2,7-diazaspiro[4.5]decan-1-one

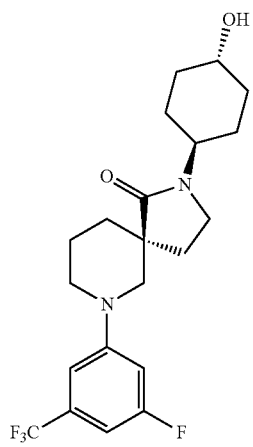 [SMILES: O=C1N([C@H]2CC[C@H](O)CC2)CC[C@]12CCCN(c1cc(F)cc(C(F)(F)F)c1)C2]

This compound was prepared by using procedures analogous to those described for the synthesis of example 472-a. LC-MS: 415.1 (M+H)$^+$.

Example 474

(5S)-7-(4-Chloro-2-methylphenyl)-2-(trans-4-hydroxycyclohexyl)-2,7-diazaspiro[4.5]decan-1-one

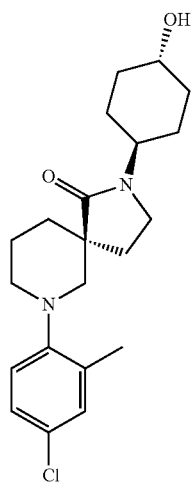

This compound was prepared by using procedures analogous to those described for the synthesis of example 472-a. LC-MS: 377.4 (M+H)$^+$.

Example 475

(5S)-7-(3-chloro-2-methylphenyl)-2-(trans-4-hydroxycyclohexyl)-2,7-diazaspiro[4.5]decan-1-one

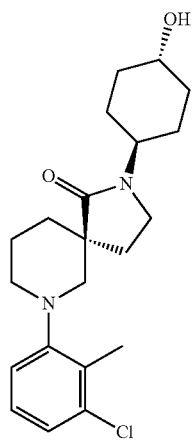 [SMILES: Cc1c(Cl)cccc1N1CCC[C@]2(CCN([C@H]3CC[C@H](O)CC3)C2=O)C1]

This compound was prepared by using procedures analogous to those described for the synthesis of example 472-a. LC-MS: 377.4 (M+H)$^+$.

Example 476

(5S)-2-(trans-4-Hydroxycyclohexyl)-7-quinolin-8-yl-2,7-diazaspiro[4.5]decan-1-one

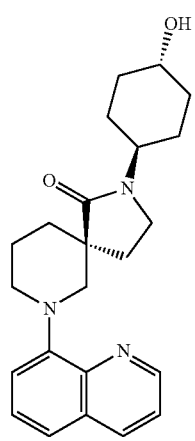 [SMILES: O=C1N([C@H]2CC[C@H](O)CC2)CC[C@]12CCCN(c1cccc3cccnc13)C2]

This compound was prepared by using procedures analogous to those described for the synthesis of example 472-a. LC-MS: 380.2 (M+H)+.

Example 477

{3-[(5S)-2-(trans-4-Hydroxycyclohexyl)-1-oxo-2,7-diazaspiro[4.5]dec-7-yl]phenyl}acetonitrile

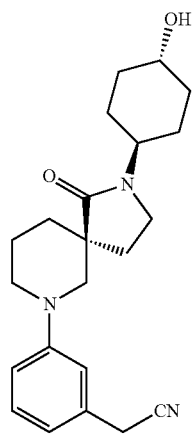 [SMILES: N#CCc1cccc(N2CCC[C@]3(CCN([C@H]4CC[C@H](O)CC4)C3=O)C2)c1]

This compound was prepared by using procedures analogous to those described for the synthesis of example 472-a. LC-MS: 368.2 (M+H)+.

Example 478

(5S)-7-(4-Fluoro-2-methylphenyl)-2-(trans-4-hydroxycyclohexyl)-2,7-diazaspiro[4.5]decan-1-one

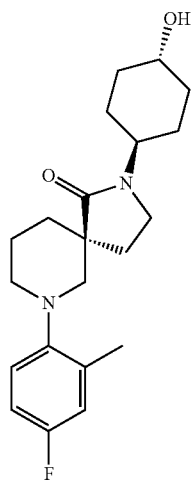 [SMILES: Cc1cc(F)ccc1N1CCC[C@]2(CCN([C@H]3CC[C@H](O)CC3)C2=O)C1]

This compound was prepared by using procedures analogous to those described for the synthesis of example 180. LC-MS: 361.2 (M+H)+.

Example 479

(5S)-2-(trans-4-Hydroxycyclohexyl)-7-[4-(2-oxopyrrolidin-1-yl)-2-(trifluoromethyl)phenyl]-2,7-diazaspiro[4.5]decan-1-one

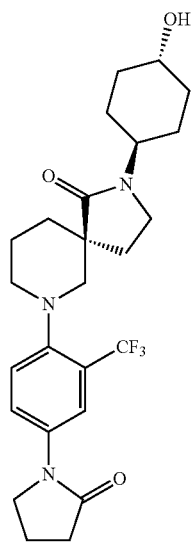 [SMILES: O=C1CCCN1c1ccc(N2CCC[C@]3(CCN([C@H]4CC[C@H](O)CC4)C3=O)C2)c(C(F)(F)F)c1]

This compound was prepared by using procedures analogous to those described for the synthesis of example 256. LC-MS: 480.2 (M+H)+.

Example 480

(5S)-2-(trans-4-Hydroxycyclohexyl)-7-[4-(2-oxo-1,3-oxazolidin-3-yl)-2-(trifluoromethyl)phenyl]-2,7-diazaspiro[4.5]decan-1-one

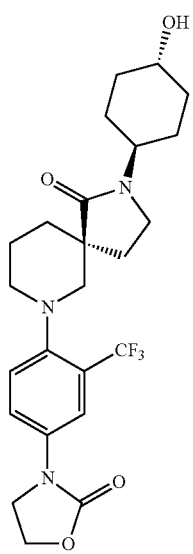

This compound was prepared by using procedures analogous to those described for the synthesis of example 256. LC-MS: 482.2 (M+H)$^+$.

Example 481

(5S)-2-(trans-4-Hydroxycyclohexyl)-7-[4-(2-oxo-1,3-oxazinan-3-yl)-2-(trifluoromethyl)phenyl]-2,7-diazaspiro[4.5]decan-1-one

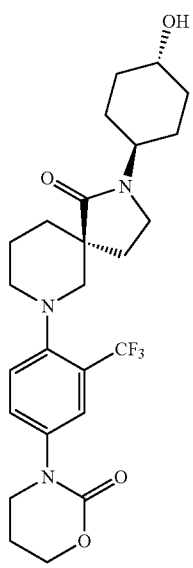

This compound was prepared by using procedures analogous to those described for the synthesis of example 256. LC-MS: 496.2 (M+H)$^+$.

Example 482

(5S)-7-[3-Fluoro-4-(pyridin-2-yloxy)phenyl]-2-(4-hydroxycyclohexyl)-2,7-diazaspiro[4.5]decan-1-one

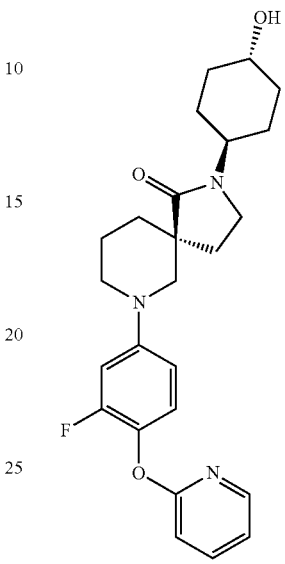 and 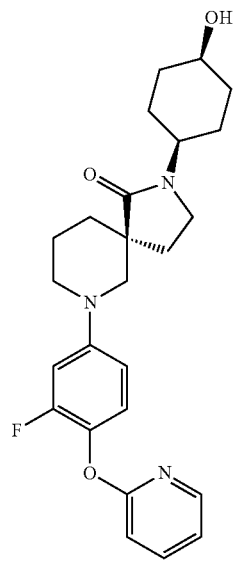

This compound was prepared by using procedures analogous to those described for the synthesis of example 180. LC-MS: 440.3 (M+H)$^+$.

Example 483

(5S)-7-[3-Fluoro-4-(pyridin-4-yloxy)phenyl]-2-(4-hydroxycyclohexyl)-2,7-diazaspiro[4.5]decan-1-one

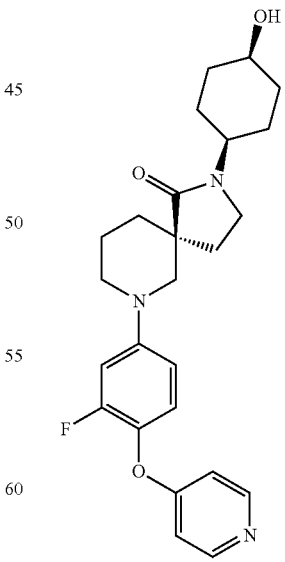 and 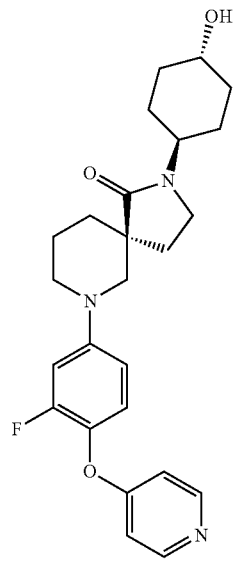

This compound was prepared by using procedures analogous to those described for the synthesis of example 180. LC-MS: 440.3 (M+H)$^+$.

Example 484

(5S)-7-[3-Fluoro-4-(pyridin-3-yloxy)phenyl]-2-(4-hydroxycyclohexyl)-2,7-diazaspiro[4.5]decan-1-one

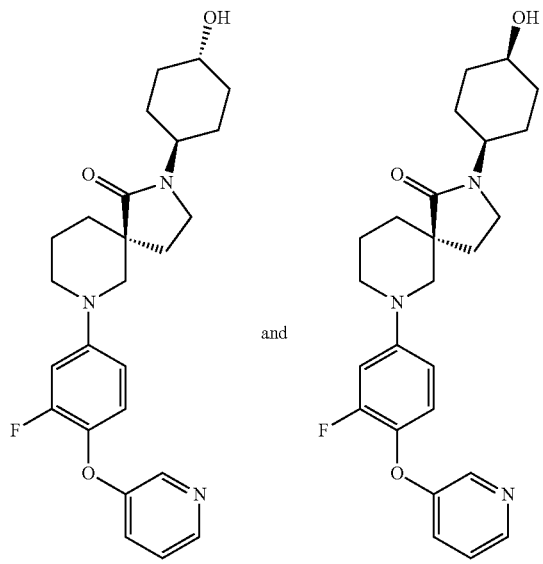 [SMILES: O=C1N([C@H]2CC[C@H](O)CC2)CC[C@]12CCCN(c1ccc(Oc3cccnc3)c(F)c1)C2 ; O=C1N([C@H]2CC[C@@H](O)CC2)CC[C@]12CCCN(c1ccc(Oc3cccnc3)c(F)c1)C2]

and

This compound was prepared by using procedures analogous to those described for the synthesis of example 180. LC-MS: 440.3 (M+H)+.

Example 485

(5S)-7-[2-Fluoro-4-(pyridin-3-yloxy)phenyl]-2-(4-hydroxycyclohexyl)-2,7-diazaspiro[4.5]decan-1-one

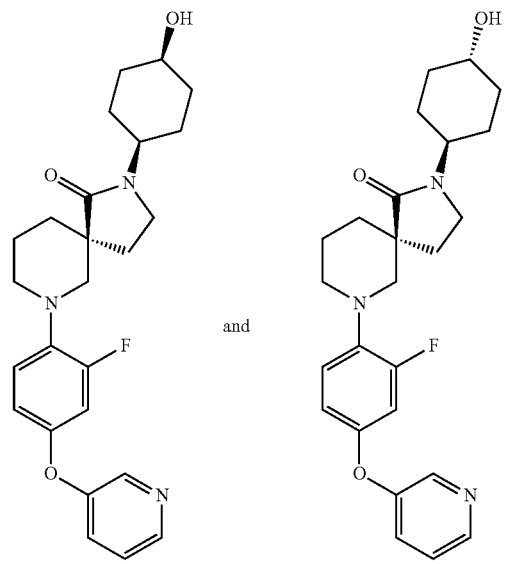 [SMILES: O=C1N([C@H]2CC[C@@H](O)CC2)CC[C@]12CCCN(c1ccc(Oc3cccnc3)cc1F)C2 ; O=C1N([C@H]2CC[C@H](O)CC2)CC[C@]12CCCN(c1ccc(Oc3cccnc3)cc1F)C2]

and

This compound was prepared by using procedures analogous to those described for the synthesis of example 180. LC-MS: 440.3 (M+H)+.

Example 486

Methyl {3-chloro-4-[(5S)-2-(trans-4-hydroxycyclohexyl)-1-oxo-2,7-diazaspiro[4.5]dec-7-yl]phenyl}carbamate

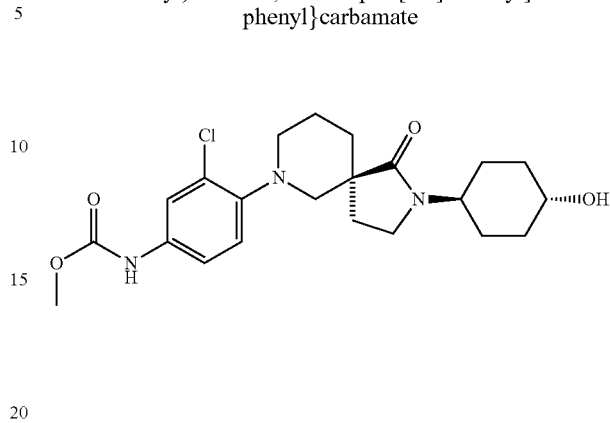

This compound was prepared by using procedures analogous to those described for the synthesis of example 105. LC-MS: 436.3 (M+H)+.

Example 487

Ethyl {3-chloro-4-[(5S)-2-(trans-4-hydroxycyclohexyl)-1-oxo-2,7-diazaspiro[4.5]dec-7-yl]phenyl}carbamate

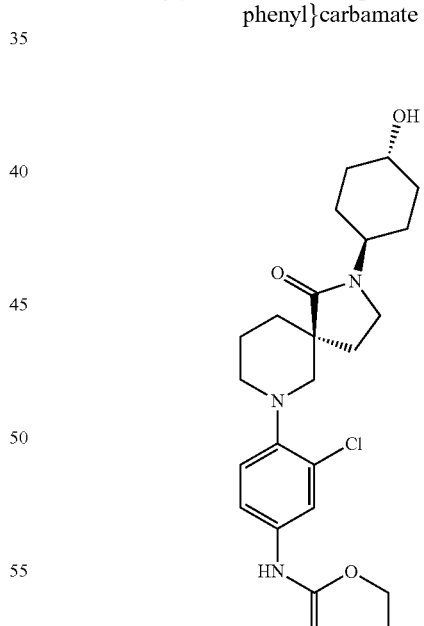

This compound was prepared by using procedures analogous to those described for the synthesis of example 105. LC-MS: 450.3 (M+H)+.

Example 488

Prop-2-yn-1-yl {3-chloro-4-[(5S)-2-(trans-4-hydroxycyclohexyl)-1-oxo-2,7-diazaspiro[4.5]dec-7-yl]phenyl}carbamate

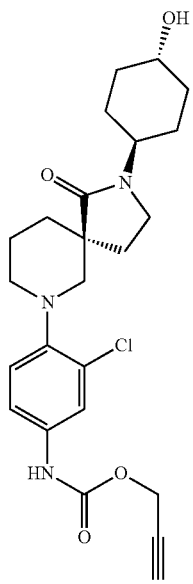 [SMILES: C#CCOC(=O)Nc1ccc(N2CCC[C@]3(CCN([C@H]4CC[C@H](O)CC4)C3=O)C2)c(Cl)c1]

This compound was prepared by using procedures analogous to those described for the synthesis of example 105. LC-MS: 460.3 (M+H)$^+$.

Example 489

Propyl {3-chloro-4-[(5S)-2-(trans-4-hydroxycyclohexyl)-1-oxo-2,7-diazaspiro[4.5]dec-7-yl]phenyl}carbamate

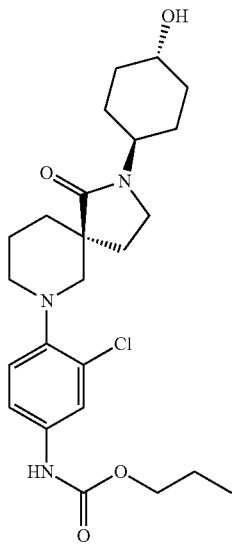 [SMILES: CCCOC(=O)Nc1ccc(N2CCC[C@]3(CCN([C@H]4CC[C@H](O)CC4)C3=O)C2)c(Cl)c1]

This compound was prepared by using procedures analogous to those described for the synthesis of example 105. LC-MS: 465.1 (M+H)$^+$.

Example 490

N-{3-Chloro-4-[(5S)-2-(trans-4-hydroxycyclohexyl)-1-oxo-2,7-diazaspiro[4.5]dec-7-yl]phenyl}cyclopentanecarboxamide

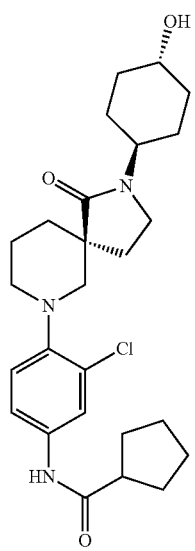 [SMILES: O=C(Nc1ccc(N2CCC[C@]3(CCN([C@H]4CC[C@H](O)CC4)C3=O)C2)c(Cl)c1)C1CCCC1]

This compound was prepared by using procedures analogous to those described for the synthesis of example 105. LC-MS: 475.1 (M+H)$^+$.

Example 491

N-{3-Chloro-4-[(5S)-2-(trans-4-hydroxycyclohexyl)-1-oxo-2,7-diazaspiro[4.5]dec-7-yl]phenyl}cyclohexanecarboxamide

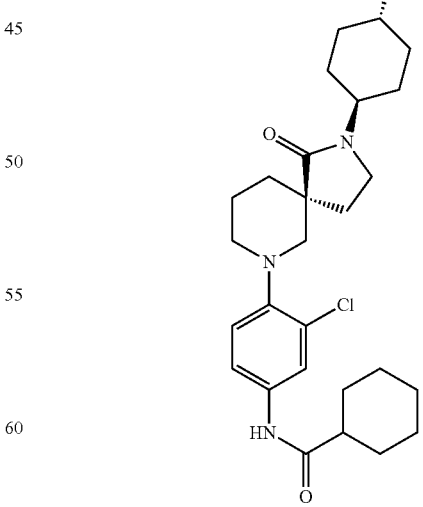

This compound was prepared by using procedures analogous to those described for the synthesis of example 105. LC-MS: 489.1 (M+H)$^+$.

Example 492

(5S)-7-(5-Fluoropyrimidin-2-yl)-2-(cis-4-hydroxycyclohexyl)-2,7-diazaspiro[4.5]decan-1-one

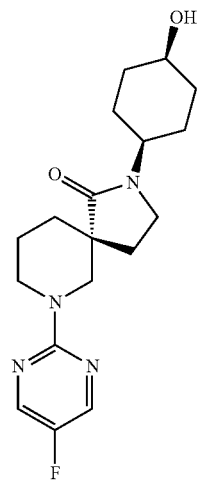 [SMILES: O=C1N([C@H]2CC[C@@H](O)CC2)CC[C@@]12CCCN(c1ncc(F)cn1)C2]

This compound was prepared by using procedures analogous to those described for the synthesis of example 93 starting from (S)-2-((cis)-4-hydroxycyclohexyl)-2,7-diazaspiro[4.5]decan-1-one (which was prepared using procedures analogous to those described in the synthesis of example 472-a followed by standard hydrogenation to remove the carbobenzyloxy (Cbz) protecting group). LC-MS: 349.1 (M+H)$^+$.

Example 493

(5S)-7-(5-Bromopyrimidin-2-yl)-2-(cis-4-hydroxycyclohexyl)-2,7-diazaspiro[4.5]decan-1-one

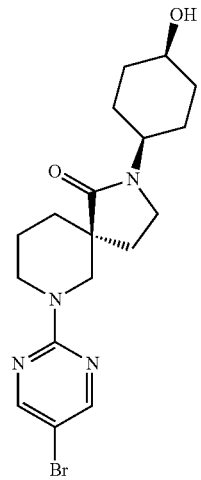 [SMILES: O=C1N([C@H]2CC[C@@H](O)CC2)CC[C@]12CCCN(c1ncc(Br)cn1)C2]

This compound was prepared by using procedures analogous to those described for the synthesis of example 93 starting from (S)-2-((cis)-4-hydroxycyclohexyl)-2,7-diazaspiro[4.5]decan-1-one (which was prepared using procedures analogous to those described in the synthesis of example 472-a and followed by standard hydrogenation to remove the carbobenzyloxy (Cbz) protecting group). LC-MS: 409.1/411.1 (M+H)$^+$.

Example 494

(5S)-7-(5-Ethylpyrimidin-2-yl)-2-(cis-4-hydroxycyclohexyl)-2,7-diazaspiro[4.5]decan-1-one

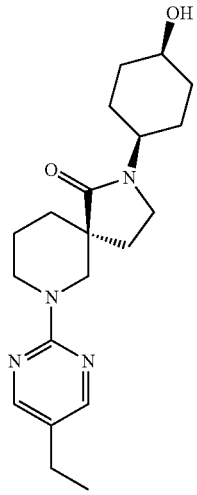 [SMILES: CCc1cnc(N2CCC[C@]3(CCN([C@H]4CC[C@@H](O)CC4)C3=O)C2)nc1]

This compound was prepared by using procedures analogous to those described for the synthesis of example 93 starting from (S)-2-((cis)-4-hydroxycyclohexyl)-2,7-diazaspiro[4.5]decan-1-one (which was prepared using procedures analogous to those described in the synthesis of example 472-a followed by standard hydrogenation to remove the carbobenzyloxy (Cbz) protecting group). LC-MS: 359.1 (M+H)$^+$.

Example 495

4-{2-[(5S)-2-(cis-4-Hydroxycyclohexyl)-1-oxo-2,7-diazaspiro[4.5]dec-7-yl]pyrimidin-5-yl}benzamide

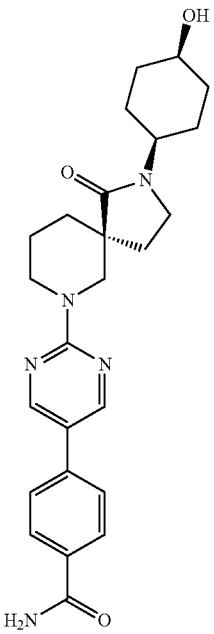 [SMILES: NC(=O)c1ccc(-c2cnc(N3CCC[C@]4(CCN([C@H]5CC[C@@H](O)CC5)C4=O)C3)nc2)cc1]

This compound was prepared by using procedures analogous to those described for the synthesis of example 257. LC-MS: 450.1 (M+H)$^+$.

Example 496

N-Cyclopropyl-4-{2-[(5S)-2-(cis-4-hydroxycyclohexyl)-1-oxo-2,7-diazaspiro[4.5]dec-7-yl]pyrimidin-5-yl}benzamide

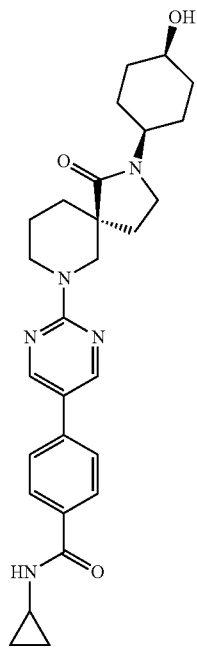 [SMILES: O=C(NC1CC1)c1ccc(-c2cnc(N3CCC[C@]4(CCN([C@H]5CC[C@@H](O)CC5)C4=O)C3)nc2)cc1]

This compound was prepared by using procedures analogous to those described for the synthesis of example 257. LC-MS: 490.1 (M+H)+.

Example 497

(5S)-2-(cis-4-Hydroxycyclohexyl)-7-[5-(4-methoxyphenyl)pyrimidin-2-yl]-2,7-diazaspiro[4.5]decan-1-one

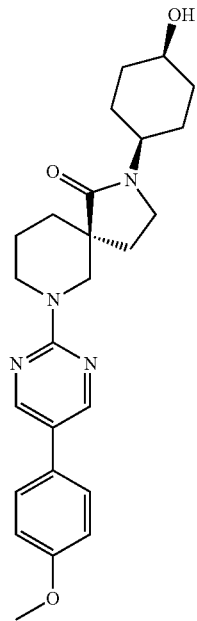 [SMILES: COc1ccc(-c2cnc(N3CCC[C@]4(CCN([C@H]5CC[C@@H](O)CC5)C4=O)C3)nc2)cc1]

This compound was prepared by using procedures analogous to those described for the synthesis of example 257. LC-MS: 437.1 (M+H)+.

Example 498

(5S)-2-(cis-4-Hydroxycyclohexyl)-7-(5-pyridin-3-ylpyrimidin-2-yl)-2,7-diazaspiro[4.5]decan-1-one

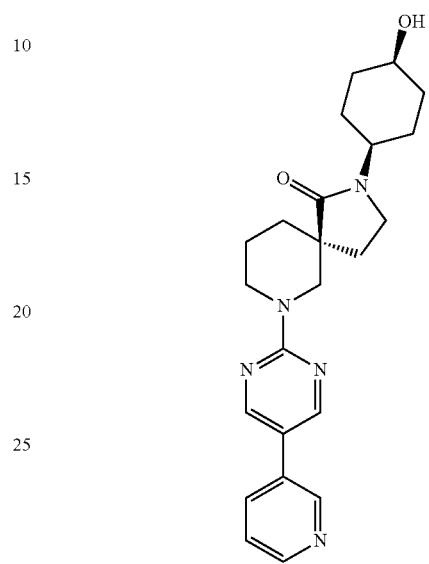

This compound was prepared by using procedures analogous to those described for the synthesis of example 257. LC-MS: 408.2 (M+H)+.

Example 499

5-{2-[(5S)-2-(cis-4-Hydroxycyclohexyl)-1-oxo-2,7-diazaspiro[4.5]dec-7-yl]pyrimidin-5-yl}-N,N-dimethylpyridine-2-carboxamide

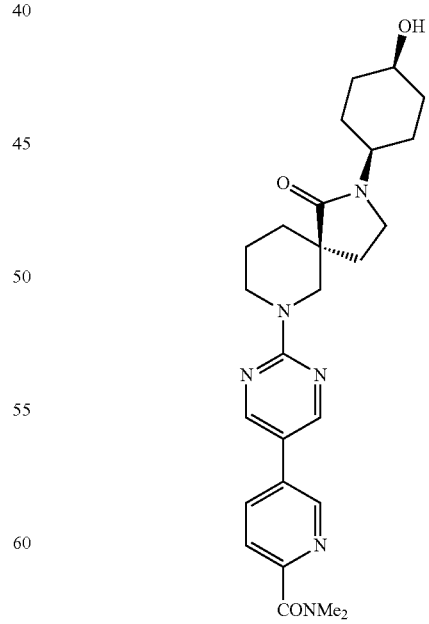

This compound was prepared by using procedures analogous to those described for the synthesis of example 257. LC-MS: 479.1 (M+H)+.

Example 500

(5S)-2-(cis-4-Hydroxycyclohexyl)-7-(5-pyridin-4-ylpyrimidin-2-yl)-2,7-diazaspiro[4.5]decan-1-one

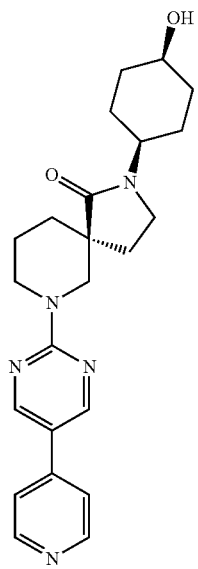

This compound was prepared by using procedures analogous to those described for the synthesis of example 257. LC-MS: 408.2 (M+H)+.

Example 501

4-{5-Chloro-6-[(5S)-2-(cis-4-hydroxycyclohexyl)-1-oxo-2,7-diazaspiro[4.5]dec-7-yl]pyridin-3-yl}-N-cyclopropylbenzamide

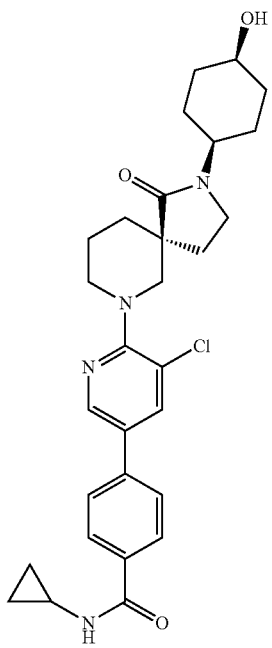 [SMILES: O=C(NC1CC1)c1ccc(-c2cnc(N3CCC[C@]4(CCN([C@H]5CC[C@@H](O)CC5)C4=O)C3)c(Cl)c2)cc1]

This compound was prepared by using procedures analogous to those described for the synthesis of example 257. LC-MS: 523.2 (M+H)+.

Example 502

5'-Chloro-N-ethyl-6'-[(5S)-2-(cis-4-hydroxycyclohexyl)-1-oxo-2,7-diazaspiro[4.5]dec-7-yl]-3,3'-bipyridine-6-carboxamide

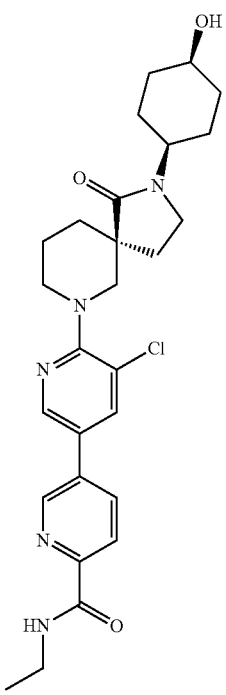 [SMILES: CCNC(=O)c1ccc(-c2cnc(N3CCC[C@]4(CCN([C@H]5CC[C@@H](O)CC5)C4=O)C3)c(Cl)c2)cn1]

This compound was prepared by using procedures analogous to those described for the synthesis of example 257. LC-MS: 512.2 (M+H)+.

Example 503

2-[(5S)-2-(trans-4-Hydroxycyclohexyl)-1-oxo-2,7-diazaspiro[4.5]dec-7-yl]isonicotinonitrile

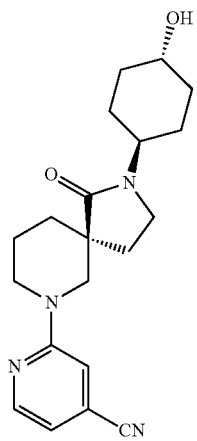

This compound was prepared by using procedures analogous to those described for the synthesis of example 93 starting from (S)-2-((trans)-4-hydroxycyclohexyl)-2,7-diazaspiro[4.5]decan-1-one (which was prepared using procedures analogous to those described in the synthesis of example 472-a followed by standard hydrogenation to remove the carbobenzyloxy (Cbz) protecting group). LC-MS: 355.2 (M+11)⁺.

Example 504

Methyl {4-[(5S)-2-(cis-4-hydroxy-4-methylcyclohexyl)-1-oxo-2,7-diazaspiro[4.5]dec-7-yl]-3-methylphenyl}carbamate

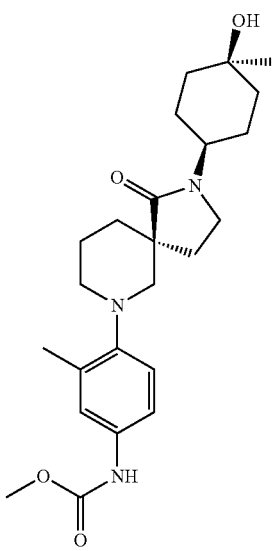

This compound was prepared by using procedures analogous to those described for the synthesis of example 105. LC-MS: 430.1 (M+H)⁺.

Example 505

Prop-2-yn-1-yl {6-[(5S)-2-(trans-4-hydroxycyclohexyl)-1-oxo-2,7-diazaspiro[4.5]dec-7-yl]-5-methoxypyridin-3-yl}carbamate

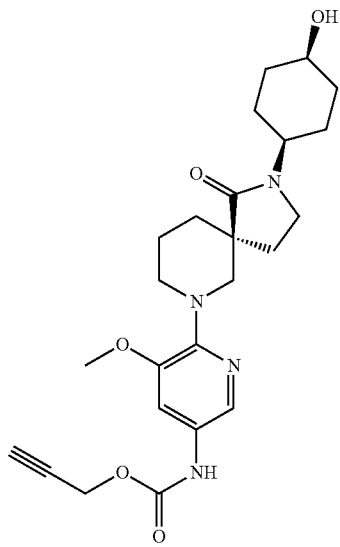 [SMILES: C#CCOC(=O)Nc1cnc(N2CCC[C@]3(CCN([C@H]4CC[C@@H](O)CC4)C3=O)C2)c(OC)c1]

This compound was prepared by using procedures analogous to those described for the synthesis of example 105. LC-MS: 457.2 (M+H)⁺.

Example 506

(5S)-7-(5-Fluoropyrimidin-2-yl)-2-(tetrahydro-2H-pyran-4-yl)-2,7-diazaspiro[4.5]decan-1-one

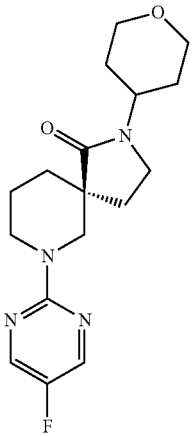 [SMILES: O=C1N(C2CCOCC2)CC[C@]12CCCN(c1ncc(F)cn1)C2]

This compound was prepared by using procedures analogous to those described for the synthesis of example 116. LC-MS: 335.1 (M+H)⁺.

Example 507

(5S)-7-(5-Ethylpyrimidin-2-yl)-2-(tetrahydro-2H-pyran-4-yl)-2,7-diazaspiro[4.5]decan-1-one

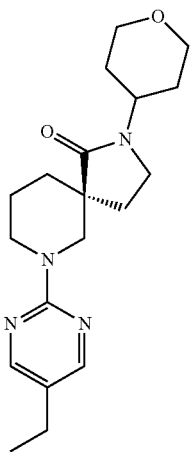 [SMILES: CCc1cnc(N2CCC[C@]3(CCN(C4CCOCC4)C3=O)C2)nc1]

This compound was prepared by using procedures analogous to those described for the synthesis of example 116. LC-MS: 345.1 (M+H)⁺.

Example 508

(5S)-2-(Tetrahydro-2H-pyran-4-yl)-7-[4-(trifluoromethyl)pyrimidin-2-yl]-2,7-diazaspiro[4.5]decan-1-one

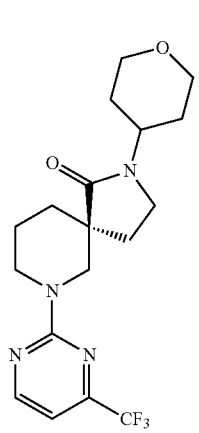 [SMILES: O=C1N(C2CCOCC2)CC[C@]12CCCN(c1nccc(C(F)(F)F)n1)C2]

This compound was prepared by using procedures analogous to those described for the synthesis of example 116. LC-MS: 385.1 (M+H)$^+$.

Example 509

(5S)-7-(4-Methoxypyrimidin-2-yl)-2-(tetrahydro-2H-pyran-4-yl)-2,7-diazaspiro[4.5]decan-1-one

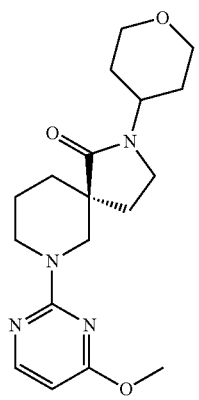 [SMILES: COc1ccnc(N2CCC[C@]3(CCN(C4CCOCC4)C3=O)C2)n1]

This compound was prepared by using procedures analogous to those described for the synthesis of example 116. LC-MS: 347.1 (M+H)$^+$.

Example 510

(5S)-7-(2-Fluorophenyl)-2-(tetrahydro-2H-pyran-4-yl)-2,7-diazaspiro[4.5]decan-1-one

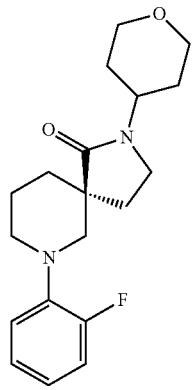 [SMILES: O=C1N(C2CCOCC2)CC[C@]12CCCN(c1ccccc1F)C2]

This compound was prepared by using procedures analogous to those described for the synthesis of example 180. LC-MS: 333.1 (M+H)$^+$.

Example 511

(5S)-2-(cis-4-Hydroxycyclohexyl)-7-[5-(1H-pyrazol-1-yl)pyrimidin-2-yl]-2,7-diazaspiro[4.5]decan-1-one

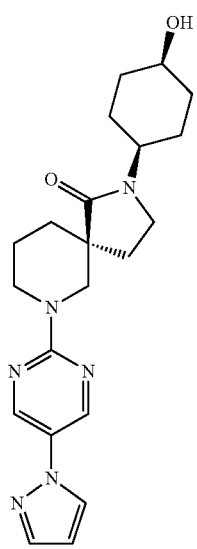

To a solution of (5S)-7-(5-bromopyrimidin-2-yl)-2-(cis-4-hydroxycyclohexyl)-2,7-diazaspiro[4.5]decan-1-one (30 mg, 0.00007 mol, this compound was prepared by using procedures that were analogous to those described for the synthesis of example 420) in 1,4-dioxane (1 mL, 0.01 mol) was added 1H-pyrazole (6.0 mg, 0.0000880 mol), (1S,2S)-N,N'-dimethylcyclohexane-1,2-diamine (2.3 µL, 0.000015 mol), copper(I) iodide (1.4 mg, 0.0000073 mol), and potassium carbonate (0.0213 g, 0.000154 mol). After stirring at 150° C. for 16 h, the reaction mixture was filtered and purified by prep-HPLC to afford the desired product. LC-MS: 397.2 (M+H)$^+$.

Example 512

(5S)-2-(cis-4-Hydroxycyclohexyl)-7-[5-(3-methyl-1H-pyrazol-1-yl)pyrimidin-2-yl]-2,7-diazaspiro[4.5]decan-1-one

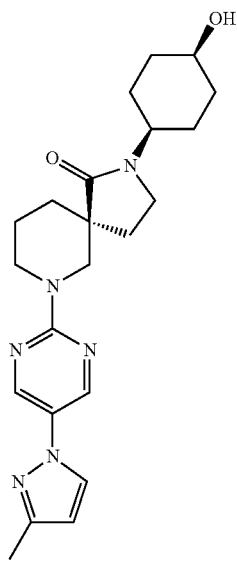 [SMILES: Cc1ccn(-c2cnc(N3CCC[C@]4(CCN([C@H]5CC[C@@H](O)CC5)C4=O)C3)nc2)n1]

This compound was prepared by using procedures analogous to those described for the synthesis of example 511. LC-MS: 411.2 (M+H)$^+$.

Example 513

(5S)-2-(cis-4-Hydroxycyclohexyl)-7-{5-[3-(trifluoromethyl)-1H-pyrazol-1-yl]pyrimidin-2-yl}-2,7-diazaspiro[4.5]decan-1-one

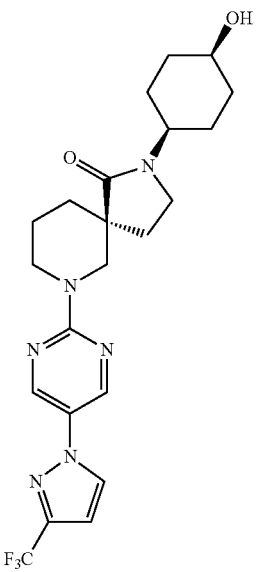 [SMILES: O=C1N([C@H]2CC[C@@H](O)CC2)CC[C@]12CCCN(c1ncc(-n3ccc(C(F)(F)F)n3)cn1)C2]

This compound was prepared by using procedures analogous to those described for the synthesis of example 511. LC-MS: 465.2 (M+H)$^+$.

Example 514

(5S)-2-(cis-4-Hydroxycyclohexyl)-7-pyrimidin-2-yl-2,7-diazaspiro[4.5]decan-1-one

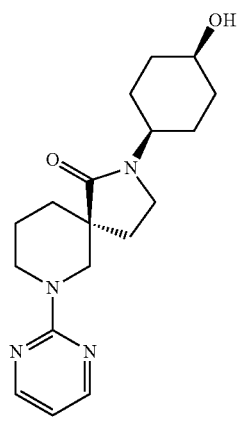 [SMILES: O=C1N([C@H]2CC[C@@H](O)CC2)CC[C@]12CCCN(c1ncccn1)C2]

This compound was prepared by using procedures analogous to those described for the synthesis of example 420. LC-MS: 331.2 (M+H)$^+$.

Example 515

(5S)-2-(cis-4-Hydroxycyclohexyl)-7-[5-(2-oxopyridin-1(2H)-yl)pyrimidin-2-yl]-2,7-diazaspiro[4.5]decan-1-one

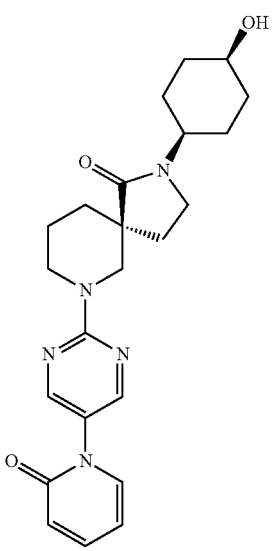 [SMILES: O=C1N([C@H]2CC[C@@H](O)CC2)CC[C@]12CCCN(c1ncc(-n3ccccc3=O)cn1)C2]

This compound was prepared by using procedures analogous to those described for the synthesis of example 511. LC-MS: 424.2 (M+H)$^+$.

Example 516

(5S)-7-(2,5-Difluoropyridin-3-yl)-2-(cis-4-hydroxy-cyclohexyl)-2,7-diazaspiro[4.5]decan-1-one

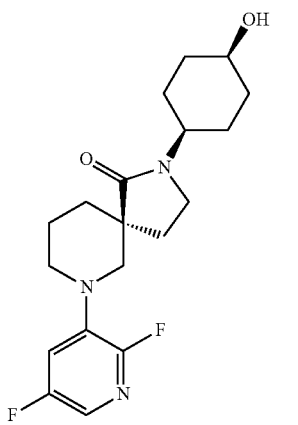 [SMILES: O=C1N([C@H]2CC[C@@H](O)CC2)CC[C@]12CCCN(c1cc(F)cnc1F)C2]

This compound was prepared by using procedures analogous to those described for the synthesis of example 420. LC-MS: 366.1 (M+H)+.

Example 517

(5S)-7-(3,5-Difluoropyridin-2-yl)-2-(cis-4-hydroxy-cyclohexyl)-2,7-diazaspiro[4.5]decan-1-one

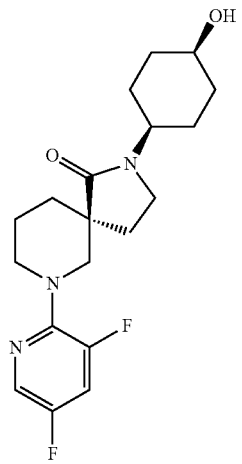

This compound was prepared by using procedures analogous to those described for the synthesis of example 420. LC-MS: 366.1 (M+H)+.

Example 518

(5S)-7-[3-Fluoro-4-(trifluoromethyl)pyridin-2-yl]-2-(cis-4-hydroxycyclohexyl)-2,7-diazaspiro[4.5]decan-1-one

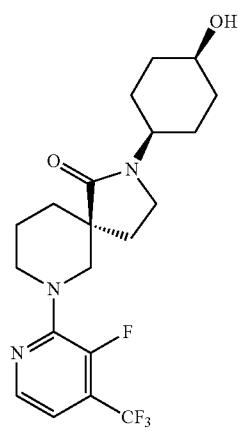 [SMILES: O=C1N([C@H]2CC[C@@H](O)CC2)CC[C@]12CCCN(c1nccc(C(F)(F)F)c1F)C2]

This compound was prepared by using procedures analogous to those described for the synthesis of example 420. LC-MS: 416.1 (M+H)+.

Example 519

(5S)-7-[3-Chloro-5-(trifluoromethyl)pyridin-2-yl]-2-(cis-4-hydroxycyclohexyl)-2,7-diazaspiro[4.5]decan-1-one

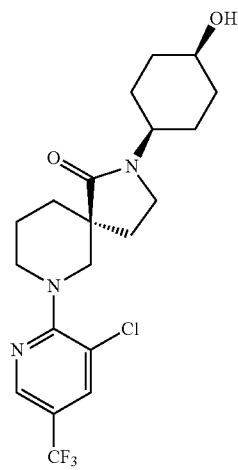 [SMILES: O=C1N([C@H]2CC[C@@H](O)CC2)CC[C@]12CCCN(c1ncc(C(F)(F)F)cc1Cl)C2]

This compound was prepared by using procedures analogous to those described for the synthesis of example 420. LC-MS: 432.2 (M+H)+.

Example 520

(5S)-2-(cis-4-Hydroxycyclohexyl)-7-[4-(trifluoromethyl)pyridin-2-yl]-2,7-diazaspiro[4.5]decan-1-one

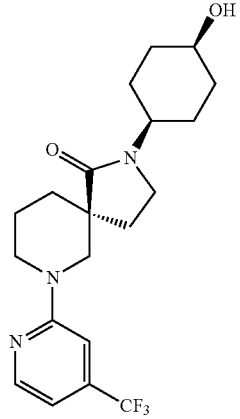 [SMILES: O=C1N([C@H]2CC[C@@H](O)CC2)CC[C@]12CCCN(c1cc(C(F)(F)F)ccn1)C2]

This compound was prepared by using procedures analogous to those described for the synthesis of example 420. LC-MS: 398.2 (M+H)+.

Example 521

(5S)-7-(5-Bromo-2-chloropyridin-3-yl)-2-(cis-4-hydroxycyclohexyl)-2,7-diazaspiro[4.5]decan-1-one

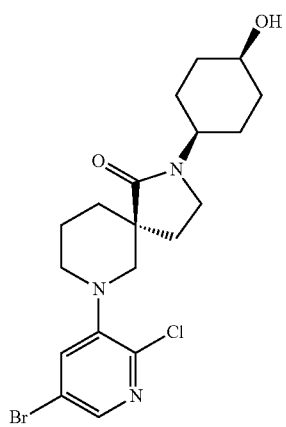 [SMILES: O=C1N([C@H]2CC[C@@H](O)CC2)CC[C@]12CCCN(c1cc(Br)cnc1Cl)C2]

This compound was prepared by using procedures analogous to those described for the synthesis of example 420. LC-MS: 442.2/444.2 (M+H)+.

Example 522a (5S)-7-(5-Bromo-3-fluoropyridin-2-yl)-2-(cis-4-hydroxycyclohexyl)-2,7-diazaspiro[4.5]decan-1-one

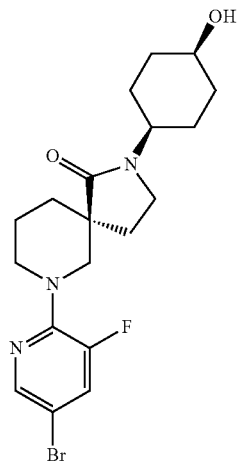 [SMILES: O=C1N([C@H]2CC[C@@H](O)CC2)CC[C@]12CCCN(c1ncc(Br)cc1F)C2]

This compound was prepared by using procedures analogous to those described for the synthesis of example 420. LC-MS: 426.1 (M+H)+.

Example 522b (5S)-7-(5-Bromo-3-chloropyridin-2-yl)-2-(cis-4-hydroxycyclohexyl)-2,7-diazaspiro[4.5]decan-1-one

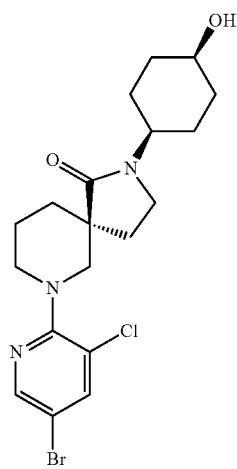 [SMILES: O=C1N([C@H]2CC[C@@H](O)CC2)CC[C@]12CCCN(c1ncc(Br)cc1Cl)C2]

This compound was prepared by using procedures analogous to those described for the synthesis of example 420. LC-MS: 442.2/444.2 (M+H)+.

Example 523

(5S)-7-(5-Bromo-3-methylpyridin-2-yl)-2-(cis-4-hydroxycyclohexyl)-2,7-diazaspiro[4.5]decan-1-one

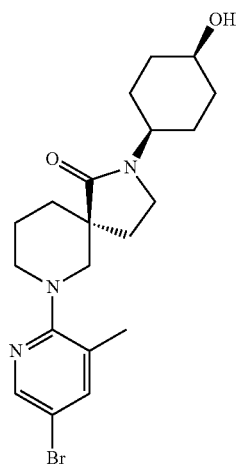 [SMILES: Cc1cc(Br)cnc1N1CCC[C@]2(CCN([C@H]3CC[C@@H](O)CC3)C2=O)C1]

This compound was prepared by using procedures analogous to those described for the synthesis of example 420. LC-MS: 422.2/424.2 (M+H)⁺.

Example 524

Methyl {6-[(5S)-2-(cis-4-hydroxycyclohexyl)-1-oxo-2,7-diazaspiro[4.5]dec-7-yl]-5-methylpyridin-3-yl}carbamate

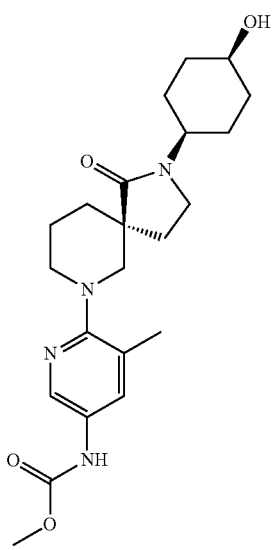 [SMILES: COC(=O)Nc1cnc(N2CCC[C@]3(CCN([C@H]4CC[C@@H](O)CC4)C3=O)C2)c(C)c1]

This compound was prepared by using procedures analogous to those described for the synthesis of examples 420, steps 1 and 2 followed by using procedures that were analogous to those described for the synthesis of example 105, steps 1 and 2. LC-MS: 417.2 (M+H)⁺.

Example 525

Ethyl {6-[(5S)-2-(cis-4-hydroxycyclohexyl)-1-oxo-2,7-diazaspiro[4.5]dec-7-yl]-5-methylpyridin-3-yl}carbamate

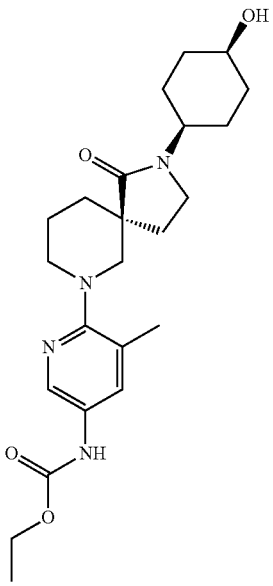

This compound was prepared by using procedures analogous to those described for the synthesis of example 524. LC-MS: 431.2 (M+H)⁺.

Example 526

Propyl {6-[(5S)-2-(cis-4-hydroxycyclohexyl)-1-oxo-2,7-diazaspiro[4.5]dec-7-yl]-5-methylpyridin-3-yl}carbamate

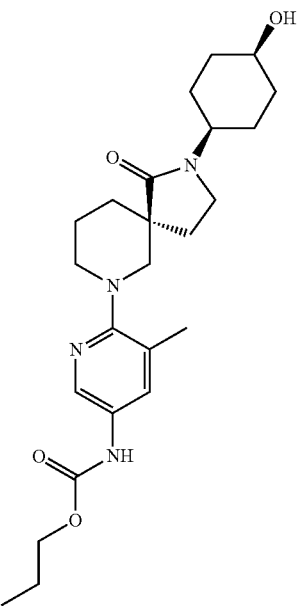 [SMILES: CCCOC(=O)Nc1cnc(N2CCC[C@]3(CCN([C@H]4CC[C@@H](O)CC4)C3=O)C2)c(C)c1]

This compound was prepared by using procedures analogous to those described for the synthesis of example 524. LC-MS: 445.2 (M+H)⁺.

Example 527

Prop-2-yn-1-yl {6-[(5S)-2-(cis-4-hydroxycyclohexyl)-1-oxo-2,7-diazaspiro[4.5]dec-7-yl]-5-methylpyridin-3-yl}carbamate

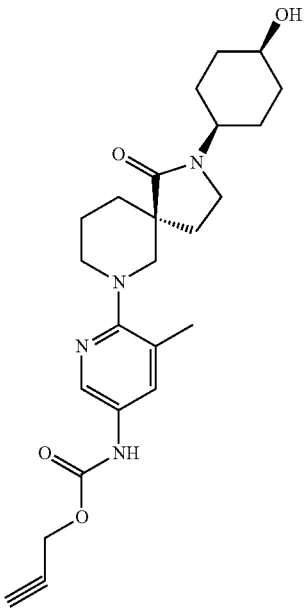 [SMILES: C#CCOC(=O)Nc1cnc(N2CCC[C@]3(CCN([C@H]4CC[C@@H](O)CC4)C3=O)C2)c(C)c1]

This compound was prepared by using procedures analogous to those described for the synthesis of example 524. LC-MS: 441.2 (M+H)$^+$.

Example 528

Methyl {6-[(5S)-2-(cis-4-hydroxycyclohexyl)-1-oxo-2,7-diazaspiro[4.5]dec-7-yl]-5-methoxypyridin-3-yl}carbamate

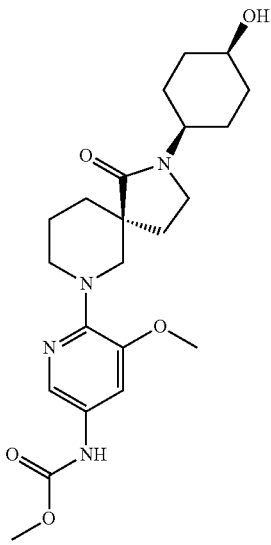 [SMILES: COC(=O)Nc1cnc(N2CCC[C@]3(CCN([C@H]4CC[C@@H](O)CC4)C3=O)C2)c(OC)c1]

This compound was prepared by using procedures analogous to those described for the synthesis of example 524. LC-MS: 433.2 (M+H)$^+$.

Example 529

Ethyl {6-[(5S)-2-(cis-4-hydroxycyclohexyl)-1-oxo-2,7-diazaspiro[4.5]dec-7-yl]-5-methoxypyridin-3-yl}carbamate

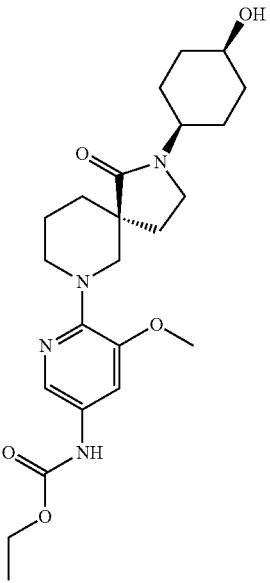 [SMILES: CCOC(=O)Nc1cnc(N2CCC[C@]3(CCN([C@H]4CC[C@@H](O)CC4)C3=O)C2)c(OC)c1]

This compound was prepared by using procedures analogous to those described for the synthesis of example 524. LC-MS: 447.2 (M+H)$^+$.

Example 530

Propyl {6-[(5S)-2-(cis-4-hydroxycyclohexyl)-1-oxo-2,7-diazaspiro[4.5]dec-7-yl]-5-methoxypyridin-3-yl}carbamate

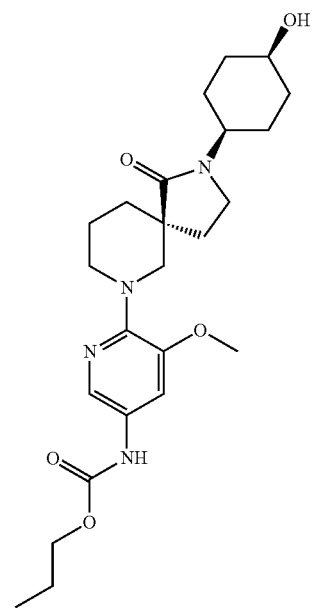 [SMILES: CCCOC(=O)Nc1cnc(N2CCC[C@]3(CCN([C@H]4CC[C@@H](O)CC4)C3=O)C2)c(OC)c1]

This compound was prepared by using procedures analogous to those described for the synthesis of example 524. LC-MS: 461.2 (M+H)$^+$.

Example 531

Prop-2-yn-1-yl {6-[(5S)-2-(cis-4-hydroxycyclohexyl)-1-oxo-2,7-diazaspiro[4.5]dec-7-yl]-5-methoxypyridin-3-yl}carbamate

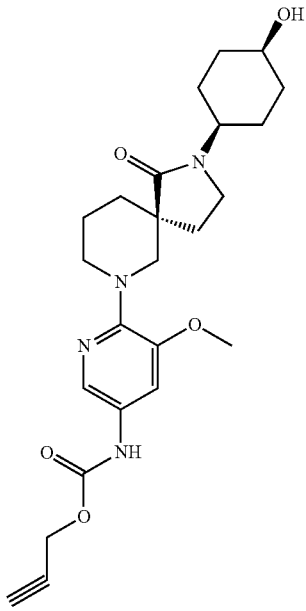

This compound was prepared by using procedures analogous to those described for the synthesis of example 524. LC-MS: 457.2 (M+H)+.

Example 532

(5S)-2-(cis-4-Hydroxycyclohexyl)-7-[3-methoxy-5-(2-oxopyrrolidin-1-yl)pyridin-2-yl]-2,7-diazaspiro[4.5]decan-1-one

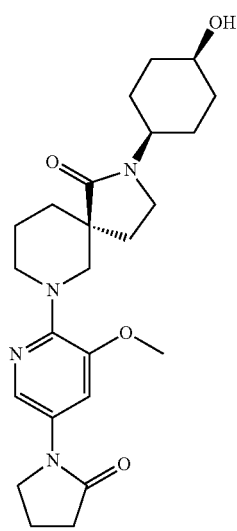 [SMILES: COc1cc(N2CCCC2=O)cnc1N1CCC[C@]2(CCN([C@H]3CC[C@@H](O)CC3)C2=O)C1]

This compound was prepared by using procedures analogous to those described for the synthesis of examples 420, steps 1 and 2 followed by using procedures that were analogous to those described for the synthesis of example 256. LC-MS: 443.2 (M+H)+.

Example 533

(5S)-2-(cis-4-Hydroxycyclohexyl)-7-[3-methoxy-5-(2-oxo-1,3-oxazolidin-3-yl)pyridin-2-yl]-2,7-diazaspiro[4.5]decan-1-one

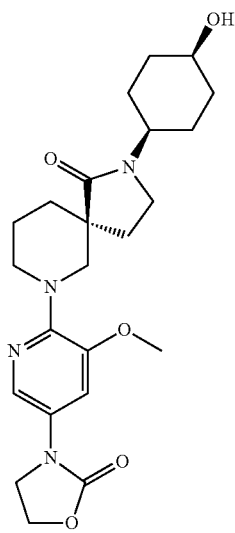 [SMILES: COc1cc(N2CCOC2=O)cnc1N1CCC[C@]2(CCN([C@H]3CC[C@@H](O)CC3)C2=O)C1]

This compound was prepared by using procedures analogous to those described for the synthesis of example 532. LC-MS: 445.2 (M+H)+.

Example 534

(5S)-2-(cis-4-Hydroxycyclohexyl)-7-[3-methoxy-5-(2-oxo-1,3-oxazinan-3-yl)pyridin-2-yl]-2,7-diazaspiro[4.5]decan-1-one

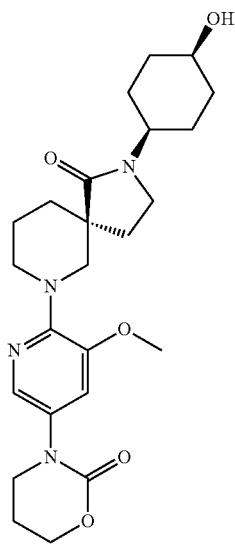 [SMILES: COc1cc(N2CCCOC2=O)cnc1N1CCC[C@]2(CCN([C@H]3CC[C@@H](O)CC3)C2=O)C1]

This compound was prepared by using procedures analogous to those described for the synthesis of example 532. LC-MS: 459.1 (M+H)+.

Example 535

(5S)-7-(3-Chloro-5-phenylpyridin-2-yl)-2-(cis-4-hydroxycyclohexyl)-2,7-diazaspiro[4.5]decan-1-one

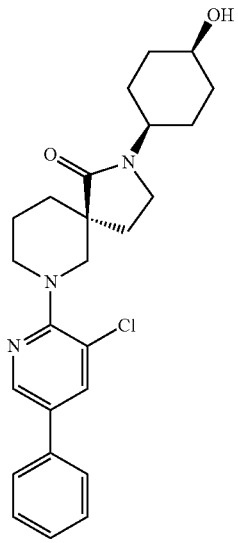 [SMILES: O=C1N([C@H]2CC[C@@H](O)CC2)CC[C@]12CCCN(c1ncc(-c3ccccc3)cc1Cl)C2]

This compound was prepared by using procedures analogous to those described for the synthesis of examples 420, steps 1 and 2 followed by using procedures that were analogous to those described for the synthesis of example 257. LC-MS: 440.2 (M+H)+.

Example 536a (5S)-7-[3-Chloro-5-(4-methoxyphenyl)pyridin-2-yl]-2-(cis-4-hydroxycyclohexyl)-2,7-diazaspiro[4.5]decan-1-one

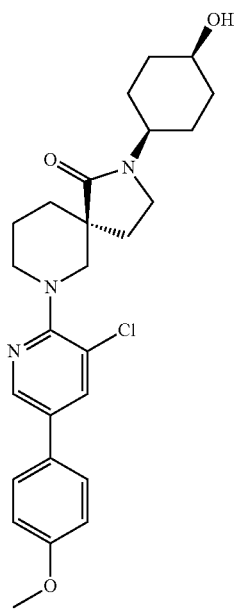 [SMILES: COc1ccc(-c2cnc(N3CCC[C@]4(CCN([C@H]5CC[C@@H](O)CC5)C4=O)C3)c(Cl)c2)cc1]

This compound was prepared by using procedures analogous to those described for the synthesis of example 535. LC-MS: 471.2 (M+H)+.

Example 536b

4-{5-Chloro-6-[(5S)-2-(cis-4-hydroxycyclohexyl)-1-oxo-2,7-diazaspiro[4.5]dec-7-yl]pyridin-3-yl}benzamide

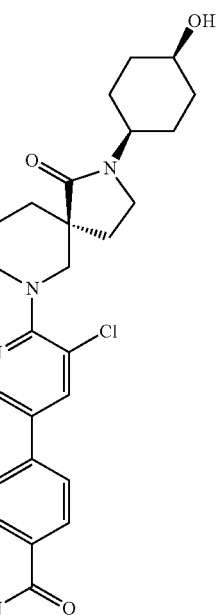

This compound was prepared by using procedures analogous to those described for the synthesis of example 535. LC-MS: 483.2 (M+H)+.

Example 537

(5S)-7-(5-Chloro-3,4'-bipyridin-6-yl)-2-(cis-4-hydroxycyclohexyl)-2,7-diazaspiro[4.5]decan-1-one

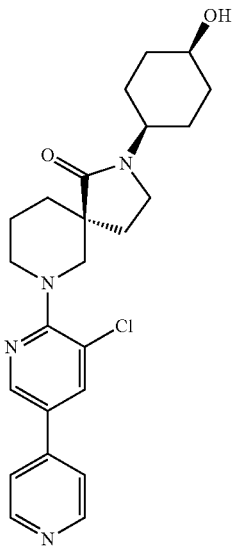 [SMILES: O=C1N([C@H]2CC[C@@H](O)CC2)CC[C@]12CCCN(c1ncc(-c3ccncc3)cc1Cl)C2]

This compound was prepared by using procedures analogous to those described for the synthesis of example 535. LC-MS: 441.2 (M+H)+.

Example 538

5'-Chloro-6'-[(5S)-2-(cis-4-hydroxycyclohexyl)-1-oxo-2,7-diazaspiro[4.5]dec-7-yl]-N,N-dimethyl-3,3'-bipyridine-6-carboxamide

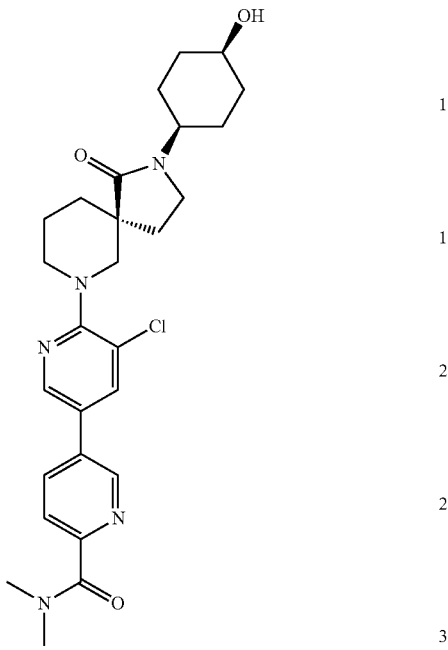

This compound was prepared by using procedures analogous to those described for the synthesis of example 535. LC-MS: 512.2 (M+H)+.

Example 539

5'-Chloro-N,N-diethyl-6'-[(5S)-2-(cis-4-hydroxycyclohexyl)-1-oxo-2,7-diazaspiro[4.5]dec-7-yl]-3,3'-bipyridine-6-carboxamide

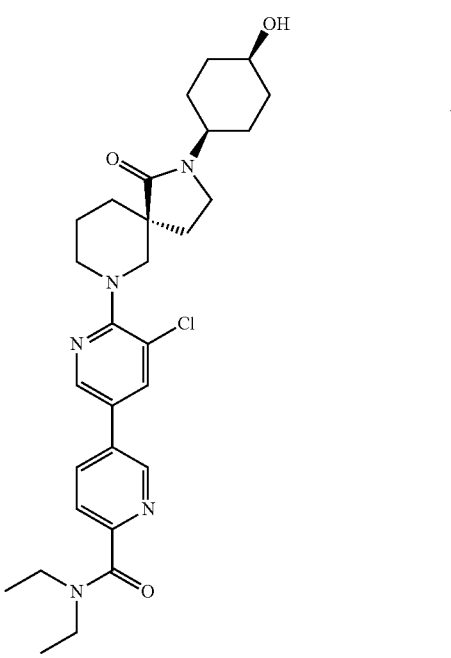

This compound was prepared by using procedures analogous to those described for the synthesis of example 535. LC-MS: 540.2 (M+H)+.

Example 540

4-{5-Chloro-6-[(5S)-2-(cis-4-hydroxycyclohexyl)-1-oxo-2,7-diazaspiro[4.5]dec-7-yl]pyridin-3-yl}-N,N-dimethylbenzamide

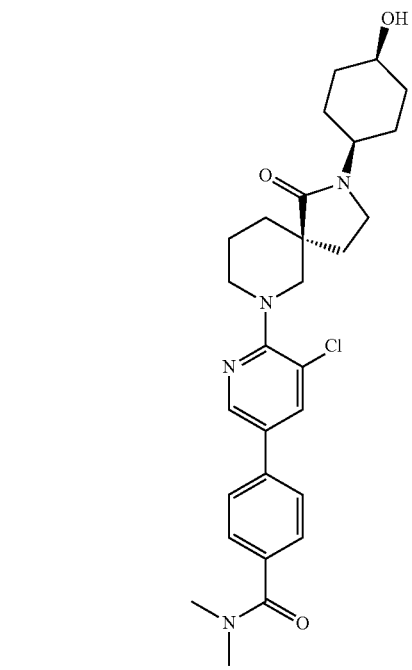 [SMILES: CN(C)C(=O)c1ccc(-c2cnc(N3CCC[C@]4(CCN([C@H]5CC[C@@H](O)CC5)C4=O)C3)c(Cl)c2)cc1]

This compound was prepared by using procedures analogous to those described for the synthesis of example 535. LC-MS: 511.2 (M+H)+.

Example 541

Methyl {5-chloro-6-[(5S)-2-(cis-4-hydroxycyclohexyl)-1-oxo-2,7-diazaspiro[4.5]dec-7-yl]pyridin-3-yl}carbamate

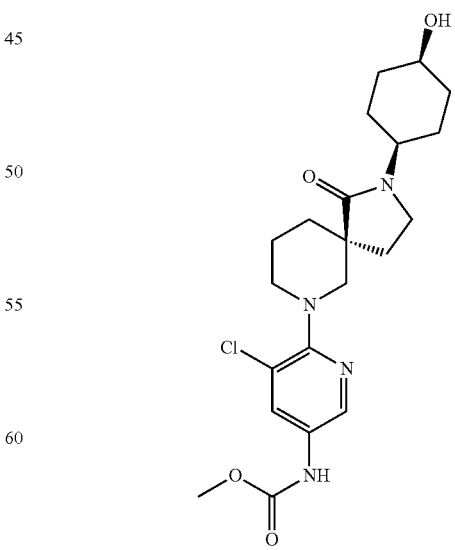

This compound was prepared by using procedures analogous to those described for the synthesis of example 524. LC-MS: 437.2 (M+H)+.

321
Example 542

Ethyl {5-chloro-6-[(5S)-2-(cis-4-hydroxycyclohexyl)-1-oxo-2,7-diazaspiro[4.5]dec-7-yl]pyridin-3-yl}carbamate

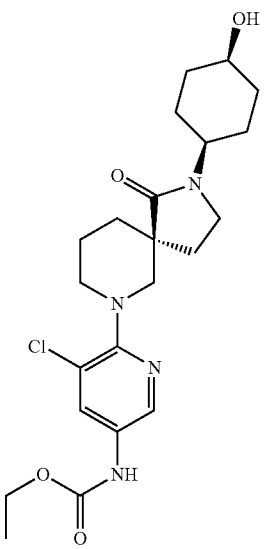 [SMILES: CCOC(=O)Nc1cnc(N2CCC[C@]3(CCN([C@H]4CC[C@@H](O)CC4)C3=O)C2)c(Cl)c1]

This compound was prepared by using procedures analogous to those described for the synthesis of example 524. LC-MS: 451.2 (M+H)+.

Example 543

Propyl {5-chloro-6-[(5S)-2-(cis-4-hydroxycyclohexyl)-1-oxo-2,7-diazaspiro[4.5]dec-7-yl]pyridin-3-yl}carbamate

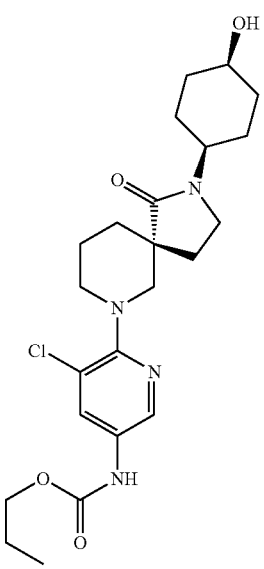 [SMILES: CCCOC(=O)Nc1cnc(N2CCC[C@@]3(CCN([C@H]4CC[C@@H](O)CC4)C3=O)C2)c(Cl)c1]

This compound was prepared by using procedures analogous to those described for the synthesis of example 524. LC-MS: 465.2 (M+H)+.

322
Example 544

Prop-2-yn-1-yl {5-chloro-6-[(5S)-2-(cis-4-hydroxycyclohexyl)-1-oxo-2,7-diazaspiro[4.5]dec-7-yl]pyridin-3-yl}carbamate

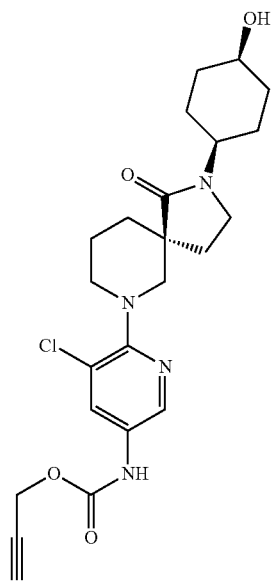 [SMILES: C#CCOC(=O)Nc1cnc(N2CCC[C@]3(CCN([C@H]4CC[C@@H](O)CC4)C3=O)C2)c(Cl)c1]

This compound was prepared by using procedures analogous to those described for the synthesis of example 524. LC-MS: 461.2 (M+H)+.

Example 545

(5S)-7-[3-Chloro-5-(2-oxo-1,3-oxazolidin-3-yl)pyridin-2-yl]-2-(cis-4-hydroxycyclohexyl)-2,7-diazaspiro[4.5]decan-1-one

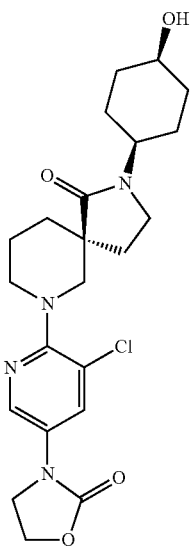 [SMILES: O=C1OCCN1c1cnc(N2CCC[C@]3(CCN([C@H]4CC[C@@H](O)CC4)C3=O)C2)c(Cl)c1]

This compound was prepared by using procedures analogous to those described for the synthesis of example 532. LC-MS: 449.2 (M+H)+.

Example 546

(5S)-7-[3-Chloro-5-(2-oxo-1,3-oxazinan-3-yl)pyridin-2-yl]-2-(cis-4-hydroxycyclohexyl)-2,7-diazaspiro[4.5]decan-1-one

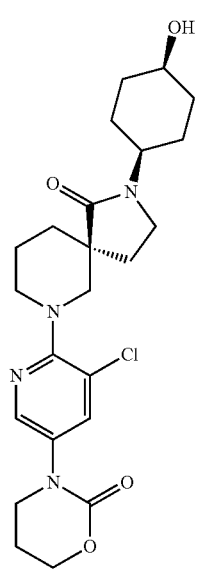 [SMILES: O=C1OCCCN1c1cnc(N2CCC[C@]3(CCN([C@H]4CC[C@@H](O)CC4)C3=O)C2)c(Cl)c1]

This compound was prepared by using procedures analogous to those described for the synthesis of example 532. LC-MS: 463.2 (M+H)$^+$.

Example 547

(5S)-7-[3-Chloro-5-(2-oxopyrrolidin-1-yl)pyridin-2-yl]-2-(cis-4-hydroxycyclohexyl)-2,7-diazaspiro[4.5]decan-1-one

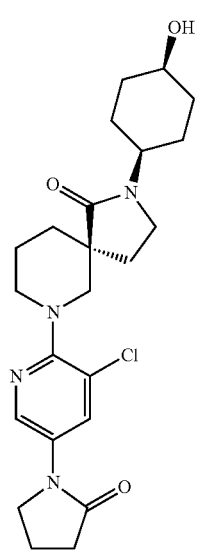

This compound was prepared by using procedures analogous to those described for the synthesis of example 532. LC-MS: 447.2 (M+H)$^+$.

Example 548

(5S)-7-(5-Chloro-3,3'-bipyridin-6-yl)-2-(cis-4-hydroxycyclohexyl)-2,7-diazaspiro[4.5]decan-1-one

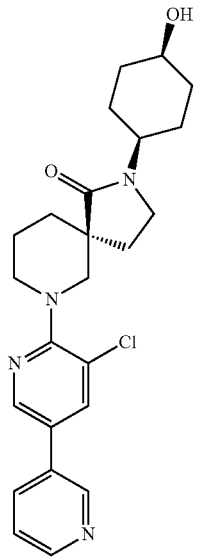 [SMILES: O=C1N([C@H]2CC[C@@H](O)CC2)CC[C@]12CCCN(c1ncc(-c3cccnc3)cc1Cl)C2]

This compound was prepared by using procedures analogous to those described for the synthesis of example 535. LC-MS: 441.2 (M+H)$^+$.

Example 549

(5S)-7-(3-Fluoro-6-methylpyridin-2-yl)-2-(trans-4-hydroxycyclohexyl)-2,7-diazaspiro[4.5]decan-1-one

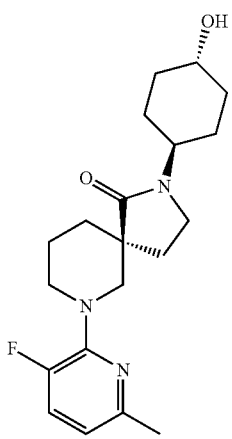 [SMILES: Cc1ccc(F)c(N2CCC[C@]3(CCN([C@H]4CC[C@H](O)CC4)C3=O)C2)n1]

This compound was prepared by using procedures analogous to those described for the synthesis of example 93 starting from (S)-2-((trans)-4-hydroxycyclohexyl)-2,7-diazaspiro[4.5]decan-1-one (which was prepared using procedures analogous to those described in the synthesis of example 472-a followed by standard hydrogenation to remove the carbobenzyloxy (Cbz) protecting group). LC-MS: 362.2 (M+H)$^+$.

Example 550

6-[(5S)-2-(trans-4-Hydroxycyclohexyl)-1-oxo-2,7-diazaspiro[4.5]dec-7-yl]-2-methylnicotinonitrile

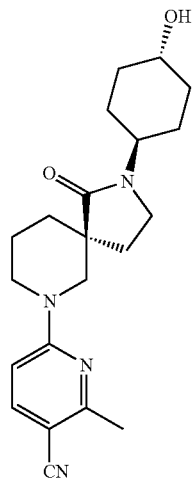 [SMILES: Cc1nc(N2CCC[C@]3(CCN([C@H]4CC[C@H](O)CC4)C3=O)C2)ccc1C#N]

This compound was prepared by using procedures analogous to those described for the synthesis of example 93 starting from (S)-2-((trans)-4-hydroxycyclohexyl)-2,7-diazaspiro[4.5]decan-1-one (which was prepared using procedures analogous to those described in the synthesis of example 472-a and followed by standard hydrogenation to remove the carbobenzyloxy (Cbz) protecting group). LC-MS: 369.2 (M+H)+.

Example 551

2-[(5S)-2-(trans-4-Hydroxycyclohexyl)-1-oxo-2,7-diazaspiro[4.5]dec-7-yl]-4,6-dimethylnicotinonitrile

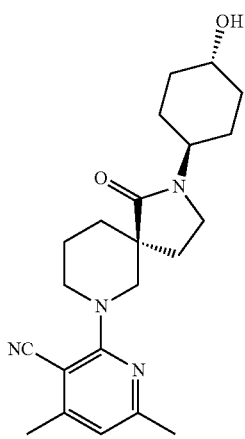 [SMILES: Cc1cc(C)c(C#N)c(N2CCC[C@]3(CCN([C@H]4CC[C@H](O)CC4)C3=O)C2)n1]

This compound was prepared by using procedures analogous to those described for the synthesis of example 93 starting from (S)-2-((trans)-4-hydroxycyclohexyl)-2,7-diazaspiro[4.5]decan-1-one (which was prepared using procedures analogous to those described in the synthesis of example 472-a followed by standard hydrogenation to remove the carbobenzyloxy (Cbz) protecting group). LC-MS: 383.2 (M+H)+.

Example 552

(5S)-2-(trans-4-Hydroxycyclohexyl)-7-[2-(trifluoromethyl)quinazolin-4-yl]-2,7-diazaspiro[4.5]decan-1-one

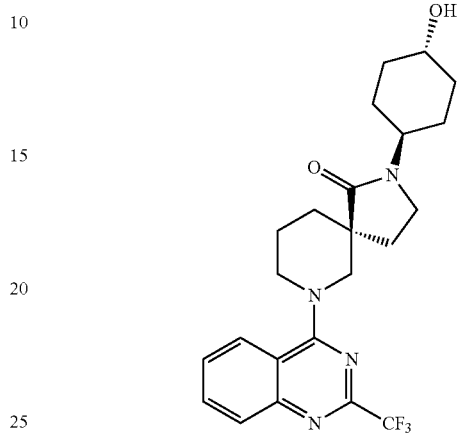

This compound was prepared by using procedures analogous to those described for the synthesis of example 93 starting from (S)-2-((trans)-4-hydroxycyclohexyl)-2,7-diazaspiro[4.5]decan-1-one (which was prepared using procedures analogous to those described in the synthesis of example 472-a followed by standard hydrogenation to remove the carbobenzyloxy (Cbz) protecting group). LC-MS: 449.2 (M+H)+.

Example 553

(5S)-2-Cyclohexyl-7-[2-fluoro-4-(2-oxopyrrolidin-1-yl)phenyl]-2,7-diazaspiro[4.5]decan-1-one

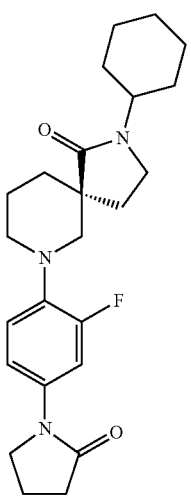 [SMILES: O=C1CCCN1c1ccc(N2CCC[C@]3(CCN(C4CCCCC4)C3=O)C2)c(F)c1]

This compound was prepared by using procedures analogous to those described for the synthesis of example 256. LC-MS: 414.2 (M+H)+.

Example 554

(5S)-2-Cyclohexyl-7-[2-fluoro-4-(2-oxo-1,3-oxazolidin-3-yl)phenyl]-2,7-diazaspiro[4.5]decan-1-one

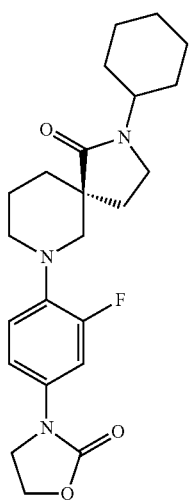 [SMILES: O=C1OCCN1c1ccc(N2CCC[C@]3(CCN(C4CCCCC4)C3=O)C2)c(F)c1]

This compound was prepared by using procedures analogous to those described for the synthesis of example 256. LC-MS: 416.2 (M+H)+.

Example 555

(5S)-7-(5-Chloro-3-methylpyridin-2-yl)-2-(trans-4-hydroxycyclohexyl)-2,7-diazaspiro[4.5]decan-1-one

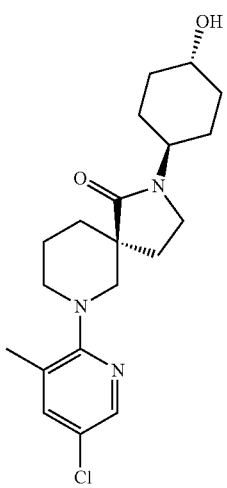 [SMILES: Cc1cc(Cl)cnc1N1CCC[C@]2(CCN([C@H]3CC[C@H](O)CC3)C2=O)C1]

This compound was prepared by using procedures analogous to those described for the synthesis of example 93 starting from (S)-2-((trans)-4-hydroxycyclohexyl)-2,7-diazaspiro[4.5]decan-1-one (which was prepared using procedures analogous to those described in the synthesis of example 472-a followed by standard hydrogenation to remove the carbobenzyloxy (Cbz) protecting group). LC-MS: 378.2 (M+H)+.

Example 556

(5S)-7-(3-Fluoro-4-methylpyridin-2-yl)-2-(trans-4-hydroxycyclohexyl)-2,7-diazaspiro[4.5]decan-1-one

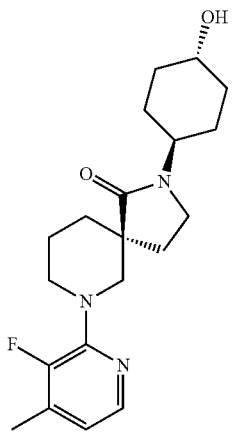 [SMILES: Cc1ccnc(N2CCC[C@]3(CCN([C@H]4CC[C@H](O)CC4)C3=O)C2)c1F]

This compound was prepared by using procedures analogous to those described for the synthesis of example 93 starting from (S)-2-((trans)-4-hydroxycyclohexyl)-2,7-diazaspiro[4.5]decan-1-one (which was prepared using procedures analogous to those described in the synthesis of example 472-a and followed by standard hydrogenation to remove the carbobenzyloxy (Cbz) protecting group). LC-MS: 362.2 (M+H)+.

Example 557

(5S)-7-(5-Fluoro-3-methylpyridin-2-yl)-2-(trans-4-hydroxycyclohexyl)-2,7-diazaspiro[4.5]decan-1-one

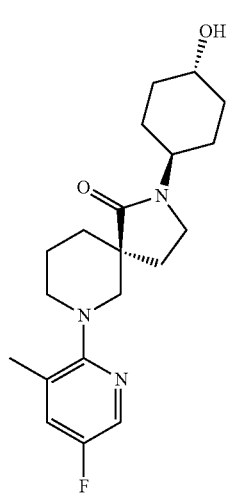 [SMILES: Cc1cc(F)cnc1N1CCC[C@]2(CCN([C@H]3CC[C@H](O)CC3)C2=O)C1]

This compound was prepared by using procedures analogous to those described for the synthesis of example 93 starting from (S)-2-((trans)-4-hydroxycyclohexyl)-2,7-diazaspiro[4.5]decan-1-one (which was prepared using procedures analogous to those described in the synthesis of example 472-a followed by standard hydrogenation to remove the carbobenzyloxy (Cbz) protecting group). LC-MS: 362.2 (M+H)+.

Example 558

(5S)-7-(5-Fluoro-6-methylpyridin-2-yl)-2-(trans-4-hydroxycyclohexyl)-2,7-diazaspiro[4.5]decan-1-one

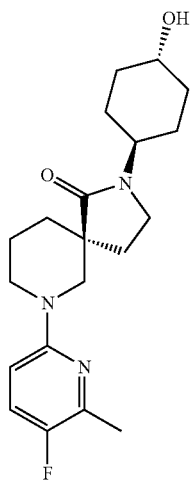 [SMILES: Cc1nc(N2CCC[C@]3(CCN([C@H]4CC[C@H](O)CC4)C3=O)C2)ccc1F]

This compound was prepared by using procedures analogous to those described for the synthesis of example 93 starting from (S)-2-((trans)-4-hydroxycyclohexyl)-2,7-diazaspiro[4.5]decan-1-one (which was prepared using procedures analogous to those described in the synthesis of example 472-a followed by standard hydrogenation to remove the carbobenzyloxy (Cbz) protecting group). LC-MS: 362.2 (M+H)$^+$.

Example 559

(5S)-2-(trans-4-Hydroxycyclohexyl)-7-(7H-pyrrolo[2,3-d]pyrimidin-4-yl)-2,7-diazaspiro[4.5]decan-1-one

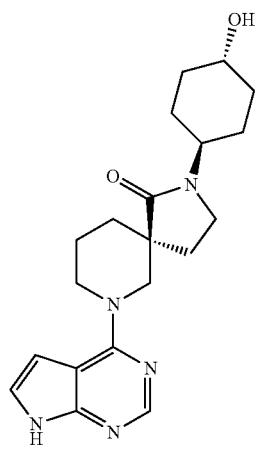 [SMILES: O=C1N([C@H]2CC[C@H](O)CC2)CC[C@]12CCCN(c1ncnc3[nH]ccc13)C2]

This compound was prepared by using procedures analogous to those described for the synthesis of example 93 starting from (S)-2-((trans)-4-hydroxycyclohexyl)-2,7-diazaspiro[4.5]decan-1-one (which was prepared using procedures analogous to those described in the synthesis of example 472-a followed by standard hydrogenation to remove the carbobenzyloxy (Cbz) protecting group). LC-MS: 370.2 (M+H)$^+$.

Example 560

(5S)-2-(trans-4-Hydroxycyclohexyl)-7-(5-methylpyridin-2-yl)-2,7-diazaspiro[4.5]decan-1-one

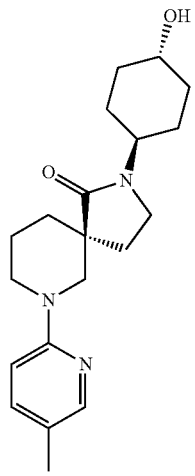 [SMILES: Cc1ccc(N2CCC[C@]3(CCN([C@H]4CC[C@H](O)CC4)C3=O)C2)nc1]

This compound was prepared by using procedures analogous to those described for the synthesis of example 93 starting from (S)-2-((trans)-4-hydroxycyclohexyl)-2,7-diazaspiro[4.5]decan-1-one (which was prepared using procedures analogous to those described in the synthesis of example 472-a followed by standard hydrogenation to remove the carbobenzyloxy (Cbz) protecting group). LC-MS: 344.2 (M+H)$^+$.

Example 561

2-[(5S)-2-(trans-4-Hydroxycyclohexyl)-1-oxo-2,7-diazaspiro[4.5]dec-7-yl]-5-phenylnicotinonitrile

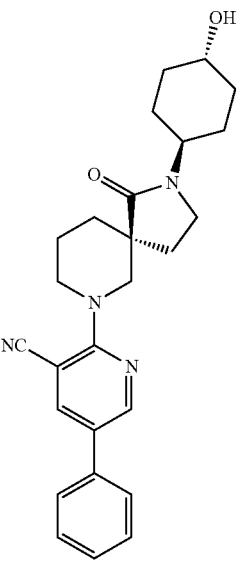 [SMILES: N#Cc1cc(-c2ccccc2)cnc1N1CCC[C@]2(CCN([C@H]3CC[C@H](O)CC3)C2=O)C1]

This compound was prepared by using procedures analogous to those described for the synthesis of example 257. LC-MS: 431.2 (M+H)$^+$.

Example 562

(5S)-7-[3-Chloro-5-(2-oxo-1,3-oxazolidin-3-yl)pyridin-2-yl]-2-cyclohexyl-2,7-diazaspiro[4.5]decan-1-one

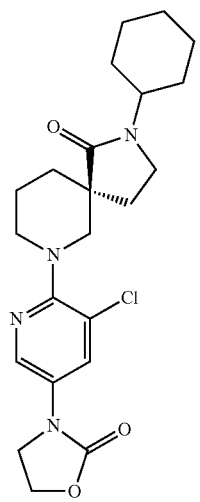 [SMILES: O=C1OCCN1c1cnc(N2CCC[C@]3(CCN(C4CCCCC4)C3=O)C2)c(Cl)c1]

This compound was prepared by using procedures analogous to those described for the synthesis of example 256. LC-MS: 433.2 (M+H)$^+$.

Example 563

(5S)-7-[3-Chloro-5-(2-oxopyrrolidin-1-yl)pyridin-2-yl]-2-cyclohexyl-2,7-diazaspiro[4.5]decan-1-one

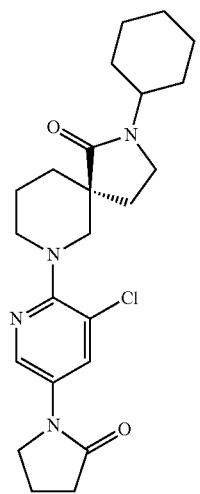 [SMILES: O=C1CCCN1c1cnc(N2CCC[C@]3(CCN(C4CCCCC4)C3=O)C2)c(Cl)c1]

This compound was prepared by using procedures analogous to those described for the synthesis of example 256. LC-MS: 431.2 (M+H)$^+$.

Example 564

(5S)-7-[3-Chloro-5-(2-oxo-1,3-oxazinan-3-yl)pyridin-2-yl]-2-cyclohexyl-2,7-diazaspiro[4.5]decan-1-one

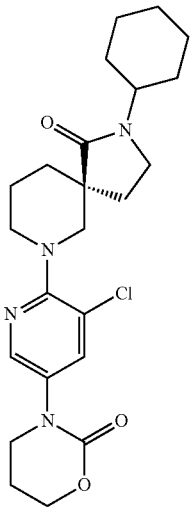 [SMILES: O=C1OCCCN1c1cnc(N2CCC[C@]3(CCN(C4CCCCC4)C3=O)C2)c(Cl)c1]

This compound was prepared by using procedures analogous to those described for the synthesis of example 256. LC-MS: 447.2 (M+H)$^+$.

Example 565

(5S)-7-[3-Chloro-5-(2-oxopiperidin-1-yl)pyridin-2-yl]-2-cyclo hexyl-2,7-diazaspiro[4.5]decan-1-one

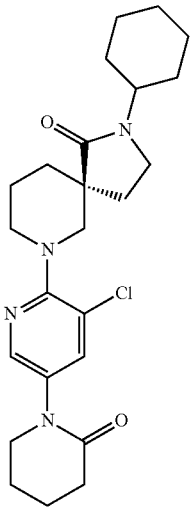 [SMILES: O=C1CCCCN1c1cnc(N2CCC[C@]3(CCN(C4CCCCC4)C3=O)C2)c(Cl)c1]

This compound was prepared by using procedures analogous to those described for the synthesis of example 256. LC-MS: 445.2 (M+H)$^+$.

Example A

Enzymatic assay of 11βHSD1

All in vitro assays were performed with clarified lysates as the source of 11βHSD1 activity. HEK-293 transient transfectants expressing an epitope-tagged version of full-length human 11βHSD1 were harvested by centrifugation. Roughly $2\times10^7$ cells were resuspended in 40 mL of lysis buffer (25 mM Tris-HCl, pH 7.5, 0.1 M NaCl, 1 mM $MgCl_2$ and 250 mM sucrose) and lysed in a microfluidizer. Lysates were clarified by centrifugation and the supernatants were aliquoted and frozen.

Inhibition of 11βHSD1 by test compounds was assessed in vitro by a Scintillation Proximity Assay (SPA). Dry test compounds were dissolved at 5 mM in DMSO. These were diluted in DMSO to suitable concentrations for the SPA assay. 0.8 μL, of 2-fold serial dilutions of compounds were dotted on 384 well plates in DMSO such that 3 logs of compound concentration were covered. 20 μL, of clarified lysate was added to each well. Reactions were initiated by addition of 20 μL of substrate-cofactor mix in assay buffer (25 mM Tris-HCl, pH 7.5, 0.1 M NaCl, 1 mM $MgCl_2$) to final concentrations of 400 μM NADPH, 25 nM $^3$H-cortisone and 0.007% Triton X-100. Plates were incubated at 37° C. for one hour. Reactions were quenched by addition of 40 μL of anti-mouse coated SPA beads that had been pre-incubated with 10 μM carbenoxolone and a cortisol-specific monoclonal antibody. Quenched plates were incubated for a minimum of 30 minutes at RT prior to reading on a Topcount scintillation counter. Controls with no lysate, inhibited lysate, and with no mAb were run routinely. Roughly 30% of input cortisone is reduced by 11βHSD1 in the uninhibited reaction under these conditions.

Test compounds having an $IC_{50}$ value less than about 20 μM according to this assay were considered active.

Example B

Cell-Based Assays for HSD Activity

Peripheral blood mononuclear cells (PBMCs) were isolated from normal human volunteers by Ficoll density centrifugation. Cells were plated at $4\times10^5$ cells/well in 200 μL of AIM V (Gibco-BRL) media in 96 well plates. The cells were stimulated overnight with 50 ng/ml recombinant human IL-4 (R&D Systems). The following morning, 200 nM cortisone (Sigma) was added in the presence or absence of various concentrations of compound. The cells were incubated for 48 hours and then supernatants were harvested. Conversion of cortisone to cortisol was determined by a commercially available ELISA (Assay Design).

Test compounds having an $IC_{50}$ value less than about 20 μM according to this assay were considered active.

Example C

Cellular Assay to Evaluate MR Antagonism

Assays for MR antagonism were performed essentially as described (Jausons-Loffreda et al. J Biolumin and Chemilumin, 1994, 9: 217-221). Briefly, HEK293/MSR cells (Invitrogen Corp.) were co-transfected with three plasmids: 1) one designed to express a fusion protein of the GAL4 DNA binding domain and the mineralocorticoid receptor ligand binding domain, 2) one containing the GAL4 upstream activation sequence positioned upstream of a firefly luciferase reporter gene (pFR-LUC, Stratagene, Inc.), and 3) one containing the Renilla luciferase reporter gene cloned downstream of a thymidine kinase promoter (Promega). Transfections were performed using the FuGENE6 reagent (Roche). Transfected cells were ready for use in subsequent assays 24 hours post-transfection.

In order to evaluate a compound's ability to antagonize the MR, test compounds are diluted in cell culture medium (E-MEM, 10% charcoal-stripped FBS, 2 mM L-glutamine) supplemented with 1 nM aldosterone and applied to the transfected cells for 16-18 hours. After the incubation of the cells with the test compound and aldosterone, the activity of firefly luciferase (indicative of MR agonism by aldosterone) and Renilla luciferase (normalization control) were determined using the Dual-Glo Luciferae Assay System (Promega). Antagonism of the mineralocorticoid receptor was determined by monitoring the ability of a test compound to attenuate the aldosterone-induced firefly luciferase activity.

Compounds having an $IC_{50}$ of 100 μM or less were considered active.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula I:

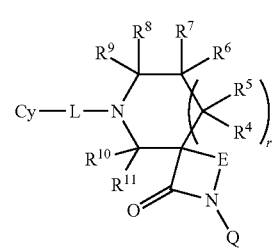

or a pharmaceutically acceptable salt thereof, wherein:

Cy is aryl, heteroaryl, cycloalkyl, or heterocycloalkyl, each optionally substituted with 1, 2, 3, 4 or 5 —W—X—Y—Z;

L is $(CR^{12}R^{13})_{q1}$, $(CR^{12}R^{13})_{q1}O(CR^{12}R^{13})_{q2}$, $(CR^{12}R^{13})_{q1}S(CR^{12}R^{13})_{q2}$, $(CR^{12}R^{13})_{q1}SO(CR^{12}R^{13})_{q2}$, $(CR^{12}R^{13})_{q1}SO(CR^{12}R^{13})_{q2}$, or $(CR^{12}R^{13})_{q1}CO(CR^{12}R^{13})_{q2}$;

Q is —$(CR^1R^2)_m$-A;

A is cycloalkyl or heterocycloalkyl, each optionally substituted with 1, 2, 3, 4 or 5 —W'—X'—Y'—Z';

E is —$(CR^{3a}R^{3b})_{n1}$—, —$(CR^{3a}R^{3b})_{n2}CO$—, —$(CR^{3a}R^{3b})_{n2}OCO$—, —$(CR^{3a}R^{3b})_{n2}SO$—, —$(CR^{3a}R^{3b})_{n2}SO_2$—, —$(CR^{3a}R^{3b})_{n2}NR^{3c}$—, or a group of formula:

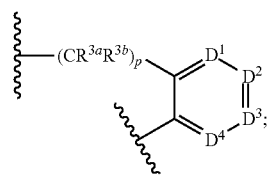

$D^1$, $D^2$, $D^3$ and $D^4$ are each N or $CR^{15}$;

$R^1$ and $R^2$ are each, independently, H or $C_{1-8}$ alkyl;

$R^{3a}$ and $R^{3b}$ are each, independently, H, OC(O)$R^{a'}$, OC(O)O$R^{b'}$, C(O)O$R^{b'}$, OC(O)N$R^{c'}R^{d'}$, N$R^{c'}R^{d'}$, N$R^{c'}$C(O)$R^{a'}$, N$R^{c'}$C(O)O$R^{b'}$, S(O)$R^{a'}$, S(O)N$R^{c'}R^{d'}$, S(O)$_2R^{a'}$, S(O)$_2$N$R^{c'}R^{d'}$, O$R^{b'}$, S$R^{b'}$, halo, $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl or heterocycloalkylalkyl, wherein said $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl or heterocycloalkylalkyl is optionally substituted by $R^{16}$;

$R^{3c}$ is H, $C_{1-4}$ alkyl, $C_{1-4}$ haloalkyl, $C_{2-4}$ alkenyl, $C_{2-4}$ alkynyl, or CO—($C_{1-4}$ alkyl);

$R^4, R^5, R^6, R^7, R^8, R^9, R^{10}$ and $R^{11}$ are each, independently, H, OC(O)$R^{a'}$, OC(O)O$R^{b'}$, C(O)O$R^{b'}$, OC(O)N$R^{c'}R^{d'}$, N$R^{c'}R^{d'}$, N$R^{c'}$C(O)$R^{a'}$, N$R^{c'}$C(O)O$R^{b'}$, S(O)$R^{a'}$, S(O)N$R^{c'}R^{d'}$, S(O)$_2R^{a'}$, S(O)$_2$N$R^{c'}R^{d'}$, O$R^{b'}$, S$R^{b'}$, halo, $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl or heterocycloalkylalkyl, wherein said $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl or heterocycloalkylalkyl is optionally substituted by $R^{14}$;

or $R^4$ and $R^5$ together with the carbon atom to which they are attached form a 3-14 membered cycloalkyl or heterocycloalkyl group which is optionally substituted by $R^{14}$;

or $R^6$ and $R^7$ together with the carbon atom to which they are attached form a 3-14 membered cycloalkyl or heterocycloalkyl group which is optionally substituted by $R^{14}$;

or $R^8$ and $R^9$ together with the carbon atom to which they are attached form a 3-14 membered cycloalkyl or heterocycloalkyl group which is optionally substituted by $R^{14}$;

or $R^{10}$ and $R^{11}$ together with the carbon atom to which they are attached form a 3-14 membered cycloalkyl or heterocycloalkyl group which is optionally substituted by $R^{14}$;

or $R^4$ and $R^6$ together with the carbon atom to which they are attached form a 3-7 membered fused cycloalkyl group or 3-7 membered fused heterocycloalkyl group which is optionally substituted by $R^{14}$;

or $R^6$ and $R^8$ together with the carbon atom to which they are attached form a 3-7 membered fused cycloalkyl group or 3-7 membered fused heterocycloalkyl group which is optionally substituted by $R^{14}$;

or $R^4$ and $R^9$ together form a $C_{1-3}$ alkylene bridge which is optionally substituted by $R^{14}$;

or $R^4$ and $R^{19}$ together form a $C_{1-3}$ alkylene bridge which is optionally substituted by $R^{14}$;

or $R^6$ and $R^{10}$ together form a $C_{1-3}$ alkylene bridge which is optionally substituted by $R^{14}$;

or $R^9$ and $R^{10}$ together form a $C_{1-3}$ alkylene bridge which is optionally substituted by $R^{14}$;

$R^{12}$ and $R^{13}$ are each, independently, H, halo, $C_{1-4}$ alkyl, $C_{1-4}$ haloalkyl, aryl, cycloalkyl, heteroaryl, heterocycloalkyl, CN, NO$_2$, O$R^{a'}$, S$R^{a'}$, C(O)$R^{b'}$, C(O)N$R^{c'}R^{d'}$, C(O)O$R^{a'}$, OC(O)$R^{b'}$, OC(O)N$R^{c'}R^{d'}$, N$R^{c'}R^{d'}$, N$R^{c'}$C(O)$R^{d'}$, N$R^{c'}$(O)$R^{a'}$, S(O)$R^{b'}$, S(O)N$R^{c'}R^{d'}$, S(O)$_2R^{b'}$, or S(O)$_2$N$R^{c'}R^{d'}$;

$R^{14}$ is halo, $C_{1-4}$ alkyl, $C_{1-4}$ haloalkyl, aryl, cycloalkyl, heteroaryl, heterocycloalkyl, CN, NO$_2$, O$R^{a'}$, S$R^{a'}$, C(O)$R^{b'}$, C(O)N$R^{c'}R^{d'}$, C(O)O$R^{a'}$, OC(O)$R^{b'}$, OC(O) N$R^{c'}R^{d'}$, N$R^{c'}R^{d'}$, N$R^{c'}$C(O)$R^{d'}$, N$R^{c'}$C(O)O$R^{a'}$, S(O)$R^{b'}$, S(O)N$R^{c'}R^{d'}$, S(O)$_2R^{b'}$, or S(O)$_2$N$R^{c'}R^{d'}$;

$R^{15}$ is H, halo, $C_{1-4}$ alkyl, $C_{1-4}$ haloalkyl, aryl, cycloalkyl, heteroaryl, heterocycloalkyl, CN, NO$_2$, O$R^{a''}$, S$R^{a''}$, C(O)$R^{b''}$, C(O)N$R^{c''}R^{d''}$, C(O)O$R^{a''}$, OC(O)$R^{b''}$, OC(O) N$R^{c''}R^{d''}$, N$R^{c''}R^{d''}$, N$R^{c''}$C(O)$R^{d''}$, N$R^{c''}$C(O)O$R^{a''}$, S(O)$R^{b''}$, S(O)N$R^{c''}R^{d''}$, S(O)$_2R^{b''}$, or S(O)$_2$N$R^{c''}R^{d''}$;

$R^{16}$ is halo, $C_{1-4}$ alkyl, $C_{1-4}$ haloalkyl, aryl, cycloalkyl, heteroaryl, heterocycloalkyl, CN, NO$_2$, O$R^{a'}$, S$R^{a'}$, C(O)$R^{b'}$, C(O)N$R^{c'}R^{d'}$, C(O)O$R^{a'}$, OC(O)$R^{b'}$, OC(O) N$R^{c'}R^{d'}$, N$R^{c'}R^{d'}$, N$R^{c'}$(O)$R^{d'}$, N$R^{c'}$(O)O$R^{a'}$, S(O)$R^{b'}$, S(O)N$R^{c'}R^{d'}$, S(O)$_2R^{b'}$, or S(O)$_2$N$R^{c'}R^{d'}$;

W, W' and W'' are each, independently, absent, $C_{1-6}$ alkylenyl, $C_{2-6}$ alkenylenyl, $C_{2-6}$ alkynylenyl, O, S, N$R^e$, CO, COO, CON$R^e$, SO, SO$_2$, SON$R^e$, or N$R^e$CON$R^f$, wherein said $C_{1-6}$ alkylenyl, $C_{2-6}$ alkenylenyl, $C_{2-6}$ alkynylenyl are each optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

X, X' and X'' are each, independently, absent, $C_{1-6}$ alkylenyl, $C_{2-6}$ alkenylenyl, $C_{2-6}$ alkynylenyl, aryl, cycloalkyl, heteroaryl or heterocycloalkyl, wherein said $C_{1-6}$ alkylenyl, $C_{2-6}$ alkenylenyl, $C_{2-6}$ alkynylenyl, aryl, cycloalkyl, heteroaryl or heterocycloalkyl is optionally substituted by one or more halo, oxo, CN, NO$_2$, OH, $C_{1-4}$ alkoxy, $C_{1-4}$ haloalkoxy, amino, $C_{1-4}$ alkylamino or $C_{2-8}$ dialkylamino;

Y, Y' and Y'' are each, independently, absent, $C_{1-6}$ alkylenyl, $C_{2-6}$ alkenylenyl, $C_{2-6}$ alkynylenyl, O, S, N$R^e$, CO, COO, CON$R^e$, SO, SO$_2$, SON$R^e$, or N$R^e$CON$R^f$, wherein said $C_{1-6}$ alkylenyl, $C_{2-6}$ alkenylenyl, $C_{2-6}$ alkynylenyl are each optionally substituted by 1, 2 or 3 halo, OH, $C_{1-4}$ alkoxy, $C_{1-4}$ haloalkoxy, amino, $C_{1-4}$ alkylamino or $C_{2-8}$ dialkylamino;

Z, Z' and Z'' are each, independently, H, halo, CN, NO$_2$, OH, $C_{1-4}$ alkoxy, $C_{1-4}$ haloalkoxy, amino, $C_{1-4}$ alkylamino, $C_{2-8}$ dialkylamino, $C_{1-6}$ alkyl, $C_{2-6}$ alkenyl, $C_{2-6}$ alkynyl, aryl, cycloalkyl, heteroaryl or heterocycloalkyl, wherein said $C_{1-6}$ alkyl, $C_{2-6}$ alkenyl, $C_{2-6}$ alkynyl, aryl, cycloalkyl, heteroaryl or heterocycloalkyl is optionally substituted by 1, 2 or 3 halo, oxo, $C_{1-6}$ alkyl, $C_{2-6}$ alkenyl, $C_{2-6}$ alkynyl, $C_{1-4}$ haloalkyl, aryl, cycloalkyl, heteroaryl, heterocycloalkyl, CN, NO$_2$, O$R^a$, S$R^a$, C(O)$R^b$, C(O)N$R^cR^d$, C(O)O$R^a$, OC(O)$R^b$, OC(O)N$R^cR^d$, N$R^cR^d$, N$R^c$C(O)$R^d$, N$R^c$C(O)O$R^a$, N$R^c$S(O)$_2R^b$, S(O)$R^b$, S(O)N$R^cR^d$, S(O)$_2R^b$, or S(O)$_2$N$R^cR^d$;

wherein two —W—X—Y—Z attached to the same atom optionally form a 3-20 membered cycloalkyl or heterocyloalkyl group, each optionally substituted by 1, 2 or 3 —W''—X''—Y''—Z'';

wherein two —W'—X'—Y'—Z' attached to the same atom optionally form a 3-20 membered cycloalkyl or heterocyloalkyl group, each optionally substituted by 1, 2 or 3 —W''—X''—Y''—Z'';

wherein —W—X—Y—Z is other than H;

wherein —W'—X'—Y'—Z' is other than H;

wherein —W''—X''—Y''—Z'' is other than H;

$R^a, R^{a'}$ and $R^{a''}$ are each, independently, H, $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl or heterocycloalkyl; heterocycloalkyl, heterocycloalkylalkyl is optionally substituted with H, OH, amino, halo, $C_{1-6}$ alkyl, $C_{1-6}$ haloalkyl, aryl, arylalkyl, heteroaryl, heteroarylalkyl, cycloalkyl or heterocycloalkyl;

$R^b$, $R^{b'}$ and $R^{b''}$ are each, independently, H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

$R^c$ and $R^d$ are each, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^c$ and $R^d$ together with the N atom to which they are attached form a 4-, 5-, or 7-membered heterocycloalkyl group;

$R^{c'}$ and $R^{d'}$ are each, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^{c'}$ and $R^{d'}$ together with the N atom to which they are attached form a 4-, 5-, 6- or 7-membered heterocycloalkyl group;

$R^{c''}$ and $R^{d''}$ are each, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^{c''}$ and $R^{d''}$ together with the N atom to which they are attached form a 4-, 5-, 6- or 7-membered heterocycloalkyl group;

$R^e$ and $R^f$ are each, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with H, OH, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^e$ and $R^f$ together with the N atom to which they are attached form a 4-, 5-, 6- or 7-membered heterocycloalkyl group;

m is 0, 1, 2 or 3;

n1 is 1, 2, 3 or 4;

n2 is 0, 1, 2, 3 or 4;

n3 is 0, 1, 2, 3 or 4;

p is 0, 1 or 2;

q1 is 0, 1 or 2;

q2 is 0, 1 or 2; and r is 0, 1 or 2;

with the proviso:

when Cy is aryl optionally substituted with 1, 2, 3, 4 or 5 —W—X—Y—Z or heteroaryl optionally substituted with 1, 2, 3, 4 or 5 —W—X—Y—Z; L is $SO_2$, $SO_2CH_2$ or $CH_2$; and m is 0, then A is other than tetrahydropyran-4-yl, 2,3-dihydroinden-2-yl or 2,2-difluoro-1,3-benzodioxol-5-yl.

2. The compound of claim 1, or a pharmaceutically acceptable salt thereof, wherein Cy is aryl or heteroaryl, each optionally substituted with 1, 2, 3, 4 or 5 —W—X—Y—Z.

3. The compound of claim 1, or a pharmaceutically acceptable salt thereof, wherein Cy is cycloalkyl or heterocycloalkyl, each optionally substituted with 1, 2, 3, 4 or 5 —W—X—Y—Z.

4. The compound of claim 1, or a pharmaceutically acceptable salt thereof, wherein L is $SO_2$.

5. The compound of claim 1, or a pharmaceutically acceptable salt thereof, wherein L is CO.

6. The compound of claim 1, or a pharmaceutically acceptable salt thereof, wherein L is $(CR^{12}R^{13})_{q1}$.

7. The compound of claim 1, or a pharmaceutically acceptable salt thereof, wherein Q is cycloalkyl or heterocycloalkyl, each optionally substituted with 1, 2, 3, 4 or 5 —W'—X'—Y'—Z'.

8. The compound of claim 1, or a pharmaceutically acceptable salt thereof, wherein Q is cyclohexyl substituted at the 4-position with at least one —W'—X'—Y'—Z'.

9. The compound of claim 1, or a pharmaceutically acceptable salt thereof, wherein Q is cyclohexyl substituted at the 4-position with at least one OH, CN, or —O—X'—Y'—Z'.

10. The compound of claim 1, or a pharmaceutically acceptable salt thereof, wherein Q is —$(CR^1R^2)_m$-A and m is 1, 2 or 3.

11. The compound of claim 1, or a pharmaceutically acceptable salt thereof, wherein E is methylene, ethylene, or propylene.

12. The compound of claim 1, or a pharmaceutically acceptable salt thereof, wherein $R^4$, $R^5$, $R^6$, $R^7$, $R^8$, $R^9$, $R^{10}$ and $R^{11}$ are each, independently, H, $C_{1-10}$ alkyl or $C_{1-10}$ haloalkyl.

13. The compound of claim 1, or a pharmaceutically acceptable salt thereof, wherein $R^4$, $R^5$, $R^6$, $R^7$, $R^8$, $R^9$, $R^{10}$ and $R^{11}$ are each H.

14. The compound of claim 1, or a pharmaceutically acceptable salt thereof, wherein $R^{12}$ and $R^{13}$ are each H.

15. The compound of claim 1 having Formula II:

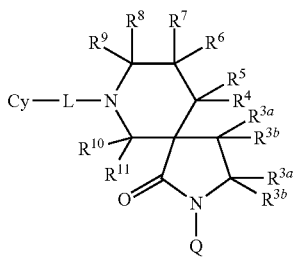

or a pharmaceutically acceptable salt thereof.

16. A compound selected from:
7-[(3-Chloro-2-methylphenyl)sulfonyl]-2-(cis-4-hydroxycyclohexyl)-2,7-diazaspiro[4.5]decan-1-one;
7-[(3-Chloro-2-methylphenyl)sulfonyl]-2-(trans-4-hydroxycyclohexyl)-2,7-diazaspiro[4.5]decan-1-one;
7-[(3-Chloro-2-methylphenyl)sulfonyl]-2-(2-methylphenyl)-2,7-diazaspiro[4.5]decan-1-one;
7-[(3-Chloro-2-methylphenyl)sulfonyl]-2-phenyl-2,7-diazaspiro[4.5]decan-1-one;
trans-4-{7-[(3-chloro-2-methylphenyl)sulfonyl]-1-oxo-2,7-diazaspiro[4.5]dec-2-yl}cyclohexanecarbonitrile;
7-[(3-Chloro-2-methylphenyl)sulfonyl]-2-cycloheptyl-2,7-diazaspiro[4.5]decan-1-one;
7-[(3-Chloro-2-methylphenyl)sulfonyl]-2-cyclohexyl-2,7-diazaspiro[4.5]decan-1-one;
7-[(3-Chloro-2-methylphenyl)sulfonyl]-2-(4-methylpyridin-3-yl)-2,7-diazaspiro[4.5]decan-1-one;
7-[(3-Chloro-2-methylphenyl)sulfonyl]-2-[cis-4-(pyridin-2-yloxy)cyclohexyl]-2,7-diazaspiro[4.5]decan-1-one;
7-[(3-Chloro-2-methylphenyl)sulfonyl]-2-[cis-4-(pyridin-3-yloxy)cyclohexyl]-2,7-diazaspiro[4.5]decan-1-one;
7-[(3-Chloro-2-methylphenyl)sulfonyl]-2-[cis-4-(pyridin-4-yloxy)cyclohexyl]-2,7-diazaspiro[4.5]decan-1-one;
2-(1-Adamantyl)-7-[(3-chloro-2-methylphenyl)sulfonyl]-2,7-diazaspiro[4.5]decan-1-one;
7-[(3-Chloro-2-methylphenyl)sulfonyl]-2-(1-methyl-2-phenylethyl)-2,7-diazaspiro[4.5]decan-1-one;
(5S)-7-[(3-Chloro-2-methylphenyl)sulfonyl]-2-cycloheptyl-2,7-diazaspiro[4.5]decan-1-one;
(5S)-7-[(3-Chloro-2-methylphenyl)sulfonyl]-2-cycloheptyl-2,7-diazaspiro[4.5]decan-1-one;
cis-4-{7-[(3-Chloro-2-methylphenyl)sulfonyl]-1-oxo-2,7-diazaspiro[4.5]dec-2-yl}cyclohexanecarbonitrile;
2-Cyclohexyl-7-(2-fluorophenyl)-2,7-diazaspiro[4.5]decan-1-one;
2-Cyclohexyl-7-(4-fluorophenyl)-2,7-diazaspiro[4.5]decan-1-one;
2-Cyclohexyl-7-(3-fluorophenyl)-2,7-diazaspiro[4.5]decan-1-one;
2-Cyclohexyl-7-phenyl-2,7-diazaspiro[4.5]decan-1-one;
7-(4-Fluorophenyl)-2-(trans-4-hydroxycyclohexyl)-2,7-diazaspiro[4.5]decan-1-one;
7-(3-Fluorophenyl)-2-(trans-4-hydroxycyclohexyl)-2,7-diazaspiro[4.5]decan-1-one;
2-(trans-4-Hydroxycyclohexyl)-7-phenyl-2,7-diazaspiro[4.5]decan-1-one;
Methyl 1-[7-(2-fluorophenyl)-1-oxo-2,7-diazaspiro[4.5]dec-2-yl]cyclopropanecarboxylate;
2-(trans-4-Hydroxycyclohexyl)-7-[5-(trifluoromethyl)pyridin-2-yl]-2,7-diazaspiro[4.5]decan-1-one;
6-[2-(trans-4-Hydroxycyclohexyl)-1-oxo-2,7-diazaspiro[4.5]dec-7-yl]nicotinonitrile;
2-(trans-4-Hydroxycyclohexyl)-7-(6-methoxypyridin-2-yl)-2,7-diazaspiro[4.5]decan-1-one;
2-(trans-4-Hydroxycyclohexyl)-7-(6-methylpyridin-2-yl)-2,7-diazaspiro[4.5]decan-1-one;
2-(trans-4-Hydroxycyclohexyl)-7-(5-methylpyridin-2-yl)-2,7-diazaspiro[4.5]decan-1-one;
7-(5-Fluoropyridin-2-yl)-2-(trans-4-hydroxycyclohexyl)-2,7-diazaspiro[4.5]decan-1-one;
2-(trans-4-Hydroxycyclohexyl)-7-[6-(trifluoromethyl)pyridin-2-yl]-2,7-diazaspiro[4.5]decan-1-one;
(5S)-2-(trans-4-Hydroxycyclohexyl)-7-[5-(trifluoromethyl)pyridin-2-yl]-2,7-diazaspiro[4.5]decan-1-one;
(5S)-2-(trans-4-Hydroxycyclohexyl)-7-[5-(trifluoromethyl)pyridin-2-yl]-2,7-diazaspiro[4.5]decan-1-one;
7-(6-Fluoropyridin-2-yl)-2-(trans-4-hydroxycyclohexyl)-2,7-diazaspiro[4.5]decan-1-one;
2-(trans-4-Hydroxycyclohexyl)-7-(3-methylpyridin-2-yl)-2,7-diazaspiro[4.5]decan-1-one;
2-(trans-4-Hydroxycyclohexyl)-7-(4-methoxypyridin-2-yl)-2,7-diazaspiro[4.5]decan-1-one;
2-(trans-4-Hydroxycyclohexyl)-7-pyridin-2-yl-2,7-diazaspiro[4.5]decan-1-one;
(5S)-2-Cyclohexyl-7-phenyl-2,7-diazaspiro[4.5]decan-1-one;
(5S)-2-Cyclohexyl-7-phenyl-2,7-diazaspiro[4.5]decan-1-one;
7-[3-Chloro-5-(trifluoromethyl)pyridin-2-yl]-2-(trans-4-hydroxycyclohexyl)-2,7-diazaspiro[4.5]decan-1-one;
4-[2-(trans-4-Hydroxycyclohexyl)-1-oxo-2,7-diazaspiro[4.5]dec-7-yl]benzonitrile;
2-(trans-4-Hydroxycyclohexyl)-7-[4-(trifluoromethyl)phenyl]-2,7-diazaspiro[4.5]decan-1-one;
3-Fluoro-4-[2-(trans-4-hydroxycyclohexyl)-1-oxo-2,7-diazaspiro[4.5]dec-7-yl]benzonitrile;
4-(2-Cyclohexyl-1-oxo-2,7-diazaspiro[4.5]dec-7-yl)benzonitrile;
4-(2-Cyclohexyl-1-oxo-2,7-diazaspiro[4.5]dec-7-yl)-3-fluorobenzonitrile;
2-(trans-4-Hydroxycyclohexyl)-7-(piperidin-1-ylcarbonyl)-2,7-diazaspiro[4.5]decan-1-one;
2-(trans-4-Hydroxycyclohexyl)-7-(pyrrolidin-1-ylcarbonyl)-2,7-diazaspiro[4.5]decan-1-one;
2-(trans-4-Hydroxycyclohexyl)-7-[(4-phenyl-3,6-dihydropyridin-1(2H)-yl)carbonyl]-2,7-diazaspiro[4.5]decan-1-one;
2-(trans-4-Hydroxycyclohexyl)-7-[(4-phenylpiperidin-1-yl)carbonyl]-2,7-diazaspiro[4.5]decan-1-one;
2-(trans-4-Hydroxycyclohexyl)-7-[(4-phenylpiperazin-1-yl)carbonyl]-2,7-diazaspiro[4.5]decan-1-one;
7-{[4-(2-Fluorophenyl)piperazin-1-yl]carbonyl}-2-(trans-4-hydroxycyclohexyl)-2,7-diazaspiro[4.5]decan-1-one;
2-(trans-4-Hydroxycyclohexyl)-7-({4-[2-(trifluoromethyl)phenyl]piperazin-1-yl}carbonyl)-2,7-diazaspiro[4.5]decan-1-one;
2-Cyclohexyl-7-isonicotinoyl-2,7-diazaspiro[4.5]decan-1-one;
7-Benzoyl-2-cyclohexyl-2,7-diazaspiro[4.5]decan-1-one;
2-Cyclohexyl-7-(pyridin-3-ylcarbonyl)-2,7-diazaspiro[4.5]decan-1-one;
7-Benzoyl-2-(trans-4-hydroxycyclohexyl)-2,7-diazaspiro[4.5]decan-1-one;
Isopropyl {4-[2-(trans-4-hydroxycyclohexyl)-1-oxo-2,7-diazaspiro[4.5]dec-7-yl]phenyl}carbamate;
Prop-2-yn-1-yl {4-[2-(trans-4-hydroxycyclohexyl)-1-oxo-2,7-diazaspiro[4.5]dec-7-yl]phenyl}carbamate;

Methyl {4-[2-(trans-4-hydroxycyclohexyl)-1-oxo-2,7-diazaspiro[4.5]dec-7-yl]phenyl}carbamate;
N-{4-[2-(trans-4-Hydroxycyclohexyl)-1-oxo-2,7-diazaspiro[4.5]dec-7-yl]phenyl}acetamide;
N-{4-[2-(trans-4-Hydroxycyclohexyl)-1-oxo-2,7-diazaspiro[4.5]dec-7-yl]phenyl}cyclopropanecarboxamide;
Isopropyl {3-fluoro-4-[2-(trans-4-hydroxycyclohexyl)-1-oxo-2,7-diazaspiro[4.5]dec-7-yl]phenyl}carbamate;
Prop-2-yn-1-yl {3-fluoro-4-[2-(trans-4-hydroxycyclohexyl)-1-oxo-2,7-diazaspiro[4.5]dec-7-yl]phenyl}carbamate;
Methyl {3-fluoro-4-[2-(trans-4-hydroxycyclohexyl)-1-oxo-2,7-diazaspiro[4.5]dec-7-yl]phenyl}carbamate;
N-{3-Fluoro-4-[2-(trans-4-hydroxycyclohexyl)-1-oxo-2,7-diazaspiro[4.5]dec-7-yl]phenyl}cyclopropanecarboxamide;
7-(4-Chloropyrimidin-2-yl)-2-(trans-4-hydroxycyclohexyl)-2,7-diazaspiro[4.5]decan-1-one;
2-Cyclohexyl-7-[5-(trifluoromethyl)pyridin-2-yl]-2,7-diazaspiro[4.5]decan-1-one;
2-Cyclohexyl-7-pyridin-2-yl-2,7-diazaspiro[4.5]decan-1-one;
7-[3-Chloro-5-(trifluoromethyl)pyridin-2-yl]-2-cyclohexyl-2,7-diazaspiro[4.5]decan-1-one;
2-Cyclohexyl-7-(piperidin-1-ylcarbonyl)-2,7-diazaspiro[4.5]decan-1-one;
2-Cyclohexyl-7-(pyrrolidin-1-ylcarbonyl)-2,7-diazaspiro[4.5]decan-1-one;
2-Cyclohexyl-7-[(4-phenyl-3,6-dihydropyridin-1(2H)-yl)carbonyl]-2,7-diazaspiro[4.5]decan-1-one;
2-Cyclohexyl-7-[(4-phenylpiperidin-1-yl)carbonyl]-2,7-diazaspiro[4.5]decan-1-one;
2-Cyclohexyl-7-[(4-phenylpiperazin-1-yl)carbonyl]-2,7-diazaspiro[4.5]decan-1-one;
2-Cyclohexyl-7-{[4-(2-fluorophenyl)piperazin-1-yl]carbonyl}-2,7-diazaspiro[4.5]decan-1-one;
2-Cyclohexyl-7-({4-[2-(trifluoromethyl)phenyl]piperazin-1-yl}carbonyl)-2,7-diazaspiro[4.5]decan-1-one;
2-[2-(trans-4-Hydroxycyclohexyl)-1-oxo-2,7-diazaspiro[4.5]dec-7-yl]nicotinonitrile;
7-(5-Chloropyridin-2-yl)-2-(trans-4-hydroxycyclohexyl)-2,7-diazaspiro[4.5]decan-1-one;
7-(3,5-Dichloropyridin-2-yl)-2-(trans-4-hydroxycyclohexyl)-2,7-diazaspiro[4.5]decan-1-one;
2-(trans-4-Hydroxycyclohexyl)-7-[4-(trifluoromethyl)pyridin-2-yl]-2,7-diazaspiro[4.5]decan-1-one;
2-(trans-4-Hydroxycyclohexyl)-7-[6-methyl-4-(trifluoromethyl)pyridin-2-yl]-2,7-diazaspiro[4.5]decan-1-one;
Methyl 6-[2-(trans-4-hydroxycyclohexyl)-1-oxo-2,7-diazaspiro[4.5]dec-7-yl]nicotinate;
2-(trans-4-Hydroxycyclohexyl)-7-isoquinolin-1-yl-2,7-diazaspiro[4.5]decan-1-one;
2-(trans-4-Hydroxycyclohexyl)-7-quinolin-2-yl-2,7-diazaspiro[4.5]decan-1-one;
N-{3-Fluoro-4-[2-(trans-4-hydroxycyclohexyl)-1-oxo-2,7-diazaspiro[4.5]dec-7-yl]phenyl}acetamide;
(5S)-2-(2-Chlorophenyl)-7-(3,5-dichloropyridin-2-yl)-2,7-diazaspiro[4.5]decan-1-one;
2-(2-Chlorophenyl)-7-[5-(trifluoromethyl)pyridin-2-yl]-2,7-diazaspiro[4.5]decan-1-one;
2-(2-Chlorophenyl)-7-(3-chloropyrazin-2-yl)-2,7-diazaspiro[4.5]decan-1-one;
2-(2-Chlorophenyl)-7-(3-chloropyridin-2-yl)-2,7-diazaspiro[4.5]decan-1-one;
2-[(5S)-2-(2-Chlorophenyl)-1-oxo-2,7-diazaspiro[4.5]dec-7-yl]nicotinonitrile;
(5S)-2-(2-Chlorophenyl)-7-[3-(trifluoromethyl)pyridin-2-yl]-2,7-diazaspiro[4.5]decan-1-one;
6-[(5S)-2-(2-Chlorophenyl)-1-oxo-2,7-diazaspiro[4.5]dec-7-yl]nicotinonitrile;
Methyl {6-[(5S)-2-(2-chlorophenyl)-1-oxo-2,7-diazaspiro[4.5]dec-7-yl]pyridin-3-yl}carbamate;
Ethyl {6-[(5S)-2-(2-chlorophenyl)-1-oxo-2,7-diazaspiro[4.5]dec-7-yl]pyridin-3-yl}carbamate;
Propyl {6-[(5S)-2-(2-chlorophenyl)-1-oxo-2,7-diazaspiro[4.5]dec-7-yl]pyridin-3-yl}carbamate;
6-[2-(2-Chlorophenyl)-1-oxo-2,7-diazaspiro[4.5]dec-7-yl]-N-methylnicotinamide;
6-[2-(2-Chlorophenyl)-1-oxo-2,7-diazaspiro[4.5]dec-7-yl]-N-ethylnicotinamide;
(5S)-2-(Tetrahydro-2H-pyran-4-yl)-7-[5-(trifluoromethyl)pyridin-2-yl]-2,7-diazaspiro[4.5]decan-1-one;
(5S)-2-(Tetrahydro-2H-pyran-4-yl)-7-[5-(trifluoromethyl)pyridin-2-yl]-2,7-diazaspiro[4.5]decan-1-one;
Methyl {6-[(5S)-1-oxo-2-(tetrahydro-2H-pyran-4-yl)-2,7-diazaspiro[4.5]dec-7-yl]pyridin-3-yl}carbamate;
Ethyl {6-[(5S)-1-oxo-2-(tetrahydro-2H-pyran-4-yl)-2,7-diazaspiro[4.5]dec-7-yl]pyridin-3-yl}carbamate;
Propyl {6-[(5S)-1-oxo-2-(tetrahydro-2H-pyran-4-yl)-2,7-diazaspiro[4.5]dec-7-yl]pyridin-3-yl}carbamate;
Isopropyl {6-[(5S)-1-oxo-2-(tetrahydro-2H-pyran-4-yl)-2,7-diazaspiro[4.5]dec-7-yl]pyridin-3-yl}carbamate;
Isobutyl {6-[(5S)-1-oxo-2-(tetrahydro-2H-pyran-4-yl)-2,7-diazaspiro[4.5]dec-7-yl]pyridin-3-yl}carbamate;
(5S)-7-(3-Chloropyrazin-2-yl)-2-(tetrahydro-2H-pyran-4-yl)-2,7-diazaspiro[4.5]decan-1-one;
3-[(5S)-1-Oxo-2-(tetrahydro-2H-pyran-4-yl)-2,7-diazaspiro[4.5]dec-7-yl]pyrazine-2-carbonitrile;
(5S)-7-(3-Chloropyridin-2-yl)-2-(tetrahydro-2H-pyran-4-yl)-2,7-diazaspiro[4.5]decan-1-one;
2-[(5S)-1-Oxo-2-(tetrahydro-2H-pyran-4-yl)-2,7-diazaspiro[4.5]dec-7-yl]nicotinonitrile;
(5S)-2-(Tetrahydro-2H-pyran-4-yl)-7-[3-(trifluoromethyl)pyridin-2-yl]-2,7-diazaspiro[4.5]decan-1-one;
(5S)-7-(3,5-Dichloropyridin-2-yl)-2-(tetrahydro-2H-pyran-4-yl)-2,7-diazaspiro[4.5]decan-1-one;
(5S)-7-(5-Chloropyridin-2-yl)-2-(tetrahydro-2H-pyran-4-yl)-2,7-diazaspiro[4.5]decan-1-one;
Methyl {5-chloro-6-[(5S)-1-oxo-2-(tetrahydro-2H-pyran-4-yl)-2,7-diazaspiro[4.5]dec-7-yl]pyridin-3-yl}carbamate;
Ethyl {5-chloro-6-[(5S)-1-oxo-2-(tetrahydro-2H-pyran-4-yl)-2,7-diazaspiro[4.5]dec-7-yl]pyridin-3-yl}carbamate;
Propyl {5-chloro-6-[(5S)-1-oxo-2-(tetrahydro-2H-pyran-4-yl)-2,7-diazaspiro[4.5]dec-7-yl]pyridin-3-yl}carbamate;
Isopropyl {5-chloro-6-[(5S)-1-oxo-2-(tetrahydro-2H-pyran-4-yl)-2,7-diazaspiro[4.5]dec-7-yl]pyridin-3-yl}carbamate;
Isobutyl {5-chloro-6-[(5S)-1-oxo-2-(tetrahydro-2H-pyran-4-yl)-2,7-diazaspiro[4.5]dec-7-yl]pyridin-3-yl}carbamate;
3-Chloro-4-[(5S)-1-oxo-2-(tetrahydro-2H-pyran-4-yl)-2,7-diazaspiro[4.5]dec-7-yl]benzonitrile;
6-[(5S)-1-oxo-2-(tetrahydro-2H-pyran-4-yl)-2,7-diazaspiro[4.5]dec-7-yl]nicotinonitrile;
(5S)-7-(3,5-Difluoropyridin-2-yl)-2-(tetrahydro-2H-pyran-4-yl)-2,7-diazaspiro[4.5]decan-1-one;
(5S)-7-Isoquinolin-1-yl-2-(tetrahydro-2H-pyran-4-yl)-2,7-diazaspiro[4.5]decan-1-one;
(5S)-7-quinolin-2-yl-2-(tetrahydro-2H-pyran-4-yl)-2,7-diazaspiro[4.5]decan-1-one;

Methyl {5-methyl-6-[(5S)-1-oxo-2-(tetrahydro-2H-pyran-4-yl)-2,7-diazaspiro[4.5]dec-7-yl]pyridin-3-yl}carbamate;
Ethyl {5-methyl-6-[(5S)-1-oxo-2-(tetrahydro-2H-pyran-4-yl)-2,7-diazaspiro[4.5]dec-7-yl]pyridin-3-yl}carbamate;
Propyl {5-methyl-6-[(5S)-1-oxo-2-(tetrahydro-2H-pyran-4-yl)-2,7-diazaspiro[4.5]dec-7-yl]pyridin-3-yl}carbamate;
Methyl {3-fluoro-4-[(5S)-1-oxo-2-(tetrahydro-2H-pyran-4-yl)-2,7-diazaspiro[4.5]dec-7-yl]phenyl}carbamate;
Ethyl {3-fluoro-4-[(5S)-1-oxo-2-(tetrahydro-2H-pyran-4-yl)-2,7-diazaspiro[4.5]dec-7-yl]phenyl}carbamate;
Propyl {3-fluoro-4-[(5S)-1-oxo-2-(tetrahydro-2H-pyran-4-yl)-2,7-diazaspiro[4.5]dec-7-yl]phenyl}carbamate;
Isopropyl {3-fluoro-4-[(5S)-1-oxo-2-(tetrahydro-2H-pyran-4-yl)-2,7-diazaspiro[4.5]dec-7-yl]phenyl}carbamate;
Isobutyl {3-fluoro-4-[(5S)-1-oxo-2-(tetrahydro-2H-pyran-4-yl)-2,7-diazaspiro[4.5]dec-7-yl]phenyl}carbamate;
Methyl {4-[(5S)-1-oxo-2-(tetrahydro-2H-pyran-4-yl)-2,7-diazaspiro[4.5]dec-7-yl]phenyl}carbamate;
Ethyl {4-[(5S)-1-oxo-2-(tetrahydro-2H-pyran-4-yl)-2,7-diazaspiro[4.5]dec-7-yl]phenyl}carbamate;
Propyl {4-[(5S)-1-oxo-2-(tetrahydro-2H-pyran-4-yl)-2,7-diazaspiro[4.5]dec-7-yl]phenyl}carbamate;
Isopropyl {4-[(5S)-1-oxo-2-(tetrahydro-2H-pyran-4-yl)-2,7-diazaspiro[4.5]dec-7-yl]phenyl}carbamate;
Isobutyl {4-[(5S)-1-oxo-2-(tetrahydro-2H-pyran-4-yl)-2,7-diazaspiro[4.5]dec-7-yl]phenyl}carbamate;
Methyl methyl {4-[(5S)-1-oxo-2-(tetrahydro-2H-pyran-4-yl)-2,7-diazaspiro[4.5]dec-7-yl]phenyl}carbamate;
3-Fluoro-4-[(5S)-1-oxo-2-(tetrahydro-2H-pyran-4-yl)-2,7-diazaspiro[4.5]dec-7-yl]benzonitrile;
2-(1-Methylpiperidin-4-yl)-7-[5-(trifluoromethyl)pyridin-2-yl]-2,7-diazaspiro[4.5]decan-1-one;
Methyl 4-{1-oxo-7-[5-(trifluoromethyl)pyridin-2-yl]-2,7-diazaspiro[4.5]dec-2-yl}piperidine-1-carboxylate;
N,N-Dimethyl-4-{1-oxo-7-[5-(trifluoromethyl)pyridin-2-yl]-2,7-diazaspiro[4.5]dec-2-yl}piperidine-1-carboxamide;
7-(3-Chloropyrazin-2-yl)-2-quinolin-5-yl-2,7-diazaspiro[4.5]decan-1-one;
7-(3-Chloropyridin-2-yl)-2-quinolin-5-yl-2,7-diazaspiro[4.5]decan-1-one;
7-(3,5-Dichloropyridin-2-yl)-2-quinolin-5-yl-2,7-diazaspiro[4.5]decan-1-one;
2-(2-Methylphenyl)-7-[4-(trifluoromethyl)pyrimidin-2-yl]-2,7-diazaspiro[4.5]decan-1-one;
7-(4-Chloropyrimidin-2-yl)-2-(2-methylphenyl)-2,7-diazaspiro[4.5]decan-1-one;
7-(6-Chloro-7H-purin-2-yl)-2-(2-methylphenyl)-2,7-diazaspiro[4.5]decan-1-one;
3-[2-(2-Methylphenyl)-1-oxo-2,7-diazaspiro[4.5]dec-7-yl]pyrazine-2-carbonitrile;
7-(6-Chloropyrazin-2-yl)-2-(2-methylphenyl)-2,7-diazaspiro[4.5]decan-1-one;
7-(3-Chloropyrazin-2-yl)-2-(2-methylphenyl)-2,7-diazaspiro[4.5]decan-1-one;
2-(2-Methylphenyl)-7-[5-(trifluoromethyl)pyridin-2-yl]-2,7-diazaspiro[4.5]decan-1-one;
2-Quinolin-5-yl-7-[5-(trifluoromethyl)pyridin-2-yl]-2,7-diazaspiro[4.5]decan-1-one;
2-Isoquinolin-5-yl-7-[5-(trifluoromethyl)pyridin-2-yl]-2,7-diazaspiro[4.5]decan-1-one;
2-(4-Bromo-2-methylphenyl)-7-[5-(trifluoromethyl)pyridin-2-yl]-2,7-diazaspiro[4.5]decan-1-one;
3-Methyl-4-{1-oxo-7-[5-(trifluoromethyl)pyridin-2-yl]-2,7-diazaspiro[4.5]dec-2-yl}benzonitrile;
N-(3-Methyl-4-{1-oxo-7-[5-(trifluoromethyl)pyridin-2-yl]-2,7-diazaspiro[4.5]dec-2-yl}phenyl)acetamide;
N-(3-Methyl-4-{1-oxo-7-[5-(trifluoromethyl)pyridin-2-yl]-2,7-diazaspiro[4.5]dec-2-yl}phenyl)methanesulfonamide;
2-(3-Methylpyridin-4-yl)-7-[5-(trifluoromethyl)pyridin-2-yl]-2,7-diazaspiro[4.5]decan-1-one;
2-(4-Methylpyridin-3-yl)-7-[5-(trifluoromethyl)pyridin-2-yl]-2,7-diazaspiro[4.5]decan-1-one;
7-(3-Chloropyrazin-2-yl)-2-(1-methylpiperidin-4-yl)-2,7-diazaspiro[4.5]decan-1-one;
Methyl [4-[(5S)-2-cyclohexyl-1-oxo-2,7-diazaspiro[4.5]dec-7-yl]-3-(trifluoromethyl)phenyl]carbamate;
Ethyl [4-[(5S)-2-cyclohexyl-1-oxo-2,7-diazaspiro[4.5]dec-7-yl]-3-(trifluoromethyl)phenyl]carbamate;
Prop-2-yn-1-yl [4-[(5S)-2-cyclohexyl-1-oxo-2,7-diazaspiro[4.5]dec-7-yl]-3-(trifluoromethyl)phenyl]carbamate;
N-[4-[(5S)-2-Cyclohexyl-1-oxo-2,7-diazaspiro[4.5]dec-7-yl]-3-(trifluoromethyl)phenyl]acetamide;
N-[4-[(5S)-2-Cyclohexyl-1-oxo-2,7-diazaspiro[4.5]dec-7-yl]-3-(trifluoromethyl)phenyl]methanesulfonamide;
Methyl methyl [4-[(5S)-2-cyclohexyl-1-oxo-2,7-diazaspiro[4.5]dec-7-yl]-3-(trifluoromethyl)phenyl]carbamate;
Prop-2-yn-1-yl {5-chloro-6-[(5S)-2-(trans-4-hydroxycyclohexyl)-1-oxo-2,7-diazaspiro[4.5]dec-7-yl]pyridin-3-yl}carbamate;
Methyl {5-chloro-6-[(5S)-2-(trans-4-hydroxycyclohexyl)-1-oxo-2,7-diazaspiro[4.5]dec-7-yl]pyridin-3-yl}carbamate;
Ethyl {5-chloro-6-[(5S)-2-(trans-4-hydroxycyclohexyl)-1-oxo-2,7-diazaspiro[4.5]dec-7-yl]pyridin-3-yl}carbamate;
N-{5-Chloro-6-[(5S)-2-(trans-4-hydroxycyclohexyl)-1-oxo-2,7-diazaspiro[4.5]dec-7-yl]pyridin-3-yl}acetamide;
N-{5-Chloro-6-[(5S)-2-(trans-4-hydroxycyclohexyl)-1-oxo-2,7-diazaspiro[4.5]dec-7-yl]pyridin-3-yl}methanesulfonamide;
4-{1-Oxo-7-[5-(trifluoromethyl)pyridin-2-yl]-2,7-diazaspiro[4.5]dec-2-yl}cyclohexanecarbonitrile;
4-{1-Oxo-7-[4-(trifluoromethyl)phenyl]-2,7-diazaspiro[4.5]dec-2-yl}cyclohexanecarbonitrile;
4-{7-[3-Chloro-5-(trifluoromethyl)pyridin-2-yl]-1-oxo-2,7-diazaspiro[4.5]dec-2-yl}cyclohexanecarbonitrile;
4-[7-(3,5-Dichloropyridin-2-yl)-1-oxo-2,7-diazaspiro[4.5]dec-2-yl]cyclohexanecarbonitrile;
4-[7-(6-Fluoropyridin-2-yl)-1-oxo-2,7-diazaspiro[4.5]dec-2-yl]cyclohexanecarbonitrile;
(5S)-7-(2-Fluoro-4-methylphenyl)-2-(trans-4-hydroxycyclohexyl)-2,7-diazaspiro[4.5]decan-1-one;
(5S)-2-(trans-4-Hydroxycyclohexyl)-7-(4-methoxyphenyl)-2,7-diazaspiro[4.5]decan-1-one;
4-[(5S)-2-(trans-4-Hydroxycyclohexyl)-1-oxo-2,7-diazaspiro[4.5]dec-7-yl]phenyl}acetonitrile;
(5S)-2-(trans-4-Hydroxycyclohexyl)-7-[3-(trifluoromethoxy)phenyl]-2,7-diazaspiro[4.5]decan-1-one;
(5S)-2-(trans-4-Hydroxycyclohexyl)-7-[3-(trifluoromethyl)phenyl]-2,7-diazaspiro[4.5]decan-1-one;
(5S)-2-(trans-4-Hydroxycyclohexyl)-7-[2-(trifluoromethoxy)phenyl]-2,7-diazaspiro[4.5]decan-1-one;

(5S)-7-(4-Chloro-2-methylphenyl)-2-(trans-4-hydroxycyclohexyl)-2,7-diazaspiro[4.5]decan-1-one;
(5S)-7-(3-Chloro-2-methylphenyl)-2-(trans-4-hydroxycyclohexyl)-2,7-diazaspiro[4.5]decan-1-one;
(5S)-7-(2-Chloro-4-methylphenyl)-2-(trans-4-hydroxycyclohexyl)-2,7-diazaspiro[4.5]decan-1-one;
2-Fluoro-6-[(5S)-2-(trans-4-hydroxycyclohexyl)-1-oxo-2,7-diazaspiro[4.5]dec-7-yl]benzonitrile;
(5S)-7-(2,5-Dichlorophenyl)-2-(trans-4-hydroxycyclohexyl)-2,7-diazaspiro[4.5]decan-1-one;
(5S)-7-(2,3-Dichlorophenyl)-2-(trans-4-hydroxycyclohexyl)-2,7-diazaspiro[4.5]decan-1-one;
(5S)-7-(3,5-Difluorophenyl)-2-(trans-4-hydroxycyclohexyl)-2,7-diazaspiro[4.5]decan-1-one;
(5S)-7-(4-Chloro-2-methylphenyl)-2-(trans-4-hydroxycyclohexyl)-2,7-diazaspiro[4.5]decan-1-one;
(5S)-7-(3-Chloro-2-methylphenyl)-2-(trans-4-hydroxycyclohexyl)-2,7-diazaspiro[4.5]decan-1-one;
(5S)-7-(2,6-Dichlorophenyl)-2-(trans-4-hydroxycyclohexyl)-2,7-diazaspiro[4.5]decan-1-one;
3-[(5S)-2-(trans-4-Hydroxycyclohexyl)-1-oxo-2,7-diazaspiro[4.5]dec-7-yl]benzonitrile;
(5S)-7-(2-Fluorophenyl)-2-(trans-4-hydroxycyclohexyl)-2,7-diazaspiro[4.5]decan-1-one;
(5S)-7-(2-Chlorophenyl)-2-(trans-4-hydroxycyclohexyl)-2,7-diazaspiro[4.5]decan-1-one;
(5S)-7-(4-Chloro-2-fluorophenyl)-2-(trans-4-hydroxycyclohexyl)-2,7-diazaspiro[4.5]decan-1-one;
(5S)-7-(2,4-Difluorophenyl)-2-(trans-4-hydroxycyclohexyl)-2,7-diazaspiro[4.5]decan-1-one;
(5S)-7-(3-Chloro-2-fluorophenyl)-2-(trans-4-hydroxycyclohexyl)-2,7-diazaspiro[4.5]decan-1-one;
(trans-4-{1-Oxo-7-[5-(trifluoromethyl)pyridin-2-yl]-2,7-diazaspiro[4.5]dec-2-yl}cyclohexyl)acetonitrile;
(trans-4-{1-Oxo-7-[4-(trifluoromethyl)phenyl]-2,7-diazaspiro[4.5]dec-2-yl}cyclohexyl)acetonitrile;
(trans-4-{7-[3-Chloro-5-(trifluoromethyl)pyridin-2-yl]-1-oxo-2,7-diazaspiro[4.5]dec-2-yl}cyclohexyl)acetonitrile;
{trans-4-[7-(3,5-Dichloropyridin-2-yl)-1-oxo-2,7-diazaspiro[4.5]dec-2-yl]cyclohexyl}acetonitrile;
{trans-4-[7-(6-Fluoropyridin-2-yl)-1-oxo-2,7-diazaspiro[4.5]dec-2-yl]cyclohexyl}acetonitrile;
(5S)-2-(trans-4-Hydroxycyclohexyl)-7-(3,5,6-trifluoropyridin-2-yl)-2,7-diazaspiro[4.5]decan-1-one;
(5S)-7-(4,6-Dimethoxypyrimidin-2-yl)-2-(trans-4-hydroxycyclohexyl)-2,7-diazaspiro[4.5]decan-1-one;
(5S)-7-[4-Fluoro-5-(trifluoromethyl)pyrimidin-2-yl]-2-(trans-4-hydroxycyclohexyl)-2,7-diazaspiro[4.5]decan-1-one;
(5S)-7-(2,5-Difluorophenyl)-2-(trans-4-hydroxycyclohexyl)-2,7-diazaspiro[4.5]decan-1-one;
(5S)-7-[2-(Difluoromethoxy)phenyl]-2-(trans-4-hydroxycyclohexyl)-2,7-diazaspiro[4.5]decan-1-one;
(5S)-7-(4-Fluoropyrimidin-2-yl)-2-(trans-4-hydroxycyclohexyl)-2,7-diazaspiro[4.5]decan-1-one;
(5S)-7-[4-Chloro-5-(trifluoromethyl)pyrimidin-2-yl]-2-(trans-4-hydroxycyclohexyl)-2,7-diazaspiro[4.5]decan-1-one;
(5S)-2-(trans-4-Hydroxycyclohexyl)-7-quinazolin-4-yl-2,7-diazaspiro[4.5]decan-1-one;
(5S)-2-(trans-4-Hydroxycyclohexyl)-7-(6-methoxypyridin-3-yl)-2,7-diazaspiro[4.5]decan-1-one;
(5S)-2-(trans-4-Hydroxycyclohexyl)-7-[6-(methylamino)-9H-purin-2-yl]-2,7-diazaspiro[4.5]decan-1-one;
7-{[4-(2-Chlorophenyl)piperazin-1-yl]carbonyl}-2-(trans-4-hydroxycyclohexyl)-2,7-diazaspiro[4.5]decan-1-one;
2-(trans-4-Hydroxycyclohexyl)-7-({4-[2-(trifluoromethyl)quinolin-4-yl]piperazin-1-yl}carbonyl)-2,7-diazaspiro[4.5]decan-1-one;
2-(trans-4-Hydroxycyclohexyl)-7-({4-[3-(trifluoromethyl)pyridin-2-yl]piperazin-1-yl}carbonyl)-2,7-diazaspiro[4.5]decan-1-one;
2-(trans-4-Hydroxycyclohexyl)-7-{[4-(2-methylphenyl)piperazin-1-yl]carbonyl}-2,7-diazaspiro[4.5]decan-1-one;
7-{[4-(3,4-Dichlorophenyl)piperazin-1-yl]carbonyl}-2-(trans-4-hydroxycyclohexyl)-2,7-diazaspiro[4.5]decan-1-one;
2-(trans-4-Hydroxycyclohexyl)-7-({4-[3-(trifluoromethyl)phenyl]piperazin-1-yl}carbonyl)-2,7-diazaspiro[4.5]decan-1-one;
7-[(4-Biphenyl-4-ylpiperazin-1-yl)carbonyl]-2-(trans-4-hydroxycyclohexyl)-2,7-diazaspiro[4.5]decan-1-one;
2-(trans-4-Hydroxycyclohexyl)-7-({4-[5-(trifluoromethyl)pyridin-2-yl]piperazin-1-yl}carbonyl)-2,7-diazaspiro[4.5]decan-1-one;
2-(trans-4-Hydroxycyclohexyl)-7-{[4-(2-methoxyphenyl)piperazin-1-yl]carbonyl}-2,7-diazaspiro[4.5]decan-1-one;
2-(trans-4-Hydroxycyclohexyl)-7-[(4-pyridin-2-ylpiperazin-1-yl)carbonyl]-2,7-diazaspiro[4.5]decan-1-one;
7-{[4-(4-Chlorophenyl)piperazin-1-yl]carbonyl}-2-(trans-4-hydroxycyclohexyl)-2,7-diazaspiro[4.5]decan-1-one;
7-{[4-(2-Ethoxyphenyl)piperazin-1-yl]carbonyl}-2-(trans-4-hydroxycyclohexyl)-2,7-diazaspiro[4.5]decan-1-one;
2-(trans-4-Hydroxycyclohexyl)-7-{[4-(3-methoxyphenyl)piperazin-1-yl]carbonyl}-2,7-diazaspiro[4.5]decan-1-one;
2-(trans-4-Hydroxycyclohexyl)-7-{[4-(3-methylphenyl)piperazin-1-yl]carbonyl}-2,7-diazaspiro[4.5]decan-1-one;
7-{[4-(3-Chlorophenyl)piperazin-1-yl]carbonyl}-2-(trans-4-hydroxycyclohexyl)-2,7-diazaspiro[4.5]decan-1-one;
2-(trans-4-Hydroxycyclohexyl)-7-{[4-(4-methoxyphenyl)piperazin-1-yl]carbonyl}-2,7-diazaspiro[4.5]decan-1-one;
4-(4-{[2-(trans-4-Hydroxycyclohexyl)-1-oxo-2,7-diazaspiro[4.5]dec-7-yl]carbonyl}piperazin-1-yl)benzonitrile;
7-{[4-(3,5-Dichloropyridin-4-yl)piperazin-1-yl]carbonyl}-2-(trans-4-hydroxycyclohexyl)-2,7-diazaspiro[4.5]decan-1-one;
(5S)-2-(trans-4-Hydroxycyclohexyl)-7-(1,3-thiazol-2-yl)-2,7-diazaspiro[4.5]decan-1-one;
2-(trans-4-Hydroxycyclohexyl)-7-({4-[4-(trifluoromethyl)phenyl]piperazin-1-yl}carbonyl)-2,7-diazaspiro[4.5]decan-1-one;
7-(3,5-Dichloropyridin-2-yl)-2-(4-hydroxy-1-adamantyl)-2,7-diazaspiro[4.5]decan-1-one;
Propyl {3-fluoro-4-[2-(4-hydroxy-1-adamantyl)-1-oxo-2,7-diazaspiro[4.5]dec-7-yl]phenyl}carbamate;
2-(4-Hydroxy-1-adamantyl)-7-[3-(trifluoromethyl)pyridin-2-yl]-2,7-diazaspiro[4.5]decan-1-one;
Ethyl {3-fluoro-4-[2-(4-hydroxy-1-adamantyl)-1-oxo-2,7-diazaspiro[4.5]dec-7-yl]phenyl}carbamate;
7-(3,5-Difluoropyridin-2-yl)-2-(4-hydroxy-1-adamantyl)-2,7-diazaspiro[4.5]decan-1-one;

3-Fluoro-4-[2-(4-hydroxy-1-adamantyl)-1-oxo-2,7-diazaspiro[4.5]dec-7-yl]benzonitrile;
2-[2-(4-Hydroxy-1-adamantyl)-1-oxo-2,7-diazaspiro[4.5]dec-7-yl]nicotinonitrile;
4-[2-(4-Hydroxy-1-adamantyl)-1-oxo-2,7-diazaspiro[4.5]dec-7-yl]benzonitrile;
N-{3-Fluoro-4-[2-(4-hydroxy-1-adamantyl)-1-oxo-2,7-diazaspiro[4.5]dec-7-yl]phenyl}cyclopropanecarboxamide;
2-(4-Hydroxy-1-adamantyl)-7-[5-(trifluoromethyl)pyridin-2-yl]-2,7-diazaspiro[4.5]decan-1-one;
7-(5-Ethylpyrimidin-2-yl)-2-(4-hydroxy-1-adamantyl)-2,7-diazaspiro[4.5]decan-1-one;
7-(3-Fluoropyridin-2-yl)-2-(4-hydroxy-1-adamantyl)-2,7-diazaspiro[4.5]decan-1-one;
N-{3-Fluoro-4-[2-(4-hydroxy-1-adamantyl)-1-oxo-2,7-diazaspiro[4.5]dec-7-yl]phenyl}acetamide;
N-{3-Fluoro-4-[2-(4-hydroxy-1-adamantyl)-1-oxo-2,7-diazaspiro[4.5]dec-7-yl]phenyl}propanamide;
N-{3-Fluoro-4-[2-(4-hydroxy-1-adamantyl)-1-oxo-2,7-diazaspiro[4.5]dec-7-yl]phenyl}methanesulfonamide;
(5S)-7-(2,3-Difluorophenyl)-2-(4-hydroxycyclohexyl)-2,7-diazaspiro[4.5]decan-1-one;
(5S)-7-(3-Fluorophenyl)-2-(4-hydroxycyclohexyl)-2,7-diazaspiro[4.5]decan-1-one;
(5S)-7-(2-Chloro-3-fluorophenyl)-2-(4-hydroxycyclohexyl)-2,7-diazaspiro[4.5]decan-1-one;
(5S)-7-(4-Fluorophenyl)-2-(4-hydroxycyclohexyl)-2,7-diazaspiro[4.5]decan-1-one;
(5S)-7-[3-Chloro-5-(2-oxo-1,3-oxazinan-3-yl)pyridin-2-yl]-2-(trans-4-hydroxycyclohexyl)-2,7-diazaspiro[4.5]decan-1-one;
(5S)-7-(3,4'-Bipyridin-6-yl)-2-(trans-4-hydroxycyclohexyl)-2,7-diazaspiro[4.5]decan-1-one;
(5S)-2-(trans-4-Hydroxycyclohexyl)-7-(6'-methoxy-3,3'-bipyridin-6-yl)-2,7-diazaspiro[4.5]decan-1-one;
4-{6-[(5S)-2-(trans-4-Hydroxycyclohexyl)-1-oxo-2,7-diazaspiro[4.5]dec-7-yl]pyridin-3-yl}-N,N-dimethylbenzamide;
4-{6-[(5S)-2-(trans-4-Hydroxycyclohexyl)-1-oxo-2,7-diazaspiro[4.5]dec-7-yl]pyridin-3-yl}benzamide;
N-Cyclopropyl-4-{6-[(5S)-2-(trans-4-hydroxycyclohexyl)-1-oxo-2,7-diazaspiro[4.5]dec-7-yl]pyridin-3-yl}benzamide;
N-(4-{6-[(5S)-2-(trans-4-Hydroxycyclohexyl)-1-oxo-2,7-diazaspiro[4.5]dec-7-yl]pyridin-3-yl}-phenyl)acetamide;
(5S)-2-(trans-4-Hydroxycyclohexyl)-7-[5-(4-methoxyphenyl)pyridin-2-yl]-2,7-diazaspiro[4.5]decan-1-one;
(5S)-7-[5-(4-Fluorophenyl)pyridin-2-yl]-2-(trans-4-hydroxycyclohexyl)-2,7-diazaspiro[4.5]decan-1-one;
(5S)-7-(3,3,1-Bipyridin-6-yl)-2-(trans-4-hydroxycyclohexyl)-2,7-diazaspiro[4.5]decan-1-one;
(5S)-7-(6'-Fluoro-3,3'-bipyridin-6-yl)-2-(trans-4-hydroxycyclohexyl)-2,7-diazaspiro[4.5]decan-1-one;
(5S)-2-(trans-4-Hydroxycyclohexyl)-7-(5-pyrimidin-5-ylpyridin-2-yl)-2,7-diazaspiro[4.5]decan-1-one;
3-{6-[(5S)-2-(trans-4-Hydroxycyclohexyl)-1-oxo-2,7-diazaspiro[4.5]dec-7-yl]pyridin-3-yl}benzamide;
N-(3-{6-[(5S)-2-(trans-4-Hydroxycyclohexyl)-1-oxo-2,7-diazaspiro[4.5]dec-7-yl]pyridin-3-yl}-phenyl)acetamide;
(5S)-7-[5-(3,5-Dimethylisoxazol-4-yl)pyridin-2-yl]-2-(trans-4-hydroxycyclohexyl)-2,7-diazaspiro[4.5]decan-1-one;
(5S)-2-(trans-4-Hydroxycyclohexyl)-7-[5-(1-methyl-1H-pyrazol-4-yl)pyridin-2-yl]-2,7-diazaspiro[4.5]decan-1-one;
4-{2-[(5S)-2-(trans-4-Hydroxycyclohexyl)-1-oxo-2,7-diazaspiro[4.5]dec-7-yl]pyrimidin-5-yl}-N,N-dimethylbenzamide;
(5S)-2-(trans-4-Methoxycyclohexyl)-7-[3-(trifluoromethyl)pyridin-2-yl]-2,7-diazaspiro[4.5]decan-1-one;
N-Cyclopropyl-4-{2-[(5S)-2-(trans-4-hydroxycyclohexyl)-1-oxo-2,7-diazaspiro[4.5]dec-7-yl]pyrimidin-5-yl}benzamide;
(5S)-7-(5-Chloro-3,3'-bipyridin-6-yl)-2-(trans-4-hydroxycyclohexyl)-2,7-diazaspiro[4.5]decan-1-one;
(5S)-7-(5-Bromopyrimidin-2-yl)-2-(trans-4-hydroxycyclohexyl)-2,7-diazaspiro[4.5]decan-1-one;
(5S)-7-[3-Chloro-5-(1-methyl-1H-pyrazol-4-yl)pyridin-2-yl]-2-(trans-4-hydroxycyclohexyl)-2,7-diazaspiro[4.5]decan-1-one;
4-{2-[(5S)-2-(trans-4-Hydroxycyclohexyl)-1-oxo-2,7-diazaspiro[4.5]dec-7-yl]pyrimidin-5-yl}benzamide;
(5S)-7-(3,5-Difluoropyridin-2-yl)-2-(trans-4-methoxycyclohexyl)-2,7-diazaspiro[4.5]decan-1-one;
(5S)-7-(5-Chloro-3,4'-bipyridin-6-yl)-2-(trans-4-hydroxycyclohexyl)-2,7-diazaspiro[4.5]decan-1-one;
(5S)-7-(5-Ethylpyrimidin-2-yl)-2-(trans-4-methoxycyclohexyl)-2,7-diazaspiro[4.5]decan-1-one;
tert-Butyl 5-chloro-6-[(5S)-2-(trans-4-hydroxycyclohexyl)-1-oxo-2,7-diazaspiro[4.5]dec-7-yl]-3',6'-dihydro-3,4'-bipyridine-1'(2'H)-carboxylate;
(5S)-7-(5-Fluoropyrimidin-2-yl)-2-(trans-4-hydroxycyclohexyl)-2,7-diazaspiro[4.5]decan-1-one;
(5S)-2-(trans-4-Hydroxycyclohexyl)-7-[4-(2-oxo-1,3-oxazolidin-3-yl)-phenyl]-2,7-diazaspiro[4.5]decan-1-one;
(5S)-7-[2-Fluoro-4-(2-oxo-1,3-oxazolidin-3-yl)phenyl]-2-(trans-4-hydroxycyclohexyl)-2,7-diazaspiro[4.5]decan-1-one;
(5S)-7-[2-Fluoro-4-(2-oxopyrrolidin-1-yl)phenyl]-2-(trans-4-hydroxycyclohexyl)-2,7-diazaspiro[4.5]decan-1-one;
(5S)-7-[3-Chloro-5-(2-oxopyrrolidin-1-yl)pyridin-2-yl]-2-(trans-4-hydroxycyclohexyl)-2,7-diazaspiro[4.5]decan-1-one;
(5S)-2-(trans-4-Hydroxycyclohexyl)-7-[4-(2-oxopyrrolidin-1-yl)phenyl]-2,7-diazaspiro[4.5]decan-1-one;
(5S)-7-[3-Chloro-5-(2-oxo-1,3-oxazolidin-3-yl)pyridin-2-yl]-2-(trans-4-hydroxycyclohexyl)-2,7-diazaspiro[4.5]decan-1-one;
(5S)-7-(2-Fluoro-4-pyrrolidin-1-ylphenyl)-2-(trans-4-hydroxycyclohexyl)-2,7-diazaspiro[4.5]decan-1-one;
(5S)-7-(3-Chloro-5-pyrrolidin-1-ylpyridin-2-yl)-2-(trans-4-hydroxycyclohexyl)-2,7-diazaspiro[4.5]decan-1-one;
(5S)-2-(trans-4-Hydroxycyclohexyl)-7-(5-pyrrolidin-1-ylpyridin-2-yl)-2,7-diazaspiro[4.5]decan-1-one;
(5S)-7-[2-Fluoro-4-(2-oxo-piperidin-1-yl)-phenyl]-2-(trans-4-hydroxy-cyclohexyl)-2,7-diaza-spiro[4.5]decan-1-one;
(5S)-7-[2-Fluoro-4-(2-oxo-1,3-oxazinan-3-yl)phenyl]-2-(trans-4-hydroxycyclohexyl)-2,7-diazaspiro[4.5]decan-1-one;
(5S)-2-(trans-4-hydroxycyclohexyl)-7-[4-(2-oxopiperidin-1-yl)phenyl]-2,7-diazaspiro[4.5]decan-1-one;
(5S)-7-(1,3-Benzothiazol-2-yl)-2-(trans-4-hydroxycyclohexyl)-2,7-diazaspiro[4.5]decan-1-one;
2-[(5S)-2-(trans-4-Methoxycyclohexyl)-1-oxo-2,7-diazaspiro[4.5]dec-7-yl]nicotinonitrile;

(5S)-2-(trans-4-Methoxycyclohexyl)-7-[5-(trifluoromethyl)pyridin-2-yl]-2,7-diazaspiro[4.5]decan-1-one;
(5S)-7-(5-Fluoropyrimidin-2-yl)-2-(trans-4-methoxycyclohexyl)-2,7-diazaspiro[4.5]decan-1-one;
(5S)-7-{3-Chloro-5-[4-(trifluoromethoxy)phenyl]pyridin-2-yl}-2-(trans-4-hydroxycyclohexyl)-2,7-diazaspiro[4.5]decan-1-one;
(5S)-7-(2-Chloro-9H-purin-6-yl)-2-(trans-4-hydroxycyclohexyl)-2,7-diazaspiro[4.5]decan-1-one;
(5S)-7-(4-Amino-5-fluoropyrimidin-2-yl)-2-(trans-4-hydroxycyclohexyl)-2,7-diazaspiro[4.5]decan-1-one;
N-{3-Fluoro-4-[(5S)-2-(trans-4-hydroxycyclohexyl)-1-oxo-2,7-diazaspiro[4.5]dec-7-yl]phenyl}cyclopropanecarboxamide;
N-3-Fluoro-4-[(5S)-2-(trans-4-hydroxycyclohexyl)-1-oxo-2,7-diazaspiro[4.5]dec-7-yl]phenyl cyclobutanecarboxamide;
N-{3-Fluoro-4-[(5S)-2-(trans-4-hydroxycyclohexyl)-1-oxo-2,7-diazaspiro[4.5]dec-7-yl]phenyl}cyclopentanecarboxamide;
N-{3-Fluoro-4-[(5S)-2-(trans-4-hydroxycyclohexyl)-1-oxo-2,7-diazaspiro[4.5]dec-7-yl]phenyl}cyclohexanecarboxamide;
Ethyl {3-fluoro-4-[(5S)-2-(trans-4-hydroxycyclohexyl)-1-oxo-2,7-diazaspiro[4.5]dec-7-yl]phenyl}carbamate;
Propyl {3-fluoro-4-[(5S)-2-(trans-4-hydroxycyclohexyl)-1-oxo-2,7-diazaspiro[4.5]dec-7-yl]phenyl}carbamate;
Isobutyl {3-fluoro-4-[(5S)-2-(trans-4-hydroxycyclohexyl)-1-oxo-2,7-diazaspiro[4.5]dec-7-yl]phenyl}carbamate;
N-{3-Fluoro-4-[(5S)-2-(trans-4-hydroxycyclohexyl)-1-oxo-2,7-diazaspiro[4.5]dec-7-yl]phenyl}propanamide;
N-{3-Fluoro-4-[(5S)-2-(trans-4-hydroxycyclohexyl)-1-oxo-2,7-diazaspiro[4.5]dec-7-yl]phenyl}-2-methylpropanamide;
N-{3-Fluoro-4-[(5S)-2-(trans-4-hydroxycyclohexyl)-1-oxo-2,7-diazaspiro[4.5]dec-7-yl]phenyl}methanesulfonamide;
N-{3-Fluoro-4-[(5S)-2-(trans-4-hydroxycyclohexyl)-1-oxo-2,7-diazaspiro[4.5]dec-7-yl]phenyl}ethane sulfonamide;
(5S)-2-(trans-4-Hydroxycyclohexyl)-7-[3-(trifluoromethyl)pyridin-2-yl]-2,7-diazaspiro[4.5]decan-1-one;
Ethyl [4-[(5S)-2-(trans-4-hydroxycyclohexyl)-1-oxo-2,7-diazaspiro[4.5]dec-7-yl]-3-(trifluoromethyl)phenyl] carbamate;
Methyl [4-[(5S)-2-(trans-4-hydroxycyclohexyl)-1-oxo-2,7-diazaspiro[4.5]dec-7-yl]-3-(trifluoromethyl)phenyl] carbamate;
Propyl [4-[(5S)-2-(trans-4-hydroxycyclohexyl)-1-oxo-2,7-diazaspiro[4.5]dec-7-yl]-3-(trifluoromethyl)phenyl] carbamate;
Isobutyl [4-[(5S)-2-(trans-4-hydroxycyclohexyl)-1-oxo-2,7-diazaspiro[4.5]dec-7-yl]-3-(trifluoromethyl)phenyl] carbamate;
Isopropyl [4-[(5S)-2-(trans-4-hydroxycyclohexyl)-1-oxo-2,7-diazaspiro[4.5]dec-7-yl]-3-(trifluoromethyl)phenyl]carbamate;
N-[4-[(5S)-2-(trans-4-Hydroxycyclohexyl)-1-oxo-2,7-diazaspiro[4.5]dec-7-yl]-3-(trifluoromethyl)phenyl]cyclopropanecarboxamide;
N-[4-[(5S)-2-(trans-4-Hydroxycyclohexyl)-1-oxo-2,7-diazaspiro[4.5]dec-7-yl]-3-(trifluoromethyl)phenyl]cyclobutanecarboxamide;
N-[4-[(5S)-2-(trans-4-Hydroxycyclohexyl)-1-oxo-2,7-diazaspiro[4.5]dec-7-yl]-3-(trifluoromethyl)phenyl]cyclopentanecarboxamide;
N-[4-[(5S)-2-(trans-4-Hydroxycyclohexyl)-1-oxo-2,7-diazaspiro[4.5]dec-7-yl]-3-(trifluoromethyl)phenyl]methanesulfonamide;
N-[4-[(5S)-2-(trans-4-Hydroxycyclohexyl)-1-oxo-2,7-diazaspiro[4.5]dec-7-yl]-3-(trifluoromethyl)phenyl]acetamide;
N-[4-[(5S)-2-(trans-4-Hydroxycyclohexyl)-1-oxo-2,7-diazaspiro[4.5]dec-7-yl]-3-(trifluoromethyl)phenyl]propanamide;
N-[4-[(5S)-2-(trans-4-Hydroxycyclohexyl)-1-oxo-2,7-diazaspiro[4.5]dec-7-yl]-3-(trifluoromethyl)phenyl]-2-methylpropanamide;
(5S)-7-[2-Fluoro-4-(pyridin-2-yloxy)phenyl]-2-(trans-4-hydroxycyclohexyl)-2,7-diazaspiro[4.5]decan-1-one;
Methyl {6-[(5S)-2-(trans-4-hydroxycyclohexyl)-1-oxo-2,7-diazaspiro[4.5]dec-7-yl]pyridin-3-yl}carbamate;
Ethyl {6-[(5S)-2-(trans-4-hydroxycyclohexyl)-1-oxo-2,7-diazaspiro[4.5]dec-7-yl]pyridin-3-yl}carbamate;
Propyl {6-[(5S)-2-(trans-4-hydroxycyclohexyl)-1-oxo-2,7-diazaspiro[4.5]dec-7-yl]pyridin-3-yl}carbamate;
Isobutyl {6-[(5S)-2-(trans-4-hydroxycyclohexyl)-1-oxo-2,7-diazaspiro[4.5]dec-7-yl]pyridin-3-yl}carbamate;
Isopropyl {6-[(5S)-2-(trans-4-hydroxycyclohexyl)-1-oxo-2,7-diazaspiro[4.5]dec-7-yl]pyridin-3-yl}carbamate;
N-{6-[(5S)-2-(trans-4-Hydroxycyclohexyl)-1-oxo-2,7-diazaspiro[4.5]dec-7-yl]pyridin-3-yl}cyclopropanecarboxamide;
N-{6-[(5S)-2-(trans-4-Hydroxycyclohexyl)-1-oxo-2,7-diazaspiro[4.5]dec-7-yl]pyridin-3-yl}cyclobutanecarboxamide;
N-{6-[(5S)-2-(trans-4-Hydroxycyclohexyl)-1-oxo-2,7-diazaspiro[4.5]dec-7-yl]pyridin-3-yl}cyclopentanecarboxamide;
N-{6-[(5S)-2-(trans-4-Hydroxycyclohexyl)-1-oxo-2,7-diazaspiro[4.5]dec-7-yl]pyridin-3-yl}acetamide;
N-{6-[(5S)-2-(trans-4-Hydroxycyclohexyl)-1-oxo-2,7-diazaspiro[4.5]dec-7-yl]pyridin-3-yl}propanamide;
N-{6-[(5S)-2-(trans-4-Hydroxycyclohexyl)-1-oxo-2,7-diazaspiro[4.5]dec-7-yl]pyridin-3-yl}-2-methylpropanamide;
N-{6-[(5S)-2-(trans-4-Hydroxycyclohexyl)-1-oxo-2,7-diazaspiro[4.5]dec-7-yl]pyridin-3-yl}cyclohexanecarboxamide;
Methyl {6-[(5S)-2-(trans-4-hydroxycyclohexyl)-1-oxo-2,7-diazaspiro[4.5]dec-7-yl]-5-methylpyridin-3-yl}carbamate;
Ethyl {6-[(5S)-2-(trans-4-hydroxycyclohexyl)-1-oxo-2,7-diazaspiro[4.5]dec-7-yl]-5-methylpyridin-3-yl}carbamate;
Propyl {6-[(5S)-2-(trans-4-hydroxycyclohexyl)-1-oxo-2,7-diazaspiro[4.5]dec-7-yl]-5-methylpyridin-3-yl}carbamate;
Methyl {3-cyano-4-[(5S)-2-(trans-4-hydroxycyclohexyl)-1-oxo-2,7-diazaspiro[4.5]dec-7-yl]phenyl}carbamate;
Ethyl {3-cyano-4-[(5S)-2-(trans-4-hydroxycyclohexyl)-1-oxo-2,7-diazaspiro[4.5]dec-7-yl]phenyl}carbamate;
Propyl {3-cyano-4-[(5S)-2-(trans-4-hydroxycyclohexyl)-1-oxo-2,7-diazaspiro[4.5]dec-7-yl]phenyl}carbamate;
Isobutyl {3-cyano-4-[(5S)-2-(trans-4-hydroxycyclohexyl)-1-oxo-2,7-diazaspiro[4.5]dec-7-yl]phenyl}carbamate;
Isopropyl {3-cyano-4-[(5S)-2-(trans-4-hydroxycyclohexyl)-1-oxo-2,7-diazaspiro[4.5]dec-7-yl]phenyl}carbamate;
N-{3-Cyano-4-[(5S)-2-(trans-4-hydroxycyclohexyl)-1-oxo-2,7-diazaspiro[4.5]dec-7-yl]phenyl}cyclopropanecarboxamide;

N-{3-Cyano-4-[(5S)-2-(trans-4-hydroxycyclohexyl)-1-oxo-2,7-diazaspiro[4.5]dec-7-yl]phenyl}cyclobutanecarboxamide;
N-{3-Cyano-4-[(5S)-2-(trans-4-hydroxycyclohexyl)-1-oxo-2,7-diazaspiro[4.5]dec-7-yl]phenyl}cyclopentanecarboxamide;
N-{3-Cyano-4-[(5S)-2-(trans-4-hydroxycyclohexyl)-1-oxo-2,7-diazaspiro[4.5]dec-7-yl]phenyl}acetamide;
N-{3-Cyano-4-[(5S)-2-(trans-4-hydroxycyclohexyl)-1-oxo-2,7-diazaspiro[4.5]dec-7-yl]phenyl}propanamide;
N-{3-Cyano-4-[(5S)-2-(trans-4-hydroxycyclohexyl)-1-oxo-2,7-diazaspiro[4.5]dec-7-yl]phenyl}-2-methylpropanamide;
N-{3-Cyano-4-[(5S)-2-(trans-4-hydroxycyclohexyl)-1-oxo-2,7-diazaspiro[4.5]dec-7-yl]phenyl}cyclohexanecarboxamide;
Methyl {4-[(5S)-2-(trans-4-hydroxycyclohexyl)-1-oxo-2,7-diazaspiro[4.5]dec-7-yl]-3-methylphenyl}carbamate;
Ethyl {4-[(5S)-2-(trans-4-hydroxycyclohexyl)-1-oxo-2,7-diazaspiro[4.5]dec-7-yl]-3-methylphenyl}carbamate;
Propyl {4-[(5S)-2-(trans-4-hydroxycyclohexyl)-1-oxo-2,7-diazaspiro[4.5]dec-7-yl]-3-methylphenyl}carbamate;
Isobutyl {4-[(5S)-2-(trans-4-hydroxycyclohexyl)-1-oxo-2,7-diazaspiro[4.5]dec-7-yl]-3-methylphenyl}carbamate;
Isopropyl {4-[(5S)-2-(trans-4-hydroxycyclohexyl)-1-oxo-2,7-diazaspiro[4.5]dec-7-yl]-3-methylphenyl}carbamate;
N-{4-[(5S)-2-(trans-4-Hydroxycyclohexyl)-1-oxo-2,7-diazaspiro[4.5]dec-7-yl]-3-methylphenyl}cyclopropanecarboxamide;
N-{4-[(5S)-2-(trans-4-Hydroxycyclohexyl)-1-oxo-2,7-diazaspiro[4.5]dec-7-yl]-3-methylphenyl}cyclobutanecarboxamide;
N-{4-[(5S)-2-(trans-4-Hydroxycyclohexyl)-1-oxo-2,7-diazaspiro[4.5]dec-7-yl]-3-methylphenyl}cyclopentanecarboxamide;
N-{4-[(5S)-2-(trans-4-Hydroxycyclohexyl)-1-oxo-2,7-diazaspiro[4.5]dec-7-yl]-3-methylphenyl}cyclohexanecarboxamide;
N-{4-[(5S)-2-(trans-4-Hydroxycyclohexyl)-1-oxo-2,7-diazaspiro[4.5]dec-7-yl]-3-methylphenyl}acetamide;
N-{4-[(5S)-2-(trans-4-Hydroxycyclohexyl)-1-oxo-2,7-diazaspiro[4.5]dec-7-yl]-3-methylphenyl}propanamide;
N-{4-[(5S)-2-(trans-4-Hydroxycyclohexyl)-1-oxo-2,7-diazaspiro[4.5]dec-7-yl]-3-methylphenyl}-2-methylpropanamide;
(5S)-2-(trans-4-Hydroxycyclohexyl)-7-[4-(trifluoromethyl)quinolin-2-yl]-2,7-diazaspiro[4.5]decan-1-one;
(5S)-7-(3-Chloropyridin-2-yl)-2-(trans-4-hydroxycyclohexyl)-2,7-diazaspiro[4.5]decan-1-one;
(5S)-7-[3-Fluoro-4-(trifluoromethyl)pyridin-2-yl]-2-(trans-4-hydroxycyclohexyl)-2,7-diazaspiro[4.5]decan-1-one;
(5S)-2-(trans-4-Hydroxycyclohexyl)-7-(3,5,6-trifluoro-4-methylpyridin-2-yl)-2,7-diazaspiro[4.5]decan-1-one;
2,3,5-Trifluoro-6-[(5S)-2-(trans-4-hydroxycyclohexyl)-1-oxo-2,7-diazaspiro[4.5]deal-yl] isonicotinonitrile;
(5S)-7-(3,5-Difluoropyridin-2-yl)-2-(trans-4-hydroxycyclohexyl)-2,7-diazaspiro[4.5]decan-1-one;
(5S)-2-(trans-4-hydroxycyclohexyl)-7-[4-(trifluoromethyl)pyridin-2-yl]-2,7-diazaspiro[4.5]decan-1-one;
(5S)-7-(3-Fluoropyridin-4-yl)-2-(trans-4-hydroxycyclohexyl)-2,7-diazaspiro[4.5]decan-1-one;
(5S)-7-(5-Chloro-3-fluoropyridin-2-yl)-2-(trans-4-hydroxycyclohexyl)-2,7-diazaspiro[4.5]decan-1-one;
(5S)-7-(3-Ethynylpyridin-2-yl)-2-(trans-4-hydroxycyclohexyl)-2,7-diazaspiro[4.5]decan-1-one;
7-(2-Fluoro-4-nitrophenyl)-2-(trans-4-hydroxy-cyclohexyl)-2,7-diazaspiro[4.5]decan-1-one;
2-[(5S)-2-(trans-4-Hydroxycyclohexyl)-1-oxo-2,7-diazaspiro[4.5]dec-7-yl]-6-methylnicotinonitrile;
(5S)-2-(trans-4-Hydroxycyclohexyl)-7-quinolin-2-yl-2,7-diazaspiro[4.5]decan-1-one;
2-(trans-4-Hydroxycyclohexyl)-7-[6-methyl-4-(trifluoromethyl)pyridin-2-yl]-2,7-diazaspiro[4.5]decan-1-one;
(5S)-7-(3-Fluoropyridin-2-yl)-2-(trans-4-hydroxycyclohexyl)-2,7-diazaspiro[4.5]decan-1-one;
7-(5-Ethylpyrimidin-2-yl)-2-(trans-4-hydroxycyclohexyl)-2,7-diazaspiro[4.5]decan-1-one;
(5S)-2-(trans-4-Hydroxycyclohexyl)-7-(3-methylquinolin-2-yl)-2,7-diazaspiro[4.5]decan-1-one;
N-{4-[(5S)-2-(trans-4-Hydroxycyclohexyl)-1-oxo-2,7-diazaspiro[4.5]dec-7-yl]phenyl}methanesulfonamide;
(5S)-7-[2-Fluoro-4-(pyridin-4-yloxy)phenyl]-2-(trans-4-hydroxycyclohexyl)-2,7-diazaspiro[4.5]decan-1-one;
(5S)-2-(trans-4-Hydroxycyclohexyl)-7-[5-(hydroxymethyl)pyridin-2-yl]-2,7-diazaspiro[4.5]decan-1-one;
6-[(5S)-2-(trans-4-Hydroxycyclohexyl)-1-oxo-2,7-diazaspiro[4.5]dec-7-yl]-N-methylnicotinamide;
(5S)-7-(3-Fluoropyridin-4-yl)-2-(trans-4-hydroxycyclohexyl)-2,7-diazaspiro[4.5]decan-1-one;
(5S)-7-(2-Chloropyridin-4-yl)-2-(trans-4-hydroxycyclohexyl)-2,7-diazaspiro[4.5]decan-1-one;
N-{3-Fluoro-4-[(5S)-2-(trans-4-hydroxycyclohexyl)-1-oxo-2,7-diazaspiro[4.5]dec-7-yl]phenyl}-N-methylmethanesulfonamide;
N-{6-[(5S)-2-(trans-4-Hydroxycyclohexyl)-1-oxo-2,7-diazaspiro[4.5]dec-7-yl]pyridin-3-yl}-2-methylpropanamide;
7-(2-Chloropyrimidin-4-yl)-2-(trans-4-hydroxycyclohexyl)-2,7-diazaspiro[4.5]decan-1-one;
6-[2-(trans-4-Hydroxycyclohexyl)-1-oxo-2,7-diazaspiro[4.5]dec-7-yl]-N,N-dimethylnicotinamide;
Ethyl {2-[(5S)-2-(trans-4-hydroxycyclohexyl)-1-oxo-2,7-diazaspiro[4.5]dec-7-yl]-6-methoxypyridin-3-yl}carbamate;
Methyl {2-[(5S)-2-(trans-4-hydroxycyclohexyl)-1-oxo-2,7-diazaspiro[4.5]dec-7-yl]-6-methoxypyridin-3-yl}carbamate;
N-{2-[(5S)-2-(trans-4-Hydroxycyclohexyl)-1-oxo-2,7-diazaspiro[4.5]dec-7-yl]-6-methoxypyridin-3-yl}acetamide;
5-[(5S)-2-(trans-4-Hydroxycyclohexyl)-1-oxo-2,7-diazaspiro[4.5]dec-7-yl]-N-methylpyridine-2-carboxamide;
(5S)-2-(trans-4-Hydroxycyclohexyl)-7-(3-methoxypyridin-2-yl)-2,7-diazaspiro[4.5]decan-1-one;
2-[8-(trans-4-Hydroxycyclohexyl)-7-oxo-2,8-diazaspiro[5.5]undec-2-yl]nicotinonitrile;
2-(trans-4-Hydroxycyclohexyl)-8-[3-(trifluoromethyl)pyridin-2-yl]-2,8-diazaspiro[5.5]undecan-1-one;
3-Cyclohexyl-7-[5-(trifluoromethyl)pyridin-2-yl]-1,3,7-triazaspiro[4.5]decane-2,4-dione;
6-(3-cyclohexyl-2,4-dioxo-1,3,7-triazaspiro[4.5]dec-7-yl)nicotinonitrile;
4-(3-Cyclohexyl-2,4-dioxo-1,3,7-triazaspiro[4.5]dec-7-yl)-3-fluorobenzonitrile;
3-Cyclohexyl-7-(5-ethylpyrimidin-2-yl)-1,3,7-triazaspiro[4.5]decane-2,4-dione;

3-Cyclohexyl-7-(3-fluoropyridin-2-yl)-1,3,7-triazaspiro[4.5]decane-2,4-dione;
3-Cyclohexyl-7-(3,5-difluoropyridin-2-yl)-1,3,7-triazaspiro[4.5]decane-2,4-dione;
3-Cyclohexyl-7-(3,5-dichloropyridin-2-yl)-1,3,7-triazaspiro[4.5]decane-2,4-dione;
2-(3-Methylpyridin-2-yl)-7-[5-(trifluoromethyl)pyridin-2-yl]-2,7-diazaspiro[4.5]decan-1-one;
N,N-Dimethyl-5-[(5S)-1-oxo-2-(tetrahydro-2H-pyran-4-yl)-2,7-diazaspiro[4.5]dec-7-yl]pyridine-2-carboxamide;
3-Fluoro-4-[(5S)-1-oxo-2-(tetrahydro-2H-pyran-4-yl)-2,7-diazaspiro[4.5]dec-7-yl]benzonitrile;
(5S)-2-(trans-4-Hydroxycyclohexyl)-7-(6-methoxy-2-methylpyridin-3-yl)-2,7-diazaspiro[4.5]decan-1-one;
(5S)-2-(4-Hydroxycyclohexyl)-7-(6-methoxy-4-methylpyridin-3-yl)-2,7-diazaspiro[4.5]decan-1-one;
(5S)-7-(2,6-Difluorophenyl)-2-(4-hydroxycyclohexyl)-2,7-diazaspiro[4.5]decan-1-one;
7-(5-Chloropyridin-2-yl)-2-(4-hydroxy-1-adamantyl)-2,7-diazaspiro[4.5]decan-1-one;
7-(3-Fluoropyridin-4-yl)-2-(4-hydroxy-1-adamantyl)-2,7-diazaspiro[4.5]decan-1-one;
N-{3-Fluoro-4-[2-(4-hydroxy-1-adamantyl)-1-oxo-2,7-diazaspiro[4.5]dec-7-yl]phenyl}propanamide;
Methyl {3-fluoro-4-[2-(4-hydroxy-1-adamantyl)-1-oxo-2,7-diazaspiro[4.5]dec-7-yl]phenyl}carbamate;
Propyl {3-fluoro-4-[2-(4-hydroxy-1-adamantyl)-1-oxo-2,7-diazaspiro[4.5]dec-7-yl]phenyl}carbamate;
N-{3-Fluoro-4-[2-(4-hydroxy-1-adamantyl)-1-oxo-2,7-diazaspiro[4.5]dec-7-yl]phenyl}ethanesulfonamide;
2-[(5S)-2-(cis-4-Hydroxycyclohexyl)-1-oxo-2,7-diazaspiro[4.5]dec-7-yl]nicotinonitrile;
(5S)-2-(cis-4-Hydroxycyclohexyl)-7-[3-(trifluoromethyl)pyridin-2-yl]-2,7-diazaspiro[4.5]decan-1-one;
(5S)-7-(3-Fluoropyridin-2-yl)-2-(cis-4-hydroxycyclohexyl)-2,7-diazaspiro[4.5]decan-1-one;
(5S)-7-(3,5-Dichloropyridin-2-yl)-2-(cis-4-hydroxycyclohexyl)-2,7-diazaspiro[4.5]decan-1-one;
(5S)-7-(5-Chloro-3-fluoropyridin-2-yl)-2-(cis-4-hydroxycyclohexyl)-2,7-diazaspiro[4.5]decan-1-one;
(5S)-7-(3-Chloropyridin-2-yl)-2-(cis-4-hydroxycyclohexyl)-2,7-diazaspiro[4.5]decan-1-one;
Methyl {4-[(5S)-2-(trans-4-hydroxycyclohexyl)-1-oxo-2,7-diazaspiro[4.5]dec-7-yl]-2-methylphenyl}carbamate;
Ethyl {4-[(5S)-2-(trans-4-hydroxycyclohexyl)-1-oxo-2,7-diazaspiro[4.5]dec-7-yl]-2-methylphenyl}carbamate;
Prop-2-yn-1-yl {4-[(5S)-2-(trans-4-hydroxycyclohexyl)-1-oxo-2,7-diazaspiro[4.5]dec-7-yl]-2-methylphenyl}carbamate;
Methyl {6-[(5S)-2-(trans-4-hydroxycyclohexyl)-1-oxo-2,7-diazaspiro[4.5]dec-7-yl]-4-methylpyridin-3-yl}carbamate;
Ethyl {6-[(5S)-2-(trans-4-hydroxycyclohexyl)-1-oxo-2,7-diazaspiro[4.5]dec-7-yl]-4-methylpyridin-3-yl}carbamate;
Prop-2-yn-1-yl {6-[(5S)-2-(trans-4-hydroxycyclohexyl)-1-oxo-2,7-diazaspiro[4.5]dec-7-yl]-4-methylpyridin-3-yl}carbamate;
Methyl {6-[(5S)-2-(trans-4-hydroxycyclohexyl)-1-oxo-2,7-diazaspiro[4.5]dec-7-yl]-5-methoxypyridin-3-yl}carbamate;
Ethyl {6-[(5S)-2-(trans-4-hydroxycyclohexyl)-1-oxo-2,7-diazaspiro[4.5]dec-7-yl]-5-methoxypyridin-3-yl}carbamate;
Prop-2-yn-1-yl {6-[(5S)-2-(trans-4-hydroxycyclohexyl)-1-oxo-2,7-diazaspiro[4.5]dec-7-yl]-5-methoxypyridin-3-yl}carbamate;
Methyl {5-fluoro-2-[(5S)-2-(trans-4-hydroxycyclohexyl)-1-oxo-2,7-diazaspiro[4.5]dec-7-yl]pyrimidin-4-yl}carbamate;
Isopropyl {3-fluoro-4-[(5S)-2-(trans-4-hydroxycyclohexyl)-1-oxo-2,7-diazaspiro[4.5]dec-7-yl]phenyl}methylcarbamate;
(5S)-7-(3-Bromo-5-methylpyridin-2-yl)-2-(trans-4-hydroxycyclohexyl)-2,7-diazaspiro[4.5]decan-1-one;
2-[(5S)-2-Cyclohexyl-1-oxo-2,7-diazaspiro[4.5]dec-7-yl]nicotinonitrile;
2-[(5S)-2-(trans-4-Hydroxycyclohexyl)-1-oxo-2,7-diazaspiro[4.5]dec-7-yl]isonicotinonitrile;
(5S)-7-(3-Fluoro-6-methylpyridin-2-yl)-2-(trans-4-hydroxycyclohexyl)-2,7-diazaspiro[4.5]decan-1-one;
6-[(5S)-2-(trans-4-Hydroxycyclohexyl)-1-oxo-2,7-diazaspiro[4.5]dec-7-yl]-2-methylnicotinonitrile;
2-[(5S)-2-(trans-4-Hydroxycyclohexyl)-1-oxo-2,7-diazaspiro[4.5]dec-7-yl]-4,6-dimethylnicotinonitrile;
(5S)-2-(trans-4-Hydroxycyclohexyl)-7-[2-(trifluoromethyl)quinazolin-4-yl]-2,7-diazaspiro[4.5]decan-1-one;
(5S)-2-Cyclohexyl-7-[2-fluoro-4-(2-oxo-1,3-oxazolidin-3-yl)phenyl]-2,7-diazaspiro[4.5]decan-1-one;
(5S)-2-Cyclohexyl-7-[2-fluoro-4-(2-oxopyrrolidin-1-yl)phenyl]-2,7-diazaspiro[4.5]decan-1-one;
(5S)-7-(3-Fluoropyridin-2-yl)-2-(tetrahydro-2H-pyran-4-yl)-2,7-diazaspiro[4.5]decan-1-one;
(5S)-7-[2-Fluoro-4-(2-oxo-1,3-oxazolidin-3-yl)phenyl]-2-(tetrahydro-2H-pyran-4-yl)-2,7-diazaspiro[4.5]decan-1-one;
(5S)-7-[2-Fluoro-4-(2-oxo-1,3-oxazinan-3-yl)phenyl]-2-(tetrahydro-2H-pyran-4-yl)-2,7-diazaspiro[4.5]decan-1-one;
(5S)-7-[2-Fluoro-4-(2-oxopiperidin-1-yl)phenyl]-2-(tetrahydro-2H-pyran-4-yl)-2,7-diazaspiro[4.5]decan-1-one;
(5S)-7-[2-Fluoro-4-(2-oxopyrrolidin-1-yl)phenyl]-2-(tetrahydro-2H-pyran-4-yl)-2,7-diazaspiro[4.5]decan-1-one;
3-Fluoro-N-methyl-4-[(5S)-1-oxo-2-(tetrahydro-2H-pyran-4-yl)-2,7-diazaspiro[4.5]dec-7-yl]benzamide;
3-Fluoro-N,N-dimethyl-4-[(5S)-1-oxo-2-(tetrahydro-2H-pyran-4-yl)-2,7-diazaspiro[4.5]dec-7-yl]benzamide;
2-[(5S)-1-Oxo-2-(tetrahydro-2H-pyran-4-yl)-2,7-diazaspiro[4.5]dec-7-yl]benzonitrile;
(5S)-7-(3,5-Dichloropyridin-2-yl)-2-(3-methylpyridin-2-yl)-2,7-diazaspiro[4.5]decan-1-one;
3-Bromo-4-[(5S)-2-(trans-4-hydroxycyclohexyl)-1-oxo-2,7-diazaspiro[4.5]dec-7-yl]benzonitrile;
(5S)-7-(2,5-difluorophenyl)-2-(4-hydroxycyclohexyl)-2,7-diazaspiro[4.5]decan-1-one;
(5S)-7-(2-Bromo-3-fluorophenyl)-2-(trans-4-hydroxycyclohexyl)-2,7-diazaspiro[4.5]decan-1-one;
(5S)-7-(5-Fluoro-2-methylphenyl)-2-(4-hydroxycyclohexyl)-2,7-diazaspiro[4.5]decan-1-one;
(5S)-7-(2,3-Dichlorophenyl)-2-(4-hydroxycyclohexyl)-2,7-diazaspiro[4.5]decan-1-one;
(5S)-7-(2,6-Dichlorophenyl)-2-(trans-4-hydroxycyclohexyl)-2,7-diazaspiro[4.5]decan-1-one;
4-Bromo-2-[(5S)-2-(cis-4-hydroxycyclohexyl)-1-oxo-2,7-diazaspiro[4.5]dec-7-yl]benzonitrile;
2-[(5S)-2-(4-Hydroxycyclohexyl)-1-oxo-2,7-diazaspiro[4.5]dec-7-yl]benzonitrile;
(5S)-7-(2-Fluorophenyl)-2-(4-hydroxycyclohexyl)-2,7-diazaspiro[4.5]decan-1-one;

2-[(5S)-2-(cis-4-Hydroxycyclohexyl)-1-oxo-2,7-diazaspiro[4.5]dec-7-yl]isonicotinonitrile;
(5S)-7-(3-Bromo-5-fluoropyridin-2-yl)-2-(cis-4-hydroxycyclohexyl)-2,7-diazaspiro[4.5]decan-1-one;
(5S)-7-(3-Fluoro-4-methylpyridin-2-yl)-2-(cis-4-hydroxycyclohexyl)-2,7-diazaspiro[4.5]decan-1-one;
6-[(5S)-2-(cis-4-Hydroxycyclohexyl)-1-oxo-2,7-diazaspiro[4.5]dec-7-yl]-2-methylnicotinonitrile;
(5S)-7-(5-Chloro-3-methylpyridin-2-yl)-2-(cis-4-hydroxycyclohexyl)-2,7-diazaspiro[4.5]decan-1-one;
4-Chloro-2-[(5S)-2-(cis-4-hydroxycyclohexyl)-1-oxo-2,7-diazaspiro[4.5]dec-7-yl]benzonitrile;
2-Fluoro-4-[(5S)-2-(cis-4-hydroxycyclohexyl)-1-oxo-2,7-diazaspiro[4.5]dec-7-yl]benzonitrile;
4-Bromo-2-[(5S)-2-(cis-4-hydroxycyclohexyl)-1-oxo-2,7-diazaspiro[4.5]dec-7-yl]benzonitrile;
7-[(3-Chloro-2-methylphenyl)sulfonyl]-2-(trans-4-hydroxycyclohexyl)-2,7-diazaspiro[4.5]decan-1-one;
(5S)-7-[2-Chloro-5-(trifluoromethyl)phenyl]-2-(trans-4-hydroxycyclohexyl)-2,7-diazaspiro[4.5]decan-1-one;
(5S)-7-[3-Fluoro-5-(trifluoromethyl)phenyl]-2-(trans-4-hydroxycyclohexyl)-2,7-diazaspiro[4.5]decan-1-one;
(5S)-7-(4-Chloro-2-methylphenyl)-2-(trans-4-hydroxycyclohexyl)-2,7-diazaspiro[4.5]decan-1-one;
(5S)-7-(3-chloro-2-methylphenyl)-2-(trans-4-hydroxycyclohexyl)-2,7-diazaspiro[4.5]decan-1-one;
(5S)-2-(trans-4-Hydroxycyclohexyl)-7-quinolin-8-yl-2,7-diazaspiro[4.5]decan-1-one;
{3-[(5S)-2-(trans-4-Hydroxycyclohexyl)-1-oxo-2,7-diazaspiro[4.5]dec-7-yl]phenyl}acetonitrile;
(5S)-7-(4-Fluoro-2-methylphenyl)-2-(trans-4-hydroxycyclohexyl)-2,7-diazaspiro[4.5]decan-1-one;
(5S)-2-(trans-4-Hydroxycyclohexyl)-7-[4-(2-oxopyrrolidin-1-yl)-2-(trifluoromethyl)phenyl]-2,7-diazaspiro[4.5]decan-1-one;
(5S)-2-(trans-4-Hydroxycyclohexyl)-7-[4-(2-oxo-1,3-oxazolidin-3-yl)-2-(trifluoromethyl)phenyl]-2,7-diazaspiro[4.5]decan-1-one;
(5S)-2-(trans-4-Hydroxycyclohexyl)-7-[4-(2-oxo-1,3-oxazinan-3-yl)-2-(trifluoromethyl)phenyl]-2,7-diazaspiro[4.5]decan-1-one;
(5S)-7-[3-Fluoro-4-(pyridin-2-yloxy)phenyl]-2-(4-hydroxycyclohexyl)-2,7-diazaspiro[4.5]decan-1-one;
(5S)-7-[3-Fluoro-4-(pyridin-4-yloxy)phenyl]-2-(4-hydroxycyclohexyl)-2,7-diazaspiro[4.5]decan-1-one;
(5S)-7-[3-Fluoro-4-(pyridin-3-yloxy)phenyl]-2-(4-hydroxycyclohexyl)-2,7-diazaspiro[4.5]decan-1-one;
(5S)-7-[2-Fluoro-4-(pyridin-3-yloxy)phenyl]-2-(4-hydroxycyclohexyl)-2,7-diazaspiro[4.5]decan-1-one;
Methyl {3-chloro-4-[(5S)-2-(trans-4-hydroxycyclohexyl)-1-oxo-2,7-diazaspiro[4.5]dec-7-yl]phenyl}carbamate;
Ethyl {3-chloro-4-[(5S)-2-(trans-4-hydroxycyclohexyl)-1-oxo-2,7-diazaspiro[4.5]dec-7-yl]phenyl}carbamate;
Prop-2-yn-1-yl {3-chloro-4-[(5S)-2-(trans-4-hydroxycyclohexyl)-1-oxo-2,7-diazaspiro[4.5]dec-7-yl]phenyl}carbamate;
Propyl {3-chloro-4-[(5S)-2-(trans-4-hydroxycyclohexyl)-1-oxo-2,7-diazaspiro[4.5]dec-7-yl]phenyl}carbamate;
N-{3-Chloro-4-[(5S)-2-(trans-4-hydroxycyclohexyl)-1-oxo-2,7-diazaspiro[4.5]dec-7-yl]phenyl}cyclopentanecarboxamide;
N-{3-Chloro-4-[(5S)-2-(trans-4-hydroxycyclohexyl)-1-oxo-2,7-diazaspiro[4.5]dec-7-yl]phenyl}cyclohexanecarboxamide;
(5S)-7-(5-Fluoropyrimidin-2-yl)-2-(cis-4-hydroxycyclohexyl)-2,7-diazaspiro[4.5]decan-1-one;
(5S)-7-(5-Bromopyrimidin-2-yl)-2-(cis-4-hydroxycyclohexyl)-2,7-diazaspiro[4.5]decan-1-one;
(5S)-7-(5-Ethylpyrimidin-2-yl)-2-(cis-4-hydroxycyclohexyl)-2,7-diazaspiro[4.5]decan-1-one;
4-{2-[(5S)-2-(cis-4-Hydroxycyclohexyl)-1-oxo-2,7-diazaspiro[4.5]dec-7-yl]pyrimidin-5-yl}benzamide;
N-Cyclopropyl-4-{2-[(5S)-2-(cis-4-hydroxycyclohexyl)-1-oxo-2,7-diazaspiro[4.5]dec-7-yl]pyrimidin-5-yl}benzamide;
(5S)-2-(cis-4-Hydroxycyclohexyl)-7-[5-(4-methoxyphenyl)pyrimidin-2-yl]-2,7-diazaspiro[4.5]decan-1-one;
(5S)-2-(cis-4-Hydroxycyclohexyl)-7-(5-pyridin-3-ylpyrimidin-2-yl)-2,7-diazaspiro[4.5]decan-1-one;
5-{2[(5S)-2-(cis-4-Hydroxycyclohexyl)-1-oxo-2,7-diazaspiro[4.5]dec-7-yl]pyrimidin-5-yl}-N,N-dimethylpyridine-2-carboxamide;
(5S)-2-(cis-4-Hydroxycyclohexyl)-7-(5-pyridin-4-ylpyrimidin-2-yl)-2,7-diazaspiro[4.5]decan-1-one;
4-{5-Chloro-6-[(5S)-2-(cis-4-hydroxycyclohexyl)-1-oxo-2,7-diazaspiro[4.5]dec-7-yl]pyridin-3-yl}-N-cyclopropylbenzamide;
5'-Chloro-N-ethyl-6'-[(5S)-2-(cis-4-hydroxycyclohexyl)-1-oxo-2,7-diazaspiro[4.5]dec-7-yl]-3,3'-bipyridine-6-carboxamide;
2-[(5S)-2-(trans-4-Hydroxycyclohexyl)-1-oxo-2,7-diazaspiro[4.5]dec-7-yl]isonicotinonitrile;
Methyl {4-[(5S)-2-(cis-4-hydroxy-4-methylcyclohexyl)-1-oxo-2,7-diazaspiro[4.5]dec-7-yl]-3-methylphenyl}carbamate;
Prop-2-yn-1-yl {6-[(5S)-2-(trans-4-hydroxycyclohexyl)-1-oxo-2,7-diazaspiro[4.5]dec-7-yl]-5-methoxypyridin-3-yl}carbamate;
(5S)-7-(5-Fluoropyrimidin-2-yl)-2-(tetrahydro-2H-pyran-4-yl)-2,7-diazaspiro[4.5]decan-1-one;
(5S)-7-(5-Ethylpyrimidin-2-yl)-2-(tetrahydro-2H-pyran-4-yl)-2,7-diazaspiro[4.5]decan-1-one;
(5S)-2-(Tetrahydro-2H-pyran-4-yl)-7-[4-(trifluoromethyl)pyrimidin-2-yl]-2,7-diazaspiro[4.5]decan-1-one;
(5S)-7-(4-Methoxypyrimidin-2-yl)-2-(tetrahydro-2H-pyran-4-yl)-2,7-diazaspiro[4.5]decan-1-one;
(5S)-7-(2-Fluorophenyl)-2-(tetrahydro-2H-pyran-4-yl)-2,7-diazaspiro[4.5]decan-1-one;
(5S)-2-(cis-4-Hydroxycyclohexyl)-7-[5-(1H-pyrazol-1-yl)pyrimidin-2-yl]-2,7-diazaspiro[4.5]decan-1-one;
(5S)-2-(cis-4-Hydroxycyclohexyl)-7-[5-(3-methyl-1H-pyrazol-1-yl)pyrimidin-2-yl]-2,7-diazaspiro[4.5]decan-1-one;
(5S)-2-(cis-4-Hydroxycyclohexyl)-7-{5-[3-(trifluoromethyl)-1H-pyrazol-1-yl]pyrimidin-2-yl}-2,7-diazaspiro[4.5]decan-1-one;
(5S)-2-(cis-4-Hydroxycyclohexyl)-7-pyrimidin-2-yl-2,7-diazaspiro[4.5]decan-1-one;
(5S)-2-(cis-4-Hydroxycyclohexyl)-7-[5-(2-oxopyridin-1(2H)-yl)pyrimidin-2-yl]-2,7-diazaspiro[4.5]decan-1-one;
(5S)-7-(2,5-Difluoropyridin-3-yl)-2-(cis-4-hydroxycyclohexyl)-2,7-diazaspiro[4.5]decan-1-one;
(5S)-7-(3,5-Difluoropyridin-2-yl)-2-(cis-4-hydroxycyclohexyl)-2,7-diazaspiro[4.5]decan-1-one;
(5S)-7-[3-Fluoro-4-(trifluoromethyl)pyridin-2-yl]-2-(cis-4-hydroxycyclohexyl)-2,7-diazaspiro[4.5]decan-1-one;
(5S)-7-[3-Chloro-5-(trifluoromethyl)pyridin-2-yl]-2-(cis-4-hydroxycyclohexyl)-2,7-diazaspiro[4.5]decan-1-one;
(5S)-2-(cis-4-Hydroxycyclohexyl)-7-[4-(trifluoromethyl)pyridin-2-yl]-2,7-diazaspiro[4.5]decan-1-one;

(5S)-7-(5-Bromo-2-chloropyridin-3-yl)-2-(cis-4-hydroxycyclohexyl)-2,7-diazaspiro[4.5]decan-1-one;
(5S)-7-(5-Bromo-3-fluoropyridin-2-yl)-2-(cis-4-hydroxycyclohexyl)-2,7-diazaspiro[4.5]decan-1-one;
(5S)-7-(5-Bromo-3-chloropyridin-2-yl)-2-(cis-4-hydroxycyclohexyl)-2,7-diazaspiro[4.5]decan-1-one;
(5S)-7-(5-Bromo-3-methylpyridin-2-yl)-2-(cis-4-hydroxycyclohexyl)-2,7-diazaspiro[4.5]decan-1-one;
Methyl {6-[(5S)-2-(cis-4-hydroxycyclohexyl)-1-oxo-2,7-diazaspiro[4.5]dec-7-yl]-5-methylpyridin-3-yl}carbamate;
Ethyl {6-[(5S)-2-(cis-4-hydroxycyclohexyl)-1-oxo-2,7-diazaspiro[4.5]dec-7-yl]-5-methylpyridin-3-yl}carbamate;
Propyl {6-[(5S)-2-(cis-4-hydroxycyclohexyl)-1-oxo-2,7-diazaspiro[4.5]dec-7-yl]-5-methylpyridin-3-yl}carbamate;
Prop-2-yn-1-yl {6-[(5S)-2-(cis-4-hydroxycyclohexyl)-1-oxo-2,7-diazaspiro[4.5]dec-7-yl]-5-methylpyridin-3-yl}carbamate;
Methyl {6-[(5S)-2-(cis-4-hydroxycyclohexyl)-1-oxo-2,7-diazaspiro[4.5]dec-7-yl]-5-methoxypyridin-3-yl}carbamate;
Ethyl {6-[(5S)-2-(cis-4-hydroxycyclohexyl)-1-oxo-2,7-diazaspiro[4.5]dec-7-yl]-5-methoxypyridin-3-yl}carbamate;
Propyl {6-[(5S)-2-(cis-4-hydroxycyclohexyl)-1-oxo-2,7-diazaspiro[4.5]dec-7-yl]-5-methoxypyridin-3-yl}carbamate;
Prop-2-yn-1-yl {6-[(5S)-2-(cis-4-hydroxycyclohexyl)-1-oxo-2,7-diazaspiro[4,5]dec-7-yl]-5-methoxypyridin-3-yl}carbamate;
(5S)-2-(cis-4-Hydroxycyclohexyl)-7-[3-methoxy-5-(2-oxopyrrolidin-1-yl)pyridin-2-yl]-2,7-diazaspiro[4.5]decan-1-one;
(5S)-2-(cis-4-Hydroxycyclohexyl)-7-[3-methoxy-5-(2-oxo-1,3-oxazolidin-3-yl)pyridin-2-yl]-2,7-diazaspiro[4.5]decan-1-one;
(5S)-2-(cis-4-Hydroxycyclohexyl)-7-[3-methoxy-5-(2-oxo-1,3-oxazinan-3-yl)pyridin-2-yl]-2,7-diazaspiro[4.5]decan-1-one;
(5S)-7-(3-Chloro-5-phenylpyridin-2-yl)-2-(cis-4-hydroxycyclohexyl)-2,7-diazaspiro[4.5]decan-1-one;
(5S)-7-[3-Chloro-5-(4-methoxyphenyl)pyridin-2-yl]-2-(cis-4-hydroxycyclohexyl)-2,7-diazaspiro[4.5]decan-1-one;
4-{5-Chloro-6-[(5S)-2-(cis-4-hydroxycyclohexyl)-1-oxo-2,7-diazaspiro[4.5]dec-7-yl]pyridin-3-yl}benzamide;
(5S)-7-(5-Chloro-3,4'-bipyridin-6-yl)-2-(cis-4-hydroxycyclohexyl)-2,7-diazaspiro[4.5]decan-1-one;
5'-Chloro-6'-[(5S)-2-(cis-4-hydroxycyclohexyl)-1-oxo-2,7-diazaspiro[4.5]dec-7-yl]-N,N-dimethyl-3,3'-bipyridine-6-carboxamide;
5'-Chloro-N,N-diethyl-6'-[(5S)-2-(cis-4-hydroxycyclohexyl)-1-oxo-2,7-diazaspiro[4.5]dec-7-yl]-3,3'-bipyridine-6-carboxamide;
4-{5-Chloro-6-[(5S)-2-(cis-4-hydroxycyclohexyl)-1-oxo-2,7-diazaspiro[4.5]dec-7-yl]pyridin-3-yl}-N,N-dimethylbenzamide;
Methyl {5-chloro-6-[(5S)-2-(cis-4-hydroxycyclohexyl)-1-oxo-2,7-diazaspiro[4.5]dec-7-yl]pyridin-3-yl}carbamate;
Ethyl {5-chloro-6-[(5S)-2-(cis-4-hydroxycyclohexyl)-1-oxo-2,7-diazaspiro[4.5]dec-7-yl]pyridin-3-yl}carbamate;
Propyl {5-chloro-6-[(5S)-2-(cis-4-hydroxycyclohexyl)-1-oxo-2,7-diazaspiro[4.5]dec-7-yl]pyridin-3-yl}carbamate;
Prop-2-yn-1-yl {5-chloro-6-[(5S)-2-(cis-4-hydroxycyclohexyl)-1-oxo-2,7-diazaspiro[4.5]dec-7-yl]pyridin-3-yl}carbamate;
(5S)-7-[3-Chloro-5-(2-oxo-1,3-oxazolidin-3-yl)pyridin-2-yl]-2-(cis-4-hydroxycyclohexyl)-2,7-diazaspiro[4.5]decan-1-one;
(5S)-7-[3-Chloro-5-(2-oxo-1,3-oxazinan-3-yl)pyridin-2-yl]-2-(cis-4-hydroxycyclohexyl)-2,7-diazaspiro[4.5]decan-1-one;
(5S)-7-[3-Chloro-5-(2-oxopyrrolidin-1-yl)pyridin-2-yl]-2-(cis-4-hydroxycyclohexyl)-2,7-diazaspiro[4.5]decan-1-one;
(5S)-7-(5-Chloro-3,3'-bipyridin-6-yl)-2-(cis-4-hydroxycyclohexyl)-2,7-diazaspiro[4.5]decan-1-one;
(5S)-7-(3-Fluoro-6-methylpyridin-2-yl)-2-(trans-4-hydroxycyclohexyl)-2,7-diazaspiro[4.5]decan-1-one;
6-[(5S)-2-(trans-4-Hydroxycyclohexyl)-1-oxo-2,7-diazaspiro[4.5]dec-7-yl]-2-methylnicotinonitrile;
2-[(5S)-2-(trans-4-Hydroxycyclohexyl)-1-oxo-2,7-diazaspiro[4.5]dec-7-yl]-4,6-dimethylnicotinonitrile;
(5S)-2-(trans-4-Hydroxycyclohexyl)-7-[2-(trifluoromethyl)quinazolin-4-yl]-2,7-diazaspiro[4.5]decan-1-one;
(5S)-2-Cyclohexyl-7-[2-fluoro-4-(2-oxopyrrolidin-1-yl)phenyl]-2,7-diazaspiro[4.5]decan-1-one;
(5S)-2-Cyclohexyl-7-[2-fluoro-4-(2-oxo-1,3-oxazolidin-3-yl)phenyl]-2,7-diazaspiro[4.5]decan-1-one;
(5S)-7-(5-Chloro-3-methylpyridin-2-yl)-2-(trans-4-hydroxycyclohexyl)-2,7-diazaspiro[4.5]decan-1-one;
(5S)-7-(3-Fluoro-4-methylpyridin-2-yl)-2-(trans-4-hydroxycyclohexyl)-2,7-diazaspho[4.5]decan-1-one;
(5S)-7-(5-Fluoro-3-methylpyridin-2-yl)-2-(trans-4-hydroxycyclohexyl)-2,7-diazaspiro[4.5]decan-1-one;
(5S)-7-(5-Fluoro-6-methylpyridin-2-yl)-2-(trans-4-hydroxycyclohexyl)-2,7-diazaspiro[4.5]decan-1-one;
(5S)-2-(trans-4-Hydroxycyclohexyl)-7-(7H-pyrrolo[2,3-d]pyrimidin-4-yl)-2,7-diazaspiro[4.5]decan-1-one;
(5S)-2-(trans-4-Hydroxycyclohexyl)-7-(5-methylpyridin-2-yl)-2,7-diazaspiro[4.5]decan-1-one;
2-[(5S)-2-(trans-4-Hydroxycyclohexyl)-1-oxo-2,7-diazaspiro[4.5]dec-7-yl]-5-phenylnicotinonitrile;
(5S)-7-[3-Chloro-5-(2-oxo-1,3-oxazolidin-3-yl)pyridin-2-yl]-2-cyclohexyl-2,7-diazaspiro[4.5]decan-1-one;
(5S)-7-[3-Chloro-5-(2-oxopyrrolidin-1-yl)pyridin-2-yl]-2-cyclohexyl-2,7-diazaspiro[4.5]decan-1-one;
(5S)-7-[3-Chloro-5-(2-oxo-1,3-oxazinan-3-yl)pyridin-2-yl]-2-cyclohexyl-2,7-diazaspiro[4.5]decan-1-one; and
(5S)-7-[3-Chloro-5-(2-oxopiperidin-1-yl)pyridin-2-yl]-2-cyclohexyl-2,7-diazaspiro[4.5]decan-1-one;
or a pharmaceutically acceptable salt thereof.

17. A composition comprising a compound of claim 1, or a pharmaceutically acceptable salt thereof, and a pharmaceutically acceptable carrier.

18. A method of treating a disease in a patient comprising administering to the patient a therapeutically effective amount of a compound according to claim 1, or a pharmaceutically acceptable salt thereof, wherein said disease is obesity, glucose intolerance, insulin resistance, hyperglycemia, hypertension, hyperlipidemia, depression, dementia, glaucoma, osteoporosis, inflammation, heart failure, atherosclerosis, arteriosclerosis, coronary artery disease, thrombosis, angina, peripheral vascular disease, vascular wall damage, stroke, dyslipidemia, hyperlipoproteinaemia, diabetic dyslipidemia, mixed dyslipidemia, hypercholesterolemia, hypertriglyceridemia, metabolic syndrome or general aldosterone-related target organ damage.

19. The compound of claim 1, or a pharmaceutically acceptable salt thereof, having Formula IIIa:

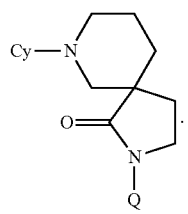

IIIa

20. The compound of claim 8, or a pharmaceutically acceptable salt thereof, having Formula IIIa:

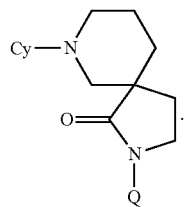

IIIa

21. The compound of claim 9, or a pharmaceutically acceptable salt thereof, having Formula IIIa:

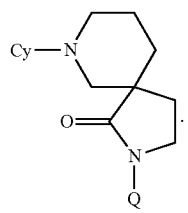

IIIa

22. The compound of claim 10, or a pharmaceutically acceptable salt thereof, having Formula IIIa:

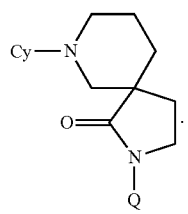

IIIa

23. The compound of claim 1, or a pharmaceutically acceptable salt thereof, having Formula IIIb or IIIc:

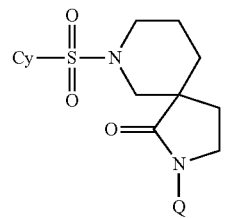

IIIb

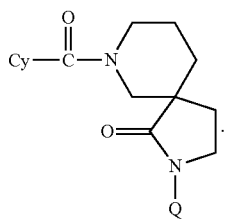

IIIc

24. The compound of claim 8, or a pharmaceutically acceptable salt thereof, having Formula IIIb or IIIc:

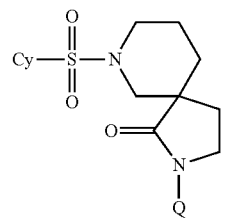

IIIb

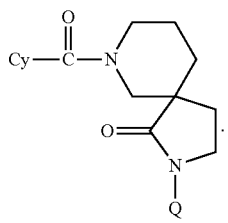

IIIc

25. The compound of claim 9, or a pharmaceutically acceptable salt thereof, having Formula IIIb or IIIc:

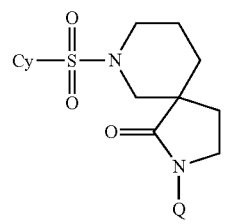

IIIb

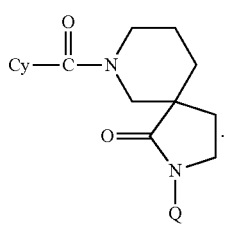

IIIc

26. The compound of claim 10, or a pharmaceutically acceptable salt thereof, having Formula IIIb or IIIc:

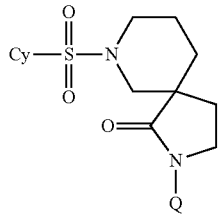

IIIb

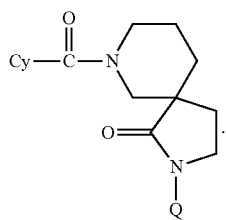

IIIc

27. A method of treating a type 2 diabetes in a patient comprising administering to the patient a therapeutically effective amount of a compound according to claim 1, or a pharmaceutically acceptable salt thereof.

28. A method of treating a type 2 diabetes in a patient comprising administering to the patient a therapeutically effective amount of a compound according to claim 19, or a pharmaceutically acceptable salt thereof.

29. A method of treating a type 2 diabetes in a patient comprising administering to the patient a therapeutically effective amount of a compound according to claim 20, or a pharmaceutically acceptable salt thereof.

30. A method of treating a type 2 diabetes in a patient comprising administering to the patient a therapeutically effective amount of a compound according to claim 21, or a pharmaceutically acceptable salt thereof.

31. A method of treating a type 2 diabetes in a patient comprising administering to the patient a therapeutically effective amount of a compound according to claim 23, or a pharmaceutically acceptable salt thereof.

* * * * *

UNITED STATES PATENT AND TRADEMARK OFFICE
CERTIFICATE OF CORRECTION

PATENT NO. : 8,563,570 B2  
APPLICATION NO. : 13/355219  
DATED : October 22, 2013  
INVENTOR(S) : Wenqing Yao et al.

It is certified that error appears in the above-identified patent and that said Letters Patent is hereby corrected as shown below:

On Title Page 2, column 1, line 27 (Other Publications): delete "2d." and insert -- 2nd. --.

IN THE CLAIMS:

Column 334, line 46 (claim 1): delete "SO" and insert -- $SO_2$ --.

Column 335, line 2 (claim 1): delete "$NR^{c'}(O)R^{a'}$," and insert -- $NR^{c'}C(O)R^{a'}$, --.

Column 335, line 3 (claim 1): delete "$NR^{c'}(O)OR^{b'}$," and insert -- $NR^{c'}C(O)OR^{b'}$, --.

Column 335, line 53 (claim 1): delete "$R^{19}$" and insert -- $R^{10}$ --.

Column 335, line 63 (claim 1): delete "$NR^{c'}(O)OR^{a'}$," and insert -- $NR^{c'}C(O)OR^{a'}$, --.

Column 336, line 12 (claim 1): delete "$NR^{c'}(O)R^{d'}$," and insert -- $NR^{c'}C(O)R^{d'}$, --.

Column 336, line 12 (claim 1): delete "$NR^{c'}(O)OR^{a'}$," and insert -- $NR^{c'}C(O)OR^{a'}$, --.

Column 336, line 51-52 (claim 1): delete "heterocyloalkyl" and insert -- heterocycloalkyl --.

Column 336, line 55-56 (claim 1): delete "heterocyloalkyl" and insert -- heterocycloalkyl --.

Column 337, line 28 (claim 1): delete "5-," and insert -- 5-, 6- --.

Column 339, line 45 (claim 16): delete "(5S)" and insert -- (5R) --.

Column 340, line 14 (claim 16): delete "(5S)" and insert -- (5R) --.

Column 340, line 24 (claim 16): delete "(5S)" and insert -- (5R) --.

Column 342, line 15 (claim 16): delete "(5S)" and insert -- (5R) --.

Column 344, line 66 (claim 16): delete "(55)" and insert -- (5S) --.

Column 348, line 57 (claim 16): delete "hydroxy-cyclohexyl" and insert -- hydroxycyclohexyl --.

Column 348, line 57 (claim 16): delete "diaza-spiro" and insert -- diazaspiro --.

Column 349, line 15 (claim 16): delete "N-3-" and insert -- N-{3- --.

Column 349, line 16 (claim 16): delete "phenyl" and insert -- phenyl} --.

Column 351, line 61 (claim 16): delete "deal" and insert -- dec-7 --.

Signed and Sealed this  
Eighth Day of September, 2015

Michelle K. Lee  
*Director of the United States Patent and Trademark Office*

CERTIFICATE OF CORRECTION (continued)
U.S. Pat. No. 8,563,570 B2

Column 358, line 67 (claim 18): delete "hyperlipoproteinaemia," and insert -- hyperlipoproteinemia, --.

Column 362, line 21 (claim 31): delete "23," and insert -- 22, --.